United States Patent (10) Patent No.: US 7,611,884 B2
Milhausen (45) Date of Patent: Nov. 3, 2009

(54) TOXOPLASMA GONDII NUCLEIC ACID MOLECULES

(75) Inventor: Michael James Milhausen, Boulder, CO (US)

(73) Assignee: Heska Corporation, Loveland, CO (US)

( * ) Notice: Subject to any disclaimer, the term of this patent is extended or adjusted under 35 U.S.C. 154(b) by 0 days.

(21) Appl. No.: 12/138,512

(22) Filed: Jun. 13, 2008

(65) Prior Publication Data

US 2009/0069264 A1    Mar. 12, 2009

Related U.S. Application Data

(60) Division of application No. 11/321,421, filed on Dec. 29, 2005, now Pat. No. 7,396,909, which is a continuation of application No. 10/321,856, filed on Dec. 17, 2002, now Pat. No. 7,052,899, which is a division of application No. 09/216,393, filed on Dec. 18, 1998, now Pat. No. 6,514,694, which is a continuation-in-part of application No. 08/994,825, filed on Dec. 19, 1997, now abandoned.

(51) Int. Cl.
C12N 1/20 (2006.01)
C12N 15/00 (2006.01)
C12N 7/00 (2006.01)
C12N 7/01 (2006.01)
C12N 15/31 (2006.01)
C12N 15/11 (2006.01)

(52) U.S. Cl. ............. 435/252.3; 435/320.1; 435/235.1; 536/23.1; 536/23.7

(58) Field of Classification Search ....................... None
See application file for complete search history.

(56) References Cited

U.S. PATENT DOCUMENTS 6,214,572 B1    4/2001    Yuan et al.

FOREIGN PATENT DOCUMENTS

| EP | 0 516 381 A | 12/1992 |
| EP | 0 687 471 A | 12/1995 |
| EP | 0 700 991 A | 3/1996 |
| EP | 0710 724 A | 5/1996 |
| WO | WO 91 00740 A | 1/1991 |

OTHER PUBLICATIONS

Bukhari et al., 1998, *Applied and Environmental Microbiology*, vol. 64, No. 11, pp. 4495-4499.
Burg et al., 1989, *Journal of Clinical Microbiology*, vol. 27, No. 8, pp. 1787-1792.
Caggana et al., 1998, *Human Mutation*, vol. 11, pp. 404-409.
Gibbons et al., 1998, *Protist*, vol. 149, pp. 127-134.
Hock, B., 1996, *Ann. Biol. Clin.*, vol. 54, pp. 243-252.
Morgan et al., 1998, *Parasitology Today*, vol. 14, No. 6, pp. 241-245.
Rochelle et al., 1997, *Applied and Environmental Microbiology*, vol. 63, No. 1, pp. 106-114.
Roy et al., 1997, *BioTechniques*, vol. 23, No. 5, pp. 942-945.
Cox-Singh et al., 1997 *International Journal for Parasitology*, vol. 27, No. 12, pp. 1575-1577.
Hehl et al., EMBL database entry TG1932, accession No. N82193, Apr. 13, 1996.
Hehl et al., EMBL database entry TGW667, accession No. W96667, Jul. 19, 1996.
Hehl et al., EMBL database entry TG5911, accession No. N61591, Feb. 29, 1996.
Marra et al., EMBL database entry TGAA20976, accession No. AA520976, Jul. 17, 1997.
Marra et al., EMBL database entry TGAA20558, accession No. AA520558, Jul. 17, 1997.
Marra et al., EMBL database entry TGAA532000, accession No. AA532000, Jul. 24, 1997.
Marra et al., EMBL database entry TGAA19977, accession No. AA519977, Jul. 17, 1997.
Marra et al., EMBL database entry TGAA20348, accession No. AA520348, Jul. 17, 1997.
Hehl et al., EMBL database entry TG0292, accession No. N82092, Apr. 13, 1996.
Marra et al., EMBL database entry TGAA31653, accession No. AA531653, Jul. 24, 1997.
Hehl et al., EMBL database entry TG1673, accession No. N82167, Apr. 13, 1996.
Hehl et al., EMBL database entry TG5032, accession No. N81503, Apr. 13, 1996.
Marra et al EMBL database entry TGAA20213, accession No. AA520213, Jul. 17, 1997.
Kennell, Progr. Nucl. Acid Res. Mol. Biol. 11:259 (1971).
Wallace, et al., Methods Enzymol., 152: 432 (1987).

*Primary Examiner*—James Martinell
(74) *Attorney, Agent, or Firm*—Sheridan Ross P.C.

(57) ABSTRACT

The present invention relates to immunogenic *Toxoplasma gondii* proteins, to *T. gondii* nucleic acid molecules, including those that encode such proteins and to antibodies raised against such proteins. The present invention also includes methods to obtain such proteins, nucleic acid molecules and antibodies. Also included in the present invention are compositions comprising such proteins, nucleic acid molecules and/or antibodies, as well as the use of such compositions to inhibit oocyst shedding by cats due to infection with *T. gondii*. The present invention also includes the use of certain *T. gondii*-based antisera to identify such nucleic acid molecules and proteins, as well as nucleic acid molecules and proteins identified by such methods. The present invention also relates to novel methods for the detection of cysts and oocysts.

12 Claims, No Drawings

TOXOPLASMA GONDII NUCLEIC ACID MOLECULES

CROSS-REFERENCE TO RELATED APPLICATIONS

This application is a divisional of application U.S. patent application Ser. No. 11/321,421, filed Dec. 29, 2005 now U.S. Pat. No. 7,396,909, entitled "*TOXOPLASMA GONDII* PROTEINS"; which is a continuation of U.S. patent application Ser. No. 10/321,856, filed Dec. 17, 2002, entitled "*TOXOPLASMA GONDII* PROTEINS, NUCLEIC ACID MOLECULES, AND USES THEREOF", now issued as U.S. Pat. No. 7,052,899 B2; which is a divisional of U.S. patent application Ser. No. 09/216,393, filed Dec. 18, 1998, entitled "METHODS FOR THE DETECTION OF ENCYSTED PARASITES", now issued as U.S. Pat. No. 6,514,694 B2; which is Continuation-in-Part of U.S. patent application Ser. No. 08/994,825, filed Dec. 19, 1997, now abandoned, entitled "*TOXOPLASMA GONDII* PROTEINS, NUCLEIC ACID MOLECULES, AND USES THEREOF, now abandoned; and all of the foregoing are incorporated herein by reference.

FIELD OF THE INVENTION

The present invention relates to *Toxoplasma gondii* nucleic acid molecules, proteins encoded by such nucleic acid molecules, antibodies raised against such proteins and methods to identify such nucleic acid molecules, proteins or antibodies. The present invention also includes compositions comprising such nucleic acid molecules, proteins and antibodies, as well as their use for inhibiting oocyst shedding by cats infected with *T. gondii* and for protecting animals from diseases caused by *T. gondii*.

BACKGROUND OF THE INVENTION

Various attempts to develop a vaccine to both the asexual systemic stage and the sexual entero-epithelial stage of the *Toxoplasma* life cycle have been reported over the last thirty years (Hermentin, K. and Aspock, H. (1988), *Zbl. Bakt. Hyg. A*, 269:423-436). These attempts can be grouped into the following categories: 1) immunization with whole killed organism, 2) immunization with selected antigens, either purified native or recombinant protein, 3) immunization with attenuated strains, and 4) immunization with irradiated organisms. Little success has been achieved with immunizations using whole killed organism (Frenkel, J. K. and Smith, D. D. (1982), *Journal of Parasitology*, 68:744-748). Partial success has been observed with the pure native protein P30 (Bulow, R., and Boothroyd, J. C. (1991), *J. Immunol.* 147: 3496) and with selected fractions of parasite lysates (Lunden, A. Lovgren, K. Uggla, A., and Araujo, P. G.; (1993) *Infection and Immunity*, 61: 2639-2643). However, attempts with purified recombinant antigens have not been successful (Lunden, A., Parmley, S. F., Bengtsson, K. L. and Araujo, F. G. (1997) *Parasitology Research*, 83:6-9). Studies with irradiated organisms have reported 0-90% protection and are complicated by the uncertainty of truly inactivated irradiated preparations. Effective vaccines have been produced using attenuated strains. Two such mutant strains, ts-4 (Waldeland, H., Pfefferkorn, E. R., and Frenkel, J. K. (1993), *Journal of Parasitology*, 69:171-175) and S48 (Hartley, W. J. and Marshall, S. C. (1957), *New Zealand Veterinary Journal*, 5:119-124), successfully protect animals against the asexual systemic disease. These strains are delivered in the tachyzoite form and do not protect cats from oocyst shedding. Another strain, T-263 (Frenkel, J. K.; Pfefferkorn, E. R.; Smith, D. D.; and Fishback, J. L. (1991), *American Journal of Veterinary Research*, 52:759-763) is an oocyst minus strain, but was shown to progress through most of the entero-epithelial stages in the cat intestine. Exposure to this strain induces immunity in the cat to oocyst shedding upon subsequent challenge. There remains a need for an effective vaccine for prevention of the diseases caused by infection with *Toxoplasma gondii*.

SUMMARY OF THE INVENTION

The present invention relates to novel compositions and methods to inhibit *Toxoplasma gondii* (*T. gondii*) oocyst shedding by cats, thereby preventing the spread of *T. gondii* infection. According to the present invention there are provided isolated immunogenic *T. gondii* proteins and mimetopes thereof; *T. gondii* nucleic acid molecules, including those that encode such proteins; recombinant molecules including such nucleic acid molecules; recombinant viruses including such nucleic acid molecules; recombinant cells including such nucleic acid molecules; and antibodies that selectively bind to such immunogenic *T. gondii* proteins.

The present invention also includes methods to obtain and/or identify proteins, nucleic acid molecules, recombinant molecules, recombinant viruses, recombinant cells, and antibodies of the present invention. Also included are compositions comprising such proteins, nucleic acid molecules, recombinant molecules, recombinant viruses, recombinant cells, and antibodies, as well as use of such compositions to inhibit *T. gondii* oocyst shedding by cats infected with *T. gondii*, or for preventing *T. gondii* infection in an animal.

The present invention further includes the use of the nucleic acid molecules or proteins of the present invention as diagnostic reagents for the detection of *T. gondii* infection. In a preferred embodiment, the present invention includes a novel detection method and kit for detecting *T. gondii* oocysts in the feces of *T. gondii* infected cats.

One embodiment of the present invention is an isolated nucleic acid molecule encoding an immunogenic *T. gondii* protein that can be identified by a method that includes the steps of: a) immunoscreening a *T. gondii* genomic expression library or cDNA expression library with an antiserum, including an antiserum derived from intestinal secretions; and b) identifying a nucleic acid molecule in the library that expresses a protein that selectively binds to an antibody in the antiserum. Antisera to be used for screening include antiserum raised against *T. gondii* oocysts, antiserum raised against *T. gondii* bradyzoites, antiserum raised against *T. gondii* infected cat gut, and antiserum isolated from a cat immune to *T. gondii* infection. Another embodiment is an isolated immunogenic *T. gondii* protein that can be identified by a method that includes the steps of: a) immunoscreening a *T. gondii* genomic expression library or cDNA expression library with such an antiserum; and b) identifying a protein expressed by the library that selectively binds to antibodies in the antiserum. Also included are methods to identify and isolate such nucleic acid molecules and proteins.

The present application also includes an isolated nucleic acid molecule that hybridizes under stringent hybridization conditions with a gene that includes a nucleic acid sequence cited in Table 1. Also included in the present invention is an isolated nucleic acid molecule that hybridizes under stringent hybridization conditions with a gene that includes a nucleic acid molecule cited in Table 1. Preferred nucleic acid molecules encode immunogenic *T. gondii* proteins. More preferred nucleic acid molecules are those cited in Table 1.

The present invention also relates to recombinant molecules, recombinant viruses and recombinant cells that include an isolated nucleic acid molecule of the present invention. Also included are methods to produce such nucleic acid molecules, recombinant molecules, recombinant viruses and recombinant cells.

Another embodiment of the present invention is an isolated immunogenic protein encoded by a nucleic acid molecule that hybridizes under stringent hybridization conditions with a gene (i.e., with either the coding strand or the non-coding strand) comprising a nucleic acid sequence cited in Table 1 and/or a nucleic acid molecule cited in Table 1. Note that the nucleic acid molecule hybridizes with the non-coding strand of the gene, that is, with the complement of the coding strand of the gene. A preferred protein is an immunogenic *T. gondii* protein. More preferred proteins are those encoded by nucleic acid molecules cited in Table 1. Also preferred are the proteins cited in Table 1.

The present invention also relates to: mimetopes of immunogenic *T. gondii* proteins and isolated antibodies that selectively bind to immunogenic *T. gondii* proteins or mimetopes thereof. Also included are methods, including recombinant methods to produce proteins, mimetopes and antibodies of the present invention.

Yet another embodiment of the present invention is a composition to inhibit *T. gondii* oocyst shedding in a cat due to infection with *T. gondii*. Such a composition includes one or more of the following protective compounds: an isolated immunogenic T. gondii protein encoded by a nucleic acid molecule that hybridizes under stringent hybridization conditions with a gene comprising a nucleic acid sequence cited in Table 1, and specifically with the non-coding-strand of that gene; an isolated antibody that selectively binds to said immunogenic *T. gondii* protein; and an isolated nucleic acid molecule that hybridizes under stringent hybridization conditions with a gene comprising a nucleic acid sequence cited in Table 1. Such a composition can also include an excipient, adjuvant or carrier. Preferred compositions comprising a nucleic acid molecule of the present invention include genetic vaccines, recombinant virus vaccines and recombinant cell vaccines. Also included in the present invention is a method to protect an animal, including a human, from disease caused by *T. gondii*, comprising the step of administering to the animal a composition of the present invention. Preferred animals to treat are cats in order to prevent oocyst shedding caused by *T. gondii* infection.

DETAILED DESCRIPTION OF THE INVENTION

The present invention provides for isolated immunogenic *T. gondii* proteins, isolated *T. gondii* nucleic acid molecules including those encoding such *T. gondii* proteins, recombinant molecules comprising such nucleic acid molecules, recombinant viruses comprising such nucleic acid molecules, cells transformed with such nucleic acid molecules (i.e., recombinant cells), and antibodies that selectively bind to immunogenic *T. gondii* proteins. As used herein, the terms isolated immunogenic *T. gondii* protein and isolated nucleic acid molecule refer to an immunogenic *T. gondii* protein and a *T. gondii* nucleic acid molecule, respectively, derived from *T. gondii* which can be obtained from its natural source or can be produced using, for example, recombinant nucleic acid technology or chemical synthesis. Also included in the present invention is the use of these proteins, nucleic acid molecules, and antibodies as compositions to protect animals from diseases caused by *T. gondii* and to inhibit *T. gondii* oocyst shedding in cats. As used herein, a cat refers to any member of the cat family (i.e., Felidae), including domestic cats, wild cats and zoo cats. Examples of cats include, but are not limited to, domestic cats, lions, tigers, leopards, panthers, cougars, bobcats, lynx, jaguars cheetahs, and servals. A preferred cat to protect is a domestic cat. Further included in the present invention is the use of these proteins, nucleic acid molecules and antibodies for the detection of *T. gondii* infection in an animal or as targets for the development of chemotherapeutic agents against parasitic infection.

Immunogenic *T. gondii* protein and nucleic acid molecules of the present invention have utility because they represent novel targets for anti-parasite vaccines or chemotherapeutic agents. Compositions of the present invention can also be used as reagents for the diagnosis of *T. gondii* infection in cats and other animals, including humans. The products and processes of the present invention are advantageous because they enable the inhibition of *T. gondii* oocyst shedding in cats, the definitive hosts for *T. gondii* (i.e., the animals in which *T. gondii* reproduction takes place). It is to be noted that the proteins and nucleic acid molecules of the present invention have uses beyond eliciting an immune response despite denoting proteins of the present invention as immunogenic proteins.

As described in more detail in the Examples, it was very difficult to isolate a nucleic acid molecule encoding an immunogenic *T. gondii* protein selectively bound by antisera directed against *T. gondii* intestinal stages. Such stages are preferred because they represent the sexual cycle of *T. gondii*, the preferred target for development of a composition to inhibit oocyst shedding. Unfortunately, however, the it gondii sexual cycle cannot currently be reproduced in culture, and, there is not a simple method by which to produce a cDNA (i.e., complementary DNA) library containing only *T. gondii* nucleic acid molecules of various stages of the sexual cycle. For example, the infected cat gut is the source of many of the sexual stages of *T. gondii*, and, as such, material to be used in identifying *T. gondii* immunogenic proteins are contaminated with cat material. The present invention describes the development of new techniques to isolate and identify nucleic acid molecules encoding immunogenic *T. gondii* proteins. These techniques include (a) the isolation and enrichment of antisera against a variety of *T. gondii* life stages, several of which are only present in infected cats, at least predominantly in infected cat guts, and (b) the use of such antisera to screen cDNA and genomic expression libraries to identify nucleic acid molecules that express *T. gondii* proteins that selectively bind to such antisera.

One embodiment of the present invention is an isolated protein that includes an immunogenic *T. gondii* protein. It is to be noted that the terms "one or more" and "at least one" can be used interchangeably herein. It is also to be noted that the terms "comprising", "including", and "having" can be used interchangeably. According to the present invention, an isolated, or biologically pure, protein is a protein that has been removed from its natural milieu. The terms "isolated" and "biologically pure" do not necessarily reflect the extent to which the protein has been purified. An isolated protein of the present invention can be obtained from its natural source, can be produced using recombinant DNA technology, or can be produced by chemical synthesis.

An isolated protein of the present invention, including a homolog, can be identified in a straight-forward manner by the protein's ability to elicit an immune response against a naturally occurring *T. gondii* protein. Examples of *T. gondii* immunogenic proteins include proteins in which amino acids have been deleted (e.g., a truncated version of the protein, such as a peptide) inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of eliciting an immune response against a *T. gondii* immunogenic protein, and/or of binding to an antibody directed against a *T. gondii* immunogenic protein. That is, when the homolog is administered to an animal as an immunogen, using techniques known to those skilled in the art, the animal will produce an immune response against at least one epitope of a *T. gondii* immunogenic protein. The ability of a protein to effect an immune response can be measured using techniques known to those skilled in the art. As used herein, the term "epitope" refers to the smallest portion of a protein or other antigen capable of selectively binding to the antigen binding site of an antibody or a T-cell receptor. It is well accepted by those skilled in the art that the minimal size of a protein epitope is about four to six amino acids. As is appreciated by those skilled in the art, an epitope can include amino acids that naturally are contiguous to each other as well as amino acids that, due to the tertiary structure of the natural protein, are in sufficiently close proximity to form an epitope. According to the present invention, an epitope includes a portion of a protein comprising at least about 4 amino acids, at least about 5 amino acids, at least about 6 amino acids, at least about 10 amino acids, at least about 15 amino acids, at least about 20 amino acids, at least about 25 amino acids, at least about 30 amino acids, at least about 35 amino acids, at least about 40 amino acids, at least about 50 amino acids, at least about 100 amino acids, at least about 150 amino acids, at least about 200 amino acids, at least about 250 amino acids, or at least about 300 amino acids.

Immunogenic *T. gondii* protein homologs can be the result of natural allelic variation or natural mutation. Immunogenic *T. gondii* protein homologs of the present invention can also be produced using techniques known in the art including, but not limited to, direct modifications to the protein or modifications to the gene encoding the protein using, for example, classic or recombinant DNA techniques to effect random or targeted mutagenesis.

As used herein, a nucleic acid molecule encoding an immunogenic *T. gondii* protein includes nucleic acid sequences related to a natural *T. gondii* gene. As used herein, a *T. gondii* gene includes all regions of the genome related to the gene, such as regulatory regions that control production of the immunogenic *T. gondii* protein encoded by the gene (for example, transcription, translation or post-translation control regions) as well as the coding region itself, and any introns or non-translated coding regions. As used herein, a gene that "includes" or "comprises" a sequence may include that sequence in one contiguous array, or may include the sequence as fragmented exons. As used herein, the term "coding region" refers to a continuous linear array of nucleotides that translates into a protein. A full-length coding region is that coding region that is translated into a full-length protein, i.e., a complete protein as would be initially translated in its natural milieu, prior to any post-translational modifications.

In one embodiment, a *T. gondii* gene of the present invention includes at least one of the nucleic acid molecules cited in Table 1 (i.e., the cited nucleic acid molecules). The coding strands of the cited nucleic acid molecules are represented, respectively, by the nucleic acid sequences (i.e., the cited nucleic acid sequences) shown in Table 1. Also presented in Table 1 are the deduced amino acid sequences encoded by each of the cited nucleic acid molecules (i.e., the cited amino acid sequences) and the protein name designations (i.e., the cited proteins).

TABLE 1

| SEQ ID NO | TYPE | Nucleic Acid Molecules | Amino Acid Molecules | Original Designation |
|---|---|---|---|---|
| 1 | DNA | $nTG1_{357}$ | | Tg-41 |
| 2 | Protein | | $PTG1_{119}$ | PTG-41 |
| 3 | DNA | $nTG2_{339}$ | | Tg-45 |
| 4 | Protein | | $PTG2_{108}$ | PTG-45 |
| 5 | DNA | $nTG4_{526}$ | | Tg-50 |
| 6 | Protein | | $PTG4_{175}$ | PTG-50 |
| 7 | cDNA | $nTG4_{1478}$ | | Tg-50c |
| 8 | Protein | | $PTG4_{381}$ | PTG-50c |
| 9 | DNA | $nTG5_{657}$ | | Q2-4 |
| 10 | Protein | | $PTG5_{219}$ | PQ2-4 |
| 11 | cDNA | $nTG5_{1029}$ | | Q2-4c |
| 12 | Protein | | $PTG5_{273}$ | PQ2-4c |
| 13 | DNA | $nTG6_{425}$ | | Q2-9 |
| 14 | Protein | | $PTG6_{142}$ | PQ2-9 |
| 15 | DNA | $nTG7_{417}$ | | Q2-10 |
| 16 | Protein | | $PTG7_{139}$ | PQ2-10 |
| 17 | DNA | $nTG8_{507}$ | | Q2-11 |
| 18 | Protein | | $PTG8_{51}$ | PQ2-11 |
| 19 | DNA | $nTG9_{718}$ | | 4499-9 |
| 20 | Protein | | $PTG9_{99}$ | P4499-9 |
| 21 | DNA | $nTG10_{441}$ | | 4604-2 |
| 22 | Protein | | $PTG10_{147}$ | P4604-2 |
| 23 | DNA | $nTG11_{428}$ | | 4604-3 |
| 24 | Protein | | $PTG11_{134}$ | P4604-3 |
| 25 | DNA | $nTG13_{282}$ | | 4604-5 |
| 26 | DNA | $nTG15_{304}$ | | 4604-10 |
| 27 | Protein | | $PTG15_{101}$ | P4604-10 |
| 28 | DNA | $nTG16_{284}$ | | 4604-17 |
| 29 | Protein | | $PTG16_{95}$ | P4604-17 |
| 30 | DNA | $nTG17_{690}$ | | 4604-54 |
| 31 | Protein | | $PTG17_{230}$ | P4604-54 |
| 32 | DNA | $nTG18_{313}$ | | 4604-62 |
| 33 | Protein | | $PTG18_{54}$ | P4604-62 |
| 34 | DNA | $nTG19_{389}$ | | 4604-63 |
| 35 | Protein | | $PTG19_{65}$ | P4604-63 |
| 36 | DNA | $nTG21_{548}$ | | 4604-69 |
| 37 | Protein | | $PTG21_{183}$ | P4604-69 |
| 38 | DNA | $nTG22_{310}$ | | BZ1-2 |
| 39 | Protein | | $PTG22_{95}$ | PBZ1-2 |
| 40 | DNA | $nTG23_{220}$ | | BZ1-3 |
| 41 | Protein | | $PTG23_{73}$ | PBZ1-3 |
| 42 | DNA | $nTG24_{642}$ | | BZ1-6 |
| 43 | Protein | | $PTG24_{34}$ | PBZ1-6 |
| 44 | DNA | $nTG25_{381}$ | | BZ2-3 |
| 45 | Protein | | $PTG25_{27}$ | PBZ2-3 |
| 46 | DNA | $nTG26_{432}$ | | BZ2-5 |
| 47 | Protein | | $PTG26_{85}$ | PBZ2-5 |
| 48 | DNA | $nTG27_{282}$ | | BZ3-2 |
| 49 | Protein | | $PTG27_{35}$ | PBZ3-2 |
| 50 | DNA | $nTG28_{466}$ | | BZ4-3 |
| 51 | Protein | | $PTG28_{71}$ | PBZ4-3 |
| 52 | DNA | $nTG30_{539}$ | | BZ4-6 |
| 53 | Protein | | $PTG30_{20}$ | PBZ4-6 |
| 54 | DNA | $nTG31_{1233}$ | | AMX/I-5 |
| 55 | DNA | $nTG32_{411}$ | | AMX/I-6 |
| 56 | Protein | | $PTG32_{60}$ | PAMX/I-6 |
| 57 | DNA | $nTG33_{441}$ | | AMX/I-7 |
| 58 | Protein | | $PTG33_{118}$ | PAMX/I-7 |
| 59 | DNA | $nTG34_{491}$ | | AMX/I-9 |
| 60 | Protein | | $PTG34_{34}$ | PAMX/I-9 |
| 61 | DNA | $nTG35_{387}$ | | AMX/I-10 |
| 62 | Protein | | $PTG35_{129}$ | PAMX/I-10 |
| 63 | DNA | $nTG36_{417}$ | | AMI-23 |
| 64 | Protein | | $PTG36_{139}$ | PAMI-23 |
| 65 | DNA | $nTG37_{416}$ | | AMI-24 |
| 66 | Protein | | $PTG37_{138}$ | PAMI-24 |
| 67 | DNA | $nTG38_{500}$ | | AMI-28 |
| 68 | DNA | $nTG40_{321}$ | | AMI-47 |
| 69 | Protein | | $PTG40_{73}$ | PAMI-47 |
| 70 | DNA | $nTG41_{513+C86}$ | | OC-1 |
| 71 | Protein | | $PTG41_{171}$ | POC-1 |
| 72 | DNA | $nTG42_{528}$ | | OC-2 |
| 73 | Protein | | $PTG42_{176}$ | POC-2 |
| 74 | DNA | $nTG43_{375}$ | | OC-13 |
| 75 | Protein | | $PTG43_{125}$ | POC-13 |
| 76 | DNA | $nTG44_{543}$ | | OC-14 |

TABLE 1-continued

| SEQ ID NO | TYPE | Nucleic Acid Molecules | Amino Acid Molecules | Original Designation |
|---|---|---|---|---|
| 77 | Protein | | PTG44$_{89}$ | POC-14 |
| 78 | DNA | nTG45$_{573}$ | | OC-22 |
| 79 | Protein | | PTG45$_{191}$ | POC-22 |
| 80 | DNA | nTG46$_{1835}$ | | OC-23 |
| 81 | Protein | | PTG46$_{612}$ | POC-23 |
| 82 | DNA | nTG48$_{604}$ | | 4CQA7f |
| 83 | Protein | | PTG48$_{112}$ | P4CQA7f |
| 84 | DNA | nTG48$_{549}$ | | 4CQA7r |
| 85 | DNA | nTG49$_{270}$ | | 4CQA11 |
| 86 | Protein | | PTG49$_{90}$ | P4CQA11 |
| 87 | DNA | nTG50$_{306}$ | | 4CQA19 |
| 88 | Protein | | PTG50$_{102}$ | P4CQA19 |
| 89 | DNA | nTG51$_{804}$ | | 4CQA21 |
| 90 | Protein | | PTG51$_{268}$ | P4CQA21 |
| 91 | DNA | nTG52$_{867}$ | | 4CQA22 |
| 92 | Protein | | PTG52$_{289}$ | P4CQA22 |
| 93 | DNA | nTG53$_{1434}$ | | 4CQA24 |
| 94 | Protein | | PTG53$_{164}$ | P4CQA24 |
| 95 | DNA | nTG54$_{680}$ | | 4CQA25 |
| 96 | Protein | | PTG54$_{227}$ | P4CQA25 |
| 97 | DNA | nTG55$_{296}$ | | 4CQA26 |
| 98 | Protein | | PTG55$_{99}$ | P4CQA26 |
| 99 | DNA | nTG56$_{723}$ | | 4CQA27 |
| 100 | Protein | | PTG56$_{53}$ | P4CQA27 |
| 101 | DNA | nTG57$_{270}$ | | 4CQA29 |
| 102 | Protein | | PTG57$_{90}$ | P4CQA29 |
| 103 | DNA | nTG58$_{503}$ | | R8050-2 |
| 104 | Protein | | PTG58$_{62}$ | PR8050-2 |
| 105 | DNA | nTG60$_{322}$ | | R8050-5 |
| 106 | Protein | | PTG60$_{73}$ | PR8050-5 |
| 107 | DNA | nTG61$_{390}$ | | R8050-6 |
| 108 | Protein | | PTG61$_{67}$ | PR8050-6 |
| 109 | DNA | nTG62$_{699}$ | | M2A1 |
| 110 | Protein | | PTG62$_{233}$ | PM2A1 |
| 111 | DNA | nTG63$_{419}$ | | M2A2 |
| 112 | Protein | | PTG63$_{140}$ | PM2A2 |
| 113 | DNA | nTG64$_{303}$ | | M2A3 |
| 114 | Protein | | PTG64$_{101}$ | PM2A3 |
| 115 | DNA | nTG65$_{696}$ | | M2A4 |
| 116 | Protein | | PTG65$_{232}$ | PM2A4 |
| 117 | DNA | nTG66$_{173}$ | | M2A5 |
| 118 | Protein | | PTG66$_{58}$ | PM2A5 |
| 119 | DNA | nTG67$_{369}$ | | M2A6 |
| 120 | Protein | | PTG67$_{123}$ | PM2A6 |
| 121 | DNA | nTG68$_{568}$ | | M2A7 |
| 122 | Protein | | PTG68$_{61}$ | PM2A7 |
| 123 | DNA | nTG69$_{616}$ | | M2A11 |
| 124 | Protein | | PTG69$_{205}$ | PM2A11 |
| 125 | DNA | nTG70$_{762}$ | | M2A16 |
| 126 | Protein | | PTG70$_{254}$ | PM2A16 |
| 127 | DNA | nTG71$_{236}$ | | M2A18 |
| 128 | Protein | | PTG71$_{79}$ | PM2A18 |
| 129 | DNA | nTG72$_{569}$ | | M2A19 |
| 130 | Protein | | PTG72$_{190}$ | PM2A19 |
| 131 | DNA | nTG73$_{232}$ | | M2A20 |
| 132 | DNA | nTG74$_{276}$ | | M2A21 |
| 133 | Protein | | PTG74$_{92}$ | PM2A21 |
| 134 | DNA | nTG75$_{309}$ | | M2A22 |
| 135 | Protein | | PTG75$_{103}$ | PM2A22 |
| 136 | DNA | nTG76$_{534}$ | | M2A23 |
| 137 | Protein | | PTG76$_{178}$ | PM2A23 |
| 138 | DNA | nTG76$_{423}$ | | M2A23 |
| 139 | DNA | nTG77$_{327}$ | | M2A24 |
| 140 | Protein | | PTG77$_{109}$ | PM2A24 |
| 141 | DNA | nTG78$_{444}$ | | M2A25 |
| 142 | Protein | | PTG78$_{148}$ | PM2A25 |
| 143 | DNA | nTG79$_{928}$ | | M2A29 |
| 144 | Protein | | PTG79$_{19}$ | PM2A29 |
| 265 | DNA | nTG22$_{310a}$ | | BZ1-2-a |
| 266 | Protein | | PTG22$_{95a}$ | PBZ1-2-a |
| 267 | DNA | nTG64$_{303a}$ | | M2A3-a |
| 268 | Protein | | PTG64$_{101a}$ | PM2A3-a |
| 269 | DNA | nTG71$_{236a}$ | | M2A18-a |
| 270 | Protein | | PTG71$_{79a}$ | PM2A18-a |
| 271 | DNA | nTG64$_{425a}$ | | Q2-9-1-a |
| 272 | Protein | | PTG6$_{142a}$ | PQ2-9-a |
| 273 | DNA | nTG41$_{513a}$ | | OC-1-a |
| 274 | Protein | | PTG41$_{171a}$ | POC-1-a |
| 282 | cDNA | nTG$_{1225}$ | | MGIS42 |
| 283 | Protein | | PTG$_{28}$ | PMGIS42 |
| 284 | DNA | nTG$_{1225}$ | | rc |
| 292 | cDNA | nTG$_{1573}$ | | MGIS44 |
| 293 | Protein | | PTG$_{73}$ | PMGIS44 |
| 294 | DNA | nTG$_{1573}$ | | rc |
| 306 | cDNA | nTG$_{2417}$ | | MGIS48 |
| 307 | Protein | | PTG$_9$ | PMGIS48 |
| 308 | DNA | nTG$_{2417}$ | | rc |
| 311 | cDNA | nTG$_{1785}$ | | MGIS65 |
| 312 | Protein | | PTG$_{24}$ | PMGIS65 |
| 313 | DNA | nTG$_{1785}$ | | rc |
| 338 | DNA | nTG$_{647}$ | | 511-44 genomic |
| 339 | DNA | nTG$_{647}$ | | rc |
| 340 | cDNA | nTG$_{867}$ | | 511-44 coding region |
| 341 | Protein | | PTG$_{288}$ | P511-44 |
| 342 | DNA | nTG$_{867}$ | | rc |
| 343 | cDNA | nTG$_{1397}$ | | 511-44cDNA |
| 345 | DNA | nTG$_{1397}$ | | rc |

It should be noted that because nucleic acid sequencing technology is not entirely error-free, the nucleic acid sequences disclosed in the present invention (as well as other nucleic acid and protein sequences presented herein) represent the apparent nucleic acid sequences of the nucleic acid molecules encoding *T. gondii* proteins of the present invention. The nucleic acid molecules cited in Table 1 also include the complementary (i.e., apparently non-coding) strands. As used herein the terms "complementary strand" and "complement" refer to the nucleic acid sequence of the DNA strand that is fully complementary to the DNA strand having the listed sequence, which can easily be determined by those skilled in the art. Likewise, a nucleic acid sequence complement of any nucleic acid sequence of the present invention refers to the nucleic acid sequence of the nucleic acid strand that is fully complementary to (i.e., can form a complete double helix with) the strand for which the sequence is cited. Production of the cited nucleic acid molecules is disclosed in the Examples as are methods to obtain nucleic acid sequences of the coding strands of such molecules and the amino acid sequences deduced therefrom.

In another embodiment, a *T. gondii* gene or nucleic acid molecule can be a naturally occurring allelic variant that includes a similar but not identical sequence to the cited nucleic acid molecules. A naturally occurring allelic variant of a *T. gondii* gene including any of the above-listed nucleic acid sequences is a gene that occurs at essentially the same locus (or loci) in the genome as the gene including at least one of the above-listed sequences, but which, due to natural variations caused by, for example, mutation or recombination, has a similar but not identical sequence. Because natural selection typically selects against alterations that affect function, allelic variants usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to be found within a given *T. gondii* organism or population, because, for example, the genome goes through a diploid stage, and sexual reproduction results in the reassortment of alleles.

In one embodiment of the present invention, an isolated immunogenic *T. gondii* protein is encoded by a nucleic acid molecule that hybridizes under stringent hybridization conditions to a gene encoding an immunogenic *T. gondii* protein. The minimal size of a *T. gondii* protein of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the *T. gondii* nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding an immunogenic *T. gondii* protein is typically at least about 12 to about 15 nucleotides in length if the nucleic acid molecule is GC-rich and at least about 15 to about 17 bases in length if it is AT-rich. The minimal size of a nucleic acid molecule used to encode an immunogenic *T. gondii* protein homolog of the present invention is from about 12 to about 18 nucleotides in length. Thus, the minimal size of an immunogenic *T. gondii* protein homolog of the present invention is from about 4 to about 6 amino acids in length. There is no limit, other than a practical limit, on the maximal size of a nucleic acid molecule encoding an immunogenic *T. gondii* protein of the present invention because a nucleic acid molecule of the present invention can include a portion of a gene, an entire gene, or multiple genes. A preferred nucleic acid molecule of the present invention is a nucleic acid molecule that is at least 12 nucleotides in length. Also preferred are nucleic acid molecules that are at least 18 nucleotides, or at least 20 nucleotides, or at least 25 nucleotides, or at least 30 nucleotides, or at least 40 nucleotides, or at least 50 nucleotides, or at least 70 nucleotides, or at least 100 nucleotides, or at least 150 nucleotides, or at least 200 nucleotides, or at least 250 nucleotides, or at least 300 nucleotides, or at least 350 nucleotides, or at least 400 nucleotides, or at least 500 nucleotides, or at least 750 nucleotides, or at least 1000 nucleotides, or at least 1500 nucleotides, or at least 1750 nucleotides, or at least 2000 nucleotides, or at least 2250 nucleotides, or at least 2417 nucleotides in length. The preferred size of a protein encoded by a nucleic acid molecule of the present invention depends on whether a full-length, fusion, multivalent, or functional portion of such a protein is desired.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267-284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$ of a given nucleic acid molecule. As defined in the formula below, $T_m$ is the temperature at which two complementary nucleic acid molecule strands will disassociate, assuming 100% complementarity between the two strands.

$$T_m = 81.5°\ C. + 16.6\ \log M + 0.41(\%\ G+C) - 500/n - 0.61(\%\ \text{formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base-pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base-pairs for hybrids greater than about 150 bp, and $T_d$ decreases about 5° C. for each mismatched base-pair for hybrids below about 50 bp. Conditions for hybrids between about 50 and about 150 base-pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid 20, hybrids with less than a specified % base-pair mismatch will hybridize. Stringent hybridization conditions are commonly understood by those skilled in the art to be those experimental conditions that will allow hybridization between molecules having about 30% or less base-pair mismatch (i.e., about 70% or greater identity). Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under stringent hybridization conditions with a *T. gondii* nucleic acid molecule of about 150 bp in length, the following conditions could preferably be used. As an example, the average G+C content of *Dirofilaria immitis* DNA is about 35%. The unknown nucleic acid molecules would be attached to a support membrane, and the 150 bp probe would be labeled, e.g. with a radioactive tag. The hybridization reaction could be carried out in a solution comprising 2×SSC and 0% formamide, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. In order to achieve high stringency hybridizations the skilled artisan would calculate the washing conditions required to allow up to 30% base-pair mismatch. For example, in a wash solution comprising 1×SSC and 0% formamide, the $T_m$ of perfect hybrids would be about 79° C.:

$$81.5° C.+16.6 \log(0.15M)+(0.41\times35)-(500/150)-(0.61\times0)=79° C.$$

Thus, to achieve hybridization with nucleic acid molecules having about 30% base-pair mismatch, hybridization washes would be carried out at a temperature of about 49° C. It is thus within the skill of one in the art to calculate additional hybridization temperatures based on the desired percentage base-pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base-pair mismatch will not vary significantly from 49° C.

Furthermore, it is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using the GCG™ program, Bestfit function with default parameter settings, or a gap weight of 12, a length weight of 4, an average match of 2.912, and an average mismatch of –2.003.

A preferred immunogenic *T. gondii* protein of the present invention is a compound that, when administered to an animal in an effective manner, is capable of protecting that animal from disease caused by *T. gondii* or, in the case of cats, is capable of preventing *T. gondii* oocyst shedding in cats infected with *T. gondii*. In accordance with the present invention, the ability of an immunogenic *T. gondii* protein of the present invention to protect an animal from *T. gondii* disease refers to the ability of that protein to, for example, treat, ameliorate and/or prevent disease caused by *T. gondii*. In one embodiment, an immunogenic *T. gondii* protein of the present invention can elicit an immune response (including a humoral and/or cellular immune response) against *T. gondii*.

The present invention also includes mimetopes of immunogenic *T. gondii* proteins of the present invention. As used herein, a mimetope of an immunogenic *T. gondii* protein of the present invention refers to any compound that is able to mimic the activity of such an immunogenic *T. gondii* protein, often because the mimetope has a structure that mimics the particular *T. gondii* protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of an immunogenic *T. gondii* protein of the present invention is a fusion protein that includes an immunogenic *T. gondii* protein-containing domain attached to one or more fusion segments. Suitable fusion segments for use with the present invention include, but are not limited for segments that can: enhance a protein's stability; act as an immunopotentiator to enhance an immune response against an immunogenic *T. gondii* protein; and/or assist in purification of an immunogenic *T. gondii* protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the immunogenic *T. gondii* protein-containing domain of the protein and can be susceptible to cleavage in order to enable straightforward recovery of an immunogenic *T. gondii* protein. Fusion proteins are preferably produced by culturing a recombinant cell transformed with a nucleic acid molecule that encodes a protein including the fusion segment attached to either the carboxyl and/or amino terminal end of an immunogenic *T. gondii* protein-containing domain. Preferred fusion segments include a metal binding domain (e.g., a polyhistidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

In another embodiment, an immunogenic *T. gondii* protein of the present invention also includes at least one additional protein segment that is capable of protecting an animal from one or more diseases. Such a multivalent protective protein can be produced, for example, by culturing a cell transformed with a nucleic acid molecule comprising two or more nucleic acid domains joined together in such a manner that the resulting nucleic acid molecule is expressed as a multivalent protective compound containing at least two protective compounds capable of protecting an animal from diseases caused, for example, by at least one infectious agent.

Examples of multivalent protective compounds include, but are not limited to, an immunogenic *T. gondii* protein of the present invention attached to one or more compounds protective against one or more other infectious agents, particularly an agent that infects cats. In another embodiment, one or more protective compounds can be included in a multivalent vaccine comprising an immunogenic *T. gondii* protein of the present invention and one or more other protective molecules as separate compounds.

A preferred isolated immunogenic *T. gondii* protein of the present invention includes a protein that is encoded by a nucleic acid molecule that hybridizes under stringent hybridization conditions with a gene (i.e., with the non-coding strand which is a complement of the coding strand) comprising at least one of the nucleic acid molecules cited in Table 1. As such, also preferred is a protein that is encoded by a nucleic acid molecule that hybridizes under stringent hybridization conditions with the non-coding strand of a gene comprising at least one of the nucleic acid sequences cited in Table 1. More preferred is a protein encoded by a nucleic acid molecule that hybridizes under stringent hybridization conditions with at least one of the cited nucleic acid molecules particularly since those nucleic acid molecules have been shown to encode proteins that selectively bind to antiserum that either was raised against *T. gondii* oocysts, bradyzoites, or infected cat gut, or was isolated from a cat immune to *T. gondii* infection. As such, also preferred is a protein encoded by a nucleic acid molecule that hybridizes under stringent hybridization conditions with the complement of at least one of the cited nucleic acid sequences.

Even more preferred are isolated proteins having an amino acid sequence encoded by a nucleic acid molecules that are at least about 75%, preferably at least about 80%, more preferably at least about 85%, even more preferably at least about 90%, even more preferably at least about 95%, and even more preferably at least about 98% identical to one of the nucleic acid molecules and/or nucleic acid sequences cited in Table 1. Also preferred are proteins that comprise one or more epitopes of any of the proteins having such amino acid sequences.

A particularly preferred isolated protein of the present invention is a protein having an amino acid sequence encoded by at least one of the cited nucleic acid molecules and/or cited nucleic acid sequences, a protein encoded by an allelic variant of at least one of the cited nucleic acid molecules and/or nucleic acid sequences, or a protein comprising an epitope of any of the proteins having such amino acid sequences.

In one embodiment, preferred immunogenic *T. gondii* proteins of the present invention include proteins that are at least about 75%, preferably at least about 80%, more preferably at least about 85%, even more preferably at least about 90%; and even more preferably at least about 95% identical to at least one of the proteins cited in Table 1. As such, also preferred are proteins that are at least about 75%, preferably at least about 80%, more preferably at least about 85%, even more preferably at least about 90%, and even more preferably at least about 95% identical to at least one of the amino acid sequences cited in Table 1. Also preferred are proteins that comprise one or more epitopes of any of such proteins. More preferred are immunogenic *T. gondii* proteins comprising the cited proteins and/or having the cited amino acid sequences, proteins encoded by allelic variants of nucleic acid molecules encoding proteins including the cited proteins and/or having the cited amino acid sequences, and proteins having one or more epitopes of such proteins.

Another embodiment of the present invention is an isolated nucleic acid molecule comprising a *T. gondii* nucleic acid molecule that encodes an immunogenic *T. gondii* protein. The identifying characteristics of such nucleic acid molecules are heretofore described. A nucleic acid molecule of the present invention can include an isolated natural *T. gondii* nucleic acid molecule or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. The minimal size of an *T. gondii* nucleic acid molecule of the present invention is from about 12 to about 18 nucleotides in length.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. Accordingly, the term "isolated", as used herein to describe a nucleic acid molecule, does not reflect the extent to which the nucleic acid molecule has been purified. An isolated *T. gondii* nucleic acid molecule of the present invention can be isolated from its natural source or produced using recombinant nucleic acid technology (e.g., polymerase chain reaction (PCR) amplification or cloning) or chemical synthesis. Isolated *T. gondii* nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode an immunogenic *T. gondii* protein of the present invention.

A homolog of a nucleic acid molecule encoding an immunogenic *T. gondii* protein can be produced using a number of methods known to those skilled in the art, see, for example, Sambrook et al., 1989, *Molecular Cloning: A Laboratory Manual*, Cold Spring Harbor Labs Press; Sambrook et al., ibid., is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologs can be selected by hybridization with a nucleic acid molecule encoding an immunogenic *T. gondii* protein or by screening the function of a protein encoded by the nucleic acid molecule (e.g., ability to elicit an immune response against at least one epitope of an immunogenic *T. gondii* protein).

An isolated nucleic acid molecule of the present invention can include a nucleic acid sequence that encodes at least one immunogenic *T. gondii* protein of the present invention, examples of which are disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, capable of encoding an *T. gondii* protein.

A preferred nucleic acid molecule of the present invention, when administered to a cat, is capable of preventing *T. gondii* oocyst shedding. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein (e.g., an immunogenic *T. gondii* protein of the present invention), the nucleic acid molecule being delivered to the animal, for example, by direct injection (i.e., as a genetic vaccine) or in a vehicle such as a recombinant virus vaccine or a recombinant cell vaccine. Another preferred nucleic acid molecule of the present invention, when administered to an animal, is capable of preventing disease in that animal caused by *T. gondii.*

One embodiment of the present invention is an isolated nucleic acid molecule that hybridizes under stringent hybridization conditions with a nucleic acid molecule comprising at least one of the nucleic acid molecules cited in Table 1. As such, also preferred is a nucleic acid molecule that hybridizes under stringent hybridization conditions with at least one of the nucleic acid sequences cited in Table 1 or with a complement of such a sequence. More preferred is a nucleic acid molecule that hybridizes under stringent hybridization conditions with at least one of the cited nucleic acid molecules. As such, also preferred is a nucleic acid molecule that hybridizes under stringent hybridization conditions with at least one of the cited nucleic acid sequences or with a complement thereof.

Even more preferred are isolated nucleic acid molecules that are at least about 75%, preferably at least about 80%, more preferably at least about 85%, even more preferably at least about 90%, even more preferably at least about 95%, and even more preferably at least about 98% identical to one of the nucleic acid molecules and/or nucleic acid sequences cited in Table 1. Also preferred are nucleic acid molecules that form stable hybrids with nucleic acid molecules having those percent identities.

A particularly preferred isolated nucleic acid molecule of the present invention is a nucleic acid molecule that comprises at least one of the cited nucleic acid molecules and/or cited nucleic acid sequences, a nucleic acid molecule that is an allelic variant of at least one of the cited nucleic acid molecules and/or nucleic acid sequences, or a nucleic acid molecule that is a portion thereof (i.e., a nucleic acid molecule that forms a stable hybrid with at least one of the cited nucleic acid molecules or allelic variants thereof).

In one embodiment, a nucleic acid molecule encoding an immunogenic *T. gondii* protein of the present invention encodes a protein that is at least about 75%, preferably at least about 80%, more preferably at least about 85%, even more preferably at least about 90%, and even more preferably at least about 95% identical to the proteins cited in Table 1. Even more preferred is a nucleic acid molecule encoding a protein cited in Table 1 or an allelic variant of such a nucleic acid molecule. Also preferred are nucleic acid molecules encoding proteins comprising one or more epitopes of proteins having the cited percent identities or epitopes of proteins cited in Table 1 or encoded by nucleic acid molecules that are allelic variants of nucleic acid molecules cited in Table 1.

In another embodiment, a nucleic acid molecule encoding an immunogenic *T. gondii* protein of the present invention encodes a protein having an amino acid sequence that is at least about 75%, preferably at least about 80%, more preferably at least about 85%, even more preferably at least about 90%, and even more preferably at least about 95% identical to at least one of the amino acid sequences cited in Table 1. Even more preferred is a nucleic acid molecule encoding a protein having an amino acid sequence cited in Table 1 or an allelic variant of such a nucleic acid molecule. Also preferred are nucleic acid molecules encoding proteins comprising one or more epitopes of proteins having the cited percent identities or epitopes of proteins having amino acid sequences cited in Table 1 or encoded by nucleic acid molecules that are allelic variants of nucleic acid molecules cited in Table 1.

Note that nucleic acid molecules of the present invention can include nucleotide sequences in addition to those disclosed above, such as, but not limited to, nucleotide sequences comprising a full-length gene, a full-length coding region, a nucleic acid molecule encoding a fusion protein, or a nucleic acid molecule encoding a multivalent protective compound. Also included in the present invention are nucleic acid molecules that have been modified to accommodate codon usage properties of the cells in which such nucleic acid molecules are to be expressed. Preferred nucleic acid molecules of the present invention include fragments of the nucleic acid molecules disclosed in Table 1.

Knowing the nucleic acid sequences of certain nucleic acid molecules encoding immunogenic *T. gondii* proteins of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other nucleic acid molecules encoding an immunogenic *T. gondii* proteins. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include *T. gondii* cDNA libraries as well as genomic DNA libraries. Similarly, preferred DNA sources from which to amplify nucleic acid molecules include *T. gondii* cDNA and genomic DNA. Techniques to clone and amplify nucleic acid molecules are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising nucleic acid molecules encoding immunogenic *T. gondii* proteins. Oligonucleotides. of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of about 100 nucleotides. The present invention includes oligonucleotides that can be used as, for example, probes to identify nucleic acid molecules encoding immunogenic *T. gondii* proteins, primers to produce nucleic acid molecules encoding immunogenic *T. gondii* proteins, or reagents to inhibit immunogenic *T. gondii* protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of nucleic acid molecule encoding immunogenic *T. gondii* proteins of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be operative in either prokaryotic or eukaryotic cells, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial yeast, *T. gondii* and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other endoparasite, or insect and mammalian cells, such as, but not limited to, tac, lac, trp, trc, oxy-pro, omp/lpp, rrnb, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, *Pichia* alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with *T. gondii*.

Suitable and preferred nucleic acid molecules to include in recombinant vectors of the present invention are as disclosed herein. Preferred nucleic acid molecules to include in recombinant vectors, and particularly in recombinant molecules, include those cited in Table 1. Particularly preferred recombinant molecules of the present invention include those recombinant molecules, the production of which are described in the Examples section.

Recombinant molecules of the present invention may also (a) contain secretory signals (i.e., signal segment nucleic acid sequences) to enable an expressed *T. gondii* protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, inicroinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include nucleic acid molecules encoding immunogenic *T. gondii* proteins disclosed herein. Particularly preferred nucleic acid molecules with which to transform a cell include those listed in Table 1.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing *T. gondii* proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), insect, other animal and plant cells. Preferred host cells include bacterial, mycobacterial, yeast, protozoan, helminth, insect and mammalian cells. More preferred host cells include *Salmonella, Escherichia, Bacillus, Listeria, Saccharomyces, Spodoptera, Mycobacteria, Trichoplusia*, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1 $_x$3987 and SR-11 $_x$4072, *Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein. Particularly preferred recombinant cells include those recombinant cells, the production of which are disclosed in the Examples section.

Recombinant cells of the present invention can also be co-transformed with one or more recombinant molecules including a nucleic acid molecule encoding at least one immunogenic *T. gondii* protein of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated *T. gondii* proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce an immunogenic *T. gondii* protein of the present invention. Effective media typically comprise an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Suitable culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase “recovering the protein”, as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in “substantially pure” form. As used herein, “substantially pure” refers to a purity that allows for the effective use of the protein as a composition to inhibit *T. gondii* oocyst shedding in a cat due to infection with *T. gondii*, or for preventing *T. gondii* infection in an animal, or as a diagnostic reagent. A composition for inhibiting *T. gondii* oocyst shedding in a cat due to infection with *T. gondii* animals, or for preventing *T. gondii* infection in an animal for example, should exhibit no substantial toxicity and preferably should be capable of stimulating the production of antibodies in a treated animal.

The present invention also includes isolated (i.e., removed from their natural milieu) antibodies that selectively bind to an immunogenic *T. gondii* protein of the present invention or a mimetope thereof (e.g., anti-*T. gondii* antibodies). As used herein, the term “selectively binds to” an immunogenic *T. gondii* protein refers to the ability of antibodies of the present invention to preferentially bind to specified proteins and mimetopes thereof of the present invention. Binding can be measured using a variety of methods standard in the art including enzyme immmunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated by reference herein in its entirety. An anti-*T. gondii* antibody of the present invention preferably selectively binds to an immunogenic *T. gondii* protein in such a way as to inhibit the function of that protein. Isolated antibodies of the present invention can include antibodies in any bodily fluid that has been collected (e.g., recovered) from an animal. Suitable bodily fluids include, but are not limited to, blood, serum, plasma, urine, tears, aqueous humor, central nervous system fluid (CNF), saliva, lymph, nasal secretions, milk and feces. Thus, serum containing antibodies (i.e., antiserum) or mucosal secretions, such as intestinal secretions, are examples of isolated antibodies. Other embodiments of antibodies include antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce *T. gondii* proteins of the present invention. Antibodies raised against defined proteins or mimetopes can be advantageous because such antibodies are not substantially contaminated with antibodies against other substances that might otherwise cause interference in a diagnostic assay or side effects if used in a composition for inhibiting *T. gondii* oocyst shedding in a cat due to infection with *T. gondii*, or for preventing *T. gondii* infection in an animal.

Antibodies of the present invention have a variety of potential uses that are within the scope of the present invention. For example, such antibodies can be used (a) as compounds to passively immunize a cat in order to inhibit the cat from shedding *T. gondii* oocysts, (b) as reagents in assays to detect infection by *T. gondii* and/or (c) as tools to screen expression libraries and/or to recover desired proteins of the present invention from a mixture of proteins and other contaminants.

One embodiment of the present invention includes a method for identifying a nucleic acid molecule encoding an immunogenic *T. gondii* protein. According to this method, antiserum (comprising either monoclonal or polyclonal antibodies) raised against a *T. gondii* developmental stage or stages, or against oocysts, is used to immunoscreen a *T. gondii* genomic expression library or a it gondii cDNA expression library, and a nucleic acid molecule expressing an immunogenic *T. gondii* protein is identified by its ability to selectively bind to at least one antibody within the antiserum. As used herein, the term immunoscreen refers to a method in which antibodies are mixed with a sample to determine whether the sample contains a substance to which the antibodies can selectively bind. A substance is identified by its ability to selectively bind to such antibodies. Although general methods to accomplishing immunoscreening of expression libraries are known to those skilled in the art, the exact method to use such a technique to identify *T. gondii* immunogenic proteins was not previously known. The present invention includes the identification of antisera that are useful in the identification and isolation of nucleic acid molecules encoding *T. gondii* immunogenic proteins. Such antisera include antiserum raised against *T. gondii* oocysts, antiserum raised against *T. gondii* bradyzoites, antiserum raised against 77 gondii infected cat gut, and antiserum isolated from a cat immune to *T. gondii* infection. In one embodiment, antiserum as described above is enriched for antibodies specific to *T. gondii* gametogenic stages. In a preferred embodiment, polyclonal antiserum is produced by exposing an animal to a *T. gondii* antigen or antigens, then isolating the antiserum from the animal so exposed. Methods to produce and use the various antisera are described in the Examples section.

In another embodiment, immunoscreening as described above can be used to identify an immunogenic *T. gondii* protein. According to this method, antiserum as described above is used to immunoscreen a *T. gondii* genomic expression library or cDNA expression library, and an immunogenic *T. gondii* protein is identified. *T. gondii* immunogenic proteins can also be identified by immunoscreening preparations containing *T. gondii* antigens (e.g., *T. gondii* oocysts, bradyzoites, infected cat guts) using antiserum as described above.

Nucleic acid molecules and proteins identified using such techniques can be isolated (i.e., recovered) and purified to a desired state of purity using techniques known to those skilled in the art.

One embodiment of the present invention is a composition that, when administered to a cat in an effective manner, is capable of preventing that cat from shedding *T. gondii* oocysts. Compositions of the present invention, useful for inhibiting *T. gondii* oocyst shedding in a cat due to infection with *T. gondii* (i.e., infection with *T. gondii* causes oocyst shedding in cats), include at least one of the following protective compounds: an isolated immunogenic *T. gondii* protein or a mimetope thereof, an isolated nucleic acid molecule that hybridizes under stringent hybridization conditions with a nucleic acid molecule comprising one of the nucleic acid molecules and/or nucleic acid sequences cited in Table 1, an isolated antibody that selectively binds to an immunogenic *T. gondii* protein, an inhibitor of *T. gondii* function identified by its ability to bind to an immunogenic *T. gondii* protein and thereby impede development and/or the production of oocysts, or a mixture thereof (i.e., combination of at least two of the compounds). As used herein, a protective compound refers to a compound that, when administered to a cat in an effective manner, is able to inhibit the cat from shedding *T. gondii* oocysts upon infection with *T. gondii*. The term protective compound also refers to a compound that, when administered to a cat or other animal, including a human, in an effective manner, is able to prevent or ameliorate disease caused by infection with *T. gondii*. Examples of proteins, nucleic acid molecules, antibodies and inhibitors of the present invention are disclosed herein.

The present invention also includes a composition comprising at least one *T. gondii* protein-based compound of the present invention in combination with at least one additional compound protective against one or more infectious agents. Examples of such compounds and infectious agents are disclosed herein.

Compositions of the present invention that are useful for preventing *T. gondii* infection can be administered to any animal susceptible to such therapy, preferably to mammals.

In order to inhibit a cat from shedding *T. gondii* oocysts, a composition of the present invention is administered to the cat in a manner effective to inhibit that cat from shedding *T. gondii* oocysts. In a preferred embodiment, compositions of the present invention are administered to cats prior to infection in order to prevent oocyst shedding (i.e., as a preventative vaccine). In another embodiment, compositions of the present invention can be administered to animals after infection in order to treat disease caused by *T. gondii* (erg., as a therapeutic vaccine).

Compositions of the present invention, useful for inhibiting *T. gondii* oocyst shedding in a cat due to infection with *T. gondii*, or for preventing *T. gondii* infection in an animal, can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal,—or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a composition useful for inhibiting oocyst shedding in a cat infected with *T. gondii*, or for preventing *T. gondii* infection in an animal, can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T-cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Supeifos Biosector A/S, Denmark). Protein adjuvants of the present invention can be delivered in the form of the protein themselves or of nucleic acid molecules encoding such proteins using the methods described herein.

In one embodiment of the present inventions a composition useful for inhibiting oocyst shedding in a cat infected with *T. gondii*, or for preventing *T. gondii* infection in an animal, can include a carrier. Carriers include compounds that increase the half-life of a composition of the present invention in the treated animal. Suitable carriers include, bit are not listed to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain dose levels of the composition effective to either inhibit oocyst shedding by cats, or to protect an animal from disease caused by *T. gondii*. The composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Compositions of the present invention can be administered to cats prior to infection in order to inhibit oocyst shedding, and/or can be administered to cats or other animals, including humans, before infection in order to prevent disease caused by *T. gondii* infection, or after infection in order to treat disease caused by *T. gondii*. For example, nucleic acid molecules, proteins, mimetopes thereof, antibodies thereof, and inhibitors thereof can be used to treat or prevent disease caused by *T. gondii* infection.

Acceptable protocols to administer compositions of the present invention include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a proteins mimetope or antibody composition of the present invention is from about 1 microgram (µg) to about 10 milligrams (mg) of the composition per kilogram body weight of the animal. Booster doses can be administered from about 2 weeks to several years after the original administration. Booster administrations preferably are administered when the immune response of the animal becomes insufficient to protect the animal from disease. A preferred administration schedule is one in which from about 10 µg to about 1 mg of the composition per kg body weight of the animal is administered from about one to about two times over a time period of from about 2 weeks to about 12 months. Modes of administration can include, but are not limited to, injection, oral administration, inhalation, nasal administration, intraocular administration, anal administration, topical administration, particle bombardment, and intradermal scarification. Preferred injection methods include intradermal, intramuscular, subcutaneous, intravenous methods, with intradermal injection and intramuscular injection being more preferred. A particularly preferred method is mucosal administration.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a nucleic acid not packaged in a viral coat or cell as a genetic vaccine (e.g., as "naked" DNA or RNA molecules with or without a non-viral/non-cellular carrier (e.g., liposome, hydrogel, etc.) or (b) administering a nucleic acid molecule packaged as a recombinant virus vaccine or as a recombinant cell vaccine (i.e., the nucleic acid molecule is delivered by a viral or cellular vehicle).

A genetic vaccine of the present invention includes a recombinant molecule of the present invention. As such, a genetic vaccine comprises at least one isolated nucleic acid molecule encoding an immunogenic *T. gondii* protein operatively linked to a eukaryotic or prokaryotic transcription control region. A genetic vaccine can be either RNA or DNA, can have components from prokaryotic as well as eukaryotic sources, and can have the ability, by methods described herein, to enter either eukaryotic or prokaryotic cells and direct expression of isolated nucleic acid molecules of the present invention in those cells. In a preferred embodiment, a genetic vaccine of the present invention includes a recombinant virus genome (i.e., a nucleic acid molecule of the present invention ligated to at least one viral genome in which transcription of the nucleic acid molecule is directed either by a transcription control region on the genome or a separate transcription control region) or a recombinant plasmid that includes a nucleic acid molecule of the present invention ligated into a vector that is not a viral genome such that the nucleic acid molecule is operatively linked to a transcription control region.

A genetic vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome (i.e., a viral vector) and a nucleic acid molecule of the present invention. Preferred viral vectors include those based on alphaviruses, poxviruses, adenoviruses, adeno-associated viruses, herpesviruses, picornaviruses, and retroviruses, with those based on alphaviruses (e.g., Sindbis virus or Semliki forest virus), picornaviruses (e.g., poliovirus or mengovirus), species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, intraocular, intranasal and oral routes of administration being preferred. A preferred single dose of a genetic vaccine ranges from about 1 nanogram (ng) to about 600 µg, depending on the route of administration and/or method of delivery, as can be determined by those skilled in the art. Suitable delivery methods include, for example, by injection, by gene gun, as drops, as inhaled aerosols, ingested in microparticles or microcapsules, and/or topical delivery. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses (e.g., Sindbis virus), picornaviruses (e.g., poliovirus, mengovirus), raccoon poxviruses, species-specific herpesviruses and species-specific poxviruses. An example of methods to produce and use alphavirus recombinant virus vaccines are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of preventing a cat from shedding oocysts as disclosed herein. For example, a recombinant virus vaccine, comprising a nucleic acid molecule encoding an immunogenic *T. gondii* protein of the present invention is administered according to a protocol that results in the subject cat producing a sufficient immune response to inhibit shedding *T. gondii* oocysts. A preferred single dose of a recombinant virus vaccine of the present invention is from about $1\times10^4$ to about $1\times10^8$ virus plaque forming units (pfu) per kilogram body weight of the animal. Administration protocols are similar to those described herein for protein-based vaccines, with subcutaneous, intramuscular, intraocular, intranasal and oral administration routes being preferred.

A recombinant cell vaccine of the present invention includes recombinant cells of the present invention that express at least one protein of the present invention. Preferred recombinant cells for this embodiment include *Salmonella, E. coli, Listeria, Mycobacterium, S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a composition of the present invention to inhibit oocyst shedding caused by *T. gondii* can be tested in a variety of ways including, but not limited to, detection of protective antibodies (using, for example, proteins or mimetopes of the present invention), detection of cellular immunity within the treated animal, or challenge of the treated animal with *T. gondii* to determine whether the treated animal is resistant to oocyst shedding. Challenge studies can include direct administration of *T. gondii* tachyzoites or tissue cysts or sporulated oocysts (the infective stages) to the treated animal. In one embodiment, compositions of the present invention can be tested in animal models such as mice. Such techniques are known to those skilled in the art.

One preferred embodiment of the present invention is the use of immunogenic *T. gondii* proteins, nucleic acid molecules encoding immunogenic *T. gondii* proteins, antibodies and inhibitors of the present invention, to inhibit a cat from shedding oocysts. It is particularly preferred to prevent intestinal stages of the parasite from developing into oocysts. Preferred compositions are those that are able to inhibit at least one step in the portion of the parasite's development cycle that occurs in the intestines prior to the development of oocysts. In cats infected with tissue cysts, for example, the prepatent period for oocyst shedding is three to five days. When cats are infected with sporulated oocysts, for example, the prepatent period can range from 19 to 45 days. Particularly preferred compositions useful for inhibiting oocyst shedding in a cat infected with *T. gondii* include *T. gondii*-based compositions of the present invention. Such compositions include nucleic acid molecules encoding immunogenic *T. gondii* proteins, immunogenic *T. gondii* proteins and mimetopes thereof and anti-*T. gondii* antibodies. Compositions of the present invention are administered to cats in a manner effective to inhibit the cats from shedding *T. gondii* oocysts. Additional protection may be obtained by administering additional protective compounds, including other *T. gondii* proteins, nucleic acid molecules and antibodies, as disclosed herein.

It is also within the scope of the present invention to use isolated proteins, mimetopes, nucleic acid molecules and antibodies of the present invention as diagnostic reagents to detect infection by *T. gondii*. These diagnostic reagents can further be supplemented with additional compounds that can specifically detect any or all phases of the parasite's life cycle. General methods to use diagnostic reagents in the diagnosis of disease are, known to those skilled in the art. A method or a kit for the detection of *T. gondii* infection could be combined with reagents for the detection of additional infectious agents, for example viruses (e.g. Coronaviruses), bacteria (e.g. *Campylobacter, Clostridium, Salmonella*), protozoa (e.g. *Cryptosporidium, Giardia, Isospora, Hammondia, Sarcocystis, Besnoitia, Microsporidium*), and/or multi-cellular organisms (e.g. *Teania, Anclostorna, Toxocara, Physaloptera, Paragonimus, Strongyloides, Trichuris*).

Another embodiment of the present invention is a method to detect microscopic parasite cysts or oocysts in feces using PCR amplification techniques. By microscopic, it is meant cysts or oocysts that are too small to be conveniently detected by simple visual observation of the feces. Preferred organisms to be detected include oocysts from infectious protozoan parasites including members of the apicomplexa and others including, for example, *Toxoplasma, Cryptosporidium, Isospora, Giardia, Eimeria, Hammorndia, Sarcocystis, Besnoitia, Microsporidium*. Additional infectious agents to detect include, for example, viruses (e.g. Coronaviruses), bacteria (e.g. *Campylobacter, Clostridium, Salmonella*), and/or multicellular organisms (e.g. *Teania, Anclostoma, Toxocara, Physaloptera, Paragonimus, Strongyloides, Trichuris*). Particularly preferred oocysts to be detected include *Toxoplasma* and *Cryptosporidium* oocysts. Preferred cysts to be detected include any cysts capable of binding to a solid support and remaining bound to the support through a washing step. Preferred cysts include *Giardia* cysts. According to this embodiment of the invention, a solid support that is capable of binding cysts or oocysts is contacted with a sample of feces, which may or may not have been partially solubilized first in an aqueous solution, and the sample of feces is allowed to dry on the support. The solid support can be of any material to which the cysts or oocyts will bind and remain bound during washing in an aqueous solution. The support can comprise one or more compounds that aid in PCR amplification of the sample, for example by allowing the inhibitors to be released in the wash step, or by binding inhibitors of PCR that are not released in the elution step, or by otherwise inactivating inhibitors of PCR amplification. Preferred supports comprise a paper substrate to which the oocysts or cysts can bind. Preferred supports include IsoCodeJ™ Stix, or their equivalent, S&S® #903™, or their equivalent, or Nobuto Blood Filter Strips, or their equivalent. The support, or the portion of the support contacted with the sample of feces, is preferably small enough to fit into a container convenient for the wash step; e.g., a size that will fit into a 1.5. ml conical centrifuge tube. The portion of the support that is contacted with the sample of feces can be removed from the rest of the support in order to achieve a convenient size. The portion of the support that includes the dried sample of feces is then washed with an aqueous solution. In a preferred embodiment the aqueous solution is water, preferably distilled water. The solution can comprise one or more compounds that aid in PCR amplification of the sample, for example by inactivating or removing inhibitors of PCR amplification. DNA associated with the sample is eluted by adding an aqueous solution to the support and then heating the solution to a temperature sufficient to elute DNA from the sample, into the solution. In a preferred embodiment, the aqueous solution into which the sample is eluted is water, preferably distilled water. This solution can comprise one or more compounds that aid in PCR amplification of the sample, for example by inactivating inhibitors of PCR amplification, or by improving reaction conditions for the PCR reaction. The heating step comprises heating to a temperature sufficient to elute DNA from the sample. A preferred temperature is approximately 95° C. Oocyst or cyst-specific DNA in the elution solution is then PCR amplified using primers specific to the oocysts or cysts being detected. The amplification products indicative of oocysts or cysts are then detected using any means available for the detection of PCR amplification products. These can include, for example, separation and observation of the PCR products on a gel, or detection and/or quantification by PCR ELISA. In a preferred embodiment of the present invention, nucleic acid molecules of the present invention are used for the detection of *T. gondii* oocysts in cat feces by PCR amplification using nucleic acid molecules of the present invention as primers. According to the present invention, detection of oocysts can be accomplished by direct analysis of feces. Methods to conduct such an assay are described further in the Examples section.

The following examples are provided for the purposes of illustration and are not intended to limit the scope of the present invention.

EXAMPLES

It is to be noted that the examples include a number of molecular biology, microbiology, immunology and biochemistry techniques considered to be familiar to those skilled in the art. Disclosure of such techniques can be found, for example, in Sambrook et al., ibid. and Ausubel, et al., 1993, *Current Protocols in Molecular Biology*, Greene/Wiley Interscience, New York, N.Y., and related references. Ausubel, et al, ibid. is incorporated by reference herein in its entirety. DNA sequence analysis and protein translations were carried out using the DNAsis program (available from Hitachi Software, San Bruno, Calif.) or MacVector program (available from International Biotechnologies, Inc., Hew Haven, Conn.). It should also be noted that since nucleic acid sequencing technology, and in particular the sequencing of PCR products, is not entirely error-free, that the nucleic acid sequences presented herein represent apparent nucleic acid sequences of the nucleic acid molecules encoding immunogenic *T gondii* proteins of the present invention.

Example 1

This example discloses the construction of a *T. gondii* genomic expression library.

Pure mRNA from *T. gondii* parasite present in the infected cat gut cannot presently be obtained. Therefore, a true cDNA library for the gametogenic stages cannot be produced. In order to get around the unavailability of pure mRNA from gut stages of *T. gondii*, a genomic expression library in λgt11 was constructed using *Toxoplasma* genomic DNA obtained from tachyzoites produced in tissue culture. This library represented genes expressed at all stages of the *Toxoplasma* life cycle, including the gametogenic genes.

Construction of the library was modeled on procedures used previously for standard lambda cloning (see, for example, Sambrook, et al., ibid.). In brief, a series of high frequency cutting restriction enzymes were used to generate near random fragments of DNA representing the tachyzoite genome. DNA fragments of approximately 500 to 2000 bp were size selected and then inserted in frame with the expressed fusion protein in λgt11. Construction of this library is described in greater detail below.

Standard Production of Tachyzoites from liquid nitrogen stocks: Liquid nitrogen stocks of *Toxoplasma* tachyzoites (TZ) (1 ml samples at $2-4 \times 10^6$ TZ/ml) were thawed in a 37° C. waterbath. The samples were thawed completely without attaining 37° C. Room temperature TMM (DMEM+3% FBS+0.1 ml 50 mg/ml gentamicin per 100 ml media) was added to the thawed sample according to the following timetable: 0.3 ml added at 0 minutes; 0.6 ml added at 5 minutes; 1.5 ml added at 10 minutes. The samples were maintained at room temperature for 5 minutes longer, then centrifuged for 10 minutes at 2,000 RPM at room temperature. The supernatant was discarded and the pellet resuspended in 12 ml of TMM.

Human foreskin fibroblasts (HSF) cells (ATCC CRL 1637) were infected with the thawed tachyzoites as follows: Passage 15-25 HSF cells were split 1:3 and grown to confluence in a 175 flask with DMEM+10% FBS (fetal bovine serum, available from Summit Biotechnology, Fort Collins, Colo.)+0.1 ml gentarnicin per 100 ml media in an incubator at 37° C. with 5% $CO_2$. HSF cells were infected by replacing the media with the thawed tachyzoites in TMM. Infections were allowed to progress until 30-50% of the cell monolayer was destroyed. The medium in the infected T75 flask was replaced with fresh TMM the day before harvesting tachyzoites for expansion of the culture.

Passage 19-25 HSF cells cultured in roller bottles (850 $cm^2$), were split 1:3 and grown to confluence in a roller bottle incubator apparatus under conditions as described above. The medium from a single roller bottle was decanted and replaced with 100 ml of TMM. The cells in this roller bottle were then infected by adding medium from an infected T75 flask (described above). Infection was allowed to progress until 30-50% of the cell monolayer was destroyed, Fresh TMM was replaced in the infected roller bottle the day before using the supernatant to infect new HSF cells. Four new roller bottles with confluent HSF cells were each infected with $2.5 \times 10^7$ tachyzoites harvested from a previously infected roller bottle. This cycle of infection of four roller bottles, for the purpose of tachyzoite production, was continued on a weekly basis.

Tachyzoite Purification: Extracellular tachyzoites were collected from tissue culture and concentrated. To collect and concentrate tachyzoites, media from roller bottles containing extracellular tachyzoites were poured into 50 ml conical tubes and centrifuged at 2,000 RPM for 10 minutes. The resulting pellets were pooled and the volume was brought up to 50 ml using TMM. The tachyzoites were diluted and counted using a haemacytometer, and then purified by either the CF-11 column method or the nucleopore method as follows:

CF-11 Method of Purifying Tachyzoites: 1.5 g of CF-11 (available from Whatman, Inc., Clifton, N.J.) was mixed thoroughly in 50 ml of DMEM (no FBS), then added to an econo-column chromatography column (available from Biorad, Hercules, Calif.) and allowed to settle, forming a flat bed. The stopcock was then opened and the excess DMEM was drained until ¼ inch of media remained above the bed. The column was washed by gently adding 50 ml of DMEM and then bringing the media level down to 1 inch above the CF-1 bed. The 50 ml of tachyzoites in TMM (prepared as described above) was then added to the column. The stopcock was opened and the tachyzoites were eluted at a rate of 1 drop/second and collected into 50 ml conical tubes on ice. The media was eluted to ¼ inch above the gel bed. Two additional 5 ml elutions were performed, followed by a 40 ml elution. The 100 ml total eluate was then centrifuged at 2,000 RPM for 10 minutes. The pellets were again pooled by resuspension in 50 ml of DMEM. The tachyzoites were counted and the final number of organisms determined. The tachyzoites were centrifuged at 2,000 rpm for 10 minutes, and the pellet resuspended in 1 ml of Hanks Balanced Salt Solution (HBSS). The tachyzoites were washed 3 times with 1 ml of HBSS by centrifugation at 5000 rpm for 5 minutes in an Eppendorf centrifuge. The pellets were stored at −70° C. until needed.

Nucleopore Method of Purifying Tachyzoites: 47 mm nucleopore units (available from Corning Costar Corp., Cambridge, Mass.) with a polycarbonate 3 um capillary pore membrane were assembled according to manufacturer's specifications. The nucleopore units were then placed on top of an open 50 ml conical tube. Five ml of DMEM was gently forced through the unit using a 30 cc syringe that connects to the top of the nucleopore unit. Twenty-five ml of the extracellular tachyzoite preparation collected from tissue culture in DMEM were passed through the unit by gently pushing on the 30 cc syringe. The maximum number of tachyzoites per nucleopore filter did not exceed $5 \times 10^8$. Filtration was followed by 2, 5 ml washes of DMEM. The nucleopore-purified tachyzoites were then centrifuged at 2,000 RPM for 10 minutes, and the pelleted tachyzoites resuspended in 50 ml of DMEM. The number of tachyzoites was determined by counting in a hemacytometer. Following centrifugation at 2,000 rpm for 10 minutes, the pellet was resuspended in 1 ml EBSS. The tachyzoites were washed 3 times with 1 ml of HBSS by centrifugation at 5,000 rpm for 5 minutes in an Eppendorf centrifuge. The pellets were stored at −70° C. until needed.

Isolation of tachyzoite DNA: DNA from all sources (for example, DNA from *Toxoplasma* or mammalian tissue) was isolated using standard techniques that can be can be found, for example, in Sambrook et alt ibid. In particular, $2 \times 10^9$ tachyzoites were resuspended in 10 ml of 10 mM Tris, pH 8, 0.1 M EDTA, 0.5% SDS and 20 μg/ml pancreatic RNase (available from Sigma Chemical Co., St. Louis, Mo.). After incubating for 1 hour at 37° C., 1 ml of 5M NaCl and 100 μl of 10 mg/ml proteinase K (available from Boehringer Mannheim Corp., Indianapolis, Ind.) was added and the solution incubated for 3 hours at 50° C. The solution was then extracted with phenol and the DNA precipitated with EtOH.

Preparation of Restricted and Size Selected DNA: Six, four-base recognition site restriction enzymes, Alu I, Mbo I, Msp I, Rsa I, Sau3A I, and Taq$^\alpha$I, (available from New England Biolabs, Beverly, Mass.) and one six-nucleotide recognition site restriction enzyme, Dra I, were used to cut *T. gondii* genomic DNA to completion. Ten μg of tachyzoite DNA was digested to completion according to the manufacturer's recommended protocols for each enzyme. All seven digests of DNA were combined and electrophoresed on an 0.8% preparative agarose gel. The region of the gel representing double stranded DNA between 500 and 2000 bp was excised and the DNA recovered using a Gene Clean Kit (available from BIO 101 Inc., Vista, Calif.). The eluted DNA was quantitated using an ethidium bromide sensitivity assay on agarose, using calf thymus DNA as a standard. The DNA was then ethanol precipitated.

Addition of Linkers: Four μg of the digested and size selected DNA was then prepared for the addition of linkers by filling in the restriction site overhangs as follows: First, the DNA was resuspended into Klenow buffer, 0.2 mM dNTPs, and Klenow fragment (available from Boehringer Mannheim Biochemicals, Indianapolis, Ind.), and the reaction mix was incubated for 30 minutes at room temperature. The reaction was stopped by incubating the reaction mix at 65° C. for 10 minutes, The DNA was then methylated using standard conditions including 0.1 mM s-adenosylmethionine and 120 units of EcoR I methylase (available from Promega Corp., Madison, Wis.). Following reprecipitation with ethanol, the DNA pellet was dissolved in water and standard T4 DNA ligase buffer (see, for example, Sambrook, et al., ibid.). Three separate EcoR I linkers, constructed to allow three different reading frames (available from Stratagene, La Jolla, Calif.) were added along with T4 DNA ligase (available from Promega, Corp.) and incubated for 16 hours at 15° C. The solution was then diluted directly into EcoR I restriction buffer and EcoR I enzyme (available from Promega Corp.) and incubated at 37° C. for 2 hours. The DNA fragments were separated from the free linkers using a Sephacryl S-400 spin column. The recovered DNA was ethanol precipitated.

Ligation and Packaging of the Restricted DNA: The entire fraction of DNA obtained from the above reaction mixture was ligated into 1 μg of EcoR I-cut and phosphatase treated λgt11 arms (available from Stratagene) with T4 DNA ligase at 15° C. for 16 hours. The phage was then packaged, titered and amplified using the Gigapack® II Packaging system (available from Stratagene) according to the manufacturer's directions. The resulting library is referred to herein as the *Toxoplasma* or *T. gondii* genomic expression library or as the λgt11:*Toxoplasma* genomnic expression library.

Example 2

This Example discloses a method of isolation of *T. gondii* nucleic acid molecules encoding immunogenic *T. gondii* proteins recognized by antisera specific for a *Toxoplasma* intestinal stage: oocysts. This Example further discloses recombinant nucleic acid molecules, proteins and cells of the present invention.

The final stage of *T. gondii* gametogony is the unsporulated oocyst. Antisera was raised directly against *Toxoplasma* oocysts. In addition to the antisera reacting with their respective immunogens, the ability of this antisera to react with *T. gondii* gametogenic stages in intestinal tissue sections from infected animals was assessed. When used in immunofluorescence assays conducted on infected cat gut samples, the anti-oocyst antisera reacted with various parasite structures in the ICG tissue sections, indicating some cross-reactivity with gametogenic stages. This antisera was made as follows.

Production of antibody to a *Toxoplasma* intestinal stage: oocysts: Oocysts from a wild type strain designated Maggie, a recent isolate from a cat with Toxoplasmosis (Veterinary Teaching Hospital, Colorado State University, 1993), were obtained from the feces of cats fed mouse brains from mice previously infected with the Maggie strain. The oocysts were purified by the standard method of repeated sugar flotation (described in Dubey, J. P. and Beattie, C. P., (1988) *Toxoplasnmosis of Animals and Man*, CRC Press, Boca Raton, Fla.). The oocysts ($3\times10^7$) were vortexed vigorously in 2 ml of PBS, and then frozen and thawed four times using liquid nitrogen and a 37° C. water bath. Each thaw was followed with vigorous vortexing. The suspension was then sonicated for 20 seconds. The protein concentration of the sonicate was determined as described above, and the suspension stored at −70° until used.

The thawed oocyst suspension was mixed with Freunds Complete Adjuvant for the first injection and Freund's Incomplete Adjuvant for three subsequent boosts. The protein concentrations of each injection in the series were 9 ug, 50 ug, 90 ug, and 90 ug respectively, delivered at four week intervals. The single cat #1959 (designated Queen 4) used for production of antibody to unsporulated oocysts had been orally infected with 100 mouse brain-derived C strain tissue cysts one month before the initial protein injection. Serum obtained from this cat (designated herein as Q4-1959) was analyzed for the presence of antibody specific to *T. gondii* oocysts by Western blot and immunohistochemistry on a monthly schedule during the injection period.

Immunoscreening the λgt11:*Toxoplasma* Genomic Expression Library and Isolation of *Toxoplasma*-Specific Nucleic Acid Molecules Reactive with Antisera to Oocysts.: Antisera Q4-1959 was used to isolate nucleic acid molecules herein designated OC-1, OC-2, OC-13, OC-14, OC-22, OC-23 as follows: *E. coli* Y1090 was infected with approximately $5\times10^6$ plaque forming units (PFU) of the λgt11:*Toxoplasma* genomic expression library, and then evenly spread on 20 LB-amp agarose culture plates. The phage were allowed to grow for about four hours at 37° C. The plates were then overlayed with nitrocellulose filters impregnated with 10 mM isopropyl-B-D-thiogalactoside (IPTG) to induce the expression of the recombinant *Toxoplasma* protein. The induction proceeded for between 4 hours to overnight and then the filters were marked to establish orientation. The filters were removed and, following several washes in TBST (Tris-buffered saline (TBS)+Tween 20: 20 in M Tris, pH 7.5, 150 mM NaCl, 0.5% Tween-20), and an incubation in blocking solution (TBS+5% powdered milk), incubated with a 1:40 dilution of antisera Q4-1959 for about 3 hours at room temperature or overnight at 4° C. After 3 to 5 washes with TBST the filters were incubated with a 1:1000 dilution of alkaline phospatase (AP)-conjugated goat anti-cat IgG (available from Kirkegaard & Perry Laboratories Inc., Gaithersburg, Md.) at room temperature for two hours. The filters were washed two times with TBST and once with TBS. The color indicator was developed in AP buffer (100 mM Tris pH 9, 100 mM NaCl, 5 mM MgCl) containing 0.7% NBT (nitroblue tetrazolium) and 0.3% BCIP (5-bromo-4-chloro-3-indolyl phosphate).

Plaques in the area corresponding to the positive signals were picked into SM buffer (50 nM Tris, pH 7.5, 100 nM NaCl, 8 mM $MgSO_4$, and 0.01% gelatin) and the phage replated at a lower density. The same screening procedure was repeated three or four times until a pure plaque was isolated. Of the approximately $5\times10^6$ plaques screened in this manner, 6 nucleic acid molecules capable of expressing proteins recognized by antisera Q4-1959 were plaque purified.

Characterization of Immunogenic *T. gondii* Proteins Encoded by Nucleic Acid Molecules Selected from the *T. gondii* Genomic Expression Library:

The nucleic acid molecules identified as positive for expression of immunogenic *T. gondii* proteins by immunoscreening with antisera Q4-1959 were screened for expression of proteins reactive with intestinal secretions from immune cats. The production of immune intestinal secretions is described in detail in Example 6, below. Prior to being used for screening, pooled intestinal secretions were preabsorbed with *E. coli* lysates as follows. Individual cultures of *E. coli* Y1090 cells and XL-1 blue cells (available from Stratagene) were grown overnight in LB Amp medium at 37° C. The cells were harvested by centrifugation, then resuspended in PBS, pH 7.4. The cell suspensions were then frozen and thawed 3 times, using a dry ice-acetone bath and a 37° C. water bath, then sonicated on ice for 10 minutes. The protein concentrations of the resulting cell lysates were adjusted to approximately 20 mg/ml, then diluted 1:10 in PBS. Fresh nitrocellulose filters (82 mm) were coated with bacterial proteins by immersing them in the diluted *E. coli* lysates at room temperature for 1 hour. The filters were further incubated in a solution of 4% (w/v) powdered milk in PBS, pH 7.4 for 30 minutes. The filters were then washed with PBS three times for 10 minutes each at room temperature. Pooled immune cat intestinal secretions were diluted 1:20 with 4% (w/v) powdered milk in PBS, pH 7.4. The diluted secreticins mixture was incubated with the *E. coli* lysate-treated filters at room temperature for 1 hour, at a ratio of 20 ml per six filters. The resulting absorbed immune intestinal secretions were used without further dilution to screen nucleic acid molecules identified as positive by immunoscreening as described below. Essentially the same protocol was followed when characterizing the proteins expressed by nucleic acid molecules isolated by immunoscreening with other antisera (as described below).

Plaque pure phage identified as positive by immunoscreening were diluted in SM buffer to approximately 50 PFU/3 μl. 3 μl of each clone was dropped onto an LB/Amp agar plate which was previously overlayed with top agar containing a 1:20 dilution of a fresh culture of *E. coli* Y1090 at mid-log growth. The plates were then incubated at 37° C. for 5 hours. IPTG-treated nitrocellulose filters were placed on the top agar and incubated for 5 hours. The filters were marked, washed in TBS buffer, pH 8.0 at room temperature for 15 minutes and then blocked with 4% (w/v) powdered milk in TBS for 30 minutes, at room temperature. The filters were incubated with absorbed intestinal secretions at 4° C. overnight. All further manipulations were at room temperature. The filters were washed in TBS buffer for 10 minutes, 3 times. The filters were incubated for 2 hours with a 1:300 dilution of horse radish peroxidase (HRP)-conjugated goat anti-cat IgA polyclonal antibody (available from Bethyl Laboratories Inc.) in TBS buffer. The filters were washed in TBS for 10 minutes, 3 times, then incubated with 4-chloro-1-naphthol substrate. Clones were judged to be either positive or negative by the intensity of the color reaction relative to wild type phage controls. The results of this assay are summarized in Table 2. Of the six nucleic acid molecules expressing proteins recognized by antisera Q4-1959, only OC-1 expressed a protein that was positive for reactivity to immune cat intestinal secretions.

TABLE 2

Nucleic Acid Molecules Selected with Cat Sera Specific to Unsporulated Oocysts

| | ORIGINAL | DETECTION | | | | EXPRESSION | | pDVAC | | REACTIVITY | |
|---|---|---|---|---|---|---|---|---|---|---|---|
| SEQ ID NO | DESIGNATION | ICG | UCG | TZ | BZ | pTrCHIS | λ CRO | IN VITRO | IN VIVO | SERUM | IS |
| 70 | OC-1 | + | + | + | + | − | ND | ND | ND | ND | + |
| 72 | OC-2 | + | − | 2+ | + | + | ND | ND | ND | ND | − |
| 74 | 0C-13 | 2+ | − | + | + | + | ND | + | + | ND | − |
| 76 | 0C-14 | + | − | + | + | − | ND | ND | ND | ND | − |
| 78 | 0C-22 | 2+ | − | + | 2+ | + | ND | + | + | ND | − |
| 80 | 0C-23 | 2+ | − | 2+ | + | + | ND | ND | ND | ND | − |

Some of the nucleic acid molecules identified as positive by immunoscreening were also assessed for expression of proteins reactive with Mozart II (immune) sera. Reactivity was assessed by spotting the purified phage directly on a lawn of host *E. coli* and inducing the expression of protein encoded by the cloned DNA insert using IPTG-soaked filters, similar to the phage screening protocol. The filters were then probed with the Mozart II sera, in essentially the same manner as was used to select the plaque purified phage identified as positive by immunoscreening. The results of these assays are summarized in Table 2.

The *Toxoplasma* inserts in λgt11, herein referred to as Xλgt11:*Toxoplasma* nucleic acid molecules were sequenced either by direct sequencing, or by first subcloning the λgt11: *Toxoplasma* nucleic acid molecules into a cloning vector, then sequencing. Direct sequencing of each insert was performed as follows: the *Toxoplasma*-specific insert in λgt11 was PCR amplified under standard conditions well known in the art using a λgt11 forward primer (5' GGTGGCGACGACTCCTGGAG 3') designated SEQ ID NO:365, and at λgt11 reverse primer (5'CCACACCAACTGOTAATGGTAG 3') designated SEQ ID NO:366, and the major PCR reaction product was separated from the rest of the PCR reaction products on a 1% agarose gel. The band representing the major PCR product was excised, and the gel slice was processed using the QIAquick kit (available from Qiagen Inc., Santa Clarita, Calif.) according to manufacturer's instructions in order to release the DNA. The isolated DNA fragment was sequenced under standard conditions using an ABI PRISM 377 automated DNA sequencer (available from Applied Biosystems, Foster City, Calif.). Each of the amplification primers were used separately as sequencing primers to obtain sequence from both directions.

Subcloning, then sequencing, was performed as follows: the *Toxoplasma*-specific insert was PCR amplified and gel purified as described above. The purified DNA was then cloned into a TA cloning vector (available from Invitrogen Corp., San Diego, Calif.) according to the manufacturer's instructions, and sequenced under standard conditions.

Sequence Analysis of Nucleic Acid Molecules Selected for Expression of Proteins Recognized by Antisera Q4-1959:

The nucleic acid molecules selected for expression of proteins recognized by antisera Q4-1959 were sequenced as described above. BLASTn and BLASTp homology searches were performed on these sequences using the NCBI GenBank™ non-redundant (nr) nucleotide (n) and amino acid (p) databases, and the dbEST (est) database as described above. The results of these searches are summarized in Table 3. Nucleic acid molecule OC-1 was sequenced again and some changes found between the first and second sequence. The resequenced nucleic acid molecule is referred to herein as OC-1-a.

TABLE 3

Homologies

| SEQ ID | Size bp | Size aa | # P (N) < 1e−10 n vs nr | # P (N) < 1e−10 n vs est | # P (N) < 1e−10 p vs nr | TOP HITS Score | TOP HITS Gene | HOMOLOGIES Name | Size | Clone/Match | Identities | % |
|---|---|---|---|---|---|---|---|---|---|---|---|---|
| 19 | 718 | 99 | — | — | — | | | | | | | |
| 21 | 441 | 147 | — | — | — | | | | | | | |
| 23 | 428 | 142 | — | — | — | | | | | | | |
| 26 | 304 | 101 | — | — | — | | | | | | | |
| 28 | 284 | 95 | — | — | — | | | | | | | |
| 30 | 690 | 230 | — | — | — | | | | | | | |
| 32 | 313 | 54 | — | — | — | | | | | | | |
| 34 | 389 | 65 | — | — | — | | | | | | | |
| 36 | 548 | 183 | — | — | — | | | | | | | |
| 82 | 604 | 112 | — | 2 | — | 1.20E−112 | AA531653 | TgESTzz29d08.r1 invivo Bradyzoite cDNA | 553 | 302-2/8-308 | 291-301 | 96 |
| | | | | | | | | | | 446-345/8-109 | 84-102 | 82 |
| | | | | | | | | | | 590-489/8-109 | 82-102 | 80 |
| | | | | | | | | | | 349-135/129/342 | 122-214 | 57 |
| | | | | | | | | | | 493-418/129-204 | 51-76 | 67 |
| | | | | | | | | | | 137-16/5-126 | 69-122 | 56 |
| | | | | | | 3.10E−33 | AA520213 | TgESTzz43d05.s1 TgME49 invivo Bradyzoite | 574 | 363-127/192-428 | 162-237 | 68 |
| | | | | | | | | | | 500-364/340-476 | 117-137 | 85 |
| | | | | | | | | | | 356-220/340-476 | 113-137 | 82 |
| | | | | | | | | | | 601-515/383-469 | 77/87 | 88 |
| | | | | | | | | | | 178-106/350-422 | 51-73 | 69 |
| | | | | | | | | | | 241-205/456-492 | 26-37 | 70 |
| | | | | | | | | | | 373-349/468-492 | 20-25 | 80 |
| 84 | 549 | | — | 2 | — | 4.30E−35 | 520213 | TgESTzz43d05.s1 TgME49 invivo Bradyzoite | 574 | 113-249/340-476 | 121-137 | 88 |
| | | | | | | | | | | 257-403/340-486 | 123-147 | 83 |
| | | | | | | | | | | 2-105/373-476 | 93-104 | 89 |
| | | | | | | | | | | 409-530/348-469 | 84-122 | 68 |
| | | | | | | | | | | 96-120/468-492 | 20/25 | 80 |
| | | | | | | 1.50E−30 | AA531653 | TgESTzz29d08.r1 TgME49 invivo Bradyzoite | 553 | 23-124/8-109 | 87-102 | 85 |
| | | | | | | | | | | 167-268/8-109 | 86/102 | 84 |
| | | | | | | | | | | 311-412/8-109 | 77-102 | 75 |
| | | | | | | | | | | 120-195/129-204 | 54-76 | 71 |
| 85 | 270 | 90 | — | — | — | | | | | | | |
| 87 | 306 | 102 | — | — | — | | | | | | | |
| 89 | 804 | 268 | — | 2 | — | 6.80E−150 | N82167 | TgESTzy44c02.r1 TgRH tachyzoite cDNA | 613 | 247-498/2-253 | 245-252 | 97 |
| | | | | | | | | | | 498-557/255-336 | 79-82 | 96 |
| | | | | | | | | | | 575-620/334-379 | 44-46 | 95 |
| | | | | | | 8.00E−40 | AA012353 | TgESTzz17b0.r1 TgME49 tachyzoite cDNA | 380 | 671-780/1-100 | 99-100 | 99 |
| | | | | | | | | | | 769-804/98-133 | 35-36 | 97 |
| 91 | 867 | 289 | — | 1 | — | 1.00E−113 | N81503 | TgESTzy57e07.r1 TgRH tachyzoite cDNA | 343 | 329-541/97-309 | 211-213 | 99 |
| | | | | | | | | | | 3-151/161-309 | 147-149 | 98 |
| 93 | 1424 | 164 | — | 2 | — | 2.40E−142 | AA531653 | TgESTzz29d08.r1 TgME49 invivo bradyzoite | 553 | 882-1086/8-212 | 198-205 | 96 |
| | | | | | | | | | | 1078-1262/206-390 | 176-185 | 95 |
| | | | | | | | | | | 452-553/8-109 | 93-102 | 91 |
| | | | | | | | | | | 24-125/8-109 | 87-102 | 85 |
| | | | | | | 1.20E−33 | AA520213 | TgESTzz43d.s1 TgME49 invivo | 574 | 114-250/340-476 | 119-137 | 86 |

TABLE 3-continued

| | | | | | | Homologies | | | | | |
|---|---|---|---|---|---|---|---|---|---|---|---|
| SEQ | Size | | # P (N) < 1e−10 | | | TOP HITS | | HOMOLOGIES | | | |
| ID | bp | aa | n vs nr | n vs est | p vs nr | Score | Gene | Name | Size | Clone/Match | Identities | % |

| SEQ ID | bp | aa | n vs nr | n vs est | p vs nr | Score | Gene | Name | Size | Clone/Match | Identities | % |
|---|---|---|---|---|---|---|---|---|---|---|---|---|
| | | | | | | | | bradyzoite | | | | |
| | | | | | | | | | | 684-820/340-476 | 117-0137 | 85 |
| | | | | | | | | | | 849-1084/220-455 | 161-236 | 68 |
| 95 | 680 | 227 | — | 2 | — | 3.80E−149 | AA520213 | TgESTzz43d05.s1 TgME49 invivo Bradyzoite | 574 | 3-352/127-476 | 343-350 | 98 |
| | | | | | | | | | | 237-493/220-476 | 202-257 | 78 |
| | | | | | | 1.50E−37 | AA531653 | TgESTzz29d08.r1 TgME49 invivo bradyzoite | 553 | 267-501/5-239 | 168-235 | 71 |
| | | | | | | | | | | 411-512/8-109 | 86-102 | 84 |
| 97 | 296 | 99 | — | — | — | | | | | | | |
| 99 | 723 | 53 | — | — | — | | | | | | | |
| 101 | 270 | 90 | — | 1 | — | 4.50E−57 | AA531653 | TgESTzz29d08.r1 TgME49 invivo bradyzoite | 553 | 3-157/236-390 | 149-155 | 96 |
| | | | | | | | | | | 80-187/283-390 | 77-108 | 71 |
| 63 | 417 | 139 | — | — | — | | | | | | | |
| 65 | 416 | 138 | — | — | — | | | | | | | |
| 67 | 500 | | — | — | | | | | | | | |
| 68 | 321 | 73 | — | — | | | | | | | | |
| 54 | 1233 | | — | 1 | | 4.50E−176 | AA520348 | TgESTzz69d04.r1 TgME49 invivo bradyzoites | 607 | 2-216/147-361 | 162-215 | 75 |
| | | | | | | | | | | 161-407/144-390 | 239-247 | 96 |
| | | | | | | | | | | 408-577/390-559 | 156-170 | 91 |
| 55 | 411 | 60 | — | — | — | | | | | | | |
| 57 | 441 | 118 | — | — | — | | | | | | | |
| 59 | 491 | 34 | — | — | — | | | | | | | |
| 61 | 387 | 129 | — | — | — | | | | | | | |
| 38 | 310 | 95 | — | — | — | | | | | | | |
| 40 | 220 | 73 | — | — | — | | | | | | | |
| 42 | 642 | 34 | — | 11 | — | 6.20E−190 | AA519977 | TgESTzz36d07.r1 TgME49 invivo bradyzoite | 653 | 385-150/199-434 | 221-236 | 93 |
| | | | | | | | | | | 642-479/32-195 | 155-164 | 94 |
| | | | | | | | | | | 148-1/435-582 | 124-148 | 83 |
| | | | | | | 9.50E−162 | AA520558 | | | | | |
| | | | | | | 8.90E−122 | AA531849 | | | | | |
| | | | | | | 1.30E−117 | AA520976 | | | | | |
| | | | | | | 4.90E−106 | AA274332 | | | | | |
| | | | | | | 5.20E−102 | W99585 | | | | | |
| | | | | | | 8.10E−94 | AA520425 | | | | | |
| | | | | | | 8.40E−90 | AA274257 | | | | | |
| | | | | | | 1.70E−87 | AA532000 | | | | | |
| | | | | | | 5.00E−81 | AA520339 | | | | | |
| | | | | | | 2.10E−55 | AA012063 | | | | | |
| 44 | 381 | 27 | — | 9 | — | 4.70E−123 | AA532000 | TgESTzz46d07.r1 TgME49 invivo bradyzoites | 577 | 328-3/11-336 | 316-326 | 96 |
| | | | | | | 5.50E−116 | AA520339 | | | | | |
| | | | | | | 1.60E−112 | AA531849 | | | | | |
| | | | | | | 1.70E−100 | AA520425 | | | | | |
| | | | | | | 3.20E−95 | AA519977 | | | | | |
| | | | | | | 1.60E−83 | AA520558 | | | | | |
| | | | | | | 6.80E−59 | AA012063 | | | | | |
| | | | | | | 4.00E−13 | AA274257 | | | | | |
| | | | | | | 7.40E−10 | W99585 | | | | | |
| 46 | 432 | 85 | — | 9 | — | 4.30E−124 | AA520558 | TgESTzz62b09.r1 TgME49 invivo bradyzoite | 441 | 207-430/91-314 | 224-224 | 100 |
| | | | | | | | | | | 119-210/2-93 | 91-92 | 98 |
| | | | | | | 8.10E−120 | AA532000 | | | | | |
| | | | | | | 8.90E−113 | AA520339 | | | | | |
| | | | | | | 2.20E−110 | AA531849 | | | | | |
| | | | | | | 2.40E−97 | AA520425 | | | | | |
| | | | | | | 9.90E−94 | AA519977 | | | | | |
| | | | | | | 8.20E−53 | AA012063 | | | | | |
| | | | | | | 8.20E−14 | AA274257 | | | | | |
| | | | | | | 1.50E−10 | W99585 | | | | | |

TABLE 3-continued

| | | | | Homologies | | | | | | | |
|---|---|---|---|---|---|---|---|---|---|---|---|
| SEQ | Size | | | # P (N) < 1e−10 | | | TOP HITS | HOMOLOGIES | | | |
| ID | bp | aa | n vs nr | n vs est | p vs nr | Score | Gene | Name | Size | Clone/Match | Identities | % |
| 48 | 282 | 35 | — | — | — | | | | | | | |
| 50 | 466 | 71 | — | 9 | — | 1.70E−125 | AA520558 | TgESTzz62b09.r1 TgME49 invivo bradyzoite | 441 | 119-418/2-316 | 314-315 | 99 |
| | | | | | | 1.30E−116 | AA532000 | | | | | |
| | | | | | | 7.70E−110 | AA520339 | | | | | |
| | | | | | | 4.70E−106 | AA531849 | | | | | |
| | | | | | | 2.60E−97 | AA520425 | | | | | |
| | | | | | | 2.90E−95 | AA519977 | | | | | |
| | | | | | | 1.60E−55 | AA012063 | | | | | |
| | | | | | | 6.40E−14 | AA274257 | | | | | |
| | | | | | | 1.20E−10 | W99585 | | | | | |
| 52 | 539 | 20 | — | 8 | — | 9.50E−130 | AA532000 | TgESTzz46d07.r1 TgME49 invivo bradyzoites | 577 | 191-400/85-294 | 208-210 | 99 |
| | | | | | | | | | | 108-190/1-83 | 80-83 | 96 |
| | | | | | | | | | | 397-443/290-336 | 46-47 | 97 |
| | | | | | | 9.00E−124 | AA531849 | | | | | |
| | | | | | | 2.50E−109 | AA520339 | | | | | |
| | | | | | | 2.90E−98 | AA520425 | | | | | |
| | | | | | | 7.70E−86 | AA519977 | | | | | |
| | | | | | | 8.30E−83 | AA520558 | | | | | |
| | | | | | | 4.40E−55 | AA012063 | | | | | |
| | | | | | | 6.30E−11 | W99585 | | | | | |
| 109 | 699 | 233 | — | — | 100 | 2.70E−40 | P46531 | Notch protein homolog *Homo sapiens* | 2444 | 36-72/658-694 | 19-37 | 51 |
| | | | | | | | | | | 42-71/243-272 | 18-30 | 60 |
| | | | | | | | | | | 188-227/893-932 | 15-40 | 37 |
| | | | | | | 3.60E−40 | A40043 | | | | | |
| | | | | | | 1.60E−35 | A36666 | | | | | |
| 111 | 419 | 140 | 1 | — | 6 | 1.30E−28 | P27951 | IGA FC/beta antigen *Streptococcus agalactiae* | 1164 | 22-139/827-944 | 40-118 | 33 |
| | | | | | | | | | | 6-128/823-945 | 41-123 | 33 |
| | | | | | | 3.40E−28 | FCSOAG | | | | | |
| | | | | | | 6.20E−22 | A60234 | | | | | |
| 113 | 303 | 101 | — | — | — | | | | | | | |
| 115 | 696 | 232 | — | — | — | | | | | | | |
| 117 | 173 | 58 | — | — | — | | | | | | | |
| 119 | 369 | 123 | — | — | — | | | | | | | |
| 121 | 566 | 61 | 1 | | — | 2.80E−13 | X60241 | *T. gondii* mitochondria-like REP2 | 1105 | 459-542/937-1020 | 69-84 | 82 |
| | | | | 1 | | 2.90E−13 | N61888 | TgESTzy31c05.r1 TgRH tachyzoite | 253 | 542-460/167-249 | 68-83 | 81 |
| 123 | 616 | 205 | — | — | — | | | | | | | |
| 125 | 762 | 254 | — | — | 2 | 5.30E−12 | d1017785 | hypothetical protein: PE . . . *Synechocystis*. | 1749 | 5-96/1137-1228 | 32-92 | 34 |
| | | | | | | 7.10E−12 | S14959 | | | | | |
| 127 | 236 | 79 | — | — | — | | | | | | | |
| 129 | 569 | 190 | — | — | — | | | | | | | |
| 131 | 232 | | — | — | | | | | | | | |
| 132 | 276 | 92 | — | — | — | | | | | | | |
| 134 | 309 | 103 | — | — | — | | | | | | | |
| 136 | 534 | 178 | — | — | — | | | | | | | |
| 139 | 327 | 109 | — | — | — | | | | | | | |
| 141 | 444 | 148 | — | — | — | | | | | | | |
| 143 | 928 | 19 | — | — | — | | | | | | | |
| 70 | 513 | 171 | — | — | 6 | 3.60E−15 | S14959 | proline-rich protein *Triticum aestivum* | 378 | 10-149/192-331 | 46-140 | 32 |
| | | | | | | 3.60E−14 | d1017785 | | | | | |
| | | | | | | 1.40E−13 | 160171 | | | | | |
| | | | | | | 4.10E−13 | 1372954 | | | | | |
| | | | | | | 4.20E−11 | S20500 | | | | | |
| | | | | | | 2.90E−10 | Q15428 | | | | | |
| 72 | 528 | 176 | — | — | — | | | | | | | |
| 74 | 375 | 125 | — | — | — | | | | | | | |
| 76 | 543 | 89 | — | 2 | — | 2.00E−72 | N82029 | TgESTzy39d03.r1 | 251 | 525-384/56-197 | 139-142 | 97 |
| | | | | | | | | | | 386-331/196-251 | 53-56 | 94 |
| | | | | | | | | | | 542-524/38-56 | 18-19 | 94 |
| | | | | | | 1.40E−49 | W00112 | TgESTzy77b07.r1 | 401 | 542-399/136-279 | 142-144 | 98 |

TABLE 3-continued

| | | | | | Homologies | | | | | | |
|---|---|---|---|---|---|---|---|---|---|---|---|
| SEQ | Size | | # P (N) < 1e–10 | | TOP HITS | | HOMOLOGIES | | | | |
| ID | bp | aa | n vs nr | n vs est | p vs nr | Score | Gene | Name | Size | Clone/Match | Identities | % |
| 78 | 573 | 191 | — | — | — | | | | | | | |
| 80 | 1835 | 612 | — | — | — | | | | | | | |
| 9 | 657 | 219 | — | — | 8 | 5.40E−31 | P27951 | IGA FC/beta antigen *Streptococcus agalactiae* | 1164 | 22-170/827-975 | 45-149 | 30 |
| | | | | | | | | | | 67-188/824-945 | 41-122 | 33 |
| | | | | | | 1.40E−30 | FCSOAG | | | | | |
| | | | | | | 2.60E−22 | A60234 | | | | | |
| | | | | | | 4.90E−14 | 1620100 | | | | | |
| | | | | | | 1.40E−12 | Q01456 | | | | | |
| | | | | | | 2.50E−10 | JC4749 | | | | | |
| | | | | | | 6.90E−10 | d1014692 | | | | | |
| | | | | | | 8.30E−10 | 703450 | | | | | |
| 11 | 1029 | 273 | 1 | — | 5 | 1.70E−27 | P27951 | IGA FC/beta antigen *Streptococcus agalactiae* | 1164 | 22-170/827-975 | 45-149 | 30 |
| | | | | | | 6.70E−27 | FCSOAG | | | 67-188/824-945 | 41-122 | 33 |
| | | | | | | 1.10E−20 | A60234 | | | | | |
| | | | | | | 7.80E−14 | 1620100 | | | | | |
| | | | | | | 3.50E−12 | Q01456 | | | | | |
| 13 | 425 | 142 | — | — | — | | | | | | | |
| 16 | 417 | 139 | — | — | — | | | | | | | |
| 17 | 507 | 51 | — | 1 | — | 1.70E−51 | N61591 | TgESTzy18d02.r1 TgRH tachyzoite | 149 | 331-446/4-149 | 144-146 | 98 |
| 103 | 503 | 62 | — | 1 | — | 1.70E−51 | N61591 | TgESTzy18d02.r1 TgRH tachyzoite | 149 | 331-446/4-149 | 144-146 | 98 |
| 105 | 322 | 73 | — | — | — | | | | | | | |
| 107 | 390 | 67 | — | — | — | | | | | | | |
| 1 | 357 | 119 | — | — | — | | | | | | | |
| 3 | 339 | 108 | — | — | — | | | | | | | |
| 5 | 526 | 175 | — | 2 | — | 4.40E−65 | W96667 | TgESTzy98f02.r1 TgME49 tachyzoite | 454 | 369-502/55-188 | 123-134 | 91 |
| | | | | | | | | | | 314-385/1-72 | 72-72 | 100 |
| | | | | | | 3.10E−43 | AA037916 | TgESTzy55c09.r1 TgRH tachyzoite | 385 | 372-502/2-132 | 128-131 | 97 |
| 7 | 1478 | 381 | — | 5 | — | 4.60E−128 | W96667 | TgESTzy98f02.r1 TgME49 tachyzoite | 454 | 864-1126/55-317 | 251-263 | 95 |
| | | | | | | | | | | 809-868/1-60 | 72-72 | 100 |
| | | | | | | 4.70E−119 | AA037916 | | | | | |
| | | | | | | 4.50E−43 | N82635 | | | | | |
| | | | | | | 1.20E−36 | N96576 | | | | | |
| | | | | | | 2.20E−36 | N82193 | | | | | |

TABLE 3 Legend:
Results of BLASTn and BLASTp search of the NCBI GenBank ™ non-redundant (nr) nucleotide (n) and amino acid (p) databases, and the dbEST (est) database. The algorithm used was as described in S. F. Altschul, W. Gish, W. Miller, E. W. Myers, and D. J. Lipman, J. Mol. Biol. 215, 403-10 (1990) and the NCBI. From left to right: are the sequence identification number (SEQ ID No), the size of the nucleic acid molecule (Size) in either base pairs (bp) or amino acids (aa), the number of hits below the sum probability score of $1^{e-10}$ (# P(N) < 1e–10), and a section of the hits with the highest homology (HOMOLOGIES). The homologies section is sub-divided to include the sum probability (Score) of the homology, the gene accession number (Gene), the name or identifier of the gene (Name), the size of the gene either in nucleotides, if it is a match in the BLASTn or amino acids if it is in the BLASTp (Size), the range of either nucleotides or amino acids in which a match was identified in the clone versus the match in the database (Clone/Match), the number of identities compared with the range matched (Identities), and the percentage homology of the match (%).
A dash (—) indicates the search was done and there were no matches.

RT-PCR Analysis of Nucleic Acid Sequences Encoding Immunogenic *T. gondii* Proteins:

The sequence data obtained as described above were used to design unique primers specific to each nucleic acid molecule of the present invention. These primer sequences are listed in Table 4.

TABLE 4

Nucleic Acid Molecules Primer Sequences

| SEQ ID NO. | ORIGINAL DESIGNATION | NAME | PRIMER SEQUENCE | BASE PAIR NUMBERS |
|---|---|---|---|---|
| 144 | | | | |
| 145 | Tg-41 (5') | nTG1 | CGCTTCTTGTGTCACCTG | 1-18 |
| 146 | Tg-41 (3') | nTG1 | GCACCTTGTTCTCTCTCTTCGCC | 317-295 |
| 147 | Tg-45-2T (5') | nTG2 | CGAGGAGACGGTGGGAGC | 1-18 |
| 148 | Tg-45-2T (3') | nTG2 | TGCCCAAGATGCCGATCTCTG | 289-269 |
| 149 | Tg-50 (5') | nTG4 | TCTCCCCCATCGACGAAAAC | 95-114 |
| 150 | Tg-50 (3') | nTG4 | GCTCATTTCCTCCGCAATTTGG | 456-435 |
| 151 | Q2-4 (5') | nTG5 | AGCTGGCAGAAATACCAAAGCTC | 67-90 |
| 152 | Q2-4 (3') | nTG5 | TGTCGGCAATACTGGGCATG | 529-510 |
| 153 | Q2-9 (5') | nTG6 | ACTGGAGTGGAAAGTCTGGTTTTG | 37-60 |
| 154 | Q2-9 (3') | nTG6 | GACGCAGAGAAGAAAGAAGAGCC | 415-393 |
| 155 | Q2-10 (5') | nTG7 | TCCAAAACTGTCTCGTCTCCCC | 165-186 |
| 156 | Q2-10 (3') | nTG7 | TCTGGATACGCCGTTCCTTTG | 305-284 |
| 157 | Q2-11 (5') | nTG8 | GACATCTACCTGTGAGTGAACCAGG | 50-74 |
| 158 | Q2-11 (3') | nTG8 | GTCAAAACCTTGCCAGCATCTC | 475-454 |
| 159 | 4499-9 (5') | nTG9 | TCCGACTGAATGACTACCTCTTTC | 45-28 |
| 160 | 4499-9 (3') | nTG9 | TCCGACCAAGTCCTCAGTGAAC | 537-516 |
| 161 | 4604-2 (5') | nTG10 | TGGGCATTTCCTGGAAGAGG | 36-55 |
| 162 | 4604-2 (3') | nTG10 | GAATCCATCTCGTGCAAACGG | 378-358 |
| 163 | 4604-3 (5') | nTG11 | CAAGACACAGGGAAACGTTGG | 102-122 |
| 164 | 4604-3 (3') | nTG11 | GAAAGAATCGCACCTCCTCTCC | 424-403 |
| 165 | 4604-5 (5') | nTG13 | TTTGAGTCTAACCGCCGTATGTC | 20-42 |
| 166 | 4604-5 (3') | nTG13 | TCAGACGATTCTCCCATTGTACG | 216-194 |
| 167 | 4604-10 (5') | nTG15 | TCGACTTGGGTCCGATTGTTAG | 43-64 |
| 168 | 4604-10 (3') | nTG15 | GATCTTTTGCGTGACTTTGTCTGC | 289-266 |
| 169 | 4604-17 (5') | nTG16 | GAAGATGCTTGTCTTGTTCGGTTC | 19-42 |
| 170 | 4604-17 (3') | nTG16 | GAGGGGTTTCCTTCTTTATTGCC | 178-156 |
| 171 | 4604-54 (5') | nTG17 | TGTTGGACATCCCGAGCATC | 23-42 |
| 172 | 4604-54 (3') | nTG17 | GGTCCTTGTTTTTCAGGCGG | 472-453 |
| 173 | 4604-62 (5') | nTG18 | TCGTGCAGACAGTGAAGCAATG | 35-56 |
| 174 | 4604-62 (3') | nTG18 | TTTTGTCAGCACAGAGTGGCG | 201-281 |
| 175 | 4604-63 (5') | nTG19 | CGCAAGTGAGTTTTGGCTTTACC | 15-37 |
| 176 | 4604-63 (3') | nTG19 | CCTGGAAGAGATATGCAGACAC | 389-368 |
| 177 | 4604-69 (5') | nTG21 | TCACCGTTCGCTCTTCTTTCTC | 12-33 |
| 178 | 4604-69 (3') | nTG21 | CGACTGAAGCATGGATTGCC | 367-348 |
| 179 | AMX/I-5 (5') | nTG31 | ACATATTCCTGAGGAGGAGTTCCC | 82-105 |
| 180 | AMX/I-5 (3') | nTG31 | AACACACCTCCGACGACACCAC | 447-426 |

TABLE 4-continued

Nucleic Acid Molecules Primer Sequences

| SEQ ID NO. | ORIGINAL DESIGNATION | NAME | PRIMER SEQUENCE | BASE PAIR NUMBERS |
|---|---|---|---|---|
| 181 | AMX/I-6 (5') | nTG32 | CTCGGCTTCTCCACATACAAGG | 8-29 |
| 182 | AMX/I-6 (3') | nTG32 | GGATCTAGGCATTTGGGTTTCAC | 411-389 |
| 183 | AMX/I-7 (5') | nTG33 | ATCGAAGAAGCTGAAGCGGAG | 4-24 |
| 184 | AMX/I-7 (3') | nTG33 | GTGCTTGTCTCTGACGAAACCC | 193-172 |
| 185 | AMX/I-9 (5') | nTG34 | TATCATTGTATCCCGTCGTCCC | 47-68 |
| 186 | AMX/I-9 (3') | nTG34 | TGATGCCTGGATTTGCACAAC | 363-343 |
| 187 | AMX/I-10 (5') | nTG35 | CGGATCGCTCTGAGTCTCTTTG | 1-22 |
| 188 | AMX/I-10 (3') | nTG35 | ATCCTGTGTCTTCTCTTCGACCC | 384-362 |
| 189 | AMI-23 (5') | nTG36 | GATCGCTCTGAGTCTCTTTG | 88-110 |
| 190 | AMI-24 (5') | nTG37 | ACGTGAGGGAGAAGAAGAGAGTGC | 21-44 |
| 191 | AMI-24 (3') | nTG37 | TTCATCGTCGCCTCTGATGTCC | 347-326 |
| 192 | AMI-28 (5') | nTG38 | TGTAGACAGCGTTTAGGGAGTGC | 21-43 |
| 193 | AMI-28 (3') | nTG38 | GTCCTTGGAAGTGCAGAAGCAG | 440-419 |
| 194 | AMI-47 (5') | nTG40 | AAGCGAGGAAAAGGAGGTGTC | 95-115 |
| 195 | AMI-47 (3') | nTG40 | CGGGAAGGTTGGTGATGTCTGTG | 252-230 |
| 196 | OC-1 (5') | nTG41 | CCCGAAGACTTTGACCTG | 34-51 |
| 197 | OC-1 (3') | nTG41 | AGTGGCATAGGAGGCTGG | 191-174 |
| 198 | OC-2 (5') | nTG42 | GCACCTTCAATGCCACAGGTATC | 90-112 |
| 199 | OC-2 (3') | nTG42 | TCGTGTGCTTCTCGCTTCTCTG | 484-463 |
| 200 | OC-13 (5') | nTG43 | CACTGTCGATCAGAAGAAGGCTTAC | 84-108 |
| 201 | OC-13 (3') | nTG43 | GCTCCGTGGGCACATTTTTG | 367-348 |
| 202 | OC-14 (5') | nTG44 | CAGTTTACGAGGTACAAGGCAACAG | 9-33 |
| 203 | OC-14 (3') | nTG44 | GATTGCGTGGGCAGTGTAGAAG | 237-216 |
| 204 | OC-22 (5') | nTG45 | TGTTTGTTTCCCCAGTCAACGAC | 89-111 |
| 205 | OC-22 (3') | nTG45 | CGGAAGAGGTTGTTGGACTCCTTC | 570-547 |
| 206 | OC-23 (5') | nTG46 | CAACCGAGAGAGAAGAGAGGAACAG | 62-86 |
| 207 | OC-23 (3') | nTG46 | TGGGGAGAACAGCAGACATCAG | 602-581 |
| 208 | 4CQA11 (5') | nTG49 | GGATGAACACTGGTGCATCATG | 6-27 |
| 209 | 4CQA11 (3') | nTG49 | CGACTTGGTCCGCTC | 270-256 |
| 210 | 4CQA19 (5') | nTG50 | CGGCGGCAACAAATGGGC | 1-18 |
| 211 | 4CQA19 (3') | nTG50 | GTCCGAGATATGAGGATGCGAC | 129-108 |
| 212 | 4CQA21 (5') | nTG51 | TCAGAGCACCATTGTTGCGAC | 39-59 |
| 213 | 4CQA21 (3') | nTG51 | TTTGACGCTCAAGTGGAGGCTG | 556-535 |
| 214 | 4CQA22 (5') | nTG52 | GCCTGCAACGCTCGATGGC | 615-633 |
| 215 | 4CQA22 (3') | nTG52 | CTTCTTGACTACCTTCACGTCTG | 810-788 |
| 216 | 4CQA24 (5') | nTG53 | AAGGACAAGCCTGGTTTG | 283-300 |

TABLE 4-continued

Nucleic Acid Molecules Primer Sequences

| SEQ ID NO. | ORIGINAL DESIGNATION | NAME | PRIMER SEQUENCE | BASE PAIR NUMBERS |
|---|---|---|---|---|
| 217 | 4CQA24 (3') | nTG53 | TTTGCCCTTCGCACAATC | 1130-1113 |
| 218 | 4CQA25 (5') | nTG54 | CCAGTTTTGCCAGAGGAAGACC | 82-103 |
| 219 | 4CQA25 (3') | nTG54 | ATCCGTCAATGCAGGTTTCATC | 459-438 |
| 220 | 4CQA26 (5') | nTG55 | AGACACCAGAGACAGCAGCAGTC | 45-67 |
| 221 | 4CQA26 (3') | nTG55 | ACTTCGCCCGACAATCGCTTTCC | 266-244 |
| 222 | 4CQA27 (5') | nTG56 | CGATCCTCCCGAGGGACC | 1-18 |
| 223 | 4CQA27 (3') | nTG56 | GCCTTTACGCATTCAAGTCGTG | 174-153 |
| 224 | 4CQA29 (3') | nTG57 | TTCAGCGGGTCTTTCCTCAC | 129-110 |
| 225 | R8050-2 (5') | nTG58 | CAACGAGAAAGATGGAGCTTCG | 34-55 |
| 226 | R8050-2 (3') | nTG58 | AACTTCTTGCACTTGGTCCCG | 404-384 |
| 227 | R8050-5 (5') | nTG60 | AAGCGAGGAAAAGGAGGTGTCTC | 95-118 |
| 228 | R8050-5 (3') | nTG60 | GGAAGGTTGGTGATGTCTGTG | 250-230 |
| 229 | R8050-6 (5') | nTG61 | TCCCCCAGGAATTGTTGAAACAG | 8-30 |
| 230 | R8050-6 (3') | nTG61 | ACTACCGACAACGTCTCAGTCCTTC | 254-230 |
| 231 | M2A1 (5') | nTG62 | CGTGCGTCTGTGAGGAAAAGTG | 2-23 |
| 232 | M2A1 (3') | nTG62 | TTGTTGCTCGTGTTGCAGGTGC | 341-320 |
| 233 | M2A3 (5') | nTG64 | TTGTTCTCGAACCCGCAGAG | 74-93 |
| 234 | M2A3 (3') | nTG64 | TGGCAAGAGACCGAATCGTG | 235-216 |
| 235 | M2A4 (5') | nTG65 | AAACTTGGCAAAGGGGAACG | 49-68 |
| 236 | M2A4 (3') | nTG65 | TGCTGTGGAGAATGATGGCTG | 483-463 |
| 237 | M2A5 (5') | nTG66 | TTTCCGACGAAGCTGCC | 25-41 |
| 238 | M2A5 (3') | nTG66 | GACTCCAACGAAAGCCTCG | 144-126 |
| 239 | M2A6 (5') | nTG67 | GGAAAGGGATAAAGACGCCG | 150-169 |
| 240 | M2A6 (3') | nTG67 | AAGCAGAGGAGAGACGAGACGAAG | 337-314 |
| 241 | M2A7 (5') | nTG68 | CTGCACCATTTCTCACTTCTTGTG | 57-80 |
| 242 | M2A7 (3') | nTG68 | GCAAAAGCGGACTCGATTCTATTG | 192-169 |
| 243 | M2A11 (5') | nTG69 | TGTGGCAGAGCAAAAGGCTC | 12-31 |
| 244 | M2A11 (3') | nTG69 | CTGTGGATGCTCCTTTGCGACT | 406-385 |
| 245 | M2A16 (5') | nTG70 | CGAGGCACCCGAAGAATTTG | 195-214 |
| 246 | M2A16 (3') | nTG70 | CTTCTCAGGTTCACTTCCTGCG | 759-738 |
| 247 | M2A18 (5') | nTG71 | TCACGCAACGAACAAGTCCTC | 42-62 |
| 248 | M2A18 (3') | nTG71 | CCCATTTTGCTTGGCTTGC | 149-130 |
| 249 | M2A19 (5') | nTG72 | AGCGGCAAACCAGTTCGTTG | 283-302 |
| 250 | M2A19 (3') | nTG72 | CACCACCTTTTCGTTGCGG | 558-539 |
| 251 | M2A20 (5') | nTG73 | CGGCGACTCAGATGGG | 1-16 |
| 252 | M2A20 (3') | nTG73 | GGGGCTGTGTCTTCTCTATTTCG | 131-109 |
| 253 | M2A21 (5') | nTG74 | AAGCAAACAGGCTCGGAAGC | 127-146 |

TABLE 4-continued

Nucleic Acid Molecules Primer Sequences

| SEQ ID NO. | ORIGINAL DESIGNATION | NAME | PRIMER SEQUENCE | BASE PAIR NUMBERS |
|---|---|---|---|---|
| 254 | M2A21 (3') | nTG74 | TCATGTTGGAGGCGTCGTTC | 241-222 |
| 255 | M2A22 (5') | nTG75 | TGTGCAGTGGAGGACAAATGG | 50-70 |
| 256 | M2A22 (3') | nTG75 | GAATCAGGGTGTTTTAGGGCG | 284-264 |
| 257 | M2A23 (5') | nTG76 | ATTCTGTGCAAGCCCAGAG | 305-323 |
| 258 | M2A23 (3') | nTG76 | CGACCAAGGGTGTTGACCAT | 136-155 |
| 259 | M2A24 (5') | nTG77 | CTAGGCAAAGAAACACCCATGC | 226-247 |
| 260 | M2A24 (3') | nTG77 | CGCTGGAACTCCTGACAC | 327-310 |
| 261 | M2A25 (5') | nTG78 | ACGAAGGGAGAGATGCGTTTG | 59-79 |
| 262 | M2A25 (3') | nTG78 | TGGCTGTTTGGGTTGTCTGG | 392-373 |
| 263 | M2A29 (5') | nTG79 | TCACCGCAGAACTTAACCCG | 62-81 |
| 264 | M2A29 (3') | nTG79 | CTCGCTTTTCCAGCTTGTCG | 249-230 |

Table 4 Legend:
Primer Sequences to Nucleic Acid Molecules. The original name (Original Designation) and the present name (Name) for each nucleic acid molecule are listed in the second and third columns. Separate 5' and 3' primer sequences are listed for the nucleic acid molecules under Primer Sequence. Identification of each primer sequence as 5' or 3' is shown in the column labeled Original Designation. The location of each primer sequences in its respective nucleic acid molecule is shown in the column, Base Pair Numbers. The sequence identification number for each primer is listed in the first column (Seq ID NO).

The unique primers listed in Table 4 were used in reverse transcriptase-polymerase chain reaction (RT-PCR) assays to assess the expression of the particular nucleic acid sequence in ICG, bradyzoites and tachyzoites. DNA templates were generated from total or poly A+ RNA using an RT-PCT kit (available from Stratagene) according to the manufacturer's instructions. The resulting DNA templates were then amplified by standard PCR reaction. The RT-PCR reactions were performed using RNA isolated from infected cat gut (ICOG), bradyzoites (BZ), tachyzoites (TZ), and the appropriate controls (e.g., uninfected cat gut (UCG) RNA). In addition to UCG controls, clone-specific primers were used in PCR reactions using DNA from the following sources: *T. gondii*, mouse cells, cat intestinal cells, and human cells. These results are, summarized in Table 2.

Subcloning *T. gondii* Nucleic Acid Molecules Encoding Immunogenic *T. gondii* Proteins into the Expression Vector pTrcHisB:

*T. gondii* nucleic acid molecules encoding immunogenic *T. gondii* proteins isolated as described above were subcloned into the expression vector pTrcHisB (available from Invitrogen Corp., San Diego, Calif.). The vector pTrcHisB is designed for expression of fusion proteins in *E. coli* and purification of proteins encoded by nucleic acid molecules of interest. Expression of fusion proteins from this vector was assessed following induction and subsequent Western blot analysis of the *E. coli* lysates using both a monoclonal antibody to the T7 phage amino acid tag sequence and the original sera used to select the nucleic acid molecule. The fusion proteins all contain a poly histidine amino acid sequence which was used to purify the fusion proteins using metal chelate chromatography.

Recombinant molecules containing nucleic acid sequences encoding immunogenic *T. gondii* proteins were produced by PCR amplifying plaque purified λgt11:*Toxoplasma* nucleic acid molecules using a λgt11 forward primer, SEQ ID NO:365 and a λgt11 reverse primer, SEQ ID NO:366. Amplifying the *Toxoplasma* inserts in this way produced DNA fragments with EcoR I sites at the jundtions between the *Toxoplasma* insert and the lambda vector. These PCR fragments were then digested with the restriction endonuclease EcoR I, gel purified and subcloned into the EcoR I-cleaved expression vector, pTrcHisB. The resultant recombinant molecules were transformed into DH5a competent cells to form recombinant cells, and assayed for the expression of an immunogenic *T. gondii* protein. The results of these assays are summarized in Table 2.

The recombinant cells were cultured in enriched bacterial growth medium containing 0.1 mg/ml ampicillin and 0.1% glucose at about 37° C. When the cells reached an $OD_{600}$ of about 0.4-0.5, expression of recombinant proteins was induced by the addition of 0.5 mM isopropyl-B-D-thiogalactoside (IPTG), and the cells were cultured for about 4 hours at about 37° C. Immunoblot analysis of the recombinant cell lysates using a T7 tag monoclonal antibody (available from Novagen Inc., Madison, Wis.) directed against the fusion portion of the recombinant *Toxoplasma* fusion protein was used to confirm the expression of the fusion proteins and to identify their size. In addition, the original selecting antisera were used to determine whether the recombinant expression molecule expressed a protein that could be recognized by the sera originally used to isolate the *Toxoplasma*-specific portion of the recombinant molecule. The results of these immunoblot assays are summarized in Table 2. Of the six nucleic acid molecules selected by immunoscreening with antiserum raised against oocysts (Q4-1959 serum), six were positive by this immunoblot assay.

Example 3

This Example discloses a method of isolation of *T. gondii* nucleic acid molecules encoding immunogenic *T. gondii* proteins recognized by antisera raised against the initiating stage of *T. gondii* gametogony: the bradyzoite. This Example further discloses recombinant nucleic acid molecules, proteins and cells of the present invention.

Antibody To Bradyzoites: Purified C strain bradyzoites ($3\times10^7$) from mouse, brain tissue cysts were used to generate stage-specific antibody to *T. gondii* as follows:

*T. gondii* C-strain tissue cysts containing bradyzoites were passaged in mice by harvesting tissue cysts from chronically infected mice that had been infected, either intraperitoneally with tachyzoites produced in vitro, or by oral gavage with tissues cysts. Between four and eight weeks post-infection, tissue cysts were harvested and used to inoculate naive mice. Harvest was accomplished by dissecting out the brains of infected mice euthanized by inhalation of $CO_2$. The brains were added to a tube of 30% Dextran in HBSS (Hanks Balanced Salt Solution, available from Life Technologies Inc. (Gibco/BRL), Gaithersburg, Md.), and placed on ice until further purified. Each tube contained a maximum of 8 brains per 20 ml of 30% Dextran solution. Tissue cysts were purified by homogenizing the brains for 20-30 seconds with a Tissuemizer (available from Tekmar-Dohrmann, Cincinnati, Ohio). The homogenized brains were centrifuged for 10 minutes at 3,300 g at 4° C. The supernatant was poured off and the pellet was resuspended in 2.0 ml of HBSS. The pellets from multiple tubes were combined and the tissue cysts were counted using a hemacytometer. To produce a new lot of chronically infected mice, tissue cysts purified as described above were diluted in HBSS to a concentration of 100 tissue cysts/ml. Mice were inoculated by oral gavage with 100 μl (10 tissue cysts). After six weeks there were approximately 600 tissue cysts per mouse.

Bradyzoites were purified from tissue cysts by pepsin digestion and passage through a CF 11 cellulose column. Pepsin digestion was initiated by adding approximately 1.0 ml of pepsin digestion fluid (0.5% pepsin, 0.17 M NaCl, and 1.16 M HCl) fluid per 1.0 ml of cyst suspension. The sample was incubated for 10 min in a 37° C. waterbath with occasional swirling. After incubation, approximately 0.9 ml of 0.5% sodium carbonate per 1.0 ml of sample was added slowly and with constant gentle mixing. The solution was then centrifuged for 10 minutes at 2,000 rpm. The supernatant was removed and the pellet resuspended in 5.0 ml of Dulbecco's Modified Eagle's Medium.

1.2 g of CF-11 cellulose was added to 50.0 ml of DMEM, and then poured into a 50 ml chromatography column. The column was equilibrated by allowing most of the DMEM to wash out. The pepsin-digested bradyzoites were diluted with 45 ml of DMEM and loaded onto the column. The column was allowed to drip slowly and the flow through was collected. The column was washed with another 50 ml of DMEM and the flow through was again collected. The two 50 ml flow through aliquots were centrifuged at 2,000 rpm for 15 min. The supernatant was carefully removed and the bradyzoite pellet was resuspended in 1 ml of sterile PBS buffer. The number of bradyzoites obtained was determined by counting an aliquot using a hemacytometer.

Bradyzoites prepared as described above were lysed in a PBS, 0.001% Triton X-100 solution by freeze-thawing four times in liquid nitrogen and a 37° C. water bath. The resulting lysate was further treated by sonication for ten, 30 second bursts, while on ice. Following protein determination using a BCA Protein Kit (available from Pierce Biochemicals, Rockford, Ill.), the bradyzoite lysate was mixed with Freunds Complete and Freunds Incomplete Adjuvants for the first and subsequent (booster) injections respectively. The first injection of rabbit #2448 contained 46 mg of soluble protein, and the two following boosts contained 6 ug of soluble protein each. Injections were given subcutaneously at four week intervals, and serum, designated 2448, was collected every three weeks.

Antiserum 2448 was used to isolate nucleic acid molecules herein designated BZ1-2, BZ1-3, BZ1-6, BZ2-3, BZ2-5, BZ3-2, BZ4-3 and BZ4-6 as follows: *E. coli* Y1090 was infected with approximately $2\times10^5$ PFU and then evenly spread on 4 LB-amp agarose culture plates. The rest of the screening procedure was as described for immunoscreening with antisera Q4-1959 (Example 2), with the following exceptions: the primary antibody was used at a 1:200 dilution, and the secondary antibody was a 1:1000 dilution of AP-conjugated goat anti-rabbit IgG. Of the $2\times10^5$ plaques screened in this manner, 8 nucleic acid molecules capable of expressing proteins recognized by antisera 2448 were plaque purified.

Characterization of Immunogenic *T. gondii* Proteins Encoded by Nucleic Acid Molecules Selected from the *T. gondii* Genomic Expression Library:

The nucleic acid molecules identified as positive for expression of *Toxoplasma* stage-specific antigenic proteins by immunoscreening with antisera 2448 were screened for expression of proteins reactive with intestinal secretions from immune cats, as described above. The results of this assay are summarized in Table 5. None of the 8 nucleic acid molecules expressing proteins recognized by antisera 2448 were positive for reactivity to immune cat intestinal secretions in this assay,

TABLE 5

Nucleic Acid Molecules Selected with Rabbit Sera Specific to Bradyzoites

| | ORIGINAL | DETECTION | | | | EXPRESSION | | pDVAC | | REACTIVITY | |
|---|---|---|---|---|---|---|---|---|---|---|---|
| SEQ ID NO | DESIGNATION | ICG | UCG | TZ | BZ | pTrCHIS | λ CRO | IN VITRO | IN VIVO | SERUM | IS |
| 38 | BZ1-2 | ND | ND | ND | ND | ND | ND | ND | ND | ND | – |
| 40 | BZ1-3 | ND | ND | ND | ND | ND | ND | ND | ND | ND | – |
| 42 | BZ1-6 | ND | ND | ND | ND | ND | ND | ND | ND | ND | – |

TABLE 5-continued Nucleic Acid Molecules Selected with Rabbit Sera Specific to Bradyzoites

| SEQ ID NO | ORIGINAL DESIGNATION | DETECTION | | | | EXPRESSION | | pDVAC | | REACTIVITY | |
|---|---|---|---|---|---|---|---|---|---|---|---|
| | | ICG | UCG | TZ | BZ | pTrCHIS | λ CRO | IN VITRO | IN VIVO | SERUM | IS |
| 44 | BZ2-3 | ND | ND | ND | ND | ND | ND | ND | ND | ND | – |
| 46 | BZ2-5 | ND | ND | ND | ND | ND | ND | ND | ND | ND | – |
| 48 | BZ3-2 | ND | ND | ND | ND | ND | ND | ND | ND | ND | – |
| 50 | BZ4-3 | ND | ND | ND | ND | ND | ND | ND | ND | ND | – |
| 52 | BZ4-6 | ND | ND | ND | ND | ND | ND | ND | ND | ND | – |

Table 5 Legend:
See Legend for Table 2.

Sequence Analysis of Nucleic Acid Molecules Selected for Expression of Proteins Recognized by Antisera 2448:

The nucleic acid molecules selected for expression of proteins recognized by antisera 2448 were sequenced as described above. BLASTn and BLASTp homology searches were performed on these sequences using the NCBI GenBank™ non-redundant (nr) nucleotide (n) and amino acid (p) databases, and the dbEST (est) database as described above. The results of these searches are summarized in Table 3. Nucleic acid molecule BZ1-2 was sequenced again and some changes found between the first and second sequence. The resequenced nucleic acid molecule is referred to herein as BZ2-1-a.

Example 4

This Example discloses a method of isolation of *T. gondii* nucleic acid molecules encoding immunogenic *T. gondii* proteins recognized by rabbit antisera raised against infected cat gut. This Example further discloses recombinant nucleic acid molecules, proteins and cells of the present invention.

Production of rabbit antisera to infected cat gut: A pregnant female cat (designated Queen 2) (available from Liberty Laboratories, Liberty Corners, N.J.) was maintained in isolation and allowed to come to term. The kittens (4) were housed with the mother and nursed normally throughout the protocol. At day seven post-partum, one kitten was selected as the control and its intestine harvested as described below. The remaining kittens were infected orally with 5000 mouse brain-derived tissue cysts of the *T. gondii* strain C, by dripping a solution of the tissue cysts in 1 ml of PBS down the back of their throats. The infected kitten intestines were obtained and processed on day 7 post-infection. The Queen 2 was also infected orally at the same time and in a similar fashion using 100 tissue cysts of *T. gondii* C strain.

In order to obtain fresh intestine, the following procedure was used for both the control and infected animals. A kitten was first anesthetized by placing it in an inhalation chamber which was flooded with both isoflurane and oxygen until the animal was anesthetized. The kitten was then euthanized with an intravenous injection of commercial pentobarbital euthanasia solution at the recommended dose (88 mg/kg). The animal was immediately dissected to expose the small intestine. This was removed by excisions at the anterior junction with the stomach and the posterior junction with the large intestine. The intestine was opened by a single cut from the anterior to the posterior end, exposing the mucosal surface. The gut was then dipped sequentially into three separate washing baths containing cold HBSS (Hanks buffered saline solution) (available from Life Technologies Inc. (Gibco/BRL), Gaithersburg, Md.). The intestine was then placed flat on a chilled laminated sterile surface with the mucosal layer up. A single piece of dry nitrocellulose (BA85; available from Schleicher and Schuell Inc., Keene, N.H.) the length of the intestine, ranging in size from 40 to 70 cm long (this varied with the animal) and 5 mm wide, was carefully placed lengthwise on the mucosal surface of the intestine to obtain an impression smear of the villus epithelial cells. After the nitrocellulose strip became wet (approximately 30 seconds after application), the strip was carefully lifted off and allowed to air dry. The orientation of the anterior and posterior ends of the intestine and strip were noted. Forty biopsy samples, approximately 4 mm by 4 mm sections, were then taken from random positions throughout the length of the intestine, and immediately fixed in either methanol or gluteraldehyde, and maintained for further histological analysis. The intestine was then cut into ten equal sections, and each section placed in a separate bag, labeled and quick frozen in a dry ice and acetone bath. The intestinal sections were maintained at −70° until further processing.

Sections of the cat gut which contained *T. gondii* were identified using PCR analysis of the DNA captured by the nitrocellulose lift with primers specific to the *T. gondii* α-tubulin gene. The presence of *T. gondii* parasite infection was confirmed by histological analysis of the biopsy sections. Portions of *T. gondii*-positive cat gut sections were then prepared as follows for subsequent injections into rabbits to produce antibody directed toward major epitopes from *T. gondii* gametogenic stages. The same methods were also used to produce antibody in cats to infected cat gut preparations, as herein described (in Example 5). A piece of intestine approximately 2 mm by 20 mm was cut from five frozen sections of infected cat gut material. The pieces were maintained at 4° C. laid flat and the mucosal layer carefully scraped from the intestine wall and muscle layers using a razor blade. This material was then minced and placed in 5 ml of sterile PBS containing 1% nystatin, 10 μg/ml gentamicin, and 1% penicillin/streptomycin in a conical centrifuge tube. The mixture was brought through 4 cycles of a freeze-thaw treatment using liquid nitrogen and a 37° C. waterbath. The sample was vortexed between each cycle. The sample was placed on ice and then sonicated using a microtip for 20 seconds followed by 20 seconds on ice. This was repeated four times. The suspension was divided among four Eppendorf tubes and centrifuged (Eppendorf 5415C centrifuge, available from Brinkmann Instruments Inc., Westbury, N.Y.) at maximum speed for 30 minutes at 4° C. The supernatant was then put through a 0.22 micron filter and a protein determination performed using the BCA Protein Determination Kit (available from Pierce Chemical Co., Rockford, Ill.) according to the manufacturer's protocol. The sample was stored as small aliquots at −70° C. until used.

Polyclonal antisera against infected cat gut (ICG) antigens (also herein referred to as anti-ICG antiserum, or anti-ICG antibody) were prepared by immunization of New Zealand White rabbits with infected cat gut tissue protein as follows. Six rabbits were injected with the solubilized cat gut material; two rabbits (designated #4603 and #8049) were injected with solubilized material from uninfected cat gut, and 4 rabbits (designated #4604, #4499, #8050, and #8051) were injected with solubilized material from infected cat gut material. For the first injection, 0.5 mg of soluble protein, prepared as described above, was brought to 0.5 ml and mixed with an equal volume of Freunds Complete Adjuvant. This solution was delivered subcutaneously (SQ). The second injection, two weeks later, was identical to the first, except Freunds Incomplete Adjuvant was used. A third injection, twelve weeks after the first injection, was similar to prior injections except that the total amount of protein injected was 1.5 mg. The animals were pre-bled prior to the first immunization and were bled at approximately monthly intervals to monitor antibody responses. The blood was allowed to clot at room temperature and serum obtained by centrifugation. The sera Were evaluated for the presence of antibody specific to *T. gondii* by both Western blot analysis using tachyzoite lysates and by indirect immunofluorescent antibody assay (section EFA) using histological sections obtained from infected cat intestine.

The rabbit antisera were preabsorbed to uninfected cat gut material prior to use in immunoscreening, either by absorbing the antisera to Sepharose beads to which solubilized uninfected cat gut material had been covalently linked, or by absorbing the antisera to nitrocellulose sheets to which uninfected cat gut protein was bound. Western analysis demonstrated that greater than 98% of the serum reactivity to uninfected cat gut was removed by preabsorption to the column. The remaining (unabsorbed) sera showed reactivity towards *T. gondii* tachyzoite lysates. The unabsorbed sera were used to screen the *Toxoplasma* genomic library.

Antisera 4604 was used to isolate nucleic acid molecules herein designated 4604-2, 4604-3, 4604-5, 4604-10, 4604-17, 4604-54, 4604-62, 4604-63 and 4604-69 as follows: Two separate immunoscreens were performed with this antisera, and *Toxoplasma*-specific nucleic acid molecules were isolated form each screen. In the first screen, *E. coli* Y1090 was infected with approximately $5 \times 10^4$ PFU and then evenly spread on. 10 LB-amp agarose culture plates. In the second screen, *E. coli* Y1090 was infected with approximately $1.5 \times 10^6$ PFU and then evenly spread on 12 LB-amp agarose culture plates. The rest of the screening procedure was as described for immunoscreening with antisera Q4-1959 (Example 2), with the following exceptions: the primary antibody was used at a 1:500 dilution, and the secondary antibody was a 1:500 dilution of AP-conjugated goat anti-rabbit IgG. Of the approximately $1.5 \times 10^6$ plaques screened in this manner, 15 nucleic acid molecules capable of expressing proteins recognized by antisera 4604 were plaque purified.

Antisera 4499 was used to isolate nucleic acid molecule 4499-9 as follows: *E. coli* Y1090 was infected with approximately $5 \times 10^4$ PFU and then evenly spread on 10 LB-amp agarose culture plates. The rest of the screening procedure was as described for immunoscreening with antisera Q4-1959 (Example 2), with the following exceptions: the primary antibody was used at a 1:200 dilution, and the secondary antibody Was a 1:500 dilution of AP-conjugated goat anti-rabbit IgG. Of the $5 \times 10^4$ plaques screened in this manner, 2 nucleic acid molecules capable of expressing proteins recognized by antisera 4499 were plaque purified.

Antisera R8050 (rabbit antisera raised against infected cat gnt) was used to isolate nucleic acid molecules herein designated R8050-2, R8050-5, and R8050-6 as follows: *E. coli* Y1090 was infected with approximately $5 \times 10^6$ PFU and then evenly spread on 10 LB-amp agarose culture plates. The rest of the screening procedure was as described for immunoscreening with antisera Q4-1959 (Example 2), with the following exceptions: the primary antibody was used at a 1:200 dilution, and the secondary antibody was a 1:1000 dilution of AP-conjugated goat anti-rabbit IgG (available from Kirkegaard Perry Laboratories). Of the $5 \times 10^6$ plaques screened in this manner, 4 nucleic acid molecules capable of expressing proteins recognized by antisera R8050 were plaque purified.

Selected nucleic acid molecules identified by screening for the expression of proteins recognized by rabbit anti-ICG antisera were subcloned and sequenced as described in Example 2. The results of assays to characterize the isolated nucleic acid molecules are summarized in Table 6.

TABLE 6

Nucleic Acid Molecules Selected with Rabbit Sera Specific to Infected Cat Gut

| SEQ ID NO | ORIGINAL DESIGNATION | DETECTION | | | | EXPRESSION | | pDVAC | | REACTIVITY | |
|---|---|---|---|---|---|---|---|---|---|---|---|
| | | ICG | UCG | TZ | BZ | pTrCHIS | λ CRO | IN VITRO | IN VIVO | SERUM | IS |
| 19 | 4499-9 | + | − | + | + | ND | + | ND | ND | + | + |
| 21 | 4604-2 | + | − | + | + | ND | + | ND | ND | ND | − |
| 23 | 4604-3 | + | − | + | − | ND | + | ND | ND | ND | − |
| 25 | 4604-5 | − | − | + | + | ND | − | ND | ND | ND | − |
| 26 | 4604-10 | − | − | + | + | ND | − | ND | ND | ND | − |
| 28 | 4604-17 | + | − | + | + | ND | − | ND | ND | ND | − |
| 30 | 4604-54 | + | − | − | 2+ | ND | + | ND | ND | ND | − |
| 32 | 4604-62 | + | − | + | + | + | ND | ND | ND | ND | − |
| 34 | 4604-63 | + | − | + | + | − | ND | ND | ND | ND | − |
| 36 | 4604-69 | + | − | 2+ | + | ND | + | ND | ND | ND | − |
| 103 | R8050-2 | + | − | 2+ | + | + | ND | ND | ND | ND | − |
| 105 | R8050-5 | − | − | + | − | + | ND | ND | ND | ND | − |
| 107 | R8050-6 | + | − | 2+ | − | − | ND | ND | ND | ND | − |

Table 6 Legend:
See Legend for Table 2.

Sequence Analysis of Nucleic Acid Molecules Selected for Expression of Proteins Recognized by Rabbit Anti-ICG Antisera 4604, 4499 and R8050:

Nucleic acid molecules 4604-2, 4604-3, 4604-5, 4604-10, 4604-17, 4604-54, 4604-62, 4604-6, 4604-69, R8050-2, R8050-5, and R8050-6 were sequenced as described above. These nucleic acid molecules were sequenced as described above. BLASTn and BLASTp homology searches were performed on these sequences using the NCBI GenBank™ non-redundant (nr) nucleotide (n) and amino acid (p) databases, and the dbEST (est) database as described above. The results of these searches are summarized in Table 3, as described above. The results of these searches are summarized in Table 3.

The sequence data described above were used to design unique primers specific to each nucleic acid molecule of the present invention. These primer sequences are listed in Table 4. The unique primers listed in Table 4 were used in reverse transcriptase-polymerase chain reaction (RT-PCR) assays to assess the expression of the particular nucleic acid sequence in ICG, bradyzoites and tachyzoites. The results of these assays are summarized in Table 6.

*T. gondii* nucleic acid molecules encoding immunogenic *T. gondii* proteins isolated by immunoscreening with rabbit anti-ICG antiserum were subcloned into either or both of two expression vectors: pTrcHisB (as described above) or Prcro/T2ori/RSET-B (described below). Expression of the fusion proteins from these vectors, and purification of their expressed fusion proteins, were as described above. The results of assays for the expression of recombinant immunogenic *T. gondii* proteins from these expression vectors is summarized in Table 6.

Recombinant nucleic acid molecules and protein molecules including sequences encoding *T. gondii* antigenic proteins and sequences from the vector Prcro/T2ori/RSET-B: Recombinant molecules containing *T. gondii* nucleic acid molecules operatively linked to lambda phage transcriptional control sequences and to a fusion sequence encoding a polyhistidine segment, were produced in the following manner. *T. gondii* DNA fragments in λgt11 were PCR amplified from nucleic acid molecules herein designated 4499-9, 4604-2, 4604-3, 4604-5, 4604-10, 4604-17, 4604-54, and 4604-69, using the λgt11 forward and reverse primers herein described. Recombinant molecules were produced by digesting the PCR product with EcoR I, gel purifying the resulting fragment, and subcloning into expression vector PRcro/T2ori/RSET-B (also referred to herein as λ CRO) that had been cleaved with EcoR I and gel purified. Expression vector PRcro/T2ori/RSET-B contains the following nucleotide segments: An about 1990-bp Pvu II to Aat II fragment from pUC19 containing the ampicillin resistance gene and *E. coli* of replication; an about 1000-bp Pvu 11 to Bgl II fragment from pRK248cIts (available from American Type Culture Collection, Rockville, Md.) containing lambda transcriptional regulatory regions (including the gene encoding cI$^{ts}$, the promoter p$_R$, and a sequence encoding 22 amino acids of the cro protein); an about 60-bp Bgl It to Xba I fragment from pGEMEX-1 (available from Promega Corp.) which contains the T7 promoter; an about 166-bp Xba I to EcoR I fragment from pRSET-B (available from Invitrogen, San Diego Calif.) which contains sequences encoding the T7-S10 translational enhancer, the His$_6$ fusion, the 14-amino acid S10 leader fusion, and an enterokinase cleavage site as well as the multiple cloning site; and an about 210-bp EcoR I to Aat II fragment containing synthetic translational and transcription termination signals including the T$_1$ translation terminators in all three reading frames, an RNA stabilization sequence from *Bacillus thurengiensis* crystal protein and the T2 rho-independent transcription terminator from the trpA operon. Expression vector PRcroIT2ori/RSET-B contains the following nucleotide segments. An about 1990-bp PvuII to AatII fragment from pUC19 containing the ampicillin resistance gene and *E. coli* of replication; an about 1000-bp PvuII to BglII fragment from pRK24ScIts (available from American Type Culture Collection, Rockville, Md.) containing lambda transcriptional regulatory regions (including the gene encoding cI$^{ts}$, the promoter p$_R$, and a sequence encoding 22 amino acids of the cro protein); an about 60-bp BglII to XbaI fragment from pGEMEX-1 (available from Promega Corp., Madison Wis.) which contains the T7 promoter; an about 166-bp XbaI to EcoRI fragment from pRSET-B (available from Invitrogen Corp., San Diego Calif.) which contains sequences encoding the T7-S10 translational enhancer, the His$_6$ fusion, the 14-amino acid S10 leader fusion, and an enterokinase cleavage site as well as the multiple cloning site; and an about 210-bp EcoRI to AatII fragment containing synthetic translational and transcription termination signals including the T$_1$ translation terminators in all three reading frames, an RNA stabilization sequence from *Bacillus thurengiensis* crystal protein and the T$_2$ rho-independent transcription terminator from the trpA operon.

The resulting recombinant molecules were transformed into *E. coli* to form recombinant cells, using standard techniques as disclosed in Sambrook et al., ibid.

The recombinant cells were cultured in shake flasks containing an enriched bacterial growth medium containing 0.1 mg/ml ampicillin and 1% glucose at about 32° C. When the cells reached an OD$_{600}$ of about 0.6, expression of the *Toxoplasma* antigen was induced by quickly adjusting the temperature to 42° C. and continuing cultivation of the cells for about 2 hours. Protein production was monitored by SDS PAGE of recombinant cell lysates, followed by immunoblot analysis using standard techniques as described herein and as known in the art. The results of these assays are summarized in Table 6.

The antisera used to originally isolate each *Toxoplasma*-specific nucleic acid molecule (i.e., either antiserum 4604, or antiserum 4499) was used to identify recombinant proteins in *E. coli* extracts as follows. The material in crude extracts from *E. coli* were separated by running 5 µg protein per lane on a 12-well 10% Tris-glycine SDS-PAGE gel at 200 volts for 1 hour, and then transferred to nitrocellulose membranes by standard methods. After transfer, the membranes were blocked in 5% (w/v) dry milk for 1 hr at 37° C. The membranes were then incubated with a 1:200 dilution in Tris buffered saline of the sera originally used to select the nucleic acid molecule encoding *Toxoplasma*-specific portion of the fusion protein. After 1 hr incubation at room temperature, the blots were washed, and antibody binding resolved using a secondary antibody bound to a substrate for a color indicator. Using the original selecting antibody, immunoblot analysis of *E. coli* lysates identified fusions proteins at or near the predicted molecular weight of the recombinant fusion protein. The results of these assays are summarized in Table 6.

Histidine tagged fusion proteins were purified from cell lysates as follows. Cell cultures containing nucleic acid molecules of the present invention inserted into either pTrcHisB or λCRO were grown to an OD$_{600}$ of approximately 0.4 to 0.5. The cultures were induced with IPTG, and the cells harvested 4 hours later. Ten ml of cell culture was centrifuged at 3000 rpm on a table top centrifuge and the protein isolated according to the manufacturer's instructions using a Ni-NTA Spin Kit (available from Qiagen Inc.). Protein purification was monitored by SDS PAGE followed by Coomassie Blue staining of the column eluate fractions. Recombinant cells including recombinant molecules 4499-9, 4604-2, 4604-3, 4604-54, and 4604-69 produced proteins that were able to bind to a T7 tag monoclonal antibody (available from Novagen Inc., Madison, Wis.) directed against the fusion portion of the recombinant fusion protein.

Recombinant Nucleic Acid Molecules and Protein Molecules Including Sequences Encoding *T. gondii* Antigenic Proteins and Sequences from the Vector pTrcHisB:

Recombinant nucleic acid molecules including sequences encoding *T. gondii* antigenic proteins and sequences from the vector pTrcHisB were produced as described in Example 2. In brief, *T. gondii* DNA fragments in λgt11 were PCR amplified from nucleic acid molecules herein designated 4604-62, 4604-63, R8050-2, R8050-5, and R8050-6, using the λgt11 forward and reverse primers herein described. The resulting recombinant molecules were transformed into *E. coli* to form recombinant cells 4604-62, 4604-63, R8050-2, R8050-5, and R8050-6. Immunoblot analysis of the recombinant cell lysates using a T7 tag monoclonal antibody (available from Novagen Inc., Madison, Wis.) directed against the fusion portion of the recombinant *Toxoplasma* fusion protein was used to confirm the expression of the fusion proteins and to identify their size. Of the six nucleic acid molecules selected by immunoscreening with rabbit anti-ICG antiserum that were subcloned into the expression vector pTrcHisB, 15(4604-62, R8050-2, and R8050-5) were positive by this immunoblot assay. The results of these assays are summarized in Table 6.

Example 5

This Example discloses a method of isolation of *T. gondii* nucleic acid molecules encoding immunogenic *T. gondii* proteins recognized by cat antisera raised against infected cat gut. This Example further discloses recombinant nucleic acid molecules, proteins and cells of the present invention.

Preparation of cat antibody against infected cat gut: Preparation of infected cat gut material and production of anti-ICC antisera in cats was performed essentially as herein described for production of rabbit anti-ICG antiserum. Polyclonal cat antisera against infected cat gut (ICG) antigens (also herein referred to as anti-ICG antiserum or antisera, or anti-ICG antibody) were prepared by immunization of cats as follows. Three cats were injected with cat gut material. One cat (#AME5) was injected with material from uninfected cat gut material and two cats (#AMI4, #AMX1) were injected with material from infected cat gut preparations. The same injection, boost and bleed regimen and antigen-preparation were used for cats as was used for rabbits, described above. Like the rabbit antisera, the cat antisera were preabsorbed to uninfected cat gut material prior to use in immunoscreening.

Anti-sera AMI was used to isolate nucleic acid molecules herein designated AMI-23, AMI-24, AMI-28, and AMI-47 as follows: *E. coli* Y1090 was infected with approximately $5 \times 10^6$ PFU and then evenly spread on 10 LB-amp agarose culture plates. The rest of the screening procedure was as described for immunoscreening with antisera Q4-1959 (Example 2), with the following exceptions: the primary antibody was used at a 1:200 dilution, and the secondary antibody was a 1:1000 dilution of AP-conjugated goat anti-cat IgG. Of the $5 \times 10^6$ plaques screened in this manner, 6 nucleic acid molecules capable of expressing proteins recognized by antisera AMI were plaque purified.

Anti-sera AMX/I was used to isolate nucleic acid molecules herein designated AMX/I-5, AMX/I-6, AMX/I-7, AMX/I-9, and AMX/I-10 as follows: *E. coli* Y1090 was infected with approximately $5 \times 10^6$ PFU and then evenly spread on 12 LB-amp agarose culture plates. The rest of the screening procedure was as described for immunoscreening with antisera Q4-1959 (Example 2), with the following exceptions: the primary antibody was used at a 1:200 dilution, and the secondary antibody was a 1:1000 dilution of AP-conjugated goat anti-cat IgG. Of the $5 \times 10^6$ plaques screened in this manner, 6 nucleic acid molecules capable of expressing proteins recognized by antisera AMX/I were plaque purified. The results of this immunoscreen are summarized in Table 7.

TABLE 7

Nucleic Acid Molecules Selected by Cat Serum Specific to Infected Cat Gut

| SEQ ID NO | ORIGINAL DESIGNATION | DETECTION | | | | EXPRESSION | | pDVAC | | REACTIVITY | |
|---|---|---|---|---|---|---|---|---|---|---|---|
| | | ICG | UCG | TZ | BZ | pTrCHIS | λ CRO | IN VITRO | IN VIVO | SERUM | IS |
| 54 | AMX/I-5 | + | − | + | + | + | + | ND | ND | ND | + |
| 55 | AMX/I-6 | 2+ | − | 2+ | + | ND | + | ND | ND | ND | − |
| 57 | AMX/I-7 | 2+ | − | − | + | ND | + | ND | ND | ND | − |
| 59 | AMX/I-9 | 2+ | − | + | + | + | ND | ND | ND | ND | − |
| 61 | AMX/I-10 | + | + | − | − | | + | ND | ND | ND | − |
| 63 | AMI-23 | + | + | − | − | ND | ND | ND | ND | ND | − |
| 65 | AMI-24 | + | − | + | 2+ | + | ND | ND | ND | ND | − |
| 67 | AMI-28 | + | − | + | 2+ | ND | ND | ND | ND | ND | − |
| 68 | AMI-47 | − | − | + | − | + | ND | ND | ND | ND | − |

Table 7 Legend:
See Legend for Table 2.

Selected nucleic acid molecules identified by screening for the expression of proteins recognized by cat anti-ICG antisera were subcloned and sequenced as described in Example 2.

Sequence Analysis of Nucleic Acid Molecules Selected for Expression of Proteins Recognized by Cat Anti-ICG Antisera AMI and AMX/I:

The nucleic acid molecules isolated using antisera AMI or AMX/I were sequenced as described above. BLASTn and BLASTp homology searches were performed on these sequences using the NCBI GenBank™ non-redundant (nr) nucleotide (n) and amino acid (p) databases, and the dbEST (est) database as described above. The results of these searches are summarized in Table 3.

The sequence data described above were used to design unique primers specific to each nucleic acid molecule of the present invention. These primer sequences are listed in table 4. The unique primers listed in Table 4 were used in reverse transcriptase-polymerase chain reaction (RT-PCR) assays to assess the expression of the particular nucleic acid sequence in ICG, bradyzoites and tachyzoites. The results of these assays are summarized in Table 7.

*T. gondii* nucleic acid molecules encoding immunogenic *T. gondii* proteins isolated by immunoscreening with cat anti-ICG antiserum (antiserum AMI or AMX/I) were subcloned into either or both of two expression vectors: pTrcHisB or Prcro/T2ori/RSET-B (as described above). Expression of the fusion proteins from these vectors, and purification of their expressed fusion proteins, were as described above.

Recombinant Nucleic Acid Molecules, Protein Molecules and Cells Including Sequences Encoding *T. gondii* Antigenic Proteins and Sequences from the Vector PrcEo/T2ori/RSET-B:

Recombinant molecules containing *T. gondii* nucleic acid molecules operatively linked to lambda phage transcriptional control sequences and to a fusion sequence encoding a poly-histidine segment in the vector Prcro/T2ori/RSET-B, were produced essentially as described above, resulting in the production of recombinant molecules. The resulting recombinant molecules were transformed into *E. coli* to form recombinant cells using standard techniques as disclosed in Sambrook et al., ibid. Assays for the expression of an immunogenic *T. gondii* fusion protein by these cells were performed as described above, and the results are summarized in Table 7.

Recombinant Nucleic Acid Molecules Protein Molecules and Cells Including Sequences Encoding *T. gondii* Antigenic Proteins and Sequences from the Vector pTrcHisB:

Recombinant nucleic acid molecules including sequences encoding *T. gondii* antigenic proteins and sequences from the vector pTrcHisB were produced as described in Example 2. In brief, *T. gondii* DNA fragments in λgt11 were PCR amplified from nucleic acid molecules herein designated AMX/I-5, AMX/I-9, AMI-24 and AMI-47 using the λgt11 forward and reverse primers herein described. The resulting recombinant molecules were transformed into *E. coli* to form recombinant cells AMX/I -5, AMX/I-9, AMI-24 and AMI-47. Immunoblot analysis of the recombinant cell lysates using a T7 tag monoclonal antibody (available from Novagen Inc., Madison, Wis.) directed against the fusion portion of the recombinant *Toxoplasma* fusion protein was used to confirm the expression of the fusion proteins and to identify their size. The results of this immunoblot analysis are summarized in Table 7.

Example 6

This Example discloses a method of isolation of *T. gondii* nucleic acid molecules encoding immunogenic *T. gondii* proteins recognized by cat immune sera. This Example further discloses recombinant nucleic acid molecules, proteins and cells of the present invention.

Production of Cat Immune Sera:

Eight specific-pathogen free (SPF) cats (available from Liberty Laboratories, Liberty Corners, N.J.), ages 8-10 months, were randomly assigned to two groups; Group 1, n=5 and Group 2, n=3 (the uninfected control group). Before the initiation of any studies with these animals, serum samples were taken from each and tested for reactivity to solubilized tachyzoites. Each animal was seronegative for *T. gondii* by standard Western and ELISA analysis using solubilized tachyzoites as the antigen. This serum also served as the pre-bleed in subsequent studies. Feces from each animal were analyzed for the presence of shed *T. gondii* oocysts using flotation by sugar solution centrifugation followed by microscopic examination. Food was removed from both groups fourteen hours prior to Day 0 and on the day prior to all sample collections. On Day 0 the cats in Group 1 were orally inoculated by syringe at the back of the throat with 1000 mouse brain derived *T. gondii* tissue cysts of the Mozart strain. This strain represents an isolate from a cat which presented with Toxoplasmosis at the Veterinary Teaching Hospital, Colorado State University, in 1992. The Group 2 cats were not infected.

The Group 1 cats were housed in individual stainless steel cages in an infectious disease isolation unit. The feces from each animal were collected every day for the first fourteen days post infection (PI) and weekly thereafter until parasite challenge. The feces were analyzed for the presence of shed *T. gondii* oocysts. Five milliliters of whole blood was collected from each animal by jugular venipuncture on the following days post primary infection: 3, 7, 10, 14, 21, 28, 42, 56, 70, 84, 112, 140, 143, 147, 154, 161, 168, and 182.

On day 140 post primary infection, all Group 1 cats were orally challenged with 1000 mouse brain-derived tissue cysts of the Mozart strain. Fecal samples were collected and monitored for the excretion of oocysts for thirty days post challenge (PC). The cats were then bled as before on days: 3, 7, 14, 21, 28, and 42 post challenge.

In addition to the serum samples collected on the bleed dates, both salivary secretions and intestinal secretions were obtained at weeks 0, 1, 2, 4, 8, 10, 16, 20, 21, 22, 23, 24, and 26. These samples were obtained by first anesthetizing each animal with an injection of thiobarbiturate, then intubating the animals and maintaining them with halothane and oxygen. Approximately 0.1 μl of saliva was collected into an equal volume of 0.1 M EDTA. The intestinal secretions were obtained from the upper portion of the small intestine using an endoscope fitted with medical tubing which allowed suction of intestinal fluid. Intestinal secretions were diluted 1:1 with sterile 0.9% NaCl and centrifuged at 10,000×g for 5 minutes in an Eppendorf centrifuge. The secretions were stored at −70° C. until use. Pooled secretions included equal aliquots from all five immune animals from week 20 through 26 post infection. These pooled secretions were used to test the reactivity of intestinal secretions from immune cats to proteins expressed by nucleic acid molecules of the present invention.

All Group 1 animals shed oocysts in their feces during the primaly infection and all seroconverted as assessed by Western blot analysis using tachyzoite lysates as the antigen. None of these animals shed oocysts when challenged, and were therefore considered immune. The sera from the immune animals was pooled, and is referred to herein as Mozart II antiserum or antisera, or as immune antiserum or antisera.

Mozart II antisera was used to isolate nucleic acid molecules herein designated 4CQA-7, 4CQA-11, 4CQA-19, 4CQA-21, 4CQA-22, 4CQA-24, 4CQA-25, 4CQA-26, 4CQA-27, and 4CQA29 as follows: *E. coli* Y1090 was infected with approximately $8.3\times10^5$ PFU and then evenly spread on 13 LB-amp agarose culture plates. The rest of the screening procedure was as described for immunoscreening with antisera Q4-1959 (Example 2), with the following exceptions: the primary antibody was used at a 1:80 dilution, and the secondary antibody was a 1:50 dilution of monoclonal mouse anti-cat α chain (available from Serotec, Oxford, England) and the tertiary antibody was a 1:1000 dilution of AP-conjugated goat anti-mouse IgG (Kirkegaard Perry Laboratories). Of the $8.3\times10^5$ plaques screened in this manner, 13 nucleic acid molecules capable of expressing proteins recognized by Mozart II antisera were plaque purified. The results of assays to characterize these nucleic acid molecules are summarized in Table 8.

conjugated goat anti-cat IgA Fce Of the $1\times10^6$ plaques screened in this manner, 4 nucleic acid molecules capable of expressing proteins recognized by Mozart II antisera were

TABLE 8

Nucleic Acid Molecules Selected with Immune Cat Sera in Screens II and III

| SEQ ID NO | ORIGINAL DESIGNATION | DETECTION | | | | EXPRESSION | | pDVAC | | REACTIVITY | |
|---|---|---|---|---|---|---|---|---|---|---|---|
| | | ICG | UCG | TZ | BZ | pTrCHIS | ICRO | IN VITRO | IN VIVO | SERUM | IS |
| 1 | Tg-41 | 2+ | − | + | 3+ | + | ND | + | + | + | − |
| 3 | Tg-45 | + | − | 2+ | + | + | ND | + | + | + | + |
| 5 | Tg-50 | + | − | + | + | + | ND | ND | ND | + | + |
| 82 | 4CQA-7 | ND | ND | ND | ND | ND | ND | ND | ND | + | − |
| 85 | 4CQA-11 | 2+ | − | + | 2+ | − | ND | + | ND | + | + |
| 87 | 4CQA-19 | + | − | + | + | − | ND | ND | ND | + | − |
| 89 | 4CQA-21 | 3+ | − | 3+ | + | + | ND | ND | ND | + | − |
| 91 | 4CQA-22 | + | − | 3+ | 2+ | − | ND | ND | ND | + | − |
| 93 | 4CQA-24 | + | − | 2+ | 3+ | − | ND | ND | ND | + | − |
| 95 | 4CQA-25 | + | − | 2+ | 3+ | − | ND | ND | ND | + | − |
| 97 | 4CQA-26 | + | + | + | + | − | ND | ND | ND | + | − |
| 99 | 4CQA-27 | + | − | + | + | + | ND | ND | ND | + | − |
| 101 | 4CQA-29 | + | − | + | 2+ | − | ND | ND | ND | + | − |
| 109 | M2A-1 | + | − | + | + | ND | ND | ND | ND | + | + |
| 111 | M2A-2 | ND | ND | ND | ND | ND | ND | ND | ND | + | − |
| 113 | M2A-3 | − | − | − | − | ND | ND | ND | ND | + | − |
| 115 | M2A-4 | + | − | + | + | ND | ND | ND | ND | + | − |
| 117 | M2A-5 | + | − | ND | ND | ND | ND | ND | ND | + | − |
| 119 | M2A-6 | − | − | − | − | ND | ND | ND | ND | + | − |
| 121 | M2A-7 | + | − | + | + | ND | ND | ND | ND | + | − |
| 123 | M2A-11 | + | − | + | + | ND | ND | ND | ND | + | − |
| 125 | M2A-16 | + | − | ND | ND | ND | ND | ND | ND | + | − |
| 127 | M2A-18 | + | − | + | + | ND | ND | ND | ND | + | − |
| 129 | M2A-19 | + | + | − | + | ND | ND | ND | ND | + | − |
| 131 | M2A-20 | + | − | + | + | ND | ND | ND | ND | + | − |
| 132 | M2A-21 | − | − | − | − | ND | ND | ND | ND | + | − |
| 134 | M2A-22 | + | − | + | + | ND | ND | ND | ND | + | − |
| 136 | M2A-23 | − | − | − | − | ND | ND | ND | ND | + | − |
| 139 | M2A-24 | − | − | − | − | ND | ND | ND | ND | + | − |
| 141 | M2A-25 | + | − | + | + | ND | ND | ND | ND | + | − |
| 143 | M2A-29 | + | − | + | + | ND | ND | ND | ND | + | − |

Table 8 Legend:
See Legend for Table 2.

In addition to the immunoscreen described above, Mozart II antisera was used in another immunoscreen to isolate nucleic acid molecules herein designated M2A1, M2A2, M2A3, M2A4, M2A5, M2A6, M2A7, M2A11, M2A16, M2A18, M2A19, M2A20, M2A21, M2A22, M2A23, M2A24, M2A25, and M2A29 as follows: E. coli Y1090 was infected with approximately $1\times10^6$ PFU and then evenly spread on 10 LB-amp agarose culture plates. The rest of the screening procedure was as described for immunoscreening with antisera Q4-1959 Example 2), with the following exceptions the primary antibody was used at a 1:50 dilution, and the secondary antibody was a 1:200 dilution of AP-conjugated goat anti-cat IgA (available from Bethyl Laboratories Inc., Montgomery, Tex.). Of the $1\times10^6$ plaques screened in this manner, 18 nucleic acid molecules capable of expressing proteins recognized by Mozart II antisera were plaque purified. The results of assays to characterize these nucleic acid molecules are summarized in Table 8.

Mozart II antisera was also used in yet another immunoscreen to isolate nucleic acid molecules herein designated Tg-41, Tg-45, and Tg-50 as follows: E. coli Y1090 was infected with approximately $1\times10^6$ PFU and then evenly spread on 12 LB-amp agarose culture plates. The rest of the screening procedure was as described for immunoscreening with antisera Q4-1959 Q3(Example 2), with the following exceptions: the primary antibody was used at a 1:50 dilution, and the secondary antibody was a 1:200 dilution of APplaque purified. The results of assays to characterize these nucleic acid molecules are summarized in Table 8.

Selected nucleic acid molecules identified by screening for the expression of proteins recognized by Mozart II (immune) antiserum were subcloned and sequenced as described in Example 2.

Sequence Analysis of Nucleic Acid Molecules Selected for Expression of Proteins Recognized by Mozart II (Immune) Antiserum:

The nucleic acid molecules isolated using Mozart II (immune) serum were sequenced as described above. BLASTn and BLASTp homology searches were performed on these sequences using the NCBI GenBank™ non-redundant (nr) nucleotide (n) and amino acid (p) databases and the dbEST (est) database as described above. The results of these searches are summarized in Table 3. Nucleic acid molecule M2A3 was sequenced again and some changes found between the first and second sequence. The resequenced nucleic acid molecule is referred to herein as M2A3-a. In addition, nucleic acid molecule M2A18 was sequenced again and some changes found between the first and second sequence. The resequenced nucleic acid molecule is referred to herein as M2A18-a.

The sequence data described above were used to design unique primers specific to each nucleic acid molecule of the present invention. These primer sequences are listed in Table 4. The unique primers listed in Table 4 were used in reverse transcriptase-polymerase chain reaction (RT-PCR) assays to assess the expression of the particular nucleic acid sequence in ICE, bradyzoites and tachyzoites. The results of these assays are summarized in Table 8.

Recombinant Nucleic Acid Molecules, Protein Molecules and Cells Including Sequences Encoding *T. gondii* Antigenic Proteins and Sequences from the Vector pTrcHisB:

Recombinant nucleic acid molecules including sequences encoding *T. gondii* antigenic proteins and sequences from the vector pTrcHisB were produced as described in Example 2. In brief, *T. gondii* DNA fragments in λgt11 were PCR amplified from nucleic acid molecules herein designated 4CQA-11, 4CQA-19, 4CQA-21, 4CQA-22, 4CQA-24, 4CQA-25, 4CQA-26, 4CQA-27, 4CQA-29, Tg-41, Tg-45, and Tg-50 using the λgt11 forward and reverse primers herein described. The resulting recombinant molecules were transformed into *E. coli* to form recombinant cells. Immunoblot analysis of the recombinant cell lysates using a T7 tag monoclonal antibody (available from Novagen Inc., Madison, Wis.) directed against the fusion portion of the recombinant *Toxoplasma* fusion protein was used to confirm the expression of the fusion proteins and to identify their size. The results of this immunoblot analysis are summarized in Table 8.

Example 7

This Example discloses a method of isolation of *T. gondii* nucleic acid molecules encoding immunogenic *T. gondii* proteins recognized by cat immune sera enriched for antibodies to gametogenic stages (herein referred to as absorbed immune sera or serum). This Example further discloses recombinant nucleic acid molecules, proteins and cells of the present invention.

Production of Cat Immune Sera Enriched for Antibodies to Gametogenic Stages:

Sera from cats which were infected and then subsequently challenged with mouse brain-derived tissue cysts were tested for reactivity to extracts of infected cat gut material by Western blot analysis. Sera from one specific cat, designated Queen 2, demonstrated reactivity to particular ICG sections in which the presence of *T. gondii* had been shown by immunofluorescence assay. Queen 2 was originally infected with 100 mouse brain-derived tissue cysts, did not shed oocysts, and seroconverted to positive for tachyzoite antigens by day 39 post-infection. This sera was highly reactive to the asexual stage, tachyzoites. Therefore, to enhance the utility of this sera as a reagent for detection of gametogenic proteins, this sera was used in conjunction with a western blot of infected cat intestinal cell lysates to obtain a fraction enriched in antibody reactive to the gametogenic proteins. The enrichment of the Queen 2 sera (also referred to herein as Q2 sera) was performed as follows:

A 12% SDS-PAGE gel was prepared according to standard methods (Laemmli, 1970, *Nature* 227, 680-685). 1000 μg of solubilized ICG protein, prepared as described above, was loaded on 20×20×0.1 cm gel and run at 8V/cm for 5 hours. *Toxoplasma* tachyzoite (TZ) antigen, prepared from solubilized tachyzoites, was used as a control. Separated proteins were transferred to nitrocellulose according to standard procedures for western blotting. After transfer, the nitrocellulose filter was blocked with 4% (w/v) dry milk powder in PBS (pH 7.5), and incubated with a 1:200 dilution of immune cat (Queen 2) antiserum at room temperature for 5 hours with gentle shaking. The filter was then washed with PBS (pH 7.5). After washing, a 0.5 cm strip was cut off the end of the filter and incubated with a 1:1000 dilution of alkaline phosphatase labeled goat anti-cat IgG antibody at room temperature for 1 hour. The strip was stained with 5-bromo-4-chloro-3-indolylphosphate p-toluene salt/nitroblue tetrazolium chloride substrates (BCIP/NBT)(available from Gibco/BRL). The areas of the gel that stained with BCIP/NBT substrates represented ICG protein bands which were recognized by IgG antibodies in immune cat serum.

The regions of interest that were visualized on the BCEP/NBT-stained end strip, were cut from the remainder of the filter, and the bound antibody eluted with 0.1 M glycine (pH 2.8), 1 mM EDTA at room temperature for 10 minutes. The antibody in glycine was neutralized with 10 mM Tris (pH 9.0), 0.02% NaN$_3$ was added, and the solution was stored at 4° C. The purified antibody was analyzed by Western blot of ICG to monitor successful recovery of the eluted antibody, verifying recovery of antibody that reacted with the appropriate molecular weight region of the ICG western blot. This antibody preparation is referred to herein as absorbed immune serum or sera.

The absorbed immune serum was used to isolate nucleic acid molecules herein designated Q2-4, Q2-9, Q2-10, and Q2-11 as follows: *E. coli* Y1090 was infected with approximately 3.2×10$^5$ PFU and then evenly spread on 8 LB-amp agarose culture plates. The rest of the screening procedure was as described for immunoscreening with antisera Q4-1959 (Example 2), with the following exceptions: the primary antibody was used at a 1:200 dilution, and the secondary antibody was a 1:1000 dilution of AP-conjugated goat anti-cat IgG. Of the 3.2×10$^5$ plaques screened in this manner, 4 nucleic acid molecules capable of expressing proteins recognized by absorbed immune serum were plaque purified. The results of assays to characterize these nucleic acid molecules are summarized in Table 9.

TABLE 9

Nucleic Acid Molecules Selected with Absorbed Immune Sera

| SEQ ID NO | ORIGINAL DESIGNATION | DETECTION | | | | EXPRESSION | | pDVAC | | REACTIVITY | |
|---|---|---|---|---|---|---|---|---|---|---|---|
| | | ICG | UCG | TZ | BZ | pTrCHIS | λ CRO | IN VITRO | IN VIVO | SERUM | IS |
| 9 | Q2-4 | 2+ | − | + | 2+ | ND | + | ND | ND | + | − |
| 13 | Q2-9 | + | − | + | + | − | − | ND | ND | + | − |
| 15 | Q2-10 | + | − | + | + | ND | + | ND | ND | + | − |
| 17 | Q2-11 | − | − | + | + | ND | + | ND | ND | + | − |

Table 9 Legend:
See Legend for Table 2.

Selected nucleic acid molecules identified by screening for the expression of proteins recognized by absorbed immune serum were subcloned and sequenced as described in Example 2.

Sequence Analysis of Nucleic Acid Molecules Selected for Expression of Proteins Recognized by Absorbed Immune Serum:

The nucleic acid molecules selected for expression of proteins recognized by absorbed immune serum were sequenced as described above. BLASTn and BLASTp homology searches were performed on these sequences using the NCBI GenBank™ non-redundant (nr) nucleotide (n) and amino acid (p) databases, and the dbEST (est) database as described above. The results of these searches are summarized in Table 3. Nucleic acid molecule Q2-9 was sequenced again and some changes found between the first and second sequence. The resequenced nucleic acid molecule is referred to herein as Q2-9-a.

The sequence data described above were used to design unique primers specific to each nucleic acid molecule of the present invention. These primer sequences are listed in Table 4. The unique primers listed in Table 4 were used in reverse transcriptase-polymerase chain reaction (RT-PCR) assays to assess the expression of the particular nucleic acid sequence in ICG, bradyzoites and tachyzoites. The results of these assays are summarized in Table 9.

Recombinant Nucleic Acid Molecules, Protein Molecules and Cells Including Sequences Encoding *T. gondii* Antigenic Proteins and Sequences from the Vector Prcro/T2ori/RSET-B:

Recombinant molecules containing *T. gondii* nucleic acid molecule operatively linked to lambda phage transcriptional control sequences and to a fusion sequence encoding a polyhistidine segment in the vector Prcro/T2ori/RSET-B, were produced essentially as described above, resulting in the production of recombinant molecule. The resulting recombinant molecules were transformed into *E. coli* to form recombinant cells using standard techniques as disclosed in Sambrook et al., ibid. Immunoblot analysis of expression of immunogenic *T. gondii* proteins by these recombinant cells is summarized in Table 9.

Example 8

This Example describes the construction of several cDNA expression libraries of the present invention.

A *T. gondii* tachyzoite cDNA expression library, a *T. gondii* infected cat gut (ICG) cDNA library (constructed from seven day post infection infected cat gut material, which is a mix of both cat intestinal cDNA and *T. gondii* gametogenic cDNA), and an uninfected cat gut (UCG) cDNA expression library were from total RNAs as follows:

Isolation of Total RNA From Tachyzoites: Total RNA from tachyzoites was prepared using Tri-Reagent™ (available from Molecular Research Center, Inc, Cincinnati, Ohio) according to the manufacturer's directions. Briefly, $4\times10^9$ tachyzoites were resuspended in 6 ml of Trikeagent with a syringe and 18 gauge needle. Successive triturations were made with 20 gauge and 22 gauge needles. A volume of $CHCl_3$ equal to one-fifth the original volume of TriReagent® was added and the mixtures were shaken for 15 seconds. The aqueous and organic phases were then separated by centrifugation. Total RNA was recovered from the aqueous phase by precipitation in isopropanol.

PolyA$^+$ RNA was isolated from total RNA using Pharmacia mRNA purification kit (available from Pharmacia Biotech Inc., Piscataway, N.J.).

Isolation of Total RNA from Other Sources: The method of isolation of total RNA from various tissues was the same for all tissues. The only variable Was the starting material. For example, to obtain RNA from infected cat gut (ICG) or uninfected cat gut (UCG), the epithelial layer of a fifteen square centimeter section of gut was scraped into 6 mil of Tri-Reagent and processed as described above. RNA from mouse was obtained from 1 gm of mouse brain and treated with Tri-Reagent as described above. RNA from 1 bradyzoites was obtained from 7,000 tissue cysts propagated in mouse brain, obtained as described, and treated with Tri-Reagent as described above.

PolyA$^+$ mRNA was isolated from total RNA using Pharmacia mRNA purification kit (available from Pharmacia Biotech Inc., Piscataway, N.J.).

Preparation of λ cDNA Libraries:

The ZAP-cDNA® synthesis kit (available from Stratagene) was used according to manufacturer's instructions to synthesize cDNA. Briefly, 5 or 10 μg of PolyA$^+$ RNA (prepared as described above) was reverse transcribed using Superscript® reverse transcriptase and 0.6 mM dGTP, DATP, dTTP, and 0.3 mM 5-methyl dCTP and 1.4 μg of oligo dT linker primer supplied with the ZAP-cDNA® Synthesis Kit. The second strand was made by digesting the RNA template with RNaseH and priming second strand synthesis with DNA polymerase I. The cDNA was then ligated into the Uni-ZAP® XR lambda insertion vector (available from Stratagene), packaged and amplified to produce tachyzoite and ICG cDNA libraries.

5 μg of polyA+ RNA was used to prepare the ICG cDNA library, and 10 μg of polyA+ RNA was used to prepare the tachyzoite cDNA library. For each library, 100 ng of double stranded cDNA was ligated and packaged and gave approximately $1.5\times10^5$ unique nucleic acid molecules. The average size of the cloned inserts was 1.9 Kb in the tachyzoite cDNA library, and 2.1 Kb in the ICG cDNA library.

Example 9

This Example describes the construction and identification of cDNA sequences encoding near full-length *T. gondii* nucleic acid molecules encoding immunogenic *T. gondii* proteins.

Two of the molecular libraries described above were used to isolate near full-length *T. gondii* nucleic acid molecules encoding immunogenic *T. gondii* proteins: the tachyzoite cDNA library and the ICG cDNA library constructed from seven day post infection infected cat gut material.

The general approach to isolating nucleic acid sequences representing full length, or near full-length cDNA sequences was as follows: First, the MacVector DNA analysis program was used to design DNA primers for each of the *Toxoplasma* sequences cloned in an expression vector as herein described. These primers were then used in a PCR reaction in which the template was either of the *Toxoplasma* cDNA libraries herein described. The presence of a positive band on an agarose gel following PCR was diagnostic of the presence in the cDNA library of a nucleic acid molecule with homology to the primers. A near full-length cDNA molecule having sequence homology with the genomic DNA sequence designated Q2-4 was obtained by a direct hybridization screen of the libraries using radiolabeled clone-specific PCR fragments as templates, The isolation of one of these near full-length sequences is herein described in detail as representative of the methods used to isolate all of the near full-length sequences identified by this strategy.

A cDNA sequence representing a near full-length gene having homology to a nucleic acid sequence herein designated Q2-4 (isolated from the *Toxoplasma* genomic DNA library) was isolated from the infected cat gut (ICG) cDNA library by hybridization screening as follows: *E. coli* Y1090 was infected with approximately $1\times10^6$ PFU of the *Toxoplasma* ICG cDNA library and then plated at a density of about 50,000 plaques per 150 mm agar plate. The resulting plaques were transferred to nitrocellulose filters. The filters were then soaked in denaturing solution (1.5 M NaCl, 0.5 M NaOH) for two minutes, neutralization solution (1.5 M NaCl, 0.5 M Tris, pH 8) for five minutes, and then rinsed several times in 2×SSC (150 mM NaCl, 15 mM Na citrate, pH 7). The DNA bound to the filters was crosslinked using a Stratalinkere UV crosslinker (available from Stratagene) according to the manufacturer's directions.

A radioactive hybridization probe was made by incorporating $^{32}P$ into clone-specific template DNA using a Prime-It® II random primer labeling kit (available from Stratagene) following the manufacturers directions. The template was a PCR fragment generated by using two primers specific for Q2-4. For each 100 μl reaction, 30 ng of *Toxoplasma* genomic DNA was PCR amplified using 200 mM of each dCTP, dGTP, dTTP, dATP, 200 nM of each specific primer, 2.5 mM $MgCl_2$, 20 mM Tris pH 8.4, 50 mM KCl, and 2.5 units Taq DNA polymerase (available from The Perkin Elmer Corp.) for thirty-five cycles in a Perkin-Bilmer Gene Amp PCR System (available from The Perkin Elmer Corp.).

The nitrocellulose filters containing crosslinked DNA were hybridized in 2×PIPES buffer (10 mM piperazine-N,N'-bis[2-ethanesulfonic acid] (pH 6.5); 400 mM, NaCl), 50% formamide, 0.5% SDS, 100 mg/ml denatured salmon sperm DNA and $10^7$ cpm/ml of the radioactive hybridization probe. The filters were incubated with this hybridization solution overnight at 42° C. The next day the filters were washed in 0.1×SSC, 0.1% SDS and then exposed to X-ray film (available from Kodak, Rochester, N.Y.) in order to visualize positive plaques.

Plaques in the area corresponding to the positive signals were picked into SM buffer (50 mM Tris, pH 7.5, 100 mM NaCl, 8 mM $MgSO_4$, and 0.01% gelatin) and the phage replated at a lower density. The same screening procedure was repeated three or four times until a pure plaque corresponding to a full length cDNA nucleic acid sequence representing Q2-4 was isolated.

After plaque purification, the nucleic acid molecules were mapped and the areas of interest sequenced using primers specific to the original clone, long fragment PCR, and cycle sequencing of the large fragments.

Example 10

This Example describes the expression in a eucaryotic cell of nucleic acid molecules encoding immunogenic *T. gondii* proteins, and DNA vaccination with nucleic acid molecules encoding immunogenic *T. gondii* proteins.

Cloning into a Eucaryotic Expression Vector(pDacI):

Inserts from eight clones (OC-2, OC-13, OC-14, OC-22, Tg-41, Tg-45, Tg-50, 4CQA-11) were ligated into the pDVacI expression vector. This vector contained a eucaryotic promoter from cytomegalovirus. (CMV), followed by the start codon and signal sequence for a mouse kappa immunoglobulin gene. An EcoR I site was inserted in frame downstream to the signal sequence. This allowed the insertion of Eco RI fragments directly from the original lambda phage. The nucleic acid molecules produced by insertion of nucleic acid molecules encoding immunogenic *T. gondii* proteins into pDVacI are referred to herein as pDVacI:*Toxoplasma* nucleic acid molecules. If the EcoR I inserts represent nucleic acid sequence that is entirely open reading frame, then the protein product expressed from these inserts may be in frame with a C-terminal fusion consisting of both a poly histidine track and amino acid sequence representing an epitope from the human myc gene as a reporter sequence. The N-terminal fusion adds 49 amino acids, or about 5.4 kD to the protein encoded by the *T. gondii* nucleic acid molecule, and the C-terminal fusion adds 38 amino acids, or about 4.2 kD, to the fusion protein.

Expression in Vitro:

Direct sequencing of the inserts in each plasmid confirmed the production of eight different pDVacI:*Toxoplasma* nucleic acid molecules. DNA from these molecules was then tested for eukaryotic expression of antigenic *T. gondii* proteins by transfecting BHK cells in vitro with DNA isolated from the pDVacI:*Toxoplasma* nucleic acid molecules. Analysis of the eukaryotic expression products of the pDVacI:*Toxoplasma* nucleic acid molecules was done by western blot on cell lysates and on supernatants from the transformed BHK cells. Either a monoclonal reactive with the myc epitope or antibody specific to each clone was used as the primary antibody. Seven out of the eight plasmid constructs expressed a protein in vitro. See Table 10.

TABLE 10

Analysis of Clones in Eucaryotic Expression Vector and DNA Vaccination

| Clone | Size (KD) Expressed in pDVac | EU/ug DNA* | Expression in vitro Pellet | Super | Sero-conversion (# of Mice)** |
|---|---|---|---|---|---|
| OC-2 | 40 | 0.3/0.4 | + | + | 5/5/5 |
| OC-13 | 38 | 0/0.23 | + | + | 0/0/4 |
| OC-14 | 32 | 7.7/3.8 | − | − | *** |
| OC-22 | 40 | 0.5/0.44 | + | + | 4/5/5 |
| Tg-41 | 33 | 23/1.8 | + | + | 0/1/5 |
| Tg-45 | 26 | 0/0 | + | + | 3/5/5 |
| Tg-50 | 55 | 4.0/4.0 | + | + | 5/5/5 |
| 4cqa-11 | 25 | 0.95/5.3 | + | + | 0/0/0 |

Table 10 legend:
*The first and second numbers represent the endotoxin units (EU)/ug of DNA for the first and second immunizations respectively.
**The numbers represent the # of mice that sero-converted at the 4, 7 and 9 week bleeds, respectively, out of the group of five that were injected.
*** Antigen for Nt4 protein was not available to analyze for these sera samples.

Expression in Vivo:

100 ug of each pDVacI:*Toxoplasma* nucleic acid molecule was injected intradermally into five mice. The administrations were at day zero and week five; bleeds were collected at weeks four, seven and nine. The mouse sera were used to determine if the DNA vaccination with each clone elicited a serological response to the cloned fusion protein. This was measured by western blot analysis with the protein expressed in the BHK lysates. Six of the eight clones induced antibodies in mice by week nine, see Table 10.

Reactivity of Antibody Raised against Recombinant OC-1 Protein:

Purified recombinant protein expressed by an expression vector containing the nucleic acid sequence referred to as OC-1 (SEQ ID NO:70) was used to immunize mice and rabbits by methods well known in the art. The animals were bled, and serum collected used in immunofluorescence assays against infected and uninfected cat gut tissue. The results of these assays showed that antibody raised, in mice and rabbits, to recombinant OC-1 protein bound to most of the enteroepithelial stages in the infected cat gut. The antiserum did not react with uninfected cat gut.

Example 11

This example describes the construction of a *Toxoplasma gondii* EMBL3 genomic library from tachyzoites grown in tissue culture. This Example further describes isolation of near full-length nucleic acid molecules encoding stage specific *T. gondii* antigenic proteins.

An EMBL3 library of *Toxoplasma* genomic DNA was constructed using standard molecular cloning methods, well known to those skilled in the art of cloning (see, for example, Sambrook, et al., ibid.). In brief, *Toxoplasma* genomic DNA, prepared from tachyzoites as herein described, was partially digested with Sau3A I, using a series of different ratios of units of enzyme to μg of DNA. Digestions were incubated at 37° C. for one hour. Ratios of 0.06, 0.03, and 0.015 units of enzyme per μg of DNA produced high molecular weight DNA fragments which were then run on a preparative agarose gel. The fraction of the gel corresponding to DNA in a size range of between 15 and 20 Kb was excised. The DNA fragments were extracted from the gel, and the amount of extracted DNA quantitated. The EMBL3 library was then constructed using this DNA and the Lambda EMBL3/BamH I Vector Kit (available from Stratagene). The manufacturer's instructions were followed for all cloning steps, and the resulting ligated DNA was packaged using the Gigapack® II XL Packaging Extract (available from Stratagene). Packaging and amplification followed the manufacturer's specifications. The resulting library is referred to herein as the ENML3:*Toxoplasma* genomic library.

The EMBL3:*Toxoplasma* genomic library was plated at a density of 50,000 plaques per 150 mM agar plate and the plaques transferred to a nitrocellulose filter. The filters were soaked in denaturing solution (1.5 M NaCl, 0.5 M NaOH) for two minutes, neutralization solution (1.5 M NaCl, 0.5 M Tris, pH 8) for five minutes, rinsed several times in 2×SSC (150 mM NaCl, 15 mM Na citrate, pH 7), and the DNA crosslinked using a Stratalinker® UV crosslinker (available from Stratagene) according to the manufacturer's instructions.

The EMBL3:*Toxoplasma* genomic library was screened with probes made from PCR amplified nucleic acid molecules isolated by immunoscreening the λgt11:*Toxoplasma* genomic library. The primers used to generate these probes were derived using the MacVector Sequence Analysis program and the sequences of nucleic acid molecules encoding *T. gondii* antigenic proteins isolated from the λgt11:*Toxoplasma* genomic library.

The filters were hybridized in 2×PIPES buffer (10 mM piperazine-N,N'-bis[2-ethanesulfonic acid] (pH 6.5), 400 mM NaCl), 50% formamide, 0.5% SDS, 100 μg/ml denatured salmon sperm DNA (available from Sigma) and $10^7$ cpm/ml of radioactive hybridization probe. The filters were hybridized overnight at 42° C. The next day the filters were washed in 0.1 X SSC, 0.1% SDS, and then exposed to X-ray film (Kodak).

Plaques in the area corresponding to the positive signals were picked into SM buffer (50 mM Tris, pH 7.5, 100 mM NaCl, 8 mM $MgSO_4$, and 0.01% gelatin) and the phage replated at a lower density. The same screening procedure was repeated three or four times until a pure plaque hybridizing with a nucleic acid molecule isolated by immunoscreening the λgt11:*Toxoplasma* genomic library was isolated. After plaque purification, the nucleic acid molecules were mapped and the areas of interest sequenced using primers specific to the original clone, long fragment PCR, and cycle sequencing of the large fragments.

Long fragment PCR was done with a Perkin-Elmer XL PCR kit (available from The Perkin-Elmer Corp., Foster City, Calif.) as follows: A 100 μl reaction was separated into two layers with a wax bead so one would have a hot-start reaction. The lower layer contained 1×XL PCR buffer supplied with the kit, 40 μM each of the forward and reverse primers, SC1011 and SC1002, (supplied by the manufacturer with the XL PCR kit, 2.5 mM each dNTP, 1.1 mM $Mg(OAc)_2$. The upper layer contained 1×XL buffer, 4 units of rTth DNA polymerase (available from The Perkin-Elmer Corp.) and about 5 ng of the plaque purified EMBL3:*Toxoplasma* genomic DNA as the template. The reaction was done in a Hybaid thermocycler (available from Hybaid Ltd., Middlesex, UK), and the reaction products were resolved on a 0.6% agarose gel.

Example 12

This Example describes the detection of *T. gondii* oocysts in cat feces by PCR amplification of nucleic acid sequences homologous to nucleic acid sequences encoding immunogenic *T. gondii* proteins of the present invention. Specifically, this example describes a rapid PCR dipstick method for the detection of oocysts in feces.

Naive cats were infected per os by 1000 mouse-brain derived tissue cysts of *T. gondii* strain C at day zero. Feces from each animal were collected, if available, on a daily basis starting at day zero and each day for 19 days post infection (PI). A portion of the feces was treated by the standard sugar floatation method (Dubey, J.P., Swan, G. V., and Frenkel, J. K. 1972, Journal of Parasitology. 58: 1005-1006) and the oocysts visualized using a microscope and counted on a haemacytometer. A portion of each feces was also suspended in PBS, vortexed and a small sample obtained by dipping an IsoCodeJ™ dipstick (available from Schleicher & Schuell, Keene, N.H.) into the fecal solution. The dipstick was allowed to air dry and then washed in 500 μl of distilled water by vortexing the stick end and water in a tube for 10 seconds. Material adhering to the filter was then eluted in 50 μl of fresh distilled water by heating to 95° C. for 30 minutes. The remaining supernatant was then used for standard hot start PCR, according to methods well known in the art, using primers representing DNA sequences from nucleic acid molecules encoding *T. gondii* antigenic proteins. The results of an experiment in which primers derived from nucleic acid molecule OC-2 were used are shown in Table 11. The results of this experiment demonstrated that the PCR detection method was at least as sensitive at detecting oocysts in fecal matter as the conventional floatation method.

TABLE 11

PCR Analysis of Cat Feces

| #3528-U | | | #3512-I | | | #3515-I | | |
|---|---|---|---|---|---|---|---|---|
| Day PI | Oocysts/gm Float | PCR Dipstick Oc2 | Day PI | Oocysts/gm Float | PCR Dipstick Oc2 | Day PI | Oocysts/gm Float | PCR Dipstick Oc2 |
| 0 | 0 | − | 0 | 0 | − | 0 | 0 | − |
| 1 | 0 | − | 1 | 0 | − | 1 | 0 | − |
| 2 | 0 | − | 2 | 0 | − | 2 | 0 | − |

TABLE 11-continued PCR Analysis of Cat Feces

| | #3528-U | | | #3512-I | | | #3515-I | |
|---|---|---|---|---|---|---|---|---|
| Day PI | Oocysts/gm Float | PCR Dipstick Oc2 | Day PI | Oocysts/gm Float | PCR Dipstick Oc2 | Day PI | Oocysts/gm Float | PCR Dipstick Oc2 |
| 3 | 0 | − | 3 | 0 | − | 3 | 0 | − |
| 4 | 0 | − | 4 | | | 4 | 1 × 10e6 | + |
| 5 | 0 | − | 5 | 1 × 10e4 | + | 5 | 5 × 10e6 | + |
| 6 | | | 6 | 3 × 10e5 | + | 6 | 1 × 10e6 | + |
| 7 | 0 | − | 7 | 1 × 10e6 | + | 7 | | |
| 8 | | | 8 | 1 × 10e6 | + | 8 | 2 × 10e5 | + |
| 9 | 0 | − | 9 | 1 × 10e6 | + | 9 | 7 × 10e4 | + |
| 10 | 0 | − | 10 | 1 × 10e5 | + | 10 | 0 | + |
| 11 | 0 | − | 11 | 1 × 10e5 | + | 11 | 0 | − |
| 12 | | | 12 | 0 | + | 12 | 0 | − |
| 13 | | | 13 | 0 | − | 13 | 0 | − |
| 14 | | | 14 | 0 | − | 14 | 0 | − |
| 15 | 0 | − | 15 | 0 | − | 15 | 0 | − |
| 16 | | | 16 | | | 16 | 0 | − |
| 17 | | | 17 | | | 17 | 0 | − |
| 18 | | | 18 | 0 | − | 18 | 0 | − |
| 19 | 0 | − | 19 | 0 | − | 19 | 0 | − |

A series of additional experiments was performed in order to investigate further the PCR dipstick method for the detection of oocyts in feces. In this set of experiments, the following methods were used to produce *T. gondii* infected cats, and to detect oocysts in the feces of the infected cats. *T. gondii* C-strain tissue cysts were obtained by orally infecting 6-8 week old Swiss Webster mice with a sub-lethal dose of mouse brain derived tissue cysts. At six weeks post infection, the animals were euthanized with $CO_2$ and the brains were removed and placed in 30% Dextran in RBSS (Gibco/BRL). The brains were then homogenized with a Tissuemizer (Tekmar Co., Cincinnati Ohio) and centrifuged at 5,000×g's for 10 min at 4° C. The pellet was resuspended in HBSS and the tissue cysts were counted. The tissue cysts were diluted with PBS to the appropriate concentration for oral administration to cats at the back of the throat using a 1 ml syringe. A total of twenty cats was used in this study: seventeen were experimentally infected with 1000 tissue cysts and three were used as uninfected controls. All cats were housed in separate cages and feces were collected at the day of infection and daily for the next 21 days. On average there were approximately twelve samples per cat. The fecal samples were stored at 4° C. until tested, which was within two weeks of collection.

Conventional quantification of oocysts in feces was based on the sugar flotation method of Dubey and Beattie, 1988, and is described in full as follows. Each fecal sample was weighed and then 2 grams of feces were mixed with 15 ml of sugar solution (53 gm sugar, 100 ml of water). Following solubilization with a tongue depressor, the mixture was passed through two layers of gauze. The filtrate was poured into a 15 ml conical tube and centrifuged at 1,200×g for 10 minutes. The top 3 ml of the sample was added to 13 ml of sugar solution and centrifuged as above. The top 3 ml of the second flotation was added to 13 ml of water and centrifuged at 1,200×g for 10 minutes. The resulting oocyst pellet was resuspended in 1 ml of water and the oocysts counted using a hemacytometer. Alternatively, the entire fecal sample was solubilized in PBS by adding five ml of PBS per gram of the pre-weighed feces in a 250 ml plastic beaker. After one hour at room temperature, a tongue depressor was used to thoroughly suspend the feces. Five ml of the fecal slurry was added to a 15 ml tube containing 5 ml of 2× sugar solution and inverted several times. The tube was then centrifuged at 1,200×g for 10 minutes. The top 3 ml of the sample was subjected to a second sugar flotation, resuspended, and counted as described above.

Analysis of the fecal samples by the PCR dipstick method was performed as follows. One ml aliquots were taken, prior to further processing for floatation, from each of the initial fecal slurries described above. Samples were collected directly onto dipsticks, either by spotting 10 ul onto each dipstick filter or by directly dipping the dipstick into the fecal slurry. The filters were then dried at room temperature and the filter portion of the dipstick was cut off into a sterile 1.5 ml centrifuge tube. The filter was washed with 500 ul of sterile distilled water by vortexing for 8 seconds. The wash was removed and 50 ul of sterile water was added to the tube and adherent oocyst DNA eluted by heating at 95° C. for 1 hour. The filter was removed with a sterile tip and the sample stored (also referred to as the dipstick eluate) at −20° C.

Primers specific to two *T. gondii* genes, B1 and OC-2, were used in the amplification reactions. The primers for the B1 gene (Burg, et al., 1989, *Journal of Clinical Microbiology*, 27: 1787-1792) were B1 forward (5'-GGA ACT OCA TCC GTT CAT GAG-3', herein referred to as SEQ ID NO:332), B1 reverse (5'-TCT TAA AGC OTT CGT GGT C-3', herein referred to as SEQ ID NO:333), and a B1 internal primer (5'-GGC GAC CAA TCT GCG AAT ACA CC-3', herein referred to as SEQ ID NO:334). The *T. gondii* OC-2 was isolated as herein described. The OC-2-derived primers were OC-2 forward (5'-GCA TCC TTG GAG ACA GAG CTT GAG-3', herein referred to as SEQ ID NO:335), OC-2 reverse (5'-OGG TTC TCT TCT CGC TCA TCT TTC-3', herein referred to as SEQ ID NO:336), and an OC-2 internal primer (5'-AGT CAG AAG CAG TCA AGG C-3' herein referred to as SEQ ID NO:337). The PCR mixture contained 1×PCR buffer (10 mM Tris-$HCl_2$, 1.5 mM $MgCl_2$, 50 mM KCl), 0.2 mM deoxynucleoside triphosphates (Perkin-Elmer Cetus Corp., Norwalk, Conn.), 0.8 uM of each primer, 0.5 U of Gold AmpliTaq™ DNA polymerase (Available from Perkin-Elmer Corp.), and 1 ul DNA template in a total volume of 25 ul. The reaction mixture was denatured at 95° C. for 10 minutes, amplified for 42 cycles including a denaturation step at 95° C. for 30 seconds, annealing at 58° C. for 30 seconds, extension at 72° C. for 30 seconds, and a final extension for 5 minutes at 75° C. on an automated DNA thermal cycler (Model 9700, Perkin-Elmer, Foster City, Calif.). PCR products were analyzed by electrophoresis on a 1.5% agarose gel, stained with ethidium bromide (0.5 ug/ml), and photographed on a UV transilluminator.

Following electrophoresis, the DNA products were denatured in 0.5 N NaOH and 1.5 M NaCl buffer for 30 minutes, transferred to a nylon membrane (Maximum Strength Nytran Plus, available from Schleicher & Schuell) overnight and cross-linked by exposure to UV light (UV Stratalinker 1800, available from Stratagene). The filters were incubated in pre-hybridization buffer (5×SSC, 1×Denhardt's reagent, 0.2% SDS, 1 mg/ml sheared DNA) at 42° C. for 2 hours and then in hybridization buffer (5×SSC, 1×Denhardt's reagent, 0.2% SDS, 1 mg/ml sheared DNA) containing $5'-\gamma^{32}P$ labeled oligonucleotide probe at 42° C. overnight. After overnight incubation, membranes were washed twice in 2×SSC, 0.1% SDS for 15 minutes at room temperature, and then washed twice in 0.2×SSC, 0.1% SDS at 55° C. for 1 hour. The filters were autoradiographed at −70° C. with Kodak XRR film.

Ethidium bromide-stained agarose gel and Southern hybridization analysis of PCR amplified products from oocyst-seeded fecal samples was performed in order to determine whether the dipstick method described herein resulted in a reduction of inhibition of PCR amplification of *T. gondii*-specific DNA in fecal slurries as compared with fecal slurries alone. Two sets of solutions, PBS and PBS/Feces (1:4 gm/ml), were seeded with four concentrations of oocysts, $2\times10^6$, $5\times10^5$ $5\times10^4$, and $5\times10^3$. Using the dipstick technique described above, this resulted in an estimated maximum number of oocysts in the PCR amplification tube to be 400, 100, 10, and 1 as indicated for the PBS solution and for the PBS/Feces solution respectively. Southern hybridization was performed using the OC-2 gene internal primer as the probe. Southern hybridization results and the ethidium bromide stained gel demonstrated that inhibition of PCR amplification of the exogenously added DNA was dramatically reduced (as compared with fecal extract alone) in samples prepared as per the dipstick assay as described above, Three different paper supports were tested for their ability to support the PCR dipstick assay: IsoCodeJ™ Stix, S&S® #903™ (available from Schleicher and Schuell) and Nobuto Blood Filter Strips (available from Advantec, Pleasantville, Calif.). First, IsoCodeJ™ Stix were tested for the ability to bind oocysts. Oocysts were diluted into either PBS or a suspension of uninfected feces and PBS. The fecal dipstick procedure as described above was used to sample and elute DNA for PCR analysis. The concentration of oocysts per reaction was adjusted so that theoretical maximum could be 1, 10, 100, and 400 oocysts respectively. The amplification products were tun on an agarose gel and stained as described above. According to this assay, oocysts diluted into PBS alone could be readily detected at 10 oocysts per ul of dipstick eluate with primers directed to the *T. gondii* OC-2 gene. In addition, oocysts in a suspension of feces and PBS could be detected when present at a concentration of between 10 and 100 oocysts per ul. This experiment demonstrates that the oocysts are bound to the IsoCodeJ™ Stix in the presence of feces, are eluted by heat, and following a wash and heat elution step are sufficiently free from inhibitors to be detected by PCR amplification.

Under these conditions, detecting 10 oocysts per ul of eluate from the IsoCodeJ™ Stix is equivalent to detecting oocysts at a concentration of $2.5\times10^5$ oocysts/gram of feces.

Several parameters were tested for their ability to increase the sensitivity of this test. First, two additional paper supports, S&S® #903™ and Nobuto Blood Filter Strips, were tested for both the ability to bind oocysts in the presence of solubilized feces, and the ability to support subsequent PCR detection of oocyst DNA. Each of these filter papers bound *T. gondii* oocysts, and subsequent PCR amplification with OC-2 primers detected the presence of *T. gondii* DNA. However, the sensitivity of detection for each of these papers was somewhat less than the sensitivity of the assay when using IsoCodeJ Stix™. All three paper supports were also tested for binding of oocysts in the presence of feces over a range of pH from 4 to 9. The S&S® #903™ and Nobuto Blood Filter Strips were most effective at pH 7. Binding of oocysts to the IsoCodeJ Stix™ was significantly increased at pH 9. All subsequent assays described below used IsoCodeJ Stix™ and pH 9 for binding of oocysts to dipsticks.

Another approach to increasing the sensitivity of the assay was to use primers from the B1 gene during the PCR amplification reaction. The B1 gene is a multicopy gene that is present at approximately 35 copies per *T. gondii* genome. Using a B1-specific primer resulted in a ten-fold increase in sensitivity, and produced an assay in which 1 oocyst/ul could routinely be detected. This level of sensitivity of the assay correlated with the ability to detect approximately $1\times10^4$ oocysts/gram of feces.

The sensitivity and specificity of the PCR detection method was tested in experimentally infected animals using flotation and visualization of oocysts as the standard for quantification of oocysts. SPF cats were infected with mouse brain-derived tissue cysts and feces were collected from the cats for twenty-one days. Each sample was analyzed by both direct visualization and the dipstick PCR technique. Following gel electrophoresis of the products from PCR amplification, the results were scored as either positive or negative depending on the presence or absence of the correct gene-specific PCR product. Table 12 shows the results of PCR detection using both the B1 and OC-2 DNA primers for each individual fecal sample. The positive and negative predicative values were 93.2% and 97.2% respectively using the B1 gene DNA primers and 80.2% and 95.8% respectively using the OC-2 DNA primers.

TABLE 12

Sensitivity, specificity and predicative values for the PCR detection of oocysts in experimentally infected cat feces.

| Method | Total Samples +/− | f/n[a] | f/p[b] | Sensitivity % | Specificity % | Predictive Value % +/− |
|---|---|---|---|---|---|---|
| Microscopy PCR | 69/176 | 0 | 0 | 100 | 100 | 100/100 |
| B1 Primers | 64/171 | 5 | 5 | 94.7 | 96.7 | 93.2/97.2 |
| OC-2 Primers | 61/161 | 7 | 16 | 89.7 | 96.4 | 80.2/95.8 |

[a]false negative
[b]false positive

Example 13

A PCR ELISA was developed for the detection and quantification of PCR amplification products from the PCR dipstick method. In general, digoxigenin-labeled amplified product produced by the PCR dipstick detection method were detected by hybridization to an internal biotinylated B1 gene primer bound to microtiter wells. The concentration of PCR labeled digoxigenin fragment was determined using an alkaline phosphatase-linked anti-digoxigenin antibody (available from Boehringer Mannheim Biochemica Gmbh). The alkaline phosphatase activity level was then determined using a standard ELISA reader. This quantitative PCR ELISA method detected oocysts at a lower limit of $1 \times 10^4$ oocysts/gram when tested with uninfected cat feces seeded with known concentrations of *T. gondii* oocysts. The method is described in detail as follows.

PCR amplification using B1 gene-specific primers was performed on eluates from the fecal dipstick method herein described. Amplification products were labeled by incorporation of digoxigenin-11-dUTP (D) IG-11-dUTP) present in the reaction mix at 2.5 uM. The concentration of dTTP in this reaction mix was reduced to 22.5 uM. The resulting labeled fragment was detected using reagents from the PCR ELISA (DIG Detection) kit (available from Boehringer Mannheim Biochemica Gmbh, Mannheim, Germany). The procedure was as follows. Four ul of the primary amplification reaction product was added to 16 ul of denaturation buffer and incubated at room temperature for 10 minutes. This was mixed with 200 ul hybridization buffer that contained 20 pmol/ml of the biotinylated B1 gene probe. One-half of the hybridization reaction mixture was transferred to a well in a streptavidin-coated microtiter plate and incubated at 50° C. for 3 hours with shaking. The plate was washed with washing buffer five times at room temperature and incubated with 100 ui of anti-digoxigenin Fab conjugated with peroxidase at 37° C. for 45 minutes. Following five washes, 100 ul of ABTS substrate solution (available from Boehringer Mannheim Biochemica) was added to each well and the color was developed at room temperature for 45 minutes. The optical densities (OD) at 405 nm were read in a spectrophotometer (SpectraMAX 250, available from Molecular Devices Inc., Sunnyvale, Calif.) and analyzed with Soft Max Pro™ software (available from Molecular Devices Inc.).

Quantification of oocysts in feces by the PCR ELISA technique was compared with quantification by the microscopic analysis. Individual feces from six different cats were collected (as available) at various days post infection. Oocysts were then quantified for each sample by two separate techniques, microscopy and PCR ELISA. The results from each of these two methods were in good agreement. Standard regression analysis produced a correlation coefficient of 0.91.

Example 14

This example describes the detection of *Cryptosporidium parvum* oocysts and *Giardia lamblia* cysts in feces using the PCR dipstick detection method described above. Oocysts and cysts from *C. parvum* and *G. lamblia* respectively were detected by the dipstick PCR detection method, thereby demonstrating the usefulness of this method for the detection of cysts or oocysts from unrelated species.

Feline fecal samples from SPF cats were seeded with either *C. parvum* oocysts or *G. lamblia* cysts and used in the PCR detection method described herein. The primers used to detect *C. parvum* were specific for the *C. parvum* AWA gene while the primers used to detect *G. lamblia* were specific for the *G. lamblia* ABB gene (Rochelle, et al.; 1997, *Applied and Environmental Microbiology* 63:106-114).

In order to demonstrate binding of *C. parvum* oocysts to a dipstick in the presence of feline fecal slurry, aliquots of feline fecal slurry (1:4, mg/ml) were seeded with between $5 \times 10^2$ and $5 \times 10^6$ *C. parvum* oocysts/ml. These samples were then tested for binding of the oocysts and subsequent PCR analysis according to the PCR detection methods described herein. The primers used in the PCR amplification were specific for the *C. parvum* AWA gene. The PCR amplified products were run on and agarose gel and stained with ethidium bromide. The *C. parvum*-specific primer primed amplification of a DNA product of the predicted mobility, in an oocyst concentration-dependent manner, from the dipstick eluate as described above, The results of this experiment demonstrated that *C. parvum* oocysts bound to a dipstick in the presence of feline fecal slurry, and that about $5 \times 10^2$ *C. parvum* oocysts/ml were detectable by the PCR detection method after binding to the dipstick under these conditions. Because $5 \times 10^2$ oocysts/ml was the lowest concentration tested, and the products were easily observable, the concentration of cysts detectable by this method is likely to be lower than $5 \times 10^2$ oocysts/ml.

In order to demonstrate binding of *Giardia* cysts to a dipstick in the presence of feline fecal slurry, aliquots of feline fecal slurry (1:4, mg/ml) were seeded with between $5 \times 10^2$ and $5 \times 10^5$ *G. lamblia* cysts/ml. These samples were then tested for binding of the cysts and subsequent PCR analysis according to the PCR detection methods described herein. The primers used in PCR amplification were specific for the *G. lamblia* ABB gene. The PCR amplified products were run on and agarose gel and stained with ethidium bromide. The *G. lamblia*-specific primer primed amplification of a DNA product of the predicted mobility, in a cyst concentration-dependent manner, from the dipstick eluate as described above. The results of this experiment demonstrated that *G. lamblia* cysts bound to a dipstick in the presence of feline fecal slurry, and that about $5 \times 10^2$ *G. lamblia* cysts/ml were detectable by the PCR detection method after binding to the dipstick under these conditions. Because $5 \times 10^2$ cysts/ml was the lowest concentration tested, and the products were easily observable, the concentration of cysts detectable by this method is likely to be lower than $5 \times 10^2$ cysts/ml.

Example 15

This Example discloses a method of isolation of *T. gondii* nucleic acid molecules encoding immunogenic *T. gondii* proteins recognized by intestinal secretions from infected cats. This Example further discloses recombinant nucleic acid molecules and proteins of the present invention.

The production of intestinal secretions and from infected cats and the use of these secretions for screening for nucleic acid molecules encoding immunogenic *T. gondii* proteins are described herein in Example 6. Intestinal secretions collected from a single cat that had been previously infected with *T. gondii* were pooled and preabsorbed to remove antibodies directed against UCG and *E. coli*. The pooled, preabsorbed intestinal secretions are also referred to herein as MGIS antiserum. MGIS antiserum was used to immune screen an ICG cDNA library in order to identify and isolate nucleic acid molecules encoding immunogenic *T. gondii* proteins recognized by intestinal secretions from infected cats. Six nucleic acid molecules encoding immunogenic *T. gondii* proteins recognized by intestinal secretions from infected cats were identified and isolated using the following methods. These six nucleic acid molecules are referred to herein as MGIS4-2 (also herein referred to as SEQ ID NO:282 and SEQ ID NO:284, representing the coding strand and its reverse complement, respectively), MGIS4-4 (also herein referred to as SEQ ID NO:292 and SEQ ID NO:294), MGIS4-8 (also herein referred to as SEQ ID NO:306 and SEQ ID NO:308), MGIS6-5 (also herein referred to as SEQ ID NO:311 and SEQ ID NO:313), MGIS6-2 (also herein referred to as SEQ ID NO:326 and SEQ ID NO:328), and MGIS1-3 (also herein referred to as SEQ ID NO:329 and SEQ ID NO:331).

Absorption of MGIS Antibody

MGIS antiserum was collected, as previously described, from the cat intestine on weeks 6, 10, and 13 after infection, and on weeks 0, 1, 2, 3, 4, and 5 after challenge. Both pools of antisera were combined and used to screen the cDNA library, and are herein referred to as MGIS antiserum.

To remove anti-cat intestinal and anti-*E. coli* tissue reactive antibodies, the MGIS pools were absorbed to nitrocellulose (NC) filters coated with either cat intestinal proteins or *E. coli* proteins. Cat intestinal proteins used to coat the nitrocellulose filters were generated as follow. The epithelial layer of uninfected cat intestine was scraped on dry ice and the cells subsequently passed through several different gauge needles (No. 18, 21, and 23) 10 times each. The sample was frozen and thawed 3 times, and then sonicated on ice for 10 minutes. The protein extract was diluted to 400 ug/ml in PBS and immersed with the nitrocellulose at room temperature for 1 hour, and was then blocked with 4% milk in PBS for 30 minutes. Similarly, XL-1 blue *E. coli* cells were resuspended in PBS and bacterial protein extracts prepared similar to the cat intestinal proteins. The bacterial extract was diluted to a final concentration of 2.3 mg/ml in PBS and bound to the filter in a manner similar as the cat intestinal extract.

MGIS antiserum was diluted 1:20 with 4% milk in PBS and absorbed sequentially 1 to both the cat intestinal and bacterial protein coated filters at room temperature for 1 hour. To demonstrate that all UCG and *E. coli*-reactive antibody had been removed from the MGIS antiserum preparation, the MGIS antiserum subjected to Western blot analysis which showed that the absorbed antibody had no reactivity to either the cat intestinal proteins or to the bacterial extract.

Immune Screening of *T. gondii* cDNA Phage Library

The ICG cDNA library was constructed from infected cat intestinal mRNA, and the cDNA product cloned into the EcoRI/XhoI sites of the Uni-Zap XR vector. *Toxoplasma*-specific nucleic acid molecules represented approximately 10% of the library. The ICG cDNA phage library was plated to approximately $2-5 \times 10^{e4-5}$ pfu per 135 mm plates with XL-1Blue MRF' cells (available from Stratagene). Ten plates were treated in the following manner after the phage were pinhead in size. Nitrocellulose filters that had been previously treated with IPTG were overlaid on top of the phage and incubated at 37° C. for 5 hours. The filters were marked, washed with TBS, pH 8.0, blocked with 4% milk in TBS, and incubated with MGIS antiserum at room temperature overnight. After washing three times with TBS, horse-radish peroxidase (HRP)-labeled goat anti-cat IgA antibody (Bethyl Lab. Inc.) was diluted 1:350, and incubated with the filters at room temperature for 2 hours. The color indicator was developed with 4-chloro-1-naphthol substrate and $H_2O_2$. Forty-one positive clones were selected for further screening.

Hybridization Screening and Clone Purification

Selected clones were replated on NZYM plates, and forty-eight individual plaques randomly picked and resuspended in 100 ul of SM buffer. Insert DNAs were PCR, amplified in a final volume of 12.5 ul containing 1 ul of template DNA, 50 mM KCL, 10 mM is —HCL (pH 8.3), 2 mM $MgCl_2$, 0.2 mM each dNTP, 0.2 mM each of T3 and T7 vector specific oligonucleotide primers, and 0.3 units of Taq polymerase. Amplification was performed by 1 cycle of 95° C. for 3 min., 35 cycles of 95° C. for 30 sec., 50° C. for 30 sec., and 72° C. for 2 min., followed by 75° C. for 5 min. on a Perkin Elmer 9600 thermocycler. The PCR amplified products were analyzed on a 1% agarose TBE gel, and the DNA transferred to a nylon membrane.

A hundred nanograms of *T. gondii* genomic DNA was labeled using the Megaprime DNA labeling systems (available from Amersham International) and used as a probe to analyze the PCR amplified DNA fragments on the nylon membrane. The membrane was pre-hybridized in 5×SSPE (1×SSPE: 0.18 M NaCl, 10 mM $NaH_2PO_4$, and 1 mM EDTA pH 7.7), 0.5% SDS, 5×Denhardt's solution, and 0.1 mg/ml single stranded salmon sperm DNA at 65° C. for 3 hours. Membranes were then hybridized overnight at 65° C., and then washed with 2×SSPE, 0.1% SDS at room temperature for 10 min., twice, and 0.2×SSPE, 0.5% SDS at 65° C. for 1 hour, twice. The membrane was exposed to film at −70° C. overnight. Twenty-three clones were thus shown to contain *T. gondii*-specific DNA, with an insert size of 1-2 Kb in length.

Clone Identification by Phage Drop Test

Each of the twenty-three *T. gondii*-specific clones were rescreened to confirm reactivity with MGIS antiserum. Phage clones were diluted 1:10e7 from the SM buffer stock, and 3 ul of this dilution (~5-50 phage) was spotted onto a NZYM/XL-1Blue MRF' agar plate, and incubated at 37° C. for 5 hours. Afterwards, an IPTG pre-treated nitrocellulose filter was overlaid onto the agar surface and incubated for another 5 hours. The filter was marked, washed with TBS buffer (pH 8.0) at room temperature for 15 minutes, and blocked with 4% milk in PBS for 30 minutes. Pre-absorbed MGIS antiserum was added to the filter and allowed to react at room temperature overnight. The filter was subsequently washed in TBS at room temperature for 10 minutes, three times. Goat anti-cat IgA polyclonal antibody labeled with HRP (available from Bethyl Laboratories, Inc.) was diluted 1:300 in TBS buffer and incubated with the filter at room temperature for 2 hours. The filter was washed and developed using 4-chloro-1-naphthol substrate and $H_2O_2$. Thirteen of the 23 clones were identified as positive for expressing antigen recognized by IgA in the MGIS antiserum.

DNA Sequencing

The DNA inserts in the thirteen clones identified as positive were subcloned into the TA vector using the TA cloning kit (available from Invitrogen). Individual clones were PCR amplified using the T3 and T7 vector-specific primers. The DNA fragments produced by PCR amplification were gel electrophoresed on a 1% agarose gel, and gel purified using a Qiagen Gel Purification kit (available from Qiagen). Plasmid DNA was purified using the 5 prime 3 prime Perfect Plasmid DNA Preparation kit (available from 5 Prime 3 Prime Inc., Boulder, Colo.). DNA sequencing was carried out on six of the *T. gondii*-specific DNA inserts using a Prizm dideoxy termination kit (available from Perkin Elmer) on an ABI 377 DNA sequencer (available from Applied Biosystems). TA sense and TA antisense oligonucleotide primers were used for DNA sequencing, and insert-specific oligonucleotide primers were used to generate internal fragment sequences. The only variation from this general protocol was in the case of MGIS4-4, where the Erase a Base system (available from Promega) was used to generate plasmids containing deleted fragments in order to facilitate sequencing. The primers used for sequencing each of the inserts were the following:

The primers used in sequencing MGIS4-2 are herein referred to as SEQ ID NO:275, SEQ ID NO:276, SEQ ID NO:277, SEQ ID NO:278, SEQ ID NO:279, SEQ ID NO:280, and SEQ ID NO:281. The primers used in sequencing MGIS4-4 are herein referred to as SEQ ID NO:285, SEQ ID NO:286, SEQ ID NO:287, SEQ ID NO:288; SEQ ID NO:289, SEQ ID NO:290, and SEQ ID NO:291. The primers used in sequencing MGIS4-8 are herein referred to as SEQ ID NO:295, SEQ ID NO:296, SEQ ID NO:297, SEQ ID NO:298, SEQ ID NO:209, SEQ ID NO:300, SEQ ID NO:301, SEQ ID NO:302, SEQ ID NO:303, SEQ ID NO:304, and SEQ ID NO:305. The primers used in sequencing MGIS6-5 are herein referred to as SEQ ID NO:309 and SEQ ID NO:310. The primers used in sequencing MGIS6-2 are herein referred to as SEQ ID NO:314, SEQ ID NO:315, SEQ ID NO:316, SEQ ID NO:317, SEQ ID NO:318, SEQ ID NO:319, SEQ BD NO:320, SEQ ID NO:321, SEQ ID NO:322, SEQ ID NO:323, SEQ ID NO: 324, and SEQ ID NO:325. And the primers used in sequencing MGIS1-3 are herein referred to as SEQ ID NO:314, SEQ ID NO:315, SEQ ID NO:316, SEQ ID NO:317, SEQ ID NO:318, SEQ ID NO:319, SEQ ID NO:320, SEQ ID NO:321, SEQ ID NO:322, SEQ ID NO:323, SEQ ID NO:324, and SEQ IL) NO:325 (note that the same primers were used for sequencing MGIS6-2 and MGIS1-3).

PCR Amplification of Feline and *T. gondii* DNA with Clone-Specific Primers

The IgA selected MGIS clones were shown to be *Toxoplasma* specific by PCR amplification analysis. The following different cDNA samples were tested for the presence of DNA representing each of the six different IgA-selected nucleic acid molecules: a) uninfected cat gut (UCG); b) infected cat gut (ICG); c) *T. gondii* tachyzoite (TgTz); d) *Toxoplasma* bradyzoite (TgBz); and e) *Toxoplasma* genomic DNA (TgTz DNA). The preparation of UCG, ICG, *Toxoplasma* tachyzoite and bradyzoite cDNA was as described above. *Toxoplasma* genomic DNA was isolated from tachyzoites by phenol/chloroform/isoamylalcohol pH 8.0 extraction. Oligonucleotide sense and anti-sense primers specific to each of five MGIS-selected nucleic acid molecules were synthesized and used as primers in the PCR amplification reactions. The reaction condition were: 95° C. for 10 min., followed by 35 cycles of 95° C. for 30 sec., 58° C. for 30 sec., 72 CC for 40 sec; this was followed by 75° C. for 5 min. afterwards to complete the reaction. The amount of the different templates used in the PCR reactions (~3-30 ng of DNA), was empirically determined by comparison with a PCR amplified *Toxoplasma* tubuhln gene product standard generated with each template. The oligonucleotide primers and the size of the expected products are listed in Table 13, below.

TABLE 13

| MGIS Clone | Sense Primer Position: Sequence | Anti-Sense Primer Position: Sequence | Product Size (bp) |
|---|---|---|---|
| 1-3 | 1513: SEQ ID NO: 319 | 1858: SEQ ID NO: 320 | 346 |
| 4-2 | 168: SEQ ID NO: 276 | 594: SEQ ID NO: 279 | 427 |
| 4-4 | 455: SEQ ID NO: 285 | 775: SEQ ID NO: 290 | 331 |
| 4-8 | 2018: SEQ ID NO: 300 | 2310: SEQ ID NO: 301 | 293 |
| 6-2 | 1301: SEQ ID NO: 319 | 1646: SEQ ID NO: 320 | 346 |

The oligonucleotide primers specific for each of the five MGIS-selected nucleic acid molecules PCR amplified products only when the template DNA contained *Toxoplasma* DNA. There were no PCR amplified products in this assay when the template DNA was UCG cDNA. These results confirm the *T. gondii* origin of the MGIS-selected nucleic acid molecules.

Sequence Analysis

Homology searches of a non-redundant protein database were performed on all six MGIS-selected nucleic acid molecules, translated into all six reading frames, using the BLASTX program available through the BLAST™ network of the National Center for Biotechnology Information (NCBI) (National Library of Medicine, National Institute of Health, Baltimore, Md.). This database includes SwissProt+ PIR+SPupdate+GenPept+GPUpdate+PDB databases. In addition, BLASTN homology searches were performed on these sequences using the NCBI databases including the non-redundant database of GenBank EST, and genembl. In all cases, the default parameters for the homology programs were used.

The highest scoring match of the homology search (BLASTX) of translation products of the nucleic acid sequence SEQ ID NO:282 (MGIS4-2) was to GenBank™ Accession No. prf 2208369A, a *Homo sapiens* signal peptidase 12kD subunit protein. The protein encoded by nucleic acid residues 742-945 of MGIS4-2 (SEQ ID NO:282) showed about 44% identity to amino acid residues 12 to 79 of the protein represented by GenBank™ Accession No. prf 2208369A. At the nucleotide level, SEQ DD NO:282 showed 97% identity over 353 nt with te sequence represented by GenBank™ Accession No. WO680 (TgESTzy81e12.r1), an EST fragment isolated from *T. gondii* tachyzoite cDNA. The homology spans the region from nt 748 to nt 1097 of SEQ ID NO:282, and nt 15 to 365 of GenBank™ Accession No. WO680. There were no other significant homology matches to SEQ ID NO:282 nucleic acid sequence.

The highest scoring matches of the homology search (BLASTX) of translation products of the nucleic acid sequence SEQ ID NO:292 (MGIS4-4) were to proteins described as elongation factor 1-gamma, with the highest match to the sequence represented by GenBank™ Accession No. gi 2160158, described as "a protein similar to elongation factor" The protein encoded by residues 47-1222 of SEQ ID NO:292 showed about 37% identity to amino acid residues 5-414 of the protein represented by GenBank™ Accession No. gi 2160158. At the nucleotide level SEQ ID NO:292 showed 94% identity over 413 nt with an EST fragment, GenBank™ Accession No. N81326 (TgESTzy40a12.r1), an EST fragment isolated from *T. gondii* cDNA. The homology spans the region from nt 420 to nt 832 of SEQ ID NO:292, and nt 15 to 427 of GenBank™ Accession No.N81326. In addition, SEQ ID NO:292 showed 99% identity over 187 nt with an EST fragment, GenBank™ Accession No. WO5869 (TgESTzyS5a09.r1), an EST fragment isolated from *T. gondii* cDNA clone. The homology spans the region from nt 757 to nt 943 of SEQ ID NO:292, and nt 62 to 248 of GenBank™ Accession No.W05869.

The highest scoring match of the homology search (BLASTX in the genembl database) of translation products of the nucleic acid sequence SEQ ID NO:329 (MGIS1-3) was to Herpesvirus Saimiri complete genome, represented by GenBank™ Accession No. X64346. The amino acid residues 777 to 1432 of the protein encoded by reading frame +2 of SEQ ID NO:329 showed about 36% identity to amino acid residues 106974 to 106517 of the protein represented by GenBank™ Accession No. X64346. At the nucleotide level, SEQ ID NO:329 showed 94% identity over 578 nt with an EST fragment, GenBank™ Accession No. AA520348 (TgESTzz69d04.r1), an EST fragment isolated from *T. gondii* bradyzoite cDNA. The homology spans the region from nt 1334 to 1910 of SEQ ID NO:329, and nt 5 to 571 of GenBank™ Accession No. AA520348.

The highest scoring match of the homology search (BLASTX of the non-redundant databases, GenBank+ EMBL+DDBJ+PDB) of SEQ ID NO:311 (MGIS6-5) was to a *T. gondii* lactate dehydrogenase gene, represented by GenBank™ Accession No. TGU35118. SEQ ID NO:311 showed 99% identity over 1619 nt.

The highest scoring match of the homology search (BLASTX in the genembl database) of translation products of the nucleic acid sequence SEQ ID NO:326 (MGIS6-2) was to Herpesvirus Saimniri complete genome, represented by Gen- Bank™ Accession No. X64346. Amino acid residues 751 to 1206 encoded by SEQ ID NO:326 showed about 36% identity to amino acid residues 106972 to 106517 of the protein represented by GenBank™ Accession No. X64346. At the nucleotide level, SEQ ID NO:326 showed 96% identity over 247 nucleotides with an EST fragment, GenBank™ Accession No. AA520348 (TgESTzz69d04.r1), an EST fragment isolated from *T. gondii* bradyzoite cDNA. The homology spans the region from nt 890 tot 136 of SEQ ID NO:326, and nt 144 to 390 of GenBank™ Accession No. AA520348.

The highest scoring match of the homology search (BLASTX of the non-redundant GenBank CDS database including Translations+PDB+SwissProt+SPupdate+PIR) of translation products of the nucleic acid sequence SEQ ID NO:306 (MGIS4-8) was to a rice 26S protease regulatory subunit 4 homolog (TAT-binding protein homolog 2), represented by GenBank™ Accession No. P46466. 26S protease regulatory subunit 4 homologs representing other species also have high homology to a translation product of SEQ ID NO:306. The protein encoded by nucleic acid residues 465 to 1565 of SEQ ID NO:306 showed about 72% identity to amino acid residues 35 to 448 of the protein represented by GenBank™ Accession No. X64346. It should be noted a gap of 42 amino acids was required in the amino acid sequence encoded by SEQ ID NO:306 in order to achieve the sequence fit resulting in this high homology. At the nucleotide level, SEQ ID NO:306 showed 98% identity over 269 nucleotides with an EST fragment, GenBank™ Accession No. W35531 (TgESTzy90g01.r1), an EST fragment isolated from *T. gondii* cDNA. The homology spans the region from nt 668 to nt 936 of SEQ ID NO:326, and nt 23 to nt 291 of GenBank™ Accession No. W35531.

Example 16

This Example discloses the isolation and sequence analysis of a 1397 bp *T. gondii* nucleic acid molecule composed of four fragments isolated by subtractive selection from an infected cat gut cDNA library. Also described is an additional nucleic acid molecule representing the genomic DNA sequence immediately upstream (5') of, and overlapping, the genomic DNA sequence encoding the cDNA sequence.

A 1397 bp *T. gondii* nucleic acid molecule, denoted $nTG_{1397}$ (the coding strand of which is herein referred to as SEQ ID NO:343, and the reverse complement of which is herein referred to as SEQ ID NO:345), is a composite of four overlapping PCR amplified products isolated from an infected cat gut (ICG) cDNA library. Specifically, a first 424 bp fragment (representing nucleotide positions 709-1132 of SEQ ID NO:343), was isolated after two rounds of selection using the PCR-Select™ Subtraction kit (available from Clontech, Palo Alto, Calif.), using day eight, RsaI restriction enzyme digested ICG cDNA as tester, and similarly digested uninfected cat gut cDNA as driver DNA. Fragments enriched by the PCR-Select™ Subtraction selection process were digested with the restriction enzyme SmaI and cloned into SmaI site in the commercially available positive selection vector, QuanToX™ (available from Quantum Biotechnologies Inc., Laval, Quebec, Canada). The cloned inserts were subsequently sequenced using the oligonucleotide primers, T7 (TAATACGACTCACTATAGGG, herein referred to as SEQ ID NO:348) and T3 (ATTAACCCTCACTAAAGGGA, herein referred to as SEQ ID NO:347). A 424 bp *T. gondii* nucleic acid molecule, referred to herein as $nTG_{424}$, was isolated, cloned and sequenced by this method.

The orientation of $nTG_{424}$, as well as additional nucleic acid sequence representing cDNA sequence occurring downstream (3') of $nTG_{424}$ was determined as follows. A 689 bp fragment including the 3'-end of the gene comprising $nTG_{424}$ was generated by PCR amplification of an ICG cDNA library constructed in the Uni-Zap XR insertion vector (available from Stratagene). The two primers used for this amplification reaction are represented by SEQ ID NO:358 ($^{709}$ACAAC-GACCACGACATCAACTAC$^{731}$, derived from the sequence of $nTG_{424}$, also referred to as pRayS), and an adaptor oligonucleotide primer that hybridized to the cDNA poly A tail (GGCCACGCGTCGACTACT$_{17}$ from BRL/GIBCO, Gaithersburg, Md., herein referred to as SEQ ID NO. 364). The superscript numbers at the beginning and end of the primer sequences described herein represent the location of the primer sequence relative to $nTG_{1397}$ (SEQ ID NO:343). A resulting 689 bp *T. gondii* nucleic acid molecule (also referred to as $nTG_{689}$) was cloned into PCR2.1 (available from Invitrogen, Carlsbad, Calif.), and sequenced using the M13 reverse oligonucleotide primers (CAGGAAACAGCTAT-GACC, herein referred to as SEQ ID NO:346) and the T7 oligonucleotide primer (SEQ ID NO:348). The sequence of $nTG_{689}$ revealed 266 bp of additional cDNA sequence (from 1133-1397 bp, relative to SEQ ID NO:343), with an overlap with $nTG_{424}$ from 709-1132 bp (relative to SEQ ID NO:343). There were three nucleotide differences between the sequence data for $nTG_{424}$ and the sequence data for $nTG_{689}$. Instead of a "T", "C" and "T" nucleotide at positions 1159, 1166, and 1169 respectively, the sequence data for $nTG_{689}$ revealed a "C", "T", and "A" at those positions.

The remainder of the nucleic acid sequence of $nTG_{1397}$ was determined in two PCR amplification steps using the ICG cDNA library as the template. The primers for the first PCR amplification were: a) an anti-sense oligonucleotide primer specific for $nTG_{424}$, having the sequence $^{929}$GTTGTCGTA-GATGTCGTTGTAGTT$^{906}$, and herein referred to as SEQ ID NO:359; and b) a Uni-Zap XR insertion vector-specific oligonucleotide primer (available from Stratagene, and referred to as Tp277) having the sequence, GGGAACAAAAGCTG-GAGCTCCACC, and herein referred to as SEQ ID NO:354. In the first PCR amplification step, SEQ ID NO:359 and SEQ ID NO:354 were used to generate an 884 bp nucleic acid molecule, (825 bp of which was $nTG_{1397}$-specific DNA sequence), that was then cloned into PCR2.1. The *T. gondii*-specific nucleic acid molecule is herein referred to as $nTG_{825}$. $nTG_{825}$ was sequenced using a TA sense oligonucleotide primer (having the sequence, CGAGCTCGGATCCACTAG, herein referred to as SEQ ID NO:350), and a TA anti-sense oligbnucleotide primer (having the sequence, GCCAGTGT-GATGGATATCTGCAG, herein referred to as SEQ ID NO:349) as well as a $nTG_{1397}$-specific internal oligonucleotide primer having the sequence, $^{564}$GAGGAGATC-GAACTTTGCTTGTGC$^{541}$, herein referred to as SEQ ID NO:361. Sequencing revealed that $nTG_{825}$ added an additional 604 bp to the sequence of $nTG_{1397}$, from nucleotides 105-708 (relative to SEQ ID NO:343). $nTG_{825}$ overlapped with $nTG_{424}$ and $nTG_{689}$ from base 709-939 (relative to SEQ ID NO:343.

The primers for the second PCR amplification step were: a) an oligonucleotide primer specific for $nTG_{424}$, having the sequence $^{225}$AGAAGCGCCTTTGCGTTTCTACGT$^{202}$, herein referred to as SEQ ID NO:360; and b) Tp277. These two primers were used to generate a 225 bp *T. gondii* DNA fragment, referred to as $nTG_{225}$. $nTG_{225}$ cloned into PCR2.1, and nucleotide sequenced with the TA oligonucleotide primers as above, thereby generating the sequence from nucleotides 1-104 of SEQ ID NO:343.

Sequence analysis revealed that $nTG_{225}$ overlapped with previously isolated $nTG_{825}$ DNA sequence from base105-225, relative to SEQ ID NO: 343.

The contiguous cDNA sequence of the overlapping fragments representing $nTG_{1397}$ was determined (and referred to herein as SEQ ID NO:343), and sequence analysis of the composite molecule revealed an 867 bp coding region (referred to as $nTG_{867}$), assuming an initiation codon at position 238-240, and a stop codon at position 1102-1104 (relative to SEQ ID NO: 343). The coding strand of $nTG_{867}$ is herein referred to as SEQ ID NO. 340, and the reverse complement is herein referred to as SEQ ID NO:342. Translation of the coding region of $nTG_{867}$ yields a 288 amino acid protein herein referred to as $PTg_{288}$, the amino acid sequence of which is herein referred to as SEQ ID NO:341.

To confirm the DNA sequence in the predicted coding region of $nTG_{1397}$, a PCR amplified fragment containing nucleotides 238 to 1271 was generated using an oligonucleotide primer having the sequence, AAGGATAGGCGGCCG-CAGGTACC $^{238}$ATGGCAGGAAGGCAGGCGGCGTT$^{260}$, herein referred to as SEQ ID NO:362, and an oligonucleotide primer having the sequence, ACCGCTCGAGAAGCTT $^{1271}$GAAGCCAAGACATCCCTTCGTGCA$^{1248}$, herein referred to as SEQ ID NO:363. The nucleotides in italics represent non-$nTG_{1397}$ nucleotide sequence, and were present to attach convenient restriction sites to the PCR product. The resulting PCR fragment was cloned into a eukaryotic expression vector, referred to as pDVacIII, and sequenced using two vector-specific oligonucleotidd primers: a) Tp244, having the sequence, GGATGCAATGAAGAGAGGGCTC, and herein referred to as SEQ ID NO:352; and b) Tp245, having the sequence, AACTAGAAGGCACAGTCGAG-GCTG, and herein referred to as SEQ ID NO:353. The PCR fragment thus generated contained two nucleotide differences as compared with the previously determined cDNA sequence of $nTG_{1397}$. Instead of an "A" at position 643, a "G" residue was found, and in place of a "T" at position 1187, a "C" residue was found. The resulting nucleotide change at position 643 altered the predicted encoded amino acid from an arginine to a glycine residue. The change at position 1187 did not change the predicted amino acid sequence of $nTG_{1397}$.

Genomic DNA sequence upstream of the gene comprising $nTG_{1397}$ was determined by generating a 747 bp fragment by PCR amplification of the λ-EMBL-3 Sau3A partial *Toxoplasma* genomic library herein described. The primers used were SEQ ID NO:360 (representing nucleotides 202-225 in $nTG_{1397}$) and a λ-EMBL-3-specific primer having the sequence, GGTTCTCTCCAGAGGTTCATTAC, and herein referred to as SEQ ID NO:351. The resulting DNA fragment was cloned in PCR2.1 and sequenced with TA oligonucleotide primers (SEQ ID NO:349, and SEQ ID NO:350) and two gene specific oligonucleotide primers, Tp310. (365CG-GACGTTGCATGTCAGTGGACA$^{343}$, herein referred to as SEQ ID NO:355) and Tp311 ($^{243}$CACGAAGCTGCATGT-TCCAGCTAG$^{265}$, herein referred to as SEQ IID NO:356). The sequence of the PCR fragment revealed a 647 bp DNA fragment, $nTG_{647}$, (herein referred to as SEQ ID NO:338, the reverse complement is herein refelTed to as SEQ ID NO:339) including 421 nucleotides of new genomic DNA sequence upstream of the 5' end of the cDNA sequence of $Tg_{1397}$. The fragment contained 327 bp of genomic DNA sequence that overlapped with the cDNA sequence, SEQ ID NO:343 (in other words, bases 422-647 of the genomic DNA sequence, SEQ ID NO:338, overlap with bases 1-225 of the cDNA sequence, SEQ ID NO:343). There was a single nucleotide difference between the genomic and the cDNA sequences at position 118 of the cDNA sequence (SEQ ID NO:343), where there is a "G" in the genomic DNA sequence and an "A", at the equivalent position in the cDNA sequence.

SEQ ID NO:343 was shown to be *T. gondii* specific by PCR amplification analysis of various DNAs, using $nTG_{1397}$-specific DNA primers to drive the reaction. The following cDNA samples were tested for the presence of $nTG_{1397}$ DNA: a) uninfected cat gut (UCG), b) infected cat gut (ICG), c) *T. gondii* tachyzoite (TgTz), and d) *Toxoplasma* bradyzoite (TgBz). To generate UCG and ICG RNA, gut tissue samples from an uninfected cat and a cat 7 days post infection with *T. gondii* tissue cysts (1000 cysts) were processed by scraping and collecting the epithelial layer of gut cells on dry ice. Cells from UCG, ICG, and *T. gondii* tachyzoites and bradyzoites were solubilized by homogenization in TRI-reagent (available from Molecular Research Center Inc., Cincinnati, Ohio), and the homogenate passed through a 18/20/and 22 gauge needle 10 times each sequentially. After standing at room temperature for 5 min., 100 ul of bromochloropropane (available from Molecular Research Center Inc.)/ml of TRI reagent was added, and the homogenate vortexed for 15 seconds. The sample was centrifuged at 14,000 rpm for 15 min. at 4° C., the aqueous layer collected, and RNA precipitated with one half volume of isopropanol. Contaminating genomic DNA was removed by digestion with 10 units of RNase free DNaseI (available from Boehringer Mannheim Corp.) at 37° C. for 30 min. The sample was then extracted with phenol/chloroform/isoamylalcohol, pH 6.0. The RNA was precipitated from the aqueous layer with ethanol and resuspended in diethylpyrocarbonate (available from Sigma) treated water. cDNA was generated from total RNA using a commercially available RT-PCR kit (available from Stratagene).

Two $nTG_{1397}$-specific oligonucleotide primers were used in the reaction: SEQ ID NO:358, having the sequence, $^{709}$ACAACGACCACGACATCAACTAC$^{731}$, and SEQ ID NO:357, having the sequence, $^{1114}$ACACTTTG-GTCTAATCGAGGGTAG$^{1091}$. The reaction conditions were: 95° C. 12 min., followed by 3 cycles of 94° C. 30 sec., 70° C. 30 sec., 72° C. 60 sec., 3 cycles of 94° C. 30 sec., 67° C. 30 sec., 72 ° C. 60 sec., 3 cycles of 94° C. 30 sec., 65° C. 30 sec., 72° C. 60 sec., 6 cycles of 94° C. 30 sec., 63° C. 30 sec., 72° C. 60 sec., 25 cycles of 94° C. 30 sec., 59° C. 30 sec., 72° C. 60 sec., and a seven minute extension at 75° C. to complete the reaction. The amount of template used in each PCR reaction (~3-30 ng of DNA), was empirically determined by comparison with a PCR amplified *Toxoplasma* tubulin gene product standard generated with each template. The PCR amplification reaction generated a 406 bp product only in the reactions containing tachyzoite and ICG cDNA template DNA, thereby confirming the *T. gondii*-specificity of SEQ ID NO:343.

Sequence Analysis

Homology searches of a non-redundant protein database were performed on SEQ ID NO:340 (representing the coding region of $nTG_{,1397}$, translated in frame I, using the BLASTP program available through the BLAST™ network of the National Center for Biotechnology Infoimation (NCBI) (National Library of Medicine, National Institute of Health, Baltimore, Md.). This database searched was PIR. In addition, a BLASTP homology search was performed on SEQ ID NO:341 (representing the amino acid sequence encoded by SEQ ID NO:340) using the NCBI database SwissProt. In all cases, the default parameters for the homology programs were used. Another homology search was run on SEQ ID NO:343 using the BLASTN search program and the database genembl.

When run against the PIR database, the highest scoring match of the homology search of translation products of the nucleic acid sequence SEQ ID NO:340 (the coding strand of the coding sequence) was to GenBank™ accession number A60095, a *Drosophila* larval glue protein precursor. Other significant homologies included homology to an African clawed frog mucin, and a promastigote surface antigen-2. When analyzed by the GCG program, using BESTFIT and default parameters, amino acid residues 145 to 281 of the protein encoded by SEQ ID NO:340 showed about 70% identity to amino acid residues 42 to 178 of the protein represented by GenBank™ accession number A60095. In addition, amino acid residues 153 to 282 of the protein encoded by SEQ ID NO:340 showed about 73% identity to amino acid residues 394 to 523 of the protein represented by GenBank™ accession number A45155 (African clawed frog mucin). When compared with the SwissProt database, the highest scoring match of the homology search of the amino acid sequence SEQ ID NO:341 (the protein encoded by SEQ ID NO:340) was to GenBank™ accession number Q05049, the African clawed frog mucin. These two amino acid sequences showed a 73% identity from amino acid 153 to 282 of SEQ ID NO:341 and amino acid 394 10 523 of the amino acid sequence represented by GenBank™ accession number Q05049. A comparison of SEQ ID NO:343 (the cDNA coding strand) using the BLASTN search program and the database genembl revealed a 76% nucleic acid sequence identity to a *D. discoideum* protein kinase, GenBank™ accession number M38703. This identity was between nt 765 to 1058 of SEQ ID NO:343 and nt 772 to 1065 of the sequence represented by GenBank™ accession number M38703. In addition, a BLASTN comparison SEQ ID NO:343 with the non-redundant GenBank™ database including GenBank EMBL+DDBJ+PDB revealed an 89% identity between nucleic acid residues 779 to 902 of SEQ ID NO:343 and nt 2150 to nt 2273 of the nucleic acid sequence represented by GenBank™ accession number DDDU86962.

Example 17

This example describes the induction of humoral and cellular responses in cats by proteins expressed by the *T. gondii* nucleic acid molecules of the present invention. Protein immunization with *T. gondii* recombinant protein and several different adjuvants induced both antibodies and T cell proliferative responses in cats. DNA immunization of cats with plasmid constructs expressing *T. gondii* immunogenic proteins of the present invention also induced antibody responses.

Protein Immunization

Protein immunization of cats was carried out with three primary subcutaneous immunizations at intervals of four weeks (prime at week 0 and boosts at weeks 4 and 8) using 50 μg protein per injection in adjuvant. The primary antigen was OC-22, which was purified as a HIS fusion protein from *E. coli*. The experimental groups were as follows: two cats were immunized with OC-22 protein in alum, two cats were immunized with OC-22 protein in polyphosphazine (PCPP), and two cats were immunized with OC-22 protein in BAYER1005 (Stunkel, K. G., et al., in *Cellular Basis of Immune Modulation*, 1989, pp. 575-579, incorporated herein by reference in its entirety). One cat was injected with two different antigens in BAYER1005: 50 ug of OC-22 and 12 ug of protein 4499-9. One control cat was injected with saline.

Whole blood was collected from all of the animals at intervals before and after the immunizations. Mononuclear cells were selected from the blood for T cell proliferation analysis (see blow) and the remaining plasma processed for detection of humoral responses. The presence of antibody was determined by western blot analysis and by ELISA using recombinant purified antigens. The western blot analysis was more sensitive at detecting a positive or negative response, while the ELISA provided a more quantitative comparison of the cat's responses to the immunogenic proteins.

Western blot analysis was performed on Recombinant purified OC-22 protein was loaded at 2 ug per lane and blotted to nitrocellulose. Samples were from pre-immune cats and cats at 1, 3, and 5 weeks after immunization. Recombinant purified OC-22 protein was loaded at 2 ug per lane and blotted to nitrocellulose. Analysis of the sera collected at three weeks following the first immunization demonstrated that all seven cats responded positively to OC-22 protein. Both anti-cat IgG and anti-cat IgA were used as secondary antibodies (on separate blots). The westerns showed that OC-22 protein elicited both IgA and IgG responses, although the IgA response was not as strong as the IgG response. The ELISA titers were monitored throughout the immunization regimen. The sera collected at week eight and a half, immediately following the second boost had detectable ELISA titers equal to or greater than 1:10,000 for all seven cats. These analyses did not demonstrate any apparent differences between the cats immunized with different adjuvants. The single cat immunized with 12 ug of 4499-9 protein was not positive to 4499-9 protein by either western blot analysis or BLISA, although the same cat demonstrated immune responses to OC-22 that were comparable to the other cats in the study.

Cellular responses to the recombinant *T. gondii* OC-22 protein were tested by in vitro proliferation of isolated peripheral blood mononuclear cells (PBMC) to purified protein at concentrations ranging from 0.5 to 8 μg/ml. At higher concentrations of protein, non-specific stimulation was evident, making interpretation difficult, but at lower concentrations of antigen, distinct differences were seen between cats. One week after the first boost, T cells from all of the cats in either the PCPP or BAY R1005 adjuvant groups demonstrated stimulation indices (SI) greater than 3, Cells from the PBS control and two alum group cats did not show any proliferative responses. Peak proliferative responses were seen one week after each boost, with the highest responses observed after the first boost. The cats immunized with protein in PCPP had the highest responses, followed by the cats immunized with protein in BAY R1005. The responses observed at 0.5 μg antigen per ml were lower than the responses observed at higher doses, but correlated well with the results observed at 2 ug/ml (data not shown). All of the immunized cats responded to antigen, at some point during the experiment, with an SI level above 3.

DNA Immunization

Cats were immunized with the recombinant eukaryotic expression vector, pDVac II, encoding *T. gondii* nucleic acid molecules encoding the immunogenic proteins OC-2, OC-22 and Tg-50. The pDVacII vector contains the CMV promoter and intron A sequences. The protein expressed by this vector includes the *T. gondii* antigen of interest, fused at the 5 prime end to the tissue plasminogen activator signal sequence and fused at the three prime end with both a stretch of poly histidines and an amino acid epitope from the mammalian myc gene. Fifteen cats were divided into four experimental groups: three cats received saline (cats 1, 8, and 16), four cats received DNA encoding OC-2 (cats 2, 5, 9, and 15), four cats received DNA encoding OC-22 (cats 3, 6, 10, and 12), and four cats received a combination of DNA encoding OC-2, OC-22, and Tg-50 (cats 4, 7, 13, and 14). Each cat was injected intramuscularly with a total 300 ug of DNA at two sites per immunization. The combined formulation included 300 ug of each plasmid per injection.

The cats were given one injection and then at eight weeks received a boost.

The serum samples collected at six weeks after the primary immunization were analyzed. Two out of eight cats immunized with OC-2 DNA were shown to sero convert to antibody positive to OC-2 protein by western blot analysis. None of the sera collected at this time from the cats immunized with OC-22 or Tg-50 DNA were positive by western blot analysis to OC-22 or Tg-50 protein respectively. When sera collected one week following the boost (week 9) were analyzed by western blots, seven of eight cats immunized with OC-2 were positive to OC-2, six of eight cats immunized with OC-22 were positive to OC-22, and one of four cats immunized with Tg-50 were positive to Tg-50. Similar to the western blot analysis for the protein immunogenicity study described above, faint IgA responses from all of the OC-22 sero-positive animals could be observed. ELISA analysis of sera taken one week after the boost indicated that four out of eight cats immunized with OC-2 and four of eight cats immunized with OC-22 had midpoint titers greater then 1:1000.

The T cell analysis demonstrated positive proliferative responses to several antigens, however the data were difficult to interpret. Cells isolated from two cats immunized with the OC-22 gene and one cat immunized with the OC-2 gene each demonstrated significant SI responses. However, the same cells from each of these cats were also stimulated by the other recombinant antigen; i.e. cells from OC-22-injected cats responded to OC-2 protein and cells from OC-2-injected cats responded to OC-22 protein. Sera from these animals did not react with the poly histidine or myc fusions on other control fusion proteins. This inability to demonstrate strong proliferative responses in PBMC is consistent with other results observed while exploring the induction of proliferative responses in T cells from DNA immunized cats. Cat peripheral blood is a poor source of responsive T cells.

Analysis of Oocyst Shedding in Protein an DNA Immunized Cats:

Analysis of oocysts shed following tissue cyst challenge of cats in both the protein and DNA immunogenicity studies showed no significant difference in oocyst shedding between any of the test groups and the control within each study. However, the number of animals in these studies varied between two and four per group, and thus this result is statistically meaningless. However, significant reduction, i.e., greater than several logs of total oocysts, was not observed in this experiment.

Example 18

This example describes immunization of cats with nucleic acid molecules encoding immunogenic *T. gondii* proteins, and subsequent challenge of the immunized cats.

Immunization Protocol:

The following set of conditions were used for the delivery of DNA-coated gold particles to cats: 1.25 ug of DNA was delivered per shot by Gene Gun (available from Biorad). 1.6 micron gold particles were used in the presence of 0.05 mg/ml PVP (polyvinyl pyrrolidine, 360 kD). The micro-carrier loading quantity was 0.5 mg DNA/cartridge, while the DNA loading ratio was 2.5 ug DNA/mg gold. The animals were anesthetized and shaved at the points of contact with the gun. A total of six shots were delivered to the animal for each immunization: three shots to the inner thigh at 300 psi and three shots to the lower side of the abdomen at 600 psi. The immunization regimen consisted of one prime and two boosts at six week intervals. Tissue cyst challenge was performed two weeks following the second boost. The challenge was with 1000 mouse brain-derived tissue cysts.

The plasmid containing the human growth hormone (hGH) gene was used in the control groups and as a marker in the other groups in all studies. In most control groups, the hGH plasmid was diluted to a concentration similar to that in the test groups. Humoral immune responses to the gene product were measured with an ELISA assay, and cellular responses were measured using hGH protein.

First immunogenicity study: The first immunization was followed by a challenge of 1000 mouse brain derived tissue cysts fourteen weeks later. Sample collection was terminated three weeks after that. There were four groups of five animals per group, as follows: Group 1: Control, hGH (0.125 ug/shot), pDVacIII (1.125 ug/shot) This group received one prime and two boosts, at 0, 6 and 12 weeks, respectively. Group 2: OC-22 in pDVacIII (1.25 ug/shot). This group received one prime and two boosts, at 0, 6 and 12 weeks, respectively. Group 3: hGH (0.125 ug/shot), 9 *Toxoplasma* nucleic acid molecules OC-2, OC-22, OC-13, OC-14, Tg-41, Tg-45, Tg-50, 4604-3, and 4CQA11 (0.125 ug/shot). This group received one prime and two boosts, at 0, 6 and 12 weeks, respectively. Group 4: hGH (0.125 ug/shot), the same DNA as in Group 3 (9 *Toxoplasma* nucleic acid molecules), but this group received one prime and one boost, at 6 and 12 weeks, respectively. ELISA analysis for hGH sero conversion using sera collected throughout the study demonstrated that five of five cats in Group 1 were positive (i.e., demonstrated an end point titer>1,000) Three of five animals in Group 3 were sero-positive to hGH. ELISA analysis for sero conversion to OC-22 protein using sera from Group 2 and Group 3 indicated that three of five and zero of five cats were positive respectively. These data suggest that competition from the other plasmids reduced the rate of sero conversion to an individual plasmid. In all cases positive titers did not occur until after the first boost. Specific-T cell proliferative responses using PBMC from animals in each group were not observed. Using the B1 gene-based PCR ELISA herein described, the average number of oocysts shed for each group was: Group1, 1.03e8; Group 2, 1.11e8; Group 3, 5.79e7 and Group 4, 8.83e7. Statistical analysis of the data indicated no significant difference between the test groups and the control.

Second Immunogenicity Study:

The first immunization for this study was followed by a challenge of 1000 mouse brain derived tissue cysts fourteen weeks later. Sample collection was terminated three weeks after that. There were four groups of five animals per group, and all animals received one prime and two boosts. Group 2 consisted of DNA representing 18 nucleic acid molecules of the present invention. Group 3 represent 14 additional nucleic acid molecules of the present invention. Group 4 was a combination of both of these groups. The specific nucleic acid molecules and concentrations used in the immunizations were as follows: (Group 1: Control, hGH (0.083 ug/shot), pDVacIII (1.125 ug/shot). Group 2: hGH (0.070 ug/shot), 18 *Toxoplasma* nucleic acid molecules (BZ1-2, 4604-2, 4604-62, 4CQA27, 4CQA29, 4CQA21, 4CQA27, 4604-62, Q2-4, R8050-6,Tg50, M2A1, M2A5, M2A7, M2A11, M2A19, M2A22, M2A29) (0.070 ug/shot). Group 3: SGH (0.083 ug/shot), 14 *Toxoplasma* nucleic acid molecules (M2A3, M2A21, M2A18, M2A20, M2A24, M2A6, Q2-9, Q2-10, Q2-11, 4604-63, 4604-17, 4604-69, 4604-54, 4CQA19) (0.083 ug/shot). Group 4: hGH (0.040 ug/shot), 32 *Toxoplasma* nucleic acid molecules (BZ1-2, 4604-2, 4604-62, 4CQA27, 4CQA29, 4CQA21, 4CQA27, 4604-62, Q2-4, R8050-6,Tg-50, M2A1, M2A5, M2A7, M2A11, M2A19, M2A22, M2A29, M2A3, M2A21, M2A18, M2A20, M2A24, M2A6, Q2-9, Q2-10, Q2-11, 4604-63, 4604-17, 4604-69, 4604-54, 4CQA19) (0.040 ug/shot).

The ELISA analysis of antibody to hGH protein demonstrated that two of five, three of five, zero of five, and two of five animals seroconverted in Groups 1, 2, 3, and 4 respectively. Using low amounts of hGH plasmid in the presence of eighteen or thirty-two additional plasmids containing nucleic acid molecules of the present invention still induced sero conversion in several animals per group. This observation suggests that there is not a strict reduction in the production of antibodies when a gene is injected with several other constructs.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated nucleic acid molecule selected from the group consisting of:
- (a) a nucleic acid molecule that hybridizes to an at least 18 contiguous nucleotide region of SEQ ID NO:72 under conditions comprising (1) hybridizing in a solution comprising 2X SSC in the absence of nucleic acid double helix destabilizing compounds, at a temperature of about 37° C.; and (2) washing in a solution comprising 1×SSC in the absence of double helix destabilizing compounds at a temperature of about 74° C.; and
- (b) a nucleic acid molecule fully complementary in sequence to the nucleic acid molecule of (a).

2. The isolated nucleic acid molecule of claim 1, wherein said nucleic acid molecule is selected from the group consisting of:
- (a) an isolated nucleic acid molecule that comprises a nucleic acid sequence at least 95% identical to the nucleic acid sequence represented by SEQ ID NO:72; and
- (b) an isolated nucleic acid molecule fully complementary in sequence to the nucleic acid molecule of (a).

3. The isolated nucleic acid molecule of claim 1, wherein said nucleic acid molecule is selected from the group consisting of:
 (a) an isolated nucleic acid molecule that comprises a nucleic acid sequence represented by SEQ ID NO:72; and
 (b) an isolated nucleic acid molecule fully complementary in sequence to the nucleic acid molecule of (a).

4. A recombinant virus comprising an isolated nucleic acid molecule as set forth in claim 1.

5. A recombinant cell comprising an isolated nucleic acid molecule as set forth in claim 1.

6. A composition comprising (a) an isolated nucleic acid molecule as set forth in claim 1, and (b) a component selected from the group consisting of an excipient, an adjuvant and a carrier.

7. An isolated nucleic acid molecule selected from the group consisting of:
 (a) an isolated nucleic acid molecule comprising a nucleic acid sequence that encodes a protein comprising an amino acid sequence at least 95% identical to SEQ ID NO:73; and
 (b) an isolated nucleic acid molecule fully complementary in sequence to the nucleic acid molecule of (a).

8. The isolated nucleic acid molecule of claim 7, wherein said isolated nucleic acid molecule is selected from the group consisting of:
 (a) an isolated nucleic acid molecule comprising a nucleic acid sequence that encodes a protein comprising SEQ ID NO:73; and
 (b) an isolated nucleic acid molecule fully complementary in sequence to the nucleic acid molecule of (a).

9. The isolated nucleic acid molecule of claim 7, wherein said isolated nucleic acid molecule is selected from the group consisting of:
 (a) an isolated nucleic acid molecule consisting of a nucleic acid sequence that encodes a protein comprising an amino acid sequence at least 95% identical to SEQ ID NO:73; and
 (b) an isolated nucleic acid molecule fully complementary in sequence to the nucleic acid molecule of (a).

10. A recombinant virus comprising an isolated nucleic acid molecule as set forth in claim 7.

11. A recombinant cell comprising an isolated nucleic acid molecule as set forth in claim 7.

12. A composition comprising (a) an isolated nucleic acid molecule as set forth in claim 7, and (b) a component selected from the group consisting of an excipient, an adjuvant and a carrier.

\* \* \* \* \*

SEQUENCE LISTING

```
<160> NUMBER OF SEQ ID NOS: 366

<210> SEQ ID NO 1
<211> LENGTH: 357
<212> TYPE: DNA
<213> ORGANISM: Toxoplasma gondii
<220> FEATURE:
<221> NAME/KEY: CDS
<222> LOCATION: (1)..(357)
<223> OTHER INFORMATION:

<400> SEQUENCE: 1 cgc ttc ttg tgt cac ctg cgg cga cgg ggg gac tct cag cag ggc tcg      48
Arg Phe Leu Cys His Leu Arg Arg Arg Gly Asp Ser Gln Gln Gly Ser
1               5                   10                  15 tgg att cca agc ggc tct gtt ctt ctc tct tct tcg ccg gcg cat tcc      96
Trp Ile Pro Ser Gly Ser Val Leu Leu Ser Ser Ser Pro Ala His Ser
 20                  25                  30 gcc ggt cct cgg aat act cga acg tct cga gtt gcg cgc gtt ggc ctg     144
Ala Gly Pro Arg Asn Thr Arg Thr Ser Arg Val Ala Arg Val Gly Leu
35                  40                  45 gaa gcc ggg cct gcg aaa ggc gag aca gaa agc aga cga agc aga cag     192
Glu Ala Gly Pro Ala Lys Gly Glu Thr Glu Ser Arg Arg Ser Arg Gln
50                  55                  60 gac gaa ggg agc gac gtc cgt ggg cgc ttt ttt cga ggc aga caa acc     240
Asp Glu Gly Ser Asp Val Arg Gly Arg Phe Phe Arg Gly Arg Gln Thr
65                  70                  75                  80 gga gac tct cgc atc cac atg ggg gtc tac gag ggt cac gat ggc aac     288
Gly Asp Ser Arg Ile His Met Gly Val Tyr Glu Gly His Asp Gly Asn
 85                  90                  95 gag ttc ggc gaa gag aga gaa caa ggt gca tgc gat ttt tcc gca tct     336
Glu Phe Gly Glu Glu Arg Glu Gln Gly Ala Cys Asp Phe Ser Ala Ser
100                 105                 110 cct cgc tcg gaa ggc gga tcg                                         357
Pro Arg Ser Glu Gly Gly Ser
115

<210> SEQ ID NO 2
<211> LENGTH: 119
<212> TYPE: PRT
<213> ORGANISM: Toxoplasma gondii

<400> SEQUENCE: 2

Arg Phe Leu Cys His Leu Arg Arg Arg Gly Asp Ser Gln Gln Gly Ser
1               5                   10                  15

Trp Ile Pro Ser Gly Ser Val Leu Leu Ser Ser Ser Pro Ala His Ser
 20                  25                  30

Ala Gly Pro Arg Asn Thr Arg Thr Ser Arg Val Ala Arg Val Gly Leu
35                  40                  45

Glu Ala Gly Pro Ala Lys Gly Glu Thr Glu Ser Arg Arg Ser Arg Gln
50                  55                  60
```

Asp Glu Gly Ser Asp Val Arg Gly Arg Phe Phe Arg Gly Arg Gln Thr
65                  70                  75                  80

Gly Asp Ser Arg Ile His Met Gly Val Tyr Glu Gly His Asp Gly Asn
        85                  90                  95

Glu Phe Gly Glu Glu Arg Glu Gln Gly Ala Cys Asp Phe Ser Ala Ser
100                 105                 110

Pro Arg Ser Glu Gly Gly Ser
115

<210> SEQ ID NO 3
<211> LENGTH: 339
<212> TYPE: DNA
<213> ORGANISM: Toxoplasma gondii
<220> FEATURE:
<221> NAME/KEY: CDS
<222> LOCATION: (1)..(324)
<223> OTHER INFORMATION:

<400> SEQUENCE: 3 cga gga gac ggt ggg agc gca ctg gcc cga ggc gcg gca ctg gga ctt      48
Arg Gly Asp Gly Gly Ser Ala Leu Ala Arg Gly Ala Ala Leu Gly Leu
1               5                   10                  15 ggg ggc gcg aca gcc gcc gaa aca gct gct gcg cga ata gct gct ctc      96
Gly Gly Ala Thr Ala Ala Glu Thr Ala Ala Ala Arg Ile Ala Ala Leu
            20                  25                  30 aaa cca tcg ctc ttc gcg gcc tcc gaa ctc cct ccc gat gag aca gca     144
Lys Pro Ser Leu Phe Ala Ala Ser Glu Leu Pro Pro Asp Glu Thr Ala
35                  40                  45 gac agt gga gac aca ggg ccg ttc cgg cga gac cgg gac ttc ttc gcc     192
Asp Ser Gly Asp Thr Gly Pro Phe Arg Arg Asp Arg Asp Phe Phe Ala
50                  55                  60 ggc acc gcg ggc gaa cac gat gcg tcg gcg atg cga gac aaa gag gcc     240
Gly Thr Ala Gly Glu His Asp Ala Ser Ala Met Arg Asp Lys Glu Ala
65                  70                  75                  80 gca ggc tcc tca ggc gaa gag aca ccc gca gag atc ggc atc ttg ggc     288
Ala Gly Ser Ser Gly Glu Glu Thr Pro Ala Glu Ile Gly Ile Leu Gly
            85                  90                  95 agc cgc gga aac agt tgg ccg gga gac caa ggc tgc tgaagcgtcg ctcgc   339
Ser Arg Gly Asn Ser Trp Pro Gly Asp Gln Gly Cys
            100                 105

<210> SEQ ID NO 4
<211> LENGTH: 108
<212> TYPE: PRT
<213> ORGANISM: Toxoplasma gondii

<400> SEQUENCE: 4

Arg Gly Asp Gly Gly Ser Ala Leu Ala Arg Gly Ala Ala Leu Gly Leu
1               5                   10                  15

Gly Gly Ala Thr Ala Ala Glu Thr Ala Ala Ala Arg Ile Ala Ala Leu
            20                  25                  30

Lys Pro Ser Leu Phe Ala Ala Ser Glu Leu Pro Pro Asp Glu Thr Ala
35                  40                  45

Asp Ser Gly Asp Thr Gly Pro Phe Arg Arg Asp Arg Asp Phe Phe Ala
50                  55                  60

Gly Thr Ala Gly Glu His Asp Ala Ser Ala Met Arg Asp Lys Glu Ala
65                  70                  75                  80

Ala Gly Ser Ser Gly Glu Glu Thr Pro Ala Glu Ile Gly Ile Leu Gly
            85                  90                  95

-continued

```
Ser Arg Gly Asn Ser Trp Pro Gly Asp Gln Gly Cys
100                 105
```

```
<210> SEQ ID NO 5
<211> LENGTH: 526
<212> TYPE: DNA
<213> ORGANISM: Toxoplasma gondii
<220> FEATURE:
<221> NAME/KEY: CDS
<222> LOCATION: (1)..(525)
<223> OTHER INFORMATION:

<400> SEQUENCE: 5
```

```
cgg aca aaa aag ttt tcc tac gct ccg aac gga gcg gat tct aac aac      48
Arg Thr Lys Lys Phe Ser Tyr Ala Pro Asn Gly Ala Asp Ser Asn Asn
1               5                   10                  15 tcc tct ctt ccg cac ttt cca tct gtg ttt cca gcg agc gcc gta gtc      96
Ser Ser Leu Pro His Phe Pro Ser Val Phe Pro Ala Ser Ala Val Val
            20                  25                  30 tcc ccc atc gac gaa aac cct gca gag atg gaa agc acc atc tcc gag     144
Ser Pro Ile Asp Glu Asn Pro Ala Glu Met Glu Ser Thr Ile Ser Glu
35                  40                  45 ggc gaa gca ggt tct gcg gtg gcg gct cct gaa caa ggt atc cag cca     192
Gly Glu Ala Gly Ser Ala Val Ala Ala Pro Glu Gln Gly Ile Gln Pro
    50                  55                  60 gag gca gaa ttt gct acc gcc agc gaa gaa cca cgt ccc ctg gaa cct     240
Glu Ala Glu Phe Ala Thr Ala Ser Glu Glu Pro Arg Pro Leu Glu Pro
65                  70                  75                  80 gtc gac ccc gaa atg gca gct cag cag ccg caa ctg cct caa gaa gct     288
Val Asp Pro Glu Met Ala Ala Gln Gln Pro Gln Leu Pro Gln Glu Ala
                85                  90                  95 atg cca act gag aat gcg gac ctt ctt gga aac cag ccc aga atg cgc     336
Met Pro Thr Glu Asn Ala Asp Leu Leu Gly Asn Gln Pro Arg Met Arg
            100                 105                 110 aat gct ctc gaa ccc tct gcc aag gtc ctc gaa ccg gaa acc ctg gaa     384
Asn Ala Leu Glu Pro Ser Ala Lys Val Leu Glu Pro Glu Thr Leu Glu
115                 120                 125 ggg tca cct gct ctc gtc ccg ccg gca gag act gaa gag ggg aca gcc     432
Gly Ser Pro Ala Leu Val Pro Pro Ala Glu Thr Glu Glu Gly Thr Ala
130                 135                 140 gcc caa att gcg gag gaa atg agc aag cag gat cag ggc atg cag gaa     480
Ala Gln Ile Ala Glu Glu Met Ser Lys Gln Asp Gln Gly Met Gln Glu
145                 150                 155                 160 gcc agg cct caa gaa gtt ctc agt aag caa tgg gtt ctt cga tat t       526
Ala Arg Pro Gln Glu Val Leu Ser Lys Gln Trp Val Leu Arg Tyr
165                 170                 175
```

```
<210> SEQ ID NO 6
<211> LENGTH: 175
<212> TYPE: PRT
<213> ORGANISM: Toxoplasma gondii

<400> SEQUENCE: 6
```

```
Arg Thr Lys Lys Phe Ser Tyr Ala Pro Asn Gly Ala Asp Ser Asn Asn
1               5                   10                  15

Ser Ser Leu Pro His Phe Pro Ser Val Phe Pro Ala Ser Ala Val Val
            20                  25                  30

Ser Pro Ile Asp Glu Asn Pro Ala Glu Met Glu Ser Thr Ile Ser Glu
35                  40                  45

Gly Glu Ala Gly Ser Ala Val Ala Ala Pro Glu Gln Gly Ile Gln Pro
    50                  55                  60
```

```
Glu Ala Glu Phe Ala Thr Ala Ser Glu Glu Pro Arg Pro Leu Glu Pro
 65                  70                  75                  80

Val Asp Pro Glu Met Ala Ala Gln Gln Pro Gln Leu Pro Gln Glu Ala
 85                  90                  95

Met Pro Thr Glu Asn Ala Asp Leu Leu Gly Asn Gln Pro Arg Met Arg
100                 105                 110

Asn Ala Leu Glu Pro Ser Ala Lys Val Leu Glu Pro Glu Thr Leu Glu
115                 120                 125

Gly Ser Pro Ala Leu Val Pro Pro Ala Glu Thr Glu Glu Gly Thr Ala
130                 135                 140

Ala Gln Ile Ala Glu Glu Met Ser Lys Gln Asp Gln Gly Met Gln Glu
145                 150                 155                 160

Ala Arg Pro Gln Glu Val Leu Ser Lys Gln Trp Val Leu Arg Tyr
165                 170                 175

<210> SEQ ID NO 7
<211> LENGTH: 1478
<212> TYPE: DNA
<213> ORGANISM: Toxoplasma gondii
<220> FEATURE:
<221> NAME/KEY: CDS
<222> LOCATION: (19)..(1161)
<223> OTHER INFORMATION:

<400> SEQUENCE: 7
gaggacgcag acgtgagt atg ctc cag agg gat cac gga atc cac gga gag         51
                    Met Leu Gln Arg Asp His Gly Ile His Gly Glu
                     1               5                  10 gaa gcc ggt ttg ttc cgc aag gct gtt ccg ggc ttg gac gac cca gct         99
Glu Ala Gly Leu Phe Arg Lys Ala Val Pro Gly Leu Asp Asp Pro Ala
 15                  20                  25 gaa gac gat gaa gcc gac ggc gaa agt gcc tcg gat gag gca gaa gcc        147
Glu Asp Asp Glu Ala Asp Gly Glu Ser Ala Ser Asp Glu Ala Glu Ala
 30                  35                  40 gac tct gac gtc ttg gcg gac gac gaa gaa ggg aca tcc ctc atc gaa        195
Asp Ser Asp Val Leu Ala Asp Asp Glu Glu Gly Thr Ser Leu Ile Glu
 45                  50                  55 aat gcg agt gag gaa gac aca gac aac tcc gag gca gac agt caa cag        243
Asn Ala Ser Glu Glu Asp Thr Asp Asn Ser Glu Ala Asp Ser Gln Gln
 60                  65                  70                  75 gag gat gac agt gtg gga gag gat tcc ttt ctc cag cag gag ggc gag        291
Glu Asp Asp Ser Val Gly Glu Asp Ser Phe Leu Gln Gln Glu Gly Glu
 80                  85                  90 gac tcc gag gaa gaa aga gca gtc gag gac ccg tat gct gcc gcc gaa        339
Asp Ser Glu Glu Glu Arg Ala Val Glu Asp Pro Tyr Ala Ala Ala Glu
 95                 100                 105 ccc tct tat ctt gaa gag gac aac act gtt gac gac agc gcg gcg gag        387
Pro Ser Tyr Leu Glu Glu Asp Asn Thr Val Asp Asp Ser Ala Ala Glu
110                 115                 120 gat tat gcc cct gct tcg ttt gtc cag atc ggc agt gga gag aga aaa        435
Asp Tyr Ala Pro Ala Ser Phe Val Gln Ile Gly Ser Gly Glu Arg Lys
125                 130                 135 atc cgg gcg cac atg cat ctt gac agc cgc caa gtt gcc ccc gaa aga        483
Ile Arg Ala His Met His Leu Asp Ser Arg Gln Val Ala Pro Glu Arg
140                 145                 150                 155 ttc gcg cat gcg ttc aac cag gat cat gtc aga ctt ctg gac cag acc        531
Phe Ala His Ala Phe Asn Gln Asp His Val Arg Leu Leu Asp Gln Thr
160                 165                 170 gcc gtc gag gac gaa ctt ctc gat gag gcc gcc ccg ggc gga ggc gcg        579
Ala Val Glu Asp Glu Leu Leu Asp Glu Ala Ala Pro Gly Gly Gly Ala
```

```
                 175                 180                 185
agc gcc gta gtc tcc ccc atc gac gaa aac cct gca gag atg gaa agc        627
Ser Ala Val Val Ser Pro Ile Asp Glu Asn Pro Ala Glu Met Glu Ser
190                 195                 200 acc atc tcc gag ggc gaa gca ggt tct gcg gtg gcg gct cct gaa caa        675
Thr Ile Ser Glu Gly Glu Ala Gly Ser Ala Val Ala Ala Pro Glu Gln
205                 210                 215 ggt atc cag cca gag gca gaa ttt gct acc gcc agc gaa gaa cca cgt        723
Gly Ile Gln Pro Glu Ala Glu Phe Ala Thr Ala Ser Glu Glu Pro Arg
220                 225                 230                 235 ccc ctg gaa cct gtc gac ccc gaa atg gca gct cag cag ccg caa ctg        771
Pro Leu Glu Pro Val Asp Pro Glu Met Ala Ala Gln Gln Pro Gln Leu
240                 245                 250 cct caa gaa gct atg cca act gag aat gcg gac ctt ctt gga aac cag        819
Pro Gln Glu Ala Met Pro Thr Glu Asn Ala Asp Leu Leu Gly Asn Gln
255                 260                 265 ccc aga atg cgc aat gct ctc gaa ccc tct gcc aag gtc ctc gaa ccg        867
Pro Arg Met Arg Asn Ala Leu Glu Pro Ser Ala Lys Val Leu Glu Pro
270                 275                 280 gaa acc ctg gaa ggg tca cct gct ctc gtc ccg ccg gca gag act gaa        915
Glu Thr Leu Glu Gly Ser Pro Ala Leu Val Pro Pro Ala Glu Thr Glu
285                 290                 295 gag ggg aca gcc gcc caa att gcg gag gaa atg agc aag cag gat cag        963
Glu Gly Thr Ala Ala Gln Ile Ala Glu Glu Met Ser Lys Gln Asp Gln
300                 305                 310                 315 ggc atg cag gaa gcc agg cct caa gaa gtt ctc aca cga cac acc tgg       1011
Gly Met Gln Glu Ala Arg Pro Gln Glu Val Leu Thr Arg His Thr Trp
320                 325                 330 caa gat atg gag aga act gag gac cta cga aag aac gac gtc ccg gct       1059
Gln Asp Met Glu Arg Thr Glu Asp Leu Arg Lys Asn Asp Val Pro Ala
335                 340                 345 gca gtg gcg aat tcc ggc agc cag atc atc acg gct gcg tcg tcc gtc       1107
Ala Val Ala Asn Ser Gly Ser Gln Ile Ile Thr Ala Ala Ser Ser Val
350                 355                 360 gcc ctt gct ggt cta ctg gtc gca gga cag ctt ttg ttc agc gtg ggc       1155
Ala Leu Ala Gly Leu Leu Val Ala Gly Gln Leu Leu Phe Ser Val Gly
365                 370                 375 atg tac tgagaataat attcttgctt cgtggaatat gttgctacc tgaaagttaa        1211
Met Tyr
380 actattttcg ctgtgaatgt ggggggggtt cgccgactgt gttccgccc aacattcgtg     1271 gttaatgagt tttgtcccat cgtgcattgc gacgctcaac cacacttcta tttggggggg   1331 gcatcttagg taatatgcta aggttatttt ctgcgtcgct gaactctggt cttgcaaaag   1391 aagctaactc ttttccggca taacttcgtt tttggtgtca aaaaaaaaaa aaaaaaaaaa   1451 aaaaaaaaaa aaaaaaaaa aaaaaaa                                        1478

<210> SEQ ID NO 8
<211> LENGTH: 381
<212> TYPE: PRT
<213> ORGANISM: Toxoplasma gondii

<400> SEQUENCE: 8

Met Leu Gln Arg Asp His Gly Ile His Gly Glu Glu Ala Gly Leu Phe
1               5                   10                  15

Arg Lys Ala Val Pro Gly Leu Asp Asp Pro Ala Glu Asp Asp Glu Ala
            20                  25                  30

Asp Gly Glu Ser Ala Ser Asp Glu Ala Glu Ala Asp Ser Asp Val Leu
```

```
                35                  40                  45
Ala Asp Asp Glu Glu Gly Thr Ser Leu Ile Glu Asn Ala Ser Glu Glu
 50                  55                  60

Asp Thr Asp Asn Ser Glu Ala Asp Ser Gln Gln Glu Asp Asp Ser Val
 65                  70                  75                  80

Gly Glu Asp Ser Phe Leu Gln Gln Glu Gly Glu Asp Ser Glu Glu Glu
 85                  90                  95

Arg Ala Val Glu Asp Pro Tyr Ala Ala Ala Glu Pro Ser Tyr Leu Glu
100                 105                 110

Glu Asp Asn Thr Val Asp Asp Ser Ala Ala Glu Asp Tyr Ala Pro Ala
115                 120                 125

Ser Phe Val Gln Ile Gly Ser Gly Glu Arg Lys Ile Arg Ala His Met
130                 135                 140

His Leu Asp Ser Arg Gln Val Ala Pro Glu Arg Phe Ala His Ala Phe
145                 150                 155                 160

Asn Gln Asp His Val Arg Leu Leu Asp Gln Thr Ala Val Glu Asp Glu
165                 170                 175

Leu Leu Asp Glu Ala Ala Pro Gly Gly Gly Ala Ser Ala Val Val Ser
180                 185                 190

Pro Ile Asp Glu Asn Pro Ala Glu Met Glu Ser Thr Ile Ser Glu Gly
195                 200                 205

Glu Ala Gly Ser Ala Val Ala Ala Pro Glu Gln Gly Ile Gln Pro Glu
210                 215                 220

Ala Glu Phe Ala Thr Ala Ser Glu Glu Pro Arg Pro Leu Glu Pro Val
225                 230                 235                 240

Asp Pro Glu Met Ala Ala Gln Gln Pro Gln Leu Pro Gln Glu Ala Met
245                 250                 255

Pro Thr Glu Asn Ala Asp Leu Leu Gly Asn Gln Pro Arg Met Arg Asn
260                 265                 270

Ala Leu Glu Pro Ser Ala Lys Val Leu Glu Pro Glu Thr Leu Glu Gly
275                 280                 285

Ser Pro Ala Leu Val Pro Pro Ala Glu Thr Glu Glu Gly Thr Ala Ala
290                 295                 300

Gln Ile Ala Glu Glu Met Ser Lys Gln Asp Gln Gly Met Gln Glu Ala
305                 310                 315                 320

Arg Pro Gln Glu Val Leu Thr Arg His Thr Trp Gln Asp Met Glu Arg
325                 330                 335

Thr Glu Asp Leu Arg Lys Asn Asp Val Pro Ala Ala Val Ala Asn Ser
340                 345                 350

Gly Ser Gln Ile Ile Thr Ala Ala Ser Ser Val Ala Leu Ala Gly Leu
355                 360                 365

Leu Val Ala Gly Gln Leu Leu Phe Ser Val Gly Met Tyr
370                 375                 380

<210> SEQ ID NO 9
<211> LENGTH: 657
<212> TYPE: DNA
<213> ORGANISM: Toxoplasma gondii
<220> FEATURE:
<221> NAME/KEY: CDS
<222> LOCATION: (1)..(657)
<223> OTHER INFORMATION:

<400> SEQUENCE: 9 gag atg agc gcc cca gat agg caa aca gga aag ctt tcc gat tta ccg      48
Glu Met Ser Ala Pro Asp Arg Gln Thr Gly Lys Leu Ser Asp Leu Pro
```

```
                  1               5                   10                  15 cca ttt gct gag ctg cca cag ctg gca gaa ata cca aag ctc tcc gaa                96
Pro Phe Ala Glu Leu Pro Gln Leu Ala Glu Ile Pro Lys Leu Ser Glu
20                  25                  30 ctt ccg aaa atc gcg gac atg ccg aaa ttt tcg gat atg ccc aag atg              144
Leu Pro Lys Ile Ala Asp Met Pro Lys Phe Ser Asp Met Pro Lys Met
35                  40                  45 gcc gag atg ccc aag tta tca gat ata ccc aag atg gct gag atg ccc              192
Ala Glu Met Pro Lys Leu Ser Asp Ile Pro Lys Met Ala Glu Met Pro
50                  55                  60 aag tta tca gat ata ccc aag atg gct gag atg ccc aag tta tca gat              240
Lys Leu Ser Asp Ile Pro Lys Met Ala Glu Met Pro Lys Leu Ser Asp
65                  70                  75                  80 ata ccc aag atg gct gag atg ccc aag ttt tca gat ata ccc aag atg              288
Ile Pro Lys Met Ala Glu Met Pro Lys Phe Ser Asp Ile Pro Lys Met
85                  90                  95 gct gag atg cca aag tta tca gat atg ccc aga atg gct gac att cca              336
Ala Glu Met Pro Lys Leu Ser Asp Met Pro Arg Met Ala Asp Ile Pro
100                 105                 110 cag ttt cca gag atg cct agg atg gtt gac atg cct cag ttt cca gaa              384
Gln Phe Pro Glu Met Pro Arg Met Val Asp Met Pro Gln Phe Pro Glu
115                 120                 125 atc ccc agg atg gct gat atg cgg aga ttt ccg gag atg tcc aag ata              432
Ile Pro Arg Met Ala Asp Met Arg Arg Phe Pro Glu Met Ser Lys Ile
130                 135                 140 gct gac atg cca aag ttt cca gac atg cca aac gtc act gag atg cca              480
Ala Asp Met Pro Lys Phe Pro Asp Met Pro Asn Val Thr Glu Met Pro
145                 150                 155                 160 aag ctt gca gat ttg cca agg ctt gct gac atg ccc agt att gcc gac              528
Lys Leu Ala Asp Leu Pro Arg Leu Ala Asp Met Pro Ser Ile Ala Asp
165                 170                 175 atg ccc cgg ctc tca gac atg ccc agt att gca gac atg ccc cgg ctc              576
Met Pro Arg Leu Ser Asp Met Pro Ser Ile Ala Asp Met Pro Arg Leu
180                 185                 190 tca gac ata ccc agt att gcc gac atg ccc cgg ctc tca gac atg ccc              624
Ser Asp Ile Pro Ser Ile Ala Asp Met Pro Arg Leu Ser Asp Met Pro
195                 200                 205 agt att gcc gac atg ccg aaa ttc tct agc cgg                                  657
Ser Ile Ala Asp Met Pro Lys Phe Ser Ser Arg
210                 215
```

<210> SE

```
Ala Glu Met Pro Lys Leu Ser Asp Met Pro Arg Met Ala Asp Ile Pro
100                 105                 110

Gln Phe Pro Glu Met Pro Arg Met Val Asp Met Pro Gln Phe Pro Glu
115                 120                 125

Ile Pro Arg Met Ala Asp Met Arg Arg Phe Pro Glu Met Ser Lys Ile
130                 135                 140

Ala Asp Met Pro Lys Phe Pro Asp Met Pro Asn Val Thr Glu Met Pro
145                 150                 155                 160

Lys Leu Ala Asp Leu Pro Arg Leu Ala Asp Met Pro Ser Ile Ala Asp
165                 170                 175

Met Pro Arg Leu Ser Asp Met Pro Ser Ile Ala Asp Met Pro Arg Leu
180                 185                 190

Ser Asp Ile Pro Ser Ile Ala Asp Met Pro Arg Leu Ser Asp Met Pro
195                 200                 205

Ser Ile Ala Asp Met Pro Lys Phe Ser Ser Arg
210                 215
```

<210> SEQ ID NO 11
<211> LENGTH: 1029
<212> TYPE: DNA
<213> ORGANISM: Toxoplasma gondii
<220> FEATURE:
<221> NAME/KEY: CDS
<222> LOCATION: (1)..(819)
<223> OTHER INFORMATION:

<400> SEQUENCE: 11

```
gag atg agc gcc cca gat agg caa aca gga aag ctt tcc gat tta ccg      48
Glu Met Ser Ala Pro Asp Arg Gln Thr Gly Lys Leu Ser Asp Leu Pro
1               5                   10                  15 cca ttt gct gag ctg cca cag ctg gca gaa ata cca aag ctc tcc gaa      96
Pro Phe Ala Glu Leu Pro Gln Leu Ala Glu Ile Pro Lys Leu Ser Glu
20                  25                  30 ctt ccg aaa atc gcg gac atg ccg aaa ttt tcg gat atg ccc aag atg     144
Leu Pro Lys Ile Ala Asp Met Pro Lys Phe Ser Asp Met Pro Lys Met
35                  40                  45 gcc gag atg ccc aag tta tca gat ata ccc aag atg gct gag atg ccc     192
Ala Glu Met Pro Lys Leu Ser Asp Ile Pro Lys Met Ala Glu Met Pro
50                  55                  60 aag tta tca gat ata ccc aag atg gct gag atg ccc aag tta tca gat     240
Lys Leu Ser Asp Ile Pro Lys Met Ala Glu Met Pro Lys Leu Ser Asp
65                  70                  75                  80 ata ccc aag atg gct gag atg ccc aag ttt tca gat ata ccc aag atg     288
Ile Pro Lys Met Ala Glu Met Pro Lys Phe Ser Asp Ile Pro Lys Met
85                  90                  95 gct gag atg cca aag tta tca gat atg ccc aga atg gct gac att cca     336
Ala Glu Met Pro Lys Leu Ser Asp Met Pro Arg Met Ala Asp Ile Pro
100                 105                 110 cag ttt cca gag atg cct agg atg gtt gac atg cct cag ttt cca gaa     384
Gln Phe Pro Glu Met Pro Arg Met Val Asp Met Pro Gln Phe Pro Glu
115                 120                 125 atc ccc agg atg gct gat atg cgg aga ttt ccg gag atg tcc aag ata     432
Ile Pro Arg Met Ala Asp Met Arg Arg Phe Pro Glu Met Ser Lys Ile
130                 135                 140 gct gac atg cca aag ttt cca gac atg cca aac gtc act gag atg cca     480
Ala Asp Met Pro Lys Phe Pro Asp Met Pro Asn Val Thr Glu Met Pro
145                 150                 155                 160 aag ctt gca gat ttg cca agg ctt gct gac atg ccc agt att gcc gac     528
Lys Leu Ala Asp Leu Pro Arg Leu Ala Asp Met Pro Ser Ile Ala Asp
```

```
atg ccc cgg ctc tca gac atg ccc agt att gca gac atg ccc cgg ctc     576
Met Pro Arg Leu Ser Asp Met Pro Ser Ile Ala Asp Met Pro Arg Leu
180                 185                 190 tca gac ata ccc agt att gcc gac atg ccc cgg ctc tca gac atg ccc     624
Ser Asp Ile Pro Ser Ile Ala Asp Met Pro Arg Leu Ser Asp Met Pro
195                 200                 205 agt att gcc gac atg ccg aaa ttc tct agt aac cga gtt cat ggg caa     672
Ser Ile Ala Asp Met Pro Lys Phe Ser Ser Asn Arg Val His Gly Gln
210                 215                 220 agt tac cat att ctg gcg ata tgg aca ccg tcc ctt tcc gga ctc aag     720
Ser Tyr His Ile Leu Ala Ile Trp Thr Pro Ser Leu Ser Gly Leu Lys
225                 230                 235                 240 gag ttt ttt acc ccg ctc tct gac cta atc aag cca gaa gct gct tcc     768
Glu Phe Phe Thr Pro Leu Ser Asp Leu Ile Lys Pro Glu Ala Ala Ser
245                 250                 255 ctg aca agc ctg gcc aag cca tct gga gtt ttt ctg aga acc ctg ctg     816
Leu Thr Ser Leu Ala Lys Pro Ser Gly Val Phe Leu Arg Thr Leu Leu
260                 265                 270 gct tgatgagaaa atgtatattg acaaatggct gtatctccat agttatagtg          869
Ala aggaatgtat tgacttattc cgaggactct atactgaacc cgcggcatac gaggaaactg   929
acaagttggt gatgtgcgtt tctgatcttc cccgaaaaga aaaaaaaatg accgtcttaa   989
aaaaaaaaaa aaaaaaaaaa aaaaaaaaaa aaaaaaaaa                         1029

<210> SEQ ID NO 12
<211> LENGTH: 273
<212> TYPE: PRT
<213> ORGANISM: Toxoplasma gondii

<400> SEQUENCE: 12

Glu Met Ser Ala Pro Asp Arg Gln Thr Gly Lys Leu Ser Asp Leu Pro
1               5                   10                  15

Pro Phe Ala Glu Leu Pro Gln Leu Ala Glu Ile Pro Lys Leu Ser Glu
            20                  25                  30

Leu Pro Lys Ile Ala Asp Met Pro Lys Phe Ser Asp Met Pro Lys Met
        35                  40                  45

Ala Glu Met Pro Lys Leu Ser Asp Ile Pro Lys Met Ala Glu Met Pro
    50                  55                  60

Lys Leu Ser Asp Ile Pro Lys Met Ala Glu Met Pro Lys Leu Ser Asp
65                  70                  75                  80

Ile Pro Lys Met Ala Glu Met Pro Lys Phe Ser Asp Ile Pro Lys Met
                85                  90                  95

Ala Glu Met Pro Lys Leu Ser Asp Met Pro Arg Met Ala Asp Ile Pro
            100                 105                 110

Gln Phe Pro Glu Met Pro Arg Met Val Asp Met Pro Gln Phe Pro Glu
        115                 120                 125

Ile Pro Arg Met Ala Asp Met Arg Arg Phe Pro Glu Met Ser Lys Ile
    130                 135                 140

Ala Asp Met Pro Lys Phe Pro Asp Met Pro Asn Val Thr Glu Met Pro
145                 150                 155                 160

Lys Leu Ala Asp Leu Pro Arg Leu Ala Asp Met Pro Ser Ile Ala Asp
                165                 170                 175

Met Pro Arg Leu Ser Asp Met Pro Ser Ile Ala Asp Met Pro Arg Leu
            180                 185                 190
```

Ser Asp Ile Pro Ser Ile Ala Asp Met Pro Arg Leu Ser Asp Met Pro
195                 200                 205

Ser Ile Ala Asp Met Pro Lys Phe Ser Ser Asn Arg Val His Gly Gln
210                 215                 220

Ser Tyr His Ile Leu Ala Ile Trp Thr Pro Ser Leu Ser Gly Leu Lys
225                 230                 235                 240

Glu Phe Phe Thr Pro Leu Ser Asp Leu Ile Lys Pro Glu Ala Ala Ser
245                 250                 255

Leu Thr Ser Leu Ala Lys Pro Ser Gly Val Phe Leu Arg Thr Leu Leu
260                 265                 270

Ala

<210> SEQ ID NO 13
<211> LENGTH: 425
<212> TYPE: DNA
<213> ORGANISM: Toxoplasma gondii
<220> FEATURE:
<221> NAME/KEY: CDS
<222> LOCATION: (1)..(423)
<223> OTHER INFORMATION:

<400> SEQUENCE: 13

```
cgc gga att ccg gat cag cgt agc agt cgc agc cac act gga gtg gaa       48
Arg Gly Ile Pro Asp Gln Arg Ser Ser Arg Ser His Thr Gly Val Glu
1               5                   10                  15 agt ctg gtt ttg ccc tcc aga ggg gag gaa gag gcg aga gag gag acg       96
Ser Leu Val Leu Pro Ser Arg Gly Glu Glu Glu Ala Arg Glu Glu Thr
            20                  25                  30 tct gca acg cgc cag atg ccg acg ctt ctc tct tcg ccg agg cct cca      144
Ser Ala Thr Arg Gln Met Pro Thr Leu Leu Ser Ser Pro Arg Pro Pro
35                  40                  45 ctc gcg ctg ggg ttg gga gac aag tct ccc tgc gga gag tgg gtg tcg      192
Leu Ala Leu Gly Leu Gly Asp Lys Ser Pro Cys Gly Glu Trp Val Ser
50                  55                  60 ccg aat gac atg gtt tct gcg ttg tcc ctc tgg gaa gca ggc gag gct      240
Pro Asn Asp Met Val Ser Ala Leu Ser Leu Trp Glu Ala Gly Glu Ala
65                  70                  75                  80 tgg cag ttc aag aca gcg aaa att ctt gac tct ttc gaa ggg gag acc      288
Trp Gln Phe Lys Thr Ala Lys Ile Leu Asp Ser Phe Glu Gly Glu Thr
            85                  90                  95 cca gaa ggg gag gga tgc ggc gca cag gaa aga agg aca gcc gca tgc      336
Pro Glu Gly Glu Gly Cys Gly Ala Gln Glu Arg Arg Thr Ala Ala Cys
            100                 105                 110 aag ctg gtg cga ctc ccg gtg aac gtg gag ggg cgg tcg aca aag gtg      384
Lys Leu Val Arg Leu Pro Val Asn Val Glu Gly Arg Ser Thr Lys Val
115                 120                 125 tgg agc ttg gct ctt ctt tct tct ctg cgt ctg aag atc cg              425
Trp Ser Leu Ala Leu Leu Ser Ser Leu Arg Leu Lys Ile
130                 135                 140
```

<210> SEQ ID NO 14
<211> LENGTH: 141
<212> TYPE: PRT
<213> ORGANISM: Toxoplasma gondii

<400> SEQUENCE: 14

Arg Gly Ile Pro Asp Gln Arg Ser Ser Arg Ser His Thr Gly Val Glu
1               5                   10                  15

Ser Leu Val Leu Pro Ser Arg Gly Glu Glu Glu Ala Arg Glu Glu Thr
            20                  25                  30

```
Ser Ala Thr Arg Gln Met Pro Thr Leu Leu Ser Ser Pro Arg Pro Pro
 35                  40                  45

Leu Ala Leu Gly Leu Gly Asp Lys Ser Pro Cys Gly Glu Trp Val Ser
 50                  55                  60

Pro Asn Asp Met Val Ser Ala Leu Ser Leu Trp Glu Ala Gly Glu Ala
 65                  70                  75                  80

Trp Gln Phe Lys Thr Ala Lys Ile Leu Asp Ser Phe Glu Gly Glu Thr
 85                  90                  95

Pro Glu Gly Glu Gly Cys Gly Ala Gln Glu Arg Arg Thr Ala Ala Cys
100                 105                 110

Lys Leu Val Arg Leu Pro Val Asn Val Glu Gly Arg Ser Thr Lys Val
115                 120                 125

Trp Ser Leu Ala Leu Leu Ser Ser Leu Arg Leu Lys Ile
130                 135                 140

<210> SEQ ID NO 15
<211> LENGTH: 417
<212> TYPE: DNA
<213> ORGANISM: Toxoplasma gondii
<220> FEATURE:
<221> NAME/KEY: CDS
<222> LOCATION: (1)..(417)
<223> OTHER INFORMATION:

<400> SEQUENCE: 15 cgc ggc ctt tcc gat gac gcc tct cac gcg gag acc cct tca ccg ctc      48
Arg Gly Leu Ser Asp Asp Ala Ser His Ala Glu Thr Pro Ser Pro Leu
 1               5                  10                  15 acg ccc tcg agg gtg gac agc ttc tca gac gga gtt gag aga aca cgc      96
Thr Pro Ser Arg Val Asp Ser Phe Ser Asp Gly Val Glu Arg Thr Arg
         20                  25                  30 aga agc tct ccg cga gtc gag gag cac cag acg agc tcg aga gag gaa     144
Arg Ser Ser Pro Arg Val Glu Glu His Gln Thr Ser Ser Arg Glu Glu
 35                  40                  45 aaa gct gcg aca gag cgc gtt cca aaa ctg tct cgt ctc ccc tcg ctc     192
Lys Ala Ala Thr Glu Arg Val Pro Lys Leu Ser Arg Leu Pro Ser Leu
 50                  55                  60 cga gct cct cta cgc agc acg gac cga cgc gcc tcg ccg cct cgt cgg     240
Arg Ala Pro Leu Arg Ser Thr Asp Arg Arg Ala Ser Pro Pro Arg Arg
 65                  70                  75                  80 ctg tcg caa ctt ctt cgc tgc tgc aca acc tcg aga ttc gcg agc aaa     288
Leu Ser Gln Leu Leu Arg Cys Cys Thr Thr Ser Arg Phe Ala Ser Lys
 85                  90                  95 gga acg gcg tat cca gac gag gag tgg ggg cat aga gtc cga gca cag     336
Gly Thr Ala Tyr Pro Asp Glu Glu Trp Gly His Arg Val Arg Ala Gln
100                 105                 110 aga aca gaa gag act gtc tcc tct ctg acg acg aag cgc ctt ctc act     384
Arg Thr Glu Glu Thr Val Ser Ser Leu Thr Thr Lys Arg Leu Leu Thr
115                 120                 125 cga agt cct aat tcg cag act gcc ttc ccg cgg                         417
Arg Ser Pro Asn Ser Gln Thr Ala Phe Pro Arg
130                 135

<210> SEQ ID NO 16
<211> LENGTH: 139
<212> TYPE: PRT
<213> ORGANISM: Toxoplasma gondii

<400> SEQUENCE: 16

Arg Gly Leu Ser Asp Asp Ala Ser His Ala Glu Thr Pro Ser Pro Leu
 1               5                  10                  15
```

Thr Pro Ser Arg Val Asp Ser Phe Ser Asp Gly Val Glu Arg Thr Arg
 20                  25                  30

Arg Ser Ser Pro Arg Val Glu Glu His Gln Thr Ser Ser Arg Glu Glu
 35                  40                  45

Lys Ala Ala Thr Glu Arg Val Pro Lys Leu Ser Arg Leu Pro Ser Leu
 50                  55                  60

Arg Ala Pro Leu Arg Ser Thr Asp Arg Arg Ala Ser Pro Pro Arg Arg
 65                  70                  75                  80

Leu Ser Gln Leu Leu Arg Cys Cys Thr Thr Ser Arg Phe Ala Ser Lys
             85                  90                  95

Gly Thr Ala Tyr Pro Asp Glu Glu Trp Gly His Arg Val Arg Ala Gln
100                 105                 110

Arg Thr Glu Glu Thr Val Ser Ser Leu Thr Thr Lys Arg Leu Leu Thr
115                 120                 125

Arg Ser Pro Asn Ser Gln Thr Ala Phe Pro Arg
130                 135

<210> SEQ ID NO 17
<211> LENGTH: 507
<212> TYPE: DNA
<213> ORGANISM: Toxoplasma gondii
<220> FEATURE:
<221> NAME/KEY: CDS
<222> LOCATION: (1)..(153)
<223> OTHER INFORMATION:

<400> SEQUENCE: 17 ggc agg gga agt gga cga cac ccg tcg ctg agc ttt cgc ctg gag tgg      48
Gly Arg Gly Ser Gly Arg His Pro Ser Leu Ser Phe Arg Leu Glu Trp
 1               5                  10                  15 aga cat cta cct gtg agt gaa cca ggc gtt ctg ctt tcg ccg ctc ctt      96
Arg His Leu Pro Val Ser Glu Pro Gly Val Leu Leu Ser Pro Leu Leu
 20                  25                  30 tgc agg cca gag gac aat gat aca aat ata agt gac act ctt ctc ttc     144
Cys Arg Pro Glu Asp Asn Asp Thr Asn Ile Ser Asp Thr Leu Leu Phe
 35                  40                  45 gat atc ggt taactgacaa agaaccacag cggagttaaa atagcagcgt             193
Asp Ile Gly
 50 ttgcagttca acgcatgcac aaactgctta actcccacat gcttgccttt gagagacgcg   253 acagcacatc gttcgagctt gcacgcagcg aagacatcta gacagcaatt aggagatgcc   313 tgccgaattt gtatgtaagg cgcaaacgtc tcctcggtgc gaatcacaat tacgcacatt   373 tgcccggact acatctgtc ttctactggg gtctttcctt gtcaaaccgt gccgctgcaa    433 ctccaaacta gctcgttagt gagatgctgg caaggttttg acaagaatcg agttctgcga   493 ctgcatcgtg gtcg                                                     507

<210> SEQ ID NO 18
<211> LENGTH: 51
<212> TYPE: PRT
<213> ORGANISM: Toxoplasma gondii

<400> SEQUENCE: 18

Gly Arg Gly Ser Gly Arg His Pro Ser Leu Ser Phe Arg Leu Glu Trp
 1               5                  10                  15

Arg His Leu Pro Val Ser Glu Pro Gly Val Leu Leu Ser Pro Leu Leu
 20                  25                  30

Cys Arg Pro Glu Asp Asn Asp Thr Asn Ile Ser Asp Thr Leu Leu Phe
35                  40                  45

Asp Ile Gly
50

<210> SEQ ID NO 19
<211> LENGTH: 718
<212> TYPE: DNA
<213> ORGANISM: Toxoplasma gondii
<220> FEATURE:
<221> NAME/KEY: CDS
<222> LOCATION: (1)..(297)
<223> OTHER INFORMATION:

<400> SEQUENCE: 19

| | | |
|---|---|---|
| gaa ttc cga ctg aat gac tac ctc ttt cag gtg cca gag ggt ccc ccc<br>Glu Phe Arg Leu Asn Asp Tyr Leu Phe Gln Val Pro Glu Gly Pro Pro<br>1               5                   10                  15 | 48 |
| gcg aga agc cat ggg ttc gac aga aga cga gca gca gcg agc aaa aac<br>Ala Arg Ser His Gly Phe Asp Arg Arg Arg Ala Ala Ala Ser Lys Asn<br>            20                  25                  30 | 96 |
| gca aca gaa gaa acg cgg agg ctg gcg ggc aaa gaa acg ccg ccg cac<br>Ala Thr Glu Glu Thr Arg Arg Leu Ala Gly Lys Glu Thr Pro Pro His<br>35                  40                  45 | 144 |
| aga gag gcc ccg gaa aag aca acg cga ggc gaa gaa gac aga caa gag<br>Arg Glu Ala Pro Glu Lys Thr Thr Arg Gly Glu Glu Asp Arg Gln Glu<br>50                  55                  60 | 192 |
| agc gag agg gaa aga agg cga gcc ggc gtg atg gac aaa aag aac cag<br>Ser Glu Arg Glu Arg Arg Arg Ala Gly Val Met Asp Lys Lys Asn Gln<br>65                  70                  75                  80 | 240 |
| gac ctt gac gat gaa acc cgg aga agg ggg acg gcg gag gag gag agg<br>Asp Leu Asp Asp Glu Thr Arg Arg Arg Gly Thr Ala Glu Glu Glu Arg<br>            85                  90                  95 | 288 |
| aat gga gac tgaaaaaagc cgaagatgac aggccagagt aagacgagga<br>Asn Gly Asp | 337 |
| ggtgcaggac aaggatgtct cttattcacc gagtctcgtt aaccagcgtt ggtcttatca | 397 |
| agaggtgcag gacacagatg agacatccgg ttcgtccaaa gaccagttgg agcactcgag | 457 |
| agaggcaaga cagaagctga gggttcgcga cagacatcca gctgcctccg cgggcgttgt | 517 |
| tcactgagga cttggtcgga aaggggagag aaacatagaa acgaagaaca ccaagacctg | 577 |
| gaagaggtgc agattcctct tgggcactcg caggagacgc cttcgtcagt ttttttgtt | 637 |
| cactcaacgg actctgtcgt cacgagggaa ctcagacaga gacctcaagg agacagagga | 697 |
| acgcaacgca cgtcggaatt c | 718 |

<210> SEQ ID NO 20
<211> LENGTH: 99
<212> TYPE: PRT
<213> ORGANISM: Toxoplasma gondii

<400> SEQUENCE: 20

Glu Phe Arg Leu Asn Asp Tyr Leu Phe Gln Val Pro Glu Gly Pro Pro
1               5                   10                  15

Ala Arg Ser His Gly Phe Asp Arg Arg Arg Ala Ala Ala Ser Lys Asn
            20                  25                  30

Ala Thr Glu Glu Thr Arg Arg Leu Ala Gly Lys Glu Thr Pro Pro His
35                  40                  45

Arg Glu Ala Pro Glu Lys Thr Thr Arg Gly Glu Glu Asp Arg Gln Glu
50                  55                  60

```
Ser Glu Arg Glu Arg Arg Ala Gly Val Met Asp Lys Lys Asn Gln
 65                  70                  75                  80

Asp Leu Asp Asp Glu Thr Arg Arg Gly Thr Ala Glu Glu Glu Arg
             85                  90                  95

Asn Gly Asp

<210> SEQ ID NO 21
<211> LENGTH: 441
<212> TYPE: DNA
<213> ORGANISM: Toxoplasma gondii
<220> FEATURE:
<221> NAME/KEY: CDS
<222> LOCATION: (1)..(441)
<223> OTHER INFORMATION:

<400> SEQUENCE: 21 cgg atc gcc tcg gca ctt cct cat tat ccg tcg cat ggg cat ttc ctg      48
Arg Ile Ala Ser Ala Leu Pro His Tyr Pro Ser His Gly His Phe Leu
 1               5                  10                  15 gaa gag gaa caa att ttg ctg ttg gat tgg cag tat caa ctt ggg caa      96
Glu Glu Glu Gln Ile Leu Leu Leu Asp Trp Gln Tyr Gln Leu Gly Gln
             20                  25                  30 cga ggc atg gag tcc ggt gta ccc ccc tgc gtg cag cat ggg gat gcg     144
Arg Gly Met Glu Ser Gly Val Pro Pro Cys Val Gln His Gly Asp Ala
         35                  40                  45 acg aga agt ttg act tca ccg aaa agg gat gtc agt cat gac ggt cac     192
Thr Arg Ser Leu Thr Ser Pro Lys Arg Asp Val Ser His Asp Gly His
 50                  55                  60 caa gga aac agc gga aca aac gca gat gaa gcc ggc caa ggg gcc atg     240
Gln Gly Asn Ser Gly Thr Asn Ala Asp Glu Ala Gly Gln Gly Ala Met
 65                  70                  75                  80 gca ggc cga gga aag tgc gag tgg agc cgc acc acc ggt gcc aac gta     288
Ala Gly Arg Gly Lys Cys Glu Trp Ser Arg Thr Thr Gly Ala Asn Val
             85                  90                  95 ggg tcg tcg tca tgt gtg gtt gat gcg tgt ttg gcg tct gcg ggt aga     336
Gly Ser Ser Ser Cys Val Val Asp Ala Cys Leu Ala Ser Ala Gly Arg
        100                 105                 110 cat cag gcg gcg agc atg cgt ccg ttt gca cga gat gga ttc ggc gag     384
His Gln Ala Ala Ser Met Arg Pro Phe Ala Arg Asp Gly Phe Gly Glu
115                 120                 125 tct act gcg gag aac aga ccc cgt cgg gac ggc gga ctg cca cgt tct     432
Ser Thr Ala Glu Asn Arg Pro Arg Arg Asp Gly Gly Leu Pro Arg Ser
130                 135                 140 ctt gga tcg                                                         441
Leu Gly Ser
145

<210> SEQ ID NO 22
<211> LENGTH: 147
<212> TYPE: PRT
<213> ORGANISM: Toxoplasma gondii

<400> SEQUENCE: 22

Arg Ile Ala Ser Ala Leu Pro His Tyr Pro Ser His Gly His Phe Leu
 1               5                  10                  15

Glu Glu Glu Gln Ile Leu Leu Leu Asp Trp Gln Tyr Gln Leu Gly Gln
             20                  25                  30

Arg Gly Met Glu Ser Gly Val Pro Pro Cys Val Gln His Gly Asp Ala
         35                  40                  45

Thr Arg Ser Leu Thr Ser Pro Lys Arg Asp Val Ser His Asp Gly His
 50                  55                  60
```

Gln Gly Asn Ser Gly Thr Asn Ala Asp Glu Ala Gly Gln Gly Ala Met
65                  70                  75                  80

Ala Gly Arg Gly Lys Cys Glu Trp Ser Arg Thr Thr Gly Ala Asn Val
            85                  90                  95

Gly Ser Ser Ser Cys Val Val Asp Ala Cys Leu Ala Ser Ala Gly Arg
        100                 105                 110

His Gln Ala Ala Ser Met Arg Pro Phe Ala Arg Asp Gly Phe Gly Glu
    115                 120                 125

Ser Thr Ala Glu Asn Arg Pro Arg Arg Asp Gly Gly Leu Pro Arg Ser
130                 135                 140

Leu Gly Ser
145

<210> SEQ ID NO 23
<211> LENGTH: 428
<212> TYPE: DNA
<213> ORGANISM: Toxoplasma gondii
<220> FEATURE:
<221> NAME/KEY: CDS
<222> LOCATION: (1)..(426)
<223> OTHER INFORMATION:

<400> SEQUENCE: 23

| cgg | cgg | cgt | cag | cgt | gca | gac | cct | tca | gac | tgg | gaa | gga | tgt | gag | aat | 48 |
|---|---|---|---|---|---|---|---|---|---|---|---|---|---|---|---|---|
| Arg | Arg | Arg | Gln | Arg | Ala | Asp | Pro | Ser | Asp | Trp | Glu | Gly | Cys | Glu | Asn | |
| 1 | | | | 5 | | | | | 10 | | | | | 15 | | |

| gtg | gaa | aag | gat | cat | ttc | ggg | agt | cgc | gag | agg | cac | tcg | aat | ggg | gaa | 96 |
|---|---|---|---|---|---|---|---|---|---|---|---|---|---|---|---|---|
| Val | Glu | Lys | Asp | His | Phe | Gly | Ser | Arg | Glu | Arg | His | Ser | Asn | Gly | Glu | |
| | 20 | | | | | 25 | | | | | 30 | | | | | |

| gag | ttc | aag | aca | cag | gga | aac | gtt | ggt | cga | ggt | tca | ctg | agg | cag | gaa | 144 |
|---|---|---|---|---|---|---|---|---|---|---|---|---|---|---|---|---|
| Glu | Phe | Lys | Thr | Gln | Gly | Asn | Val | Gly | Arg | Gly | Ser | Leu | Arg | Gln | Glu | |
| 35 | | | | | 40 | | | | | 45 | | | | | | |

| ccc | ttt | acc | gat | gga | gtg | tac | cac | gac | agg | cag | cag | cgc | ttc | tcg | gag | 192 |
|---|---|---|---|---|---|---|---|---|---|---|---|---|---|---|---|---|
| Pro | Phe | Thr | Asp | Gly | Val | Tyr | His | Asp | Arg | Gln | Gln | Arg | Phe | Ser | Glu | |
| 50 | | | | | 55 | | | | | 60 | | | | | | |

| aaa | gaa | cct | gcg | aag | ccg | atg | ttc | act | tcc | ctc | gcg | gat | ccg | agc | gtg | 240 |
|---|---|---|---|---|---|---|---|---|---|---|---|---|---|---|---|---|
| Lys | Glu | Pro | Ala | Lys | Pro | Met | Phe | Thr | Ser | Leu | Ala | Asp | Pro | Ser | Val | |
| 65 | | | | | 70 | | | | | 75 | | | | | 80 | |

| agg | aga | cat | ttt | aag | gag | gaa | gaa | gaa | cga | cgg | aaa | ttc | cag | gaa | aag | 288 |
|---|---|---|---|---|---|---|---|---|---|---|---|---|---|---|---|---|
| Arg | Arg | His | Phe | Lys | Glu | Glu | Glu | Glu | Arg | Arg | Lys | Phe | Gln | Glu | Lys | |
| 85 | | | | | 90 | | | | | 95 | | | | | | |

| gca | gaa | gag | gag | atc | ttg | cgc | ctt | ctc | aaa | cgc | gca | gct | gag | tgc | agc | 336 |
|---|---|---|---|---|---|---|---|---|---|---|---|---|---|---|---|---|
| Ala | Glu | Glu | Glu | Ile | Leu | Arg | Leu | Leu | Lys | Arg | Ala | Ala | Glu | Cys | Ser | |
| 100 | | | | | 105 | | | | | 110 | | | | | | |

| gag | gaa | gat | ttg | aaa | agg | gaa | gaa | cgc | tcc | gaa | aag | gct | acc | gaa | aag | 384 |
|---|---|---|---|---|---|---|---|---|---|---|---|---|---|---|---|---|
| Glu | Glu | Asp | Leu | Lys | Arg | Glu | Glu | Arg | Ser | Glu | Lys | Ala | Thr | Glu | Lys | |
| 115 | | | | | 120 | | | | | 125 | | | | | | |

| ggg | tcc | cgt | ctc | ttc | tct | gga | gag | gag | gtg | cga | ttc | ttt | ccg | cc | | 428 |
|---|---|---|---|---|---|---|---|---|---|---|---|---|---|---|---|---|
| Gly | Ser | Arg | Leu | Phe | Ser | Gly | Glu | Glu | Val | Arg | Phe | Phe | Pro | | | |
| 130 | | | | | 135 | | | | | 140 | | | | | | |

<210> SEQ ID NO 24
<211> LENGTH: 142
<212> TYPE: PRT
<213> ORGANISM: Toxoplasma gondii

<400> SEQUENCE: 24

Arg Arg Arg Gln Arg Ala Asp Pro Ser Asp Trp Glu Gly Cys Glu Asn
1               5                   10                  15

Val Glu Lys Asp His Phe Gly Ser Arg Glu Arg His Ser Asn Gly Glu

```
              20                  25                  30

Glu Phe Lys Thr Gln Gly Asn Val Gly Arg Gly Ser Leu Arg Gln Glu
 35                  40                  45

Pro Phe Thr Asp Gly Val Tyr His Asp Arg Gln Gln Arg Phe Ser Glu
 50                  55                  60

Lys Glu Pro Ala Lys Pro Met Phe Thr Ser Leu Ala Asp Pro Ser Val
 65                  70                  75                  80

Arg Arg His Phe Lys Glu Glu Glu Arg Arg Lys Phe Gln Glu Lys
 85                  90                  95

Ala Glu Glu Glu Ile Leu Arg Leu Leu Lys Arg Ala Ala Glu Cys Ser
100                 105                 110

Glu Glu Asp Leu Lys Arg Glu Glu Arg Ser Glu Lys Ala Thr Glu Lys
115                 120                 125

Gly Ser Arg Leu Phe Ser Gly Glu Glu Val Arg Phe Phe Pro
130                 135                 140

<210> SEQ ID NO 25
<211> LENGTH: 282
<212> TYPE: DNA
<213> ORGANISM: Toxoplasma gondii

<400> SEQUENCE: 25
cgcgacccgc tgccagtgtt ttgagtctaa ccgccgtatg tcgcggattc cacgtggaaa    60
acgacggacc gtcaagacgc ccgagagtgc cgcaatttca cggaccgttc gttcgattcc   120
accaacacct tacgctagcg cttgctagga aacacacatg cgacggcggc tggggcctgg   180
tcgcggatct atccgtacaa tgggagaatc gtctgatgtc tccactgtcc cgctaccgca   240
caggtcctct acaggccaca ccggtagaca gtgagcggcg gc                      282

<210> SEQ ID NO 26
<211> LENGTH: 304
<212> TYPE: DNA
<213> ORGANISM: Toxoplasma gondii
<220> FEATURE:
<221> NAME/KEY: CDS
<222> LOCATION: (1)..(303)
<223> OTHER INFORMATION:

<400> SEQUENCE: 26 cgg act ggc aca gga ccg aag cgc agt tcc tcg aaa ccg acg tcg act     48
Arg Thr Gly Thr Gly Pro Lys Arg Ser Ser Ser Lys Pro Thr Ser Thr
  1               5                  10                  15 tgg gtc cga ttg tta gtc cat act gaa aca aca atg gaa aac gaa ttg     96
Trp Val Arg Leu Leu Val His Thr Glu Thr Thr Met Glu Asn Glu Leu
 20                  25                  30 atg aac caa gta agc gac ctc tcg aat gag gct tgg caa aag aaa gaa    144
Met Asn Gln Val Ser Asp Leu Ser Asn Glu Ala Trp Gln Lys Lys Glu
 35                  40                  45 ctt ccc gtc cta cac aag tgg aca aac agc cct gaa cac tcc ctc ttg    192
Leu Pro Val Leu His Lys Trp Thr Asn Ser Pro Glu His Ser Leu Leu
 50                  55                  60 aca tcg gaa gac aga gaa aat agt ctt tca aag cca acc gcg gac tca    240
Thr Ser Glu Asp Arg Glu Asn Ser Leu Ser Lys Pro Thr Ala Asp Ser
 65                  70                  75                  80 cca gac agc ttc cgg tat ggc aca cgc aga caa agt cac gca aaa gat    288
Pro Asp Ser Phe Arg Tyr Gly Thr Arg Arg Gln Ser His Ala Lys Asp
 85                  90                  95 ctg ttc tcc gat ccc g                                               304
Leu Phe Ser Asp Pro
```

<210> SEQ ID NO 27
<211> LENGTH: 101
<212> TYPE: PRT
<213> ORGANISM: Toxoplasma gondii

<400> SEQUENCE: 27

```
Arg Thr Gly Thr Gly Pro Lys Arg Ser Ser Lys Pro Thr Ser Thr
1               5                   10                  15

Trp Val Arg Leu Leu Val His Thr Glu Thr Thr Met Glu Asn Glu Leu
 20                  25                  30

Met Asn Gln Val Ser Asp Leu Ser Asn Glu Ala Trp Gln Lys Lys Glu
 35                  40                  45

Leu Pro Val Leu His Lys Trp Thr Asn Ser Pro Glu His Ser Leu Leu
 50                  55                  60

Thr Ser Glu Asp Arg Glu Asn Ser Leu Ser Lys Pro Thr Ala Asp Ser
 65                  70                  75                  80

Pro Asp Ser Phe Arg Tyr Gly Thr Arg Arg Gln Ser His Ala Lys Asp
             85                  90                  95

Leu Phe Ser Asp Pro
100
```

<210> SEQ ID NO 28
<211> LENGTH: 284
<212> TYPE: DNA
<213> ORGANISM: Toxoplasma gondii
<220> FEATURE:
<221> NAME/KEY: CDS
<222> LOCATION: (1)..(282)
<223> OTHER INFORMATION:

<400> SEQUENCE: 28

```
ccg gac ttc ctc atg tct gaa gat gct tgt ctt gtt cgg ttc gtg cga     48
Pro Asp Phe Leu Met Ser Glu Asp Ala Cys Leu Val Arg Phe Val Arg
1               5                   10                  15 cac gcg tcg gcc aca cac gcg tat aca cgc agg gca agt gcg agg acg     96
His Ala Ser Ala Thr His Ala Tyr Thr Arg Arg Ala Ser Ala Arg Thr
 20                  25                  30 gta aag ccg ctc aaa ggc caa gga gac aaa gaa cag ggt gcg aca gga    144
Val Lys Pro Leu Lys Gly Gln Gly Asp Lys Glu Gln Gly Ala Thr Gly
 35                  40                  45 aga aat gtt gag gca ata aag aag gaa acc cct ctg aga cgg gaa gcg    192
Arg Asn Val Glu Ala Ile Lys Lys Glu Thr Pro Leu Arg Arg Glu Ala
 50                  55                  60 aga gaa aac gcg ttt ttt tcg acg ttt tcc ccc gac aga gcg agc gcc    240
Arg Glu Asn Ala Phe Phe Ser Thr Phe Ser Pro Asp Arg Ala Ser Ala
 65                  70                  75                  80 tcc tgt ctc cgc att cac gcg tgt gcc gcg gca gag gaa ccc gg         284
Ser Cys Leu Arg Ile His Ala Cys Ala Ala Glu Glu Pro
             85                  90
```

<210> SEQ ID NO 29
<211> LENGTH: 94
<212> TYPE: PRT
<213> ORGANISM: Toxoplasma gondii

<400> SEQUENCE: 29

```
Pro Asp Phe Leu Met Ser Glu Asp Ala Cys Leu Val Arg Phe Val Arg
1               5                   10                  15

His Ala Ser Ala Thr His Ala Tyr Thr Arg Arg Ala Ser Ala Arg Thr
```

```
                    20                  25                  30

Val Lys Pro Leu Lys Gly Gln Gly Asp Lys Glu Gln Gly Ala Thr Gly
 35                  40                  45

Arg Asn Val Glu Ala Ile Lys Lys Glu Thr Pro Leu Arg Arg Glu Ala
 50                  55                  60

Arg Glu Asn Ala Phe Phe Ser Thr Phe Ser Pro Asp Arg Ala Ser Ala
 65                  70                  75                  80

Ser Cys Leu Arg Ile His Ala Cys Ala Ala Glu Glu Pro
 85                  90

<210> SEQ ID NO 30
<211> LENGTH: 690
<212> TYPE: DNA
<213> ORGANISM: Toxoplasma gondii
<220> FEATURE:
<221> NAME/KEY: CDS
<222> LOCATION: (1)..(690)
<223> OTHER INFORMATION:

<400> SEQUENCE: 30 cga cgt ccc tac cac tat gaa atg ttg gac atc ccg agc atc cgg cgt    48
Arg Arg Pro Tyr His Tyr Glu Met Leu Asp Ile Pro Ser Ile Arg Arg
  1               5                  10                  15 gtg gag ttg cca ggt gcg cag gtc cgt atg cca atg gcc aaa gag ctc    96
Val Glu Leu Pro Gly Ala Gln Val Arg Met Pro Met Ala Lys Glu Leu
 20                  25                  30 gta cgc gat tgg ggt tct gtc gtc cag cag cag acg act tct gat tct   144
Val Arg Asp Trp Gly Ser Val Val Gln Gln Gln Thr Thr Ser Asp Ser
 35                  40                  45 tct agt gac aca cca gct acc cgc agt cgc tct gct gaa gca ctc tgt   192
Ser Ser Asp Thr Pro Ala Thr Arg Ser Arg Ser Ala Glu Ala Leu Cys
 50                  55                  60 gtc ttt tcg acg cct tgt aca gca gac agc gac caa cgt atg aaa ggc   240
Val Phe Ser Thr Pro Cys Thr Ala Asp Ser Asp Gln Arg Met Lys Gly
 65                  70                  75                  80 cgc cat tac cca cag tca tat cat acg ccg agg gac agc gcc acc aaa   288
Arg His Tyr Pro Gln Ser Tyr His Thr Pro Arg Asp Ser Ala Thr Lys
 85                  90                  95 aga gaa aaa cct ctc aaa agt aca ttt atc tgg ggc act aca gtg gaa   336
Arg Glu Lys Pro Leu Lys Ser Thr Phe Ile Trp Gly Thr Thr Val Glu
100                 105                 110 gac aga aac cac ccc atc agc cca gac ccg ttc tca agg ctg cag gga   384
Asp Arg Asn His Pro Ile Ser Pro Asp Pro Phe Ser Arg Leu Gln Gly
115                 120                 125 tgt ggc cag acc ctc cag gac gag ctc cca tca gct cgc act aga ccg   432
Cys Gly Gln Thr Leu Gln Asp Glu Leu Pro Ser Ala Arg Thr Arg Pro
130                 135                 140 gga tgg gcc gca ttg gac tcc cgc ctg aaa aac aag gac ccg cag att   480
Gly Trp Ala Ala Leu Asp Ser Arg Leu Lys Asn Lys Asp Pro Gln Ile
145                 150                 155                 160 agc gca gga gac gaa gcc gcg aag gtc gac gac acg tca gcg gaa cct   528
Ser Ala Gly Asp Glu Ala Ala Lys Val Asp Asp Thr Ser Ala Glu Pro
165                 170                 175 tgc ctg gga acg gta ccg tcc ttt tgt cgg ctt gta aca agt cac gac   576
Cys Leu Gly Thr Val Pro Ser Phe Cys Arg Leu Val Thr Ser His Asp
180                 185                 190 ttg cta gag gct gga gcg cag gtt cgt gtg ctt ggg cca acg aca gac   624
Leu Leu Glu Ala Gly Ala Gln Val Arg Val Leu Gly Pro Thr Thr Asp
195                 200                 205 ccg gag aca gag acc gct tct cag ctc cag aca act gag ctt gcc acg   672
Pro Glu Thr Glu Thr Ala Ser Gln Leu Gln Thr Thr Glu Leu Ala Thr
```

```
Pro Glu Thr Glu Thr Ala Ser Gln Leu Gln Thr Thr Glu Leu Ala Thr
210                 215                 220 ctg aca act gtg gat ccg                                              690
Leu Thr Thr Val Asp Pro
225                 230

<210> SEQ ID NO 31
<211> LENGTH: 230
<212> TYPE: PRT
<213> ORGANISM: Toxoplasma gondii

<400> SEQUENCE: 31

Arg Arg Pro Tyr His Tyr Glu Met Leu Asp Ile Pro Ser Ile Arg Arg
1               5                   10                  15

Val Glu Leu Pro Gly Ala Gln Val Arg Met Pro Met Ala Lys Glu Leu
            20                  25                  30

Val Arg Asp Trp Gly Ser Val Val Gln Gln Thr Thr Ser Asp Ser
        35                  40                  45

Ser Ser Asp Thr Pro Ala Thr Arg Ser Arg Ser Ala Glu Ala Leu Cys
50                  55                  60

Val Phe Ser Thr Pro Cys Thr Ala Asp Ser Asp Gln Arg Met Lys Gly
65                  70                  75                  80

Arg His Tyr Pro Gln Ser Tyr His Thr Pro Arg Asp Ser Ala Thr Lys
                85                  90                  95

Arg Glu Lys Pro Leu Lys Ser Thr Phe Ile Trp Gly Thr Thr Val Glu
            100                 105                 110

Asp Arg Asn His Pro Ile Ser Pro Asp Pro Phe Ser Arg Leu Gln Gly
        115                 120                 125

Cys Gly Gln Thr Leu Gln Asp Glu Leu Pro Ser Ala Arg Thr Arg Pro
130                 135                 140

Gly Trp Ala Ala Leu Asp Ser Arg Leu Lys Asn Lys Asp Pro Gln Ile
145                 150                 155                 160

Ser Ala Gly Asp Glu Ala Ala Lys Val Asp Asp Thr Ser Ala Glu Pro
                165                 170                 175

Cys Leu Gly Thr Val Pro Ser Phe Cys Arg Leu Val Thr Ser His Asp
            180                 185                 190

Leu Leu Glu Ala Gly Ala Gln Val Arg Val Leu Gly Pro Thr Thr Asp
        195                 200                 205

Pro Glu Thr Glu Thr Ala Ser Gln Leu Gln Thr Thr Glu Leu Ala Thr
210                 215                 220

Leu Thr Thr Val Asp Pro
225                 230

<210> SEQ ID NO 32
<211> LENGTH: 313
<212> TYPE: DNA
<213> ORGANISM: Toxoplasma gondii
<220> FEATURE:
<221> NAME/KEY: CDS
<222> LOCATION: (1)..(162)
<223> OTHER INFORMATION:

<400> SEQUENCE: 32 cgc agg aat aat cct gac ggt cag acg cag cgg ttc gtg cag aca gtg   48
Arg Arg Asn Asn Pro Asp Gly Gln Thr Gln Arg Phe Val Gln Thr Val
1               5                   10                  15 aag caa tgg cag agt gta aaa agc aga acc aga gcg tgt ctg tcg gcc   96
Lys Gln Trp Gln Ser Val Lys Ser Arg Thr Arg Ala Cys Leu Ser Ala
            20                  25                  30
```

```
aaa gga aag aga agg caa atc aca cag cga ata aac ctc acc tct gtc      144
Lys Gly Lys Arg Arg Gln Ile Thr Gln Arg Ile Asn Leu Thr Ser Val
 35                  40                  45 tcg cac ccc gaa gca acg taggagagcc actggtgccg ccactctgtg             192
Ser His Pro Glu Ala Thr
 50 ctgacaaaaa agaaccggcc cttcttcggc aggggcgtag ccagtctgca gacatttcaa    252 tttcgaagcg accggaagca gtgaaatttc cagggaagac gcccaggaga cgtcaacagc    312 g                                                                    313

<210> SEQ ID NO 33
<211> LENGTH: 54
<212> TYPE: PRT
<213> ORGANISM: Toxoplasma gondii

<400> SEQUENCE: 33

Arg Arg Asn Asn Pro Asp Gly Gln Thr Gln Arg Phe Val Gln Thr Val
 1               5                  10                  15

Lys Gln Trp Gln Ser Val Lys Ser Arg Thr Arg Ala Cys Leu Ser Ala
 20                  25                  30

Lys Gly Lys Arg Arg Gln Ile Thr Gln Arg Ile Asn Leu Thr Ser Val
 35                  40                  45

Ser His Pro Glu Ala Thr
 50

<210> SEQ ID NO 34
<211> LENGTH: 389
<212> TYPE: DNA
<213> ORGANISM: Toxoplasma gondii
<220> FEATURE:
<221> NAME/KEY: CDS
<222> LOCATION: (1)..(195)
<223> OTHER INFORMATION:

<400> SEQUENCE: 34 cgc tct cac gga ggc gca agt gag ttt tgg ctt tac ctc ttg aga aaa      48
Arg Ser His Gly Gly Ala Ser Glu Phe Trp Leu Tyr Leu Leu Arg Lys
 1               5                  10                  15 cgg aac tct cca gaa gat cct cgt tcc gtc cgt cct cca cgt ccg tgt      96
Arg Asn Ser Pro Glu Asp Pro Arg Ser Val Arg Pro Pro Arg Pro Cys
 20                  25                  30 gtc ttt cga gag atg gac aaa cag aga agc aga atc aag aaa gga ttc     144
Val Phe Arg Glu Met Asp Lys Gln Arg Ser Arg Ile Lys Lys Gly Phe
 35                  40                  45 gca ttt gca ctt ggg tct gtc ttt tac ttc caa ggt cgt gaa ttt cat     192
Ala Phe Ala Leu Gly Ser Val Phe Tyr Phe Gln Gly Arg Glu Phe His
 50                  55                  60 gcg tgacgaataa gagagacagg agtaggccgc aacttctcgt ctcttggcag          245
Ala
 65 tttccgattt ctcttccttc cgaagcccct gctgccaagc actccatccg gtccggttgg   305 tctctctcag gttcttcgag caatcgacgc gatgttctct gctgtcgatg cggggcttg    365 gcgtgtctgc atatctcttc cagg                                          389

<210> SEQ ID NO 35
<211> LENGTH: 65
<212> TYPE: PRT
<213> ORGANISM: Toxoplasma gondii
```

<400> SEQUENCE: 35

```
Arg Ser His Gly Gly Ala Ser Glu Phe Trp Leu Tyr Leu Leu Arg Lys
1               5                   10                  15

Arg Asn Ser Pro Glu Asp Pro Arg Ser Val Arg Pro Arg Pro Cys
            20                  25                  30

Val Phe Arg Glu Met Asp Lys Gln Arg Ser Arg Ile Lys Lys Gly Phe
 35                  40                  45

Ala Phe Ala Leu Gly Ser Val Phe Tyr Phe Gln Gly Arg Glu Phe His
 50                  55                  60

Ala
 65
```

<210> SEQ ID NO 36
<211> LENGTH: 548
<212> TYPE: DNA
<213> ORGANISM: Toxoplasma gondii
<220> FEATURE:
<221> NAME/KEY: CDS
<222> LOCATION: (1)..(546)
<223> OTHER INFORMATION:

<400> SEQUENCE: 36

```
cga tct tct tct cac cgt tcg ctc ttc ttt ctc tcc gtt gtc tgc gtc      48
Arg Ser Ser Ser His Arg Ser Leu Phe Phe Leu Ser Val Val Cys Val
1               5                   10                  15 ctc tcc cca ctg cct ctc gcc gtc cgc gtc gtt cgc ctc cgg ggg agc      96
Leu Ser Pro Leu Pro Leu Ala Val Arg Val Val Arg Leu Arg Gly Ser
            20                  25                  30 cgg cag tgt ggc gag cac ggc ggc ttc gct cga aga gca gcg cct cgc     144
Arg Gln Cys Gly Glu His Gly Gly Phe Ala Arg Arg Ala Ala Pro Arg
 35                  40                  45 gcg ttc ctt cgg gga cgc ccg aca agc ctg cgt tca tcc cag aga acg     192
Ala Phe Leu Arg Gly Arg Pro Thr Ser Leu Arg Ser Ser Gln Arg Thr
 50                  55                  60 cct cgg tct gcg caa atg cgc cgt cgc tcc cca cac atg aga tgc ttt     240
Pro Arg Ser Ala Gln Met Arg Arg Arg Ser Pro His Met Arg Cys Phe
 65                  70                  75                  80 tgc gag act ggc agc agc gcc tgt tgc gag cga agg aag agg agc gcg     288
Cys Glu Thr Gly Ser Ser Ala Cys Cys Glu Arg Arg Lys Arg Ser Ala
                 85                  90                  95 agg gat ggc aac ctc cag gag agc gcg aag aag gcc cgt ccc tcg aat     336
Arg Asp Gly Asn Leu Gln Glu Ser Ala Lys Lys Ala Arg Pro Ser Asn
            100                 105                 110 ccg atg agc aag gca atc cat gct tca gtc gac cga gtc cag tgc ggt     384
Pro Met Ser Lys Ala Ile His Ala Ser Val Asp Arg Val Gln Cys Gly
 115                 120                 125 caa cag gac tcg aaa agg tcg agg aga tgg ccg gcg gct tcg act tct     432
Gln Gln Asp Ser Lys Arg Ser Arg Arg Trp Pro Ala Ala Ser Thr Ser
 130                 135                 140 gcg ggg gtg cag gcg att cgt gga aga aac agc gaa gtc ccg agg gtg     480
Ala Gly Val Gln Ala Ile Arg Gly Arg Asn Ser Glu Val Pro Arg Val
 145                 150                 155                 160 gac agg tcc gcc aag tcg cct acg cca ctc tcg aag aag ccg aaa atg     528
Asp Arg Ser Ala Lys Ser Pro Thr Pro Leu Ser Lys Lys Pro Lys Met
 165                 170                 175 cgg tct ctg ccg cat acg gc                                           548
Arg Ser Leu Pro His Thr
 180
```

<210> SEQ ID NO 37

```
<211> LENGTH: 182
<212> TYPE: PRT
<213> ORGANISM: Toxoplasma gondii

<400> SEQUENCE: 37

Arg Ser Ser Ser His Arg Ser Leu Phe Phe Leu Ser Val Val Cys Val
1               5                   10                  15

Leu Ser Pro Leu Pro Leu Ala Val Arg Val Val Arg Leu Arg Gly Ser
            20                  25                  30

Arg Gln Cys Gly Glu His Gly Gly Phe Ala Arg Arg Ala Ala Pro Arg
        35                  40                  45

Ala Phe Leu Arg Gly Arg Pro Thr Ser Leu Arg Ser Ser Gln Arg Thr
    50                  55                  60

Pro Arg Ser Ala Gln Met Arg Arg Ser Pro His Met Arg Cys Phe
65                  70                  75                  80

Cys Glu Thr Gly Ser Ser Ala Cys Cys Glu Arg Arg Lys Arg Ser Ala
        85                  90                  95

Arg Asp Gly Asn Leu Gln Glu Ser Ala Lys Lys Ala Arg Pro Ser Asn
100                 105                 110

Pro Met Ser Lys Ala Ile His Ala Ser Val Asp Arg Val Gln Cys Gly
115                 120                 125

Gln Gln Asp Ser Lys Arg Ser Arg Arg Trp Pro Ala Ala Ser Thr Ser
130                 135                 140

Ala Gly Val Gln Ala Ile Arg Gly Arg Asn Ser Glu Val Pro Arg Val
145                 150                 155                 160

Asp Arg Ser Ala Lys Ser Pro Thr Pro Leu Ser Lys Lys Pro Lys Met
165                 170                 175

Arg Ser Leu Pro His Thr
180

<210> SEQ ID NO 38
<211> LENGTH: 310
<212> TYPE: DNA
<213> ORGANISM: Toxoplasma gondii
<220> FEATURE:
<221> NAME/KEY: CDS
<222> LOCATION: (1)..(285)
<223> OTHER INFORMATION:
<220> FEATURE:
<221> NAME/KEY: misc_feature
<222> LOCATION: (46)..(46)
<223> OTHER INFORMATION: At nucleotide 46, y = c or t/u
      At amino acid residue 16, Xaa = Arg or Cys
<220> FEATURE:
<221> NAME/KEY: misc_feature
<222> LOCATION: (69)..(69)
<223> OTHER INFORMATION: At nucleotide 69, m = a or c
      At amino acid residue 23, Xaa = Thr
<220> FEATURE:
<221> NAME/KEY: misc_feature
<222> LOCATION: (72)..(72)
<223> OTHER INFORMATION: At nucleotide 72, m = a or c
      At amino acid residue 24, Xaa = Glu or Asp
<220> FEATURE:
<221> NAME/KEY: misc_feature
<222> LOCATION: (74)..(75)
<223> OTHER INFORMATION: At nucleotide 74, m = a or c
      At nucleotide 75, w = a or t/u
      At amino acid residue 25, Xaa = Glu, Asp or Ala
<220> FEATURE:
<221> NAME/KEY: misc_feature
<222> LOCATION: (94)..(94)
<223> OTHER INFORMATION: At nucleotide 94, s = c or g
      At amino acid residue 32, Xaa = Val or Leu
<220> FEATURE:
<221> NAME/KEY: misc_feature
```

```
<222> LOCATION: (112)..(112)
<223> OTHER INFORMATION: At nucleotide 112, s = c or g
      At amino acid residue 38, Xaa = Gly or Arg
<220> FEATURE:
<221> NAME/KEY: misc_feature
<222> LOCATION: (135)..(135)
<223> OTHER INFORMATION: At nucleotide 135, w = a or t/u
      At amino acid residue 45, Xaa = Gln or His
<220> FEATURE:
<221> NAME/KEY: misc_feature
<222> LOCATION: (169)..(169)
<223> OTHER INFORMATION: At nucleotide 169, s = c or g
      At amino acid residue 57, Xaa = Gly, Glu, Arg or Gln
<220> FEATURE:
<221> NAME/KEY: misc_feature
<222> LOCATION: (238)..(238)
<223> OTHER INFORMATION: At nucleotide 238, m = a or c
      At amino acid residue 80, Xaa = Arg

<400> SEQUENCE: 38 cgg gat cca gct gca cct aac agc aca cag gct gtg gca gcc gct ygt      48
Arg Asp Pro Ala Ala Pro Asn Ser Thr Gln Ala Val Ala Ala Ala Xaa
1               5                   10                  15 acc gtg gta gtg atg aaa acm gam gmw gaa gtg tcc ggt gac aac stc      96
Thr Val Val Val Met Lys Xaa Xaa Xaa Glu Val Ser Gly Asp Asn Xaa
            20                  25                  30 agt caa ccg ggt agg sgt ccg ccg tcg cca aag ccg caw acg acg aag     144
Ser Gln Pro Gly Arg Xaa Pro Pro Ser Pro Lys Pro Xaa Thr Thr Lys
35                  40                  45 ttt ccg cgg aga gag tca cca gac srg cag ggg acg agg cgg aga act     192
Phe Pro Arg Arg Glu Ser Pro Asp Xaa Gln Gly Thr Arg Arg Arg Thr
50                  55                  60 gaa agc cga ggc gct gtt agc agg gta tgg cca ggg gaa aac cag mga     240
Glu Ser Arg Gly Ala Val Ser Arg Val Trp Pro Gly Glu Asn Gln Xaa
65                  70                  75                  80 aga ctg tct gcc gtc gac gat tcg ata ccg gct aac cca tcg ctt         285
Arg Leu Ser Ala Val Asp Asp Ser Ile Pro Ala Asn Pro Ser Leu
85                  90                  95 tgaacgggtg gcgccctgcg atccg                                         310

<210> SEQ ID NO 39
<211> LENGTH: 95
<212> TYPE: PRT
<213> ORGANISM: Toxoplasma gondii
<220> FEATURE:
<221> NAME/KEY: misc_feature
<222> LOCATION: (16)..(16)
<223> OTHER INFORMATION: The 'Xaa' at location 16 stands for Arg, or Cys.
<220> FEATURE:
<221> NAME/KEY: misc_feature
<222> LOCATION: (23)..(23)
<223> OTHER INFORMATION: The 'Xaa' at location 23 stands for Thr.
<220> FEATURE:
<221> NAME/KEY: misc_feature
<222> LOCATION: (24)..(24)
<223> OTHER INFORMATION: The 'Xaa' at location 24 stands for Glu, or Asp.
<220> FEATURE:
<221> NAME/KEY: misc_feature
<222> LOCATION: (25)..(25)
<223> OTHER INFORMATION: The 'Xaa' at location 25 stands for Glu, Asp,
      or Ala.
<220> FEATURE:
<221> NAME/KEY: misc_feature
<222> LOCATION: (32)..(32)
<223> OTHER INFORMATION: The 'Xaa' at location 32 stands for Val, or Leu.
<220> FEATURE:
<221> NAME/KEY: misc_feature
<222> LOCATION: (38)..(38)
<223> OTHER INFORMATION: The 'Xaa' at location 38 stands for Gly, or Arg.
<220> FEATURE:
<221> NAME/KEY: misc_feature
```

```
<222> LOCATION: (45)..(45)
<223> OTHER INFORMATION: The 'Xaa' at location 45 stands for Gln, or His.
<220> FEATURE:
<221> NAME/KEY: misc_feature
<222> LOCATION: (57)..(57)
<223> OTHER INFORMATION: The 'Xaa' at location 57 stands for Gly, Glu,
      Arg, or Gln.
<220> FEATURE:
<221> NAME/KEY: misc_feature
<222> LOCATION: (80)..(80)
<223> OTHER INFORMATION: The 'Xaa' at location 80 stands for Arg.
<220> FEATURE:
<221> NAME/KEY: misc_feature
<222> LOCATION: (46)..(46)
<223> OTHER INFORMATION: At nucleotide 46, y = c or t/u
      At amino acid residue 16, Xaa = Arg or Cys
<220> FEATURE:
<221> NAME/KEY: misc_feature
<222> LOCATION: (69)..(69)
<223> OTHER INFORMATION: At nucleotide 69, m = a or c
      At amino acid residue 23, Xaa = Thr
<220> FEATURE:
<221> NAME/KEY: misc_feature
<222> LOCATION: (72)..(72)
<223> OTHER INFORMATION: At nucleotide 72, m = a or c
      At amino acid residue 24, Xaa = Glu or Asp
<220> FEATURE:
<221> NAME/KEY: misc_feature
<222> LOCATION: (74)..(75)
<223> OTHER INFORMATION: At nucleotide 74, m = a or c
      At nucleotide 75, w = a or t/u
      At amino acid residue 25, Xaa = Glu, Asp or Ala
<220> FEATURE:
<221> NAME/KEY: misc_feature
<222> LOCATION: (94)..(94)
<223> OTHER INFORMATION: At nucleotide 94, s = c or g
      At amino acid residue 32, Xaa = Val or Leu
<220> FEATURE:
<221> NAME/KEY: misc_feature
<222> LOCATION: (112)..(112)
<223> OTHER INFORMATION: At nucleotide 112, s = c or g
      At amino acid residue 38, Xaa = Gly or Arg
<220> FEATURE:
<221> NAME/KEY: misc_feature
<222> LOCATION: (135)..(135)
<223> OTHER INFORMATION: At nucleotide 135, w = a or t/u
      At amino acid residue 45, Xaa = Gln or His
<220> FEATURE:
<221> NAME/KEY: misc_feature
<222> LOCATION: (169)..(169)
<223> OTHER INFORMATION: At nucleotide 169, s = c or g
      At amino acid residue 57, Xaa = Gly, Glu, Arg or Gln
<220> FEATURE:
<221> NAME/KEY: misc_feature
<222> LOCATION: (238)..(238)
<223> OTHER INFORMATION: At nucleotide 238, m = a or c
      At amino acid residue 80, Xaa = Arg

<400> SEQUENCE: 39

Arg Asp Pro Ala Ala Pro Asn Ser Thr Gln Ala Val Ala Ala Ala Xaa
1               5                   10                  15

Thr Val Val Val Met Lys Xaa Xaa Xaa Glu Val Ser Gly Asp Asn Xaa
            20                  25                  30

Ser Gln Pro Gly Arg Xaa Pro Pro Ser Pro Lys Pro Xaa Thr Thr Lys
        35                  40                  45

Phe Pro Arg Arg Glu Ser Pro Asp Xaa Gln Gly Thr Arg Arg Thr
50                  55                  60

Glu Ser Arg Gly Ala Val Ser Arg Val Trp Pro Gly Glu Asn Gln Xaa
65                  70                  75                  80

Arg Leu Ser Ala Val Asp Asp Ser Ile Pro Ala Asn Pro Ser Leu
85                  90                  95
```

```
<210> SEQ ID NO 40
<211> LENGTH: 220
<212> TYPE: DNA
<213> ORGANISM: Toxoplasma gondii
<220> FEATURE:
<221> NAME/KEY: CDS
<222> LOCATION: (1)..(219)
<223> OTHER INFORMATION:

<400> SEQUENCE: 40 cgg gat cct tgc ctc agt gtc agg gac atc gag cgt atg ttc cgt ata        48
Arg Asp Pro Cys Leu Ser Val Arg Asp Ile Glu Arg Met Phe Arg Ile
1               5                   10                  15 tgt cac cat cgt tct ctg tct cgc ctc ctt ggc gcc tct gtt gct tgg        96
Cys His His Arg Ser Leu Ser Arg Leu Leu Gly Ala Ser Val Ala Trp
            20                  25                  30 gat gca gtt gac tgc tct tcg gct tcg tcg cgc aca cac tgg tcc ttg       144
Asp Ala Val Asp Cys Ser Ser Ala Ser Ser Arg Thr His Trp Ser Leu
35                  40                  45 ctt gcg tct gag ctc cct tcc gaa cgg gtt ctt ttt cga ctg cag gtt       192
Leu Ala Ser Glu Leu Pro Ser Glu Arg Val Leu Phe Arg Leu Gln Val
50                  55                  60 ctt cta aaa ttg cca gtt ccc gat ccc g                                 220
Leu Leu Lys Leu Pro Val Pro Asp Pro
65                  70

<210> SEQ ID NO 41
<211> LENGTH: 73
<212> TYPE: PRT
<213> ORGANISM: Toxoplasma gondii

<400> SEQUENCE: 41

Arg Asp Pro Cys Leu Ser Val Arg Asp Ile Glu Arg Met Phe Arg Ile
1               5                   10                  15

Cys His His Arg Ser Leu Ser Arg Leu Leu Gly Ala Ser Val Ala Trp
            20                  25                  30

Asp Ala Val Asp Cys Ser Ser Ala Ser Ser Arg Thr His Trp Ser Leu
35                  40                  45

Leu Ala Ser Glu Leu Pro Ser Glu Arg Val Leu Phe Arg Leu Gln Val
50                  55                  60

Leu Leu Lys Leu Pro Val Pro Asp Pro
65                  70

<210> SEQ ID NO 42
<211> LENGTH: 642
<212> TYPE: DNA
<213> ORGANISM: Toxoplasma gondii
<220> FEATURE:
<221> NAME/KEY: CDS
<222> LOCATION: (1)..(102)
<223> OTHER INFORMATION:
<220> FEATURE:
<221> NAME/KEY: misc_feature
<222> LOCATION: (19)..(19)
<223> OTHER INFORMATION: At nucleotide 19, n = unknown
     At amino acid residue 7, Xaa = Ile, Val, Leu or Phe
<220> FEATURE:
<221> NAME/KEY: misc_feature
<222> LOCATION: (23)..(23)
<223> OTHER INFORMATION: At nucleotide 23, n = unknown
     At amino acid residue 8, Xaa = Ser or Leu
<220> FEATURE:
<221> NAME/KEY: misc_feature
<222> LOCATION: (27)..(27)
<223> OTHER INFORMATION: At nucleotide 27, n = unknown
     At amino acid residue 9, Xaa = Tyr
<220> FEATURE:
```

-continued

```
<221> NAME/KEY: misc_feature
<222> LOCATION: (28)..(29)
<223> OTHER INFORMATION: At nucleotides 28 and 29, n = unknown
      At amino acid residue 10, Xaa = Asn, Ser, Thr, Ile, Asp, Gly, Ala
      , Val, His, Arg, Pro, Leu, Tyr, Cys or Phe
<220> FEATURE:
<221> NAME/KEY: misc_feature
<222> LOCATION: (41)..(41)
<223> OTHER INFORMATION: At nucleotide 41, n = unknown
      At amino acid residue 14, Xaa = Lys, Arg, Thr or ILE
<220> FEATURE:
<221> NAME/KEY: misc_feature
<222> LOCATION: (86)..(86)
<223> OTHER INFORMATION: At nucleotide 86, n = unknown
      At amino acid residue 29, Xaa = Lys, Arg, Thr or Met
<220> FEATURE:
<221> NAME/KEY: misc_feature
<222> LOCATION: (88)..(88)
<223> OTHER INFORMATION: At nucleotide 88, n = unknown
      At amino acid residue 30, Xaa = Lys, Glu or Gln
<220> FEATURE:
<221> NAME/KEY: misc_feature
<222> LOCATION: (96)..(96)
<223> OTHER INFORMATION: At nucleotide 96, n = unknown
      At amino acid residue 32, Xaa = Thr
<220> FEATURE:
<221> NAME/KEY: misc_feature
<222> LOCATION: (110)..(111)
<223> OTHER INFORMATION: n = unknown
<220> FEATURE:
<221> NAME/KEY: misc_feature
<222> LOCATION: (113)..(113)
<223> OTHER INFORMATION: n = unknown
<220> FEATURE:
<221> NAME/KEY: misc_feature
<222> LOCATION: (119)..(119)
<223> OTHER INFORMATION: n = unknown
<220> FEATURE:
<221> NAME/KEY: misc_feature
<222> LOCATION: (122)..(122)
<223> OTHER INFORMATION: n = unknown
<220> FEATURE:
<221> NAME/KEY: misc_feature
<222> LOCATION: (132)..(132)
<223> OTHER INFORMATION: n = unknown
<220> FEATURE:
<221> NAME/KEY: misc_feature
<222> LOCATION: (137)..(137)
<223> OTHER INFORMATION: n = unknown
<220> FEATURE:
<221> NAME/KEY: misc_feature
<222> LOCATION: (149)..(149)
<223> OTHER INFORMATION: n = unknown
<220> FEATURE:
<221> NAME/KEY: misc_feature
<222> LOCATION: (164)..(164)
<223> OTHER INFORMATION: n = unknown
<220> FEATURE:
<221> NAME/KEY: misc_feature
<222> LOCATION: (169)..(169)
<223> OTHER INFORMATION: n = unknown
<220> FEATURE:
<221> NAME/KEY: misc_feature
<222> LOCATION: (172)..(173)
<223> OTHER INFORMATION: n = unknown
<220> FEATURE:
<221> NAME/KEY: misc_feature
<222> LOCATION: (209)..(209)
<223> OTHER INFORMATION: n = unknown
<220> FEATURE:
<221> NAME/KEY: misc_feature
<222> LOCATION: (217)..(217)
<223> OTHER INFORMATION: n = unknown
<220> FEATURE:
<221> NAME/KEY: misc_feature
<222> LOCATION: (220)..(220)
<223> OTHER INFORMATION: n = unknown
<220> FEATURE:
<221> NAME/KEY: misc_feature
```

```
<222> LOCATION: (234)..(234)
<223> OTHER INFORMATION: n = unknown
<220> FEATURE:
<221> NAME/KEY: misc_feature
<222> LOCATION: (236)..(236)
<223> OTHER INFORMATION: n = unknown
<220> FEATURE:
<221> NAME/KEY: misc_feature
<222> LOCATION: (250)..(250)
<223> OTHER INFORMATION: n = unknown
<220> FEATURE:
<221> NAME/KEY: misc_feature
<222> LOCATION: (257)..(257)
<223> OTHER INFORMATION: n = unknown
<220> FEATURE:
<221> NAME/KEY: misc_feature
<222> LOCATION: (492)..(492)
<223> OTHER INFORMATION: n = unknown
<220> FEATURE:
<221> NAME/KEY: misc_feature
<222> LOCATION: (505)..(505)
<223> OTHER INFORMATION: n = unknown
<220> FEATURE:
<221> NAME/KEY: misc_feature
<222> LOCATION: (512)..(512)
<223> OTHER INFORMATION: n = unknown
<220> FEATURE:
<221> NAME/KEY: misc_feature
<222> LOCATION: (524)..(524)
<223> OTHER INFORMATION: n = unknown
<220> FEATURE:
<221> NAME/KEY: misc_feature
<222> LOCATION: (527)..(527)
<223> OTHER INFORMATION: n = unknown
<220> FEATURE:
<221> NAME/KEY: misc_feature
<222> LOCATION: (533)..(533)
<223> OTHER INFORMATION: n = unknown

<400> SEQUENCE: 42 cgg cgg gaa acc atg gag ntt tna tan nnt aca act tcc ana tgc atg      48
Arg Arg Glu Thr Met Glu Xaa Xaa Xaa Xaa Thr Thr Ser Xaa Cys Met
1               5                   10                  15 gta ggt acc caa aat gca aac tat aga cac aaa caa ang naa aat acn      96
Val Gly Thr Gln Asn Ala Asn Tyr Arg His Lys Gln Xaa Xaa Asn Xaa
        20                  25                  30 tgg ggg tgatgcanna ngggggangtn ggggacagan aaatngtcct tcagttntca     152
Trp Gly tctttgcccg cngcgtngan nacgcaatac agcgggcgca gcggctcatc acaccantac   212
acganttntg caaagaagca cntntcttct ctcttcangt ctctntacca cttctaccac   272
ctgcaccccc gcttcgtcca caaaacacat ttgaacgatg tgaccaaaat gatccacaaa   332
aacacgattg tttcgtcaca tgaaacctca gcaaattcag gcgccaggac ggctccttca   392
aacgtctaat ccagagtcct ctccgctcaa aaacacgatt gtttcgtcac atggaacctc   452
agcaaattca ggcgccagga cggcctccct tcaaacgtcn taatccagag tcntttccgn   512
tccatcccca cnttntgccc nttcacgttt ccagtggtgg catgtcatcg tctcccctg    572 tcaacgtccc atcacctgag tacaggcgcg aagcagcgga cagctgttct tccatctccc   632
tgtattccgg                                                         642

<210> SEQ ID NO 43
<211> LENGTH: 34
<212> TYPE: PRT
<213> ORGANISM: Toxoplasma gondii
<220> FEATURE:
<221> NAME/KEY: misc_feature
<222> LOCATION: (7)..(7)
<223> OTHER INFORMATION: The 'Xaa' at location 7 stands for Ile, Val,
```

```
            Leu, or Phe.
<220> FEATURE:
<221> NAME/KEY: misc_feature
<222> LOCATION: (8)..(8)
<223> OTHER INFORMATION: The 'Xaa' at location 8 stands for a stop
      codon, Ser, or Leu.
<220> FEATURE:
<221> NAME/KEY: misc_feature
<222> LOCATION: (9)..(9)
<223> OTHER INFORMATION: The 'Xaa' at location 9 stands for a stop
      codon, or Tyr.
<220> FEATURE:
<221> NAME/KEY: misc_feature
<222> LOCATION: (10)..(10)
<223> OTHER INFORMATION: The 'Xaa' at location 10 stands for Asn, Ser,
      Thr, Ile, Asp, Gly, Ala, Val, His, Arg, Pro, Leu, Tyr, Cys, or
      Phe.
<220> FEATURE:
<221> NAME/KEY: misc_feature
<222> LOCATION: (14)..(14)
<223> OTHER INFORMATION: The 'Xaa' at location 14 stands for Lys,
      Arg, Thr, or Ile.
<220> FEATURE:
<221> NAME/KEY: misc_feature
<222> LOCATION: (29)..(29)
<223> OTHER INFORMATION: The 'Xaa' at location 29 stands for Lys, Arg,
      Thr, or Met.
<220> FEATURE:
<221> NAME/KEY: misc_feature
<222> LOCATION: (30)..(30)
<223> OTHER INFORMATION: The 'Xaa' at location 30 stands for Lys, Glu,
      Gln, or a stop codon.
<220> FEATURE:
<221> NAME/KEY: misc_feature
<222> LOCATION: (32)..(32)
<223> OTHER INFORMATION: The 'Xaa' at location 32 stands for Thr.
<220> FEATURE:
<221> NAME/KEY: misc_feature
<222> LOCATION: (19)..(19)
<223> OTHER INFORMATION: At nucleotide 19, n = unknown
      At amino acid residue 7, Xaa = Ile, Val, Leu or Phe
<220> FEATURE:
<221> NAME/KEY: misc_feature
<222> LOCATION: (23)..(23)
<223> OTHER INFORMATION: At nucleotide 23, n = unknown
      At amino acid residue 8, Xaa = Ser or Leu
<220> FEATURE:
<221> NAME/KEY: misc_feature
<222> LOCATION: (27)..(27)
<223> OTHER INFORMATION: At nucleotide 27, n = unknown
      At amino acid residue 9, Xaa = Tyr
<220> FEATURE:
<221> NAME/KEY: misc_feature
<222> LOCATION: (28)..(29)
<223> OTHER INFORMATION: At nucleotides 28 and 29, n = unknown
      At amino acid residue 10, Xaa = Asn, Ser, Thr, Ile, Asp, Gly, Ala
      , Val, His, Arg, Pro, Leu, Tyr, Cys or Phe
<220> FEATURE:
<221> NAME/KEY: misc_feature
<222> LOCATION: (41)..(41)
<223> OTHER INFORMATION: At nucleotide 41, n = unknown
      At amino acid residue 14, Xaa = Lys, Arg, Thr or ILE
<220> FEATURE:
<221> NAME/KEY: misc_feature
<222> LOCATION: (86)..(86)
<223> OTHER INFORMATION: At nucleotide 86, n = unknown
      At amino acid residue 29, Xaa = Lys, Arg, Thr or Met
<220> FEATURE:
<221> NAME/KEY: misc_feature
<222> LOCATION: (88)..(88)
<223> OTHER INFORMATION: At nucleotide 88, n = unknown
      At amino acid residue 30, Xaa = Lys, Glu or Gln
<220> FEATURE:
<221> NAME/KEY: misc_feature
<222> LOCATION: (96)..(96)
<223> OTHER INFORMATION: At nucleotide 96, n = unknown
      At amino acid residue 32, Xaa = Thr
<220> FEATURE:
<221> NAME/KEY: misc_feature
```

```
<222> LOCATION: (110)..(111)
<223> OTHER INFORMATION: n = unknown
<220> FEATURE:
<221> NAME/KEY: misc_feature
<222> LOCATION: (113)..(113)
<223> OTHER INFORMATION: n = unknown
<220> FEATURE:
<221> NAME/KEY: misc_feature
<222> LOCATION: (119)..(119)
<223> OTHER INFORMATION: n = unknown
<220> FEATURE:
<221> NAME/KEY: misc_feature
<222> LOCATION: (122)..(122)
<223> OTHER INFORMATION: n = unknown
<220> FEATURE:
<221> NAME/KEY: misc_feature
<222> LOCATION: (132)..(132)
<223> OTHER INFORMATION: n = unknown
<220> FEATURE:
<221> NAME/KEY: misc_feature
<222> LOCATION: (137)..(137)
<223> OTHER INFORMATION: n = unknown
<220> FEATURE:
<221> NAME/KEY: misc_feature
<222> LOCATION: (149)..(149)
<223> OTHER INFORMATION: n = unknown
<220> FEATURE:
<221> NAME/KEY: misc_feature
<222> LOCATION: (164)..(164)
<223> OTHER INFORMATION: n = unknown
<220> FEATURE:
<221> NAME/KEY: misc_feature
<222> LOCATION: (169)..(169)
<223> OTHER INFORMATION: n = unknown
<220> FEATURE:
<221> NAME/KEY: misc_feature
<222> LOCATION: (172)..(173)
<223> OTHER INFORMATION: n = unknown
<220> FEATURE:
<221> NAME/KEY: misc_feature
<222> LOCATION: (209)..(209)
<223> OTHER INFORMATION: n = unknown
<220> FEATURE:
<221> NAME/KEY: misc_feature
<222> LOCATION: (217)..(217)
<223> OTHER INFORMATION: n = unknown
<220> FEATURE:
<221> NAME/KEY: misc_feature
<222> LOCATION: (220)..(220)
<223> OTHER INFORMATION: n = unknown
<220> FEATURE:
<221> NAME/KEY: misc_feature
<222> LOCATION: (234)..(234)
<223> OTHER INFORMATION: n = unknown
<220> FEATURE:
<221> NAME/KEY: misc_feature
<222> LOCATION: (236)..(236)
<223> OTHER INFORMATION: n = unknown
<220> FEATURE:
<221> NAME/KEY: misc_feature
<222> LOCATION: (250)..(250)
<223> OTHER INFORMATION: n = unknown
<220> FEATURE:
<221> NAME/KEY: misc_feature
<222> LOCATION: (257)..(257)
<223> OTHER INFORMATION: n = unknown
<220> FEATURE:
<221> NAME/KEY: misc_feature
<222> LOCATION: (492)..(492)
<223> OTHER INFORMATION: n = unknown
<220> FEATURE:
<221> NAME/KEY: misc_feature
<222> LOCATION: (505)..(505)
<223> OTHER INFORMATION: n = unknown
<220> FEATURE:
<221> NAME/KEY: misc_feature
<222> LOCATION: (512)..(512)
<223> OTHER INFORMATION: n = unknown
<220> FEATURE:
```

<221> NAME/KEY: misc_feature
<222> LOCATION: (524)..(524)
<223> OTHER INFORMATION: n = unknown
<220> FEATURE:
<221> NAME/KEY: misc_feature
<222> LOCATION: (527)..(527)
<223> OTHER INFORMATION: n = unknown
<220> FEATURE:
<221> NAME/KEY: misc_feature
<222> LOCATION: (533)..(533)
<223> OTHER INFORMATION: n = unknown

<400> SEQUENCE: 43

Arg Arg Glu Thr Met Glu Xaa Xaa Xaa Xaa Thr Thr Ser Xaa Cys Met
1               5                   10                  15

Val Gly Thr Gln Asn Ala Asn Tyr Arg His Lys Gln Xaa Xaa Asn Xaa
            20                  25                  30

Trp Gly

<210> SEQ ID NO 44
<211> LENGTH: 381
<212> TYPE: DNA
<213> ORGANISM: Toxoplasma gondii
<220> FEATURE:
<221> NAME/KEY: CDS
<222> LOCATION: (1)..(81)
<223> OTHER INFORMATION:

<400> SEQUENCE: 44 cgg atc cac aaa aac acg att gtt tcg tca cat gga acc tca gca aat         48
Arg Ile His Lys Asn Thr Ile Val Ser Ser His Gly Thr Ser Ala Asn
1               5                   10                  15 tca ggc gcc agg acg gcc tcc ctt caa acg tcc taatccagag tcctctccgc      101
Ser Gly Ala Arg Thr Ala Ser Leu Gln Thr Ser
            20                  25 tccatcccca ccttctgccc cttcacgttt ccagtggtgg catgtcatcg tctcccctg       161 tcaacgtccc atcacctgag tacaggcgcg aagcagcgga cagctgttct tccatctccc      221
tgtattccgg agtctctatc gcttgcaagg cgagcaggcg ggcctcgaca gaagggttaa      281
tcaacttgta aaccagaagt ttcacgttct ctggcacccg ccggcacctc gaaaaaaga      341 attcgacact gtattcgtac cccgattttg tatcgggagg                              381

<210> SEQ ID NO 45
<211> LENGTH: 27
<212> TYPE: PRT
<213> ORGANISM: Toxoplasma gondii

<400> SEQUENCE: 45

Arg Ile His Lys Asn Thr Ile Val Ser Ser His Gly Thr Ser Ala Asn
1               5                   10                  15

Ser Gly Ala Arg Thr Ala Ser Leu Gln Thr Ser
            20                  25

<210> SEQ ID NO 46
<211> LENGTH: 432
<212> TYPE: DNA
<213> ORGANISM: Toxoplasma gondii
<220> FEATURE:
<221> NAME/KEY: CDS
<222> LOCATION: (1)..(255)
<223> OTHER INFORMATION:

<400> SEQUENCE: 46 ttt ttt tcg agg tgc cgg cgg gtg cca gag aac gtg aaa ctt ctg gtt         48

```
Phe Phe Ser Arg Cys Arg Arg Val Pro Glu Asn Val Lys Leu Leu Val
1               5                  10                  15 tac aag ttg att aac cct tct gtc gag gcc cgc ctg ctc gcc ttg caa    96
Tyr Lys Leu Ile Asn Pro Ser Val Glu Ala Arg Leu Leu Ala Leu Gln
 20                  25                  30 gcg ata gag act ccg gaa tac agg gag atg gaa gaa cag ctg tcc gct   144
Ala Ile Glu Thr Pro Glu Tyr Arg Glu Met Glu Glu Gln Leu Ser Ala
 35                  40                  45 gct tcg cgc ctg tac tca ggt gat ggg acg ttg aca ggg gga gac gat   192
Ala Ser Arg Leu Tyr Ser Gly Asp Gly Thr Leu Thr Gly Gly Asp Asp
 50                  55                  60 gac atg cca cca ctg aaa cgt gaa ggg gca gaa ggt ggg gat gga gcg   240
Asp Met Pro Pro Leu Lys Arg Glu Gly Ala Glu Gly Gly Asp Gly Ala
 65                  70                  75                  80 gag agg act ctg gat taggacgttt gaagggaggc cgtcctggcg cctgaatttg   295
Glu Arg Thr Leu Asp
 85 ctgaggttcc atgtgacgaa acaatcgtgt ttttgagcgg agaggactct ggattaggac  355 gtttgaaggg aggccgtcct ggcgcctgaa tttgctgagg tttcatgtga cgaaacaatc  415 gtgtttttgt ggatccg                                                 432

<210> SEQ ID NO 47
<211> LENGTH: 85
<212> TYPE: PRT
<213> ORGANISM: Toxoplasma gondii

<400> SEQUENCE: 47

Phe Phe Ser Arg Cys Arg Arg Val Pro Glu Asn Val Lys Leu Leu Val
1               5                  10                  15

Tyr Lys Leu Ile Asn Pro Ser Val Glu Ala Arg Leu Leu Ala Leu Gln
 20                  25                  30

Ala Ile Glu Thr Pro Glu Tyr Arg Glu Met Glu Glu Gln Leu Ser Ala
 35                  40                  45

Ala Ser Arg Leu Tyr Ser Gly Asp Gly Thr Leu Thr Gly Gly Asp Asp
 50                  55                  60

Asp Met Pro Pro Leu Lys Arg Glu Gly Ala Glu Gly Gly Asp Gly Ala
 65                  70                  75                  80

Glu Arg Thr Leu Asp
 85

<210> SEQ ID NO 48
<211> LENGTH: 282
<212> TYPE: DNA
<213> ORGANISM: Toxoplasma gondii
<220> FEATURE:
<221> NAME/KEY: CDS
<222> LOCATION: (1)..(105)
<223> OTHER INFORMATION:

<400> SEQUENCE: 48 cgg cgg gct gct tcc cag gaa cgt ttc gcg gct gcg tgt gga cag caa    48
Arg Arg Ala Ala Ser Gln Glu Arg Phe Ala Ala Ala Cys Gly Gln Gln
1               5                  10                  15 agc ctt acc ctc gag ttt tct ctc gtg gct gcc gac gtc ggc gac gcc    96
Ser Leu Thr Leu Glu Phe Ser Leu Val Ala Ala Asp Val Gly Asp Ala
 20                  25                  30 gcg aac tcc tgagatcaaa cacacaaaaa ggccctcgtt gaaacatccc            145
Ala Asn Ser
 35
```

```
cacgcacgag cagaaggacg cgagcaagaa aacgtctcca gccttctctt gcggtcgctt      205
gcaagcggga gtgtcgtctc cctctgtctt tctctgtgta ctcgaagccc agcgacttcc      265
ttgtcgagtt tctccgg                                                    282
```

```
<210> SEQ ID NO 49
<211> LENGTH: 35
<212> TYPE: PRT
<213> ORGANISM: Toxoplasma gondii

<400> SEQUENCE: 49

Arg Arg Ala Ala Ser Gln Glu Arg Phe Ala Ala Ala Cys Gly Gln Gln
1               5                   10                  15

Ser Leu Thr Leu Glu Phe Ser Leu Val Ala Ala Asp Val Gly Asp Ala
            20                  25                  30

Ala Asn Ser
        35

<210> SEQ ID NO 50
<211> LENGTH: 466
<212> TYPE: DNA
<213> ORGANISM: Toxoplasma gondii
<220> FEATURE:
<221> NAME/KEY: CDS
<222> LOCATION: (1)..(213)
<223> OTHER INFORMATION:
<220> FEATURE:
<221> NAME/KEY: misc_feature
<222> LOCATION: (8)..(8)
<223> OTHER INFORMATION: At nucleotide 8, s = c or g
      At amino acid residue 3, Xaa = Trp or Ser
<220> FEATURE:
<221> NAME/KEY: misc_feature
<222> LOCATION: (33)..(33)
<223> OTHER INFORMATION: At nucleotide 33, m = a or c
      At amino acid residue 11, Xaa = Lys or Asn
<220> FEATURE:
<221> NAME/KEY: misc_feature
<222> LOCATION: (107)..(107)
<223> OTHER INFORMATION: At nucleotide 107, y = c or t/u
      At amino acid residue 36, Xaa = Thr or Ile

<400> SEQUENCE: 50 ttt ttt tsg agg tgc cgg cgg gtg cca gag aam gtg aaa ttc tgg ttt       48
Phe Phe Xaa Arg Cys Arg Arg Val Pro Glu Xaa Val Lys Phe Trp Phe
1               5                   10                  15 aac aag ttg att aac cct tct gtc gag gcc cgc ctg ttc gcc ttg caa       96
Asn Lys Leu Ile Asn Pro Ser Val Glu Ala Arg Leu Phe Ala Leu Gln
            20                  25                  30 gcg ata gag ayt ccg gaa tac agg gag atg gaa gaa cag ctg tcc gct      144
Ala Ile Glu Xaa Pro Glu Tyr Arg Glu Met Glu Glu Gln Leu Ser Ala
35                  40                  45 gct tcg cgc ctg tac tca ggt gat ggg acg ttg aca ggg gga gac gat      192
Ala Ser Arg Leu Tyr Ser Gly Asp Gly Thr Leu Thr Gly Gly Asp Asp
50                  55                  60 gac atg cca cca ctg gaa acg tgaaggggca gaaggtgggg atggagcgga         243
Asp Met Pro Pro Leu Glu Thr
65                  70 gaggactctg gattaggacg tttgaaggga ggccgtcctg gcgcctgaat tgctgaggt      303 tccatgtgac gaaacaatcg tgtttttgag cggagaggac tctggattag gacgtttgaa    363
gggaggccgt cctggcgcct gaatttgctg aggtttcatg tgacgaaaca atcgtgtttt    423
tgtggatcct cccgatacaa aatcggggta cgaatacagt gtc                      466
```

```
<210> SEQ ID NO 51
<211> LENGTH: 71
<212> TYPE: PRT
<213> ORGANISM: Toxoplasma gondii
<220> FEATURE:
<221> NAME/KEY: misc_feature
<222> LOCATION: (3)..(3)
<223> OTHER INFORMATION: The 'Xaa' at location 3 stands for Trp, or Ser.
<220> FEATURE:
<221> NAME/KEY: misc_feature
<222> LOCATION: (11)..(11)
<223> OTHER INFORMATION: The 'Xaa' at location 11 stands for Lys, or
      Asn.
<220> FEATURE:
<221> NAME/KEY: misc_feature
<222> LOCATION: (36)..(36)
<223> OTHER INFORMATION: The 'Xaa' at location 36 stands for Thr, or Ile.
<220> FEATURE:
<221> NAME/KEY: misc_feature
<222> LOCATION: (8)..(8)
<223> OTHER INFORMATION: At nucleotide 8, s = c or g
      At amino acid residue 3, Xaa = Trp or Ser
<220> FEATURE:
<221> NAME/KEY: misc_feature
<222> LOCATION: (33)..(33)
<223> OTHER INFORMATION: At nucleotide 33, m = a or c
      At amino acid residue 11, Xaa = Lys or Asn
<220> FEATURE:
<221> NAME/KEY: misc_feature
<222> LOCATION: (107)..(107)
<223> OTHER INFORMATION: At nucleotide 107, y = c or t/u
      At amino acid residue 36, Xaa = Thr or Ile

<400> SEQUENCE: 51

Phe Phe Xaa Arg Cys Arg Arg Val Pro Glu Xaa Val Lys Phe Trp Phe
1               5                   10                  15

Asn Lys Leu Ile Asn Pro Ser Val Glu Ala Arg Leu Phe Ala Leu Gln
            20                  25                  30

Ala Ile Glu Xaa Pro Glu Tyr Arg Glu Met Glu Glu Gln Leu Ser Ala
        35                  40                  45

Ala Ser Arg Leu Tyr Ser Gly Asp Gly Thr Leu Thr Gly Gly Asp Asp
    50                  55                  60

Asp Met Pro Pro Leu Glu Thr
65                  70

<210> SEQ ID NO 52
<211> LENGTH: 539
<212> TYPE: DNA
<213> ORGANISM: Toxoplasma gondii
<220> FEATURE:
<221> NAME/KEY: CDS
<222> LOCATION: (1)..(60)
<223> OTHER INFORMATION:
<220> FEATURE:
<221> NAME/KEY: misc_feature
<222> LOCATION: (22)..(22)
<223> OTHER INFORMATION: At nucleotide 22, n = unknown
      At amino acid residue 8, Xaa = Met, Val or Leu
<220> FEATURE:
<221> NAME/KEY: misc_feature
<222> LOCATION: (26)..(26)
<223> OTHER INFORMATION: At nucleotide 26, r = a or g
      At amino acid residue 9, Xaa = Gly or Glu
<220> FEATURE:
<221> NAME/KEY: misc_feature
<222> LOCATION: (47)..(47)
<223> OTHER INFORMATION: At nucleotide 47, n = unknown
      At amino acid residue 16, Xaa = Tyr, Cys, Ser or Phe

<400> SEQUENCE: 52 gat agc aca cgg aat gga tgc ntg grg gtt ggg agc gac tat att tnt    48
Asp Ser Thr Arg Asn Gly Cys Xaa Xaa Val Gly Ser Asp Tyr Ile Xaa
```

-continued

```
1               5                    10                   15
tat ttg gtg ctt taaagctcca actacaggac ctgaagagga atactccatc          100
Tyr Leu Val Leu
20 gaattcttgt tctcattgtg ccggcgggca ccagagaacg tgaaactact ggtttacaag   160 ttgattaacc cttctgtcga ggcccgcctg tcgccttgca agctacggag actccggaat   220 acagggagat ggaagaacag ctgtccgctg cttcgcgcct gtactcaggt gatgggacgt   280 tgacaggggg agacgatgac atgccaccac cggaaacgtg aaggggcaga aggtggggat   340 ggagcggaga ggactctgga ttaggacgtt tgaaggagg ccgtcctggc gcctgaattt    400 tgctgaggtt tcatgtgacg aaacaatcgt gttttgtgg atccggaatt ccggatcggg    460 gaatttcctc tcacaccgct tggggccgag acacgcgcag agacgttgtt gggcctccac   520 aacacagggg ggattaagg                                                 539
```

```
<210> SEQ ID NO 53
<211> LENGTH: 20
<212> TYPE: PRT
<213> ORGANISM: Toxoplasma gondii
<220> FEATURE:
<221> NAME/KEY: misc_feature
<222> LOCATION: (8)..(8)
<223> OTHER INFORMATION: The 'Xaa' at location 8 stands for Met, Val,
      or Leu.
<220> FEATURE:
<221> NAME/KEY: misc_feature
<222> LOCATION: (9)..(9)
<223> OTHER INFORMATION: The 'Xaa' at location 9 stands for Gly, or Glu.
<220> FEATURE:
<221> NAME/KEY: misc_feature
<222> LOCATION: (16)..(16)
<223> OTHER INFORMATION: The 'Xaa' at location 16 stands for Tyr, Cys,
      Ser, or Phe.
<220> FEATURE:
<221> NAME/KEY: misc_feature
<222> LOCATION: (22)..(22)
<223> OTHER INFORMATION: At nucleotide 22, n = unknown
      At amino acid residue 8, Xaa = Met, Val or Leu
<220> FEATURE:
<221> NAME/KEY: misc_feature
<222> LOCATION: (26)..(26)
<223> OTHER INFORMATION: At nucleotide 26, r = a or g
      At amino acid residue 9, Xaa = Gly or Glu
<220> FEATURE:
<221> NAME/KEY: misc_feature
<222> LOCATION: (47)..(47)
<223> OTHER INFORMATION: At nucleotide 47, n = unknown
      At amino acid residue 16, Xaa = Tyr, Cys, Ser or Phe

<400> SEQUENCE: 53

Asp Ser Thr Arg Asn Gly Cys Xaa Xaa Val Gly Ser Asp Tyr Ile Xaa
1               5                   10                  15

Tyr Leu Val Leu
20

<210> SEQ ID NO 54
<211> LENGTH: 1233
<212> TYPE: DNA
<213> ORGANISM: Toxoplasma gondii

<400> SEQUENCE: 54
cgggatccct gaaggagagc atattcctga agagttccca gaaggcgagc atgttcctga   60
ggaggaaatc cctgaaggag aacatattcc tgaggaggag ttccctgaag gagagcatgt   120
tcctgaggag gagatccctg aaggcgagca tgttcctgag gaggagctcc ctggaggaga   180
```

```
acttattcct gaggaggaga tccctgaagg agagcatgtt cctgaagagc tccctgaagg    240
cgagcatgtt cctgaggagg agatccctga aggagagcat gttcctgaag aggaaatccc    300
tgaaggcgag catgttcctg aggaggagat ccctgaagga gaacatgctc cagaggaaga    360
gactcctgca cctgaggaga ccgaaaagga ggaggaagaa ggcgtgccag tcgcagcgat    420
tgccggtggt gtcgtcggag gtgtgttgct cattgctggt ggtgcaggtg ctgccgtgta    480
cacaaaccaa ggtggcgttg aagcagctga agacgaagtg atgtttgaga gcaagaaga    540 cggaacccag gctggcgaga accgcgagag gagacggtca ttgagatcga agatgacgca    600
tgggcagaca ttggactaaa ggagactagg aggtctgtgt gggcacatgc aggcgtgcga    660
caaaaccgtg atcgcgaggt attctgtgtt acgggcggag cgtctgcggc tgtccttcga    720
aggggaggcg gagtgacact ctgagctagg taccagacga acgcagccat ttgtgtccgt    780
ccgctgtttc ttgatcctgg acacagacca gacccgacac gggtgctgaa cggtaatgca    840
aactgtcggg aaaacctctc cggcgcgaaa acagagattt acacccgtt gagatctgag    900 tagcggaagt gcatgcgcat gtgtgtccac gagaaggaa gattttcttt cgagaacgtt    960 tcccttgtt cgcacattcc tacgcggggc tcgtgccgca tgcatgtcga aggactgcg    1020 ttcgagtgct ctttcgccgt tgcagtgctg acattgcgg cgtgggcaaa ggatagaagt    1080
gacgacctct gacatggcag tgaaggtggc agagactcgc ggaaaatcca aaaactctct    1140
gccgtttcgg tcgaggaatc acctttcttt ttttcgtctc tggacccgcc tccgtggtgt    1200
tcccttgccc ttgcaagccg ctgctatgta gcg                                1233

<210> SEQ ID NO 55
<211> LENGTH: 411
<212> TYPE: DNA
<213> ORGANISM: Toxoplasma gondii
<220> FEATURE:
<221> NAME/KEY: CDS
<222> LOCATION: (1)..(180)
<223> OTHER INFORMATION:

<400> SEQUENCE: 55 cga cga cct cgg ctt ctc cac ata caa gga atg tct tcc tgt ttt gga        48
Arg Arg Pro Arg Leu Leu His Ile Gln Gly Met Ser Ser Cys Phe Gly
1               5                   10                  15 cct aag caa ccc gac ctt tat ctt ttg cac cag ctg tgc ttc ttt tac        96
Pro Lys Gln Pro Asp Leu Tyr Leu Leu His Gln Leu Cys Phe Phe Tyr
            20                  25                  30 ttg tgt gaa tca ctg tgt aaa caa act gag aag cgt gta tgc atg gtc       144
Leu Cys Glu Ser Leu Cys Lys Gln Thr Glu Lys Arg Val Cys Met Val
        35                  40                  45 gcc ttt gca tgt gga cga ggc cgc cgt cgc aca gcg tgattctcat            190
Ala Phe Ala Cys Gly Arg Gly Arg Arg Arg Thr Ala
    50                  55                  60 ctctgttgcg tggggcgcg gatgagaatc aactccttag tgtcacagca tcagtgcagt     250
gcgtggagca caattctttt cgtgcacag acaagacaca ccagatatga agaacacta      310 acgggcactt accgttgtcc gtctatatat ttatatttag tcaatgctga gattagacct    370
agacttgtga gagagagtgt gaaacccaaa tgcctagatc c                        411

<210> SEQ ID NO 56
<211> LENGTH: 60
<212> TYPE: PRT
<213> ORGANISM: Toxoplasma gondii

<400> SEQUENCE: 56
```

```
Arg Arg Pro Arg Leu Leu His Ile Gln Gly Met Ser Ser Cys Phe Gly
1               5                   10                  15

Pro Lys Gln Pro Asp Leu Tyr Leu Leu His Gln Leu Cys Phe Phe Tyr
            20                  25                  30

Leu Cys Glu Ser Leu Cys Lys Gln Thr Glu Lys Arg Val Cys Met Val
35                  40                  45

Ala Phe Ala Cys Gly Arg Gly Arg Arg Thr Ala
50                  55                  60

<210> SEQ ID NO 57
<211> LENGTH: 441
<212> TYPE: DNA
<213> ORGANISM: Toxoplasma gondii
<220> FEATURE:
<221> NAME/KEY: CDS
<222> LOCATION: (1)..(354)
<223> OTHER INFORMATION:
<220> FEATURE:
<221> NAME/KEY: misc_feature
<222> LOCATION: (152)..(152)
<223> OTHER INFORMATION: At nucleotide 152, k = g or t/u
      At amino acid residue 51, Xaa = Trp or Leu
<220> FEATURE:
<221> NAME/KEY: misc_feature
<222> LOCATION: (238)..(238)
<223> OTHER INFORMATION: At nucleotide 238, k = g or t/u
      At amino acid residue 80, Xaa = Aal or Ser
<220> FEATURE:
<221> NAME/KEY: misc_feature
<222> LOCATION: (226)..(226)
<223> OTHER INFORMATION: At nucleotide 226, k = s = c or g
      At amino acid residue 109, Xaa = Arg or Pro

<400> SEQUENCE: 57 cgg atc gaa gaa gct gaa gcg gag aca cga atc gcc gag aca ggc aaa      48
Arg Ile Glu Glu Ala Glu Ala Glu Thr Arg Ile Ala Glu Thr Gly Lys
1               5                   10                  15 cac agc ggg aat gag aat cga ctc tgc gat aga agt ggg cgc cat gga      96
His Ser Gly Asn Glu Asn Arg Leu Cys Asp Arg Ser Gly Arg His Gly
            20                  25                  30 atc aag gaa ccg agg cga agg agg ccc atg ctg ttg gcc gag gtg ccc     144
Ile Lys Glu Pro Arg Arg Arg Arg Pro Met Leu Leu Ala Glu Val Pro
35                  40                  45 tgc ttg tkg gag ggc gcc cga cga aca ggg ttt cgt cag aga caa gca     192
Cys Leu Xaa Glu Gly Ala Arg Arg Thr Gly Phe Arg Gln Arg Gln Ala
50                  55                  60 ctt cgc tcg cgt ttg tgg ccc ctt gcc gtg cgg cac gcg tgc gta kcc     240
Leu Arg Ser Arg Leu Trp Pro Leu Ala Val Arg His Ala Cys Val Xaa
65                  70                  75                  80 ttc aag aga gac tgc gga agc aga gag agg cca ttg agg ctg tcc gag     288
Phe Lys Arg Asp Cys Gly Ser Arg Glu Arg Pro Leu Arg Leu Ser Glu
85                  90                  95 gtc ggc tcc agc cga gct gga tcc gaa tcc tgc agc csg gga tcc act     336
Val Gly Ser Ser Arg Ala Gly Ser Glu Ser Cys Ser Xaa Gly Ser Thr
100                 105                 110 agt cta gac gcg cac ccg tgacccactt caggaygcgg vmatwatrcm            384
Ser Leu Asp Ala His Pro
115 ggggcagatt tttwmggyta actatcattt ccccstwgtt gattmttcca gcaattg      441

<210> SEQ ID NO 58
<211> LENGTH: 118
<212> TYPE: PRT
<213> ORGANISM: Toxoplasma gondii
```

```
<220> FEATURE:
<221> NAME/KEY: misc_feature
<222> LOCATION: (51)..(51)
<223> OTHER INFORMATION: The 'Xaa' at location 51 stands for Trp, or
      Leu.
<220> FEATURE:
<221> NAME/KEY: misc_feature
<222> LOCATION: (80)..(80)
<223> OTHER INFORMATION: The 'Xaa' at location 80 stands for Ala, or
      Ser.
<220> FEATURE:
<221> NAME/KEY: misc_feature
<222> LOCATION: (109)..(109)
<223> OTHER INFORMATION: The 'Xaa' at location 109 stands for Arg, or
      Pro.
<220> FEATURE:
<221> NAME/KEY: misc_feature
<222> LOCATION: (152)..(152)
<223> OTHER INFORMATION: At nucleotide 152, k = g or t/u
      At amino acid residue 51, Xaa = Trp or Leu
<220> FEATURE:
<221> NAME/KEY: misc_feature
<222> LOCATION: (238)..(238)
<223> OTHER INFORMATION: At nucleotide 238, k = g or t/u
      At amino acid residue 80, Xaa = Aal or Ser
<220> FEATURE:
<221> NAME/KEY: misc_feature
<222> LOCATION: (226)..(226)
<223> OTHER INFORMATION: At nucleotide 226, k = s = c or g
      At amino acid residue 109, Xaa = Arg or Pro

<400> SEQUENCE: 58

Arg Ile Glu Glu Ala Glu Ala Glu Thr Arg Ile Ala Glu Thr Gly Lys
1               5                   10                  15

His Ser Gly Asn Glu Asn Arg Leu Cys Asp Arg Ser Gly Arg His Gly
            20                  25                  30

Ile Lys Glu Pro Arg Arg Arg Arg Pro Met Leu Leu Ala Glu Val Pro
        35                  40                  45

Cys Leu Xaa Glu Gly Ala Arg Arg Thr Gly Phe Arg Gln Arg Gln Ala
    50                  55                  60

Leu Arg Ser Arg Leu Trp Pro Leu Ala Val Arg His Ala Cys Val Xaa
65                  70                  75                  80

Phe Lys Arg Asp Cys Gly Ser Arg Glu Arg Pro Leu Arg Leu Ser Glu
                85                  90                  95

Val Gly Ser Ser Arg Ala Gly Ser Glu Ser Cys Ser Xaa Gly Ser Thr
            100                 105                 110

Ser Leu Asp Ala His Pro
115

<210> SEQ ID NO 59
<211> LENGTH: 491
<212> TYPE: DNA
<213> ORGANISM: Toxoplasma gondii
<220> FEATURE:
<221> NAME/KEY: CDS
<222> LOCATION: (1)..(102)
<223> OTHER INFORMATION:

<400> SEQUENCE: 59 cgg cgg tat tat agg aca cgg ccg cct gct ggt aac atc tgt aat tta    48
Arg Arg Tyr Tyr Arg Thr Arg Pro Pro Ala Gly Asn Ile Cys Asn Leu
1               5                   10                  15 tca ttg tat ccc gtc gtc ccg tgt tcc aaa ctg gga atc ttt tct ttc    96
Ser Leu Tyr Pro Val Val Pro Cys Ser Lys Leu Gly Ile Phe Ser Phe
            20                  25                  30 ctg agc tgacggtttg gcccgcaagc tcagccgagt acgaaaccat gattaggttg    152
Leu Ser
```

```
gaggcctaat gtgctttttc gccagctgtc aaacgggcag ccaaggttga tttctctatg    212
agttgtcctc cgcgctctcg aattggtatt tcgtggtttc agattgaaag cgtcactcga    272
gctattacga ggcgtttcag caaaaaggaa gaatcactca gacacctgac cgacgcttga    332
tgtgctggcg gttgtgcaaa tccaggcatc actcaacgcc gatgctcagc aggacccatg    392
gatcttaaga ggttctgttc cactacatca gtgagagttt caaaaagaat cctgataact    452
acgcgcttct acaggtgccg cctttatggc aacgatccg                           491
```

<210> SEQ ID NO 60
<211> LENGTH: 34
<212> TYPE: PRT
<213> ORGANISM: Toxoplasma gondii

<400> SEQUENCE: 60

```
Arg Arg Tyr Tyr Arg Thr Arg Pro Ala Gly Asn Ile Cys Asn Leu
1               5                   10                  15

Ser Leu Tyr Pro Val Val Pro Cys Ser Lys Leu Gly Ile Phe Ser Phe
            20                  25                  30

Leu Ser
```

<210> SEQ ID NO 61
<211> LENGTH: 387
<212> TYPE: DNA
<213> ORGANISM: Toxoplasma gondii
<220> FEATURE:
<221> NAME/KEY: CDS
<222> LOCATION: (1)..(387)
<223> OTHER INFORMATION:

<400> SEQUENCE: 61

```
cgg atc gct ctg agt ctc ttt ggg ctc cct gcc gca tgc agg cat gaa      48
Arg Ile Ala Leu Ser Leu Phe Gly Leu Pro Ala Ala Cys Arg His Glu
1               5                   10                  15 agt gtc tcg ccg cga gag aca gag aag gaa gtg cag agc gag cgt ggg      96
Ser Val Ser Pro Arg Glu Thr Glu Lys Glu Val Gln Ser Glu Arg Gly
            20                  25                  30 cga gaa cgg acg cag aaa ggc gca ggc gag aag gag acc ggc gta gac     144
Arg Glu Arg Thr Gln Lys Gly Ala Gly Glu Lys Glu Thr Gly Val Asp
35                  40                  45 gga gtg act gga gag cag gtc tta gcg ctc act aag ggt gaa cct gaa     192
Gly Val Thr Gly Glu Gln Val Leu Ala Leu Thr Lys Gly Glu Pro Glu
50                  55                  60 gcg gca gaa gaa gcg aga gaa gag gac gag gga aag gga gaa gac aga     240
Ala Ala Glu Glu Ala Arg Glu Glu Asp Glu Gly Lys Gly Glu Asp Arg
65                  70                  75                  80 tgg tac gag gaa ggc gcg agg cga gag aaa gag gcg gct cga gtc atg     288
Trp Tyr Glu Glu Gly Ala Arg Arg Glu Lys Glu Ala Ala Arg Val Met
85                  90                  95 tcc act ccg cag acg tat gcc gaa gcc acc gac aca aca gct gca tgc     336
Ser Thr Pro Gln Thr Tyr Ala Glu Ala Thr Asp Thr Thr Ala Ala Cys
100                 105                 110 aga gac gaa agg gag ctc gcc tcg ggg gtc gaa gag aag aca cag gat     384
Arg Asp Glu Arg Glu Leu Ala Ser Gly Val Glu Glu Lys Thr Gln Asp
115                 120                 125 ccg                                                                 387
Pro
```

<210> SEQ ID NO 62
<211> LENGTH: 129

```
<212> TYPE: PRT
<213> ORGANISM: Toxoplasma gondii

<400> SEQUENCE: 62

Arg Ile Ala Leu Ser Leu Phe Gly Leu Pro Ala Ala Cys Arg His Glu
1               5                   10                  15

Ser Val Ser Pro Arg Glu Thr Glu Lys Glu Val Gln Ser Glu Arg Gly
            20                  25                  30

Arg Glu Arg Thr Gln Lys Gly Ala Gly Glu Lys Glu Thr Gly Val Asp
        35                  40                  45

Gly Val Thr Gly Glu Gln Val Leu Ala Leu Thr Lys Gly Glu Pro Glu
    50                  55                  60

Ala Ala Glu Glu Ala Arg Glu Glu Asp Glu Gly Lys Gly Glu Asp Arg
65                  70                  75                  80

Trp Tyr Glu Glu Gly Ala Arg Arg Glu Lys Glu Ala Ala Arg Val Met
            85                  90                  95

Ser Thr Pro Gln Thr Tyr Ala Glu Ala Thr Asp Thr Thr Ala Ala Cys
        100                 105                 110

Arg Asp Glu Arg Glu Leu Ala Ser Gly Val Glu Glu Lys Thr Gln Asp
    115                 120                 125

Pro

<210> SEQ ID NO 63
<211> LENGTH: 417
<212> TYPE: DNA
<213> ORGANISM: Toxoplasma gondii
<220> FEATURE:
<221> NAME/KEY: CDS
<222> LOCATION: (1)..(417)
<223> OTHER INFORMATION:
<220> FEATURE:
<221> NAME/KEY: misc_feature
<222> LOCATION: (72)..(72)
<223> OTHER INFORMATION: At nucleotide 72, n = unknown
<220> FEATURE:
<221> NAME/KEY: misc_feature
<222> LOCATION: (74)..(74)
<223> OTHER INFORMATION: At nucleotide 74, n = unknown
      At amino acid residue 25, Xaa = Tyr, Cys, Ser or Phe
<220> FEATURE:
<221> NAME/KEY: misc_feature
<222> LOCATION: (139)..(139)
<223> OTHER INFORMATION: At nucleotide 139, n = unknown
      At amino acid residue 47, Xaa = Ile, Met, Val, Leu or Phe
<220> FEATURE:
<221> NAME/KEY: misc_feature
<222> LOCATION: (141)..(141)
<223> OTHER INFORMATION: At nucleotide 141, n = unknown
      At amino acid residue 47, Xaa = Ile, Met, Val, Leu or Phe

<400> SEQUENCE: 63 ctt gca tgc gct gtg gca atg gaa gaa gca ccc gcg cca ggg caa cca      48
Leu Ala Cys Ala Val Ala Met Glu Glu Ala Pro Ala Pro Gly Gln Pro
1               5                   10                  15 ccc gaa gaa ggg gac gat ggc ggn tnt cag cag cgc ctg gag atc gct      96
Pro Glu Glu Gly Asp Asp Gly Gly Xaa Gln Gln Arg Leu Glu Ile Ala
            20                  25                  30 ctg agt ctc ttt ggg ctc cct gcc gca tgc agg cat gaa agt ntn tcg      144
Leu Ser Leu Phe Gly Leu Pro Ala Ala Cys Arg His Glu Ser Xaa Ser
        35                  40                  45 ccg cga gag aca gag aag gaa gtg cag agc gag cgt ggg cga gaa cgg      192
Pro Arg Glu Thr Glu Lys Glu Val Gln Ser Glu Arg Gly Arg Glu Arg
    50                  55                  60 acg cag aaa ggc gca ggc gag aag gag acc ggc gta gac gga gtg act      240
```

```
Thr Gln Lys Gly Ala Gly Glu Lys Glu Thr Gly Val Asp Gly Val Thr
 65                  70                  75                  80 gga gag cag ctc tta gcg ctc act aag ggt gaa cct gaa gcg gca gaa      288
Gly Glu Gln Leu Leu Ala Leu Thr Lys Gly Glu Pro Glu Ala Ala Glu
 85                  90                  95 gaa gcg aga gaa gag gac gag gga aag gga gaa gac aga tgg aac gag      336
Glu Ala Arg Glu Glu Asp Glu Gly Lys Gly Glu Asp Arg Trp Asn Glu
100                 105                 110 gaa ggc gcg agg cga gag aaa gag gcg gct cga gtc atg tcc act ccg      384
Glu Gly Ala Arg Arg Glu Lys Glu Ala Ala Arg Val Met Ser Thr Pro
115                 120                 125 cag acg tat gcc gaa gcc acc gac aca aca gcg                          417
Gln Thr Tyr Ala Glu Ala Thr Asp Thr Thr Ala
130                 135

<210> SEQ ID NO 64
<211> LENGTH: 139
<212> TYPE: PRT
<213> ORGANISM: Toxoplasma gondii
<220> FEATURE:
<221> NAME/KEY: misc_feature
<222> LOCATION: (25)..(25)
<223> OTHER INFORMATION: The 'Xaa' at location 25 stands for Tyr, Cys,
      Ser, or Phe.
<220> FEATURE:
<221> NAME/KEY: misc_feature
<222> LOCATION: (47)..(47)
<223> OTHER INFORMATION: The 'Xaa' at location 47 stands for Ile, Met,
      Val, Leu, or Phe.
<220> FEATURE:
<221> NAME/KEY: misc_feature
<222> LOCATION: (72)..(72)
<223> OTHER INFORMATION: At nucleotide 72, n = unknown
<220> FEATURE:
<221> NAME/KEY: misc_feature
<222> LOCATION: (74)..(74)
<223> OTHER INFORMATION: At nucleotide 74, n = unknown
      At amino acid residue 25, Xaa = Tyr, Cys, Ser or Phe
<220> FEATURE:
<221> NAME/KEY: misc_feature
<222> LOCATION: (139)..(139)
<223> OTHER INFORMATION: At nucleotide 139, n = unknown
      At amino acid residue 47, Xaa = Ile, Met, Val, Leu or Phe
<220> FEATURE:
<221> NAME/KEY: misc_feature
<222> LOCATION: (141)..(141)
<223> OTHER INFORMATION: At nucleotide 141, n = unknown
      At amino acid residue 47, Xaa = Ile, Met, Val, Leu or Phe

<400> SEQUENCE: 64

Leu Ala Cys Ala Val Ala Met Glu Glu Ala Pro Ala Pro Gly Gln Pro
 1               5                  10                  15

Pro Glu Glu Gly Asp Asp Gly Gly Xaa Gln Gln Arg Leu Glu Ile Ala
 20                  25                  30

Leu Ser Leu Phe Gly Leu Pro Ala Ala Cys Arg His Glu Ser Xaa Ser
 35                  40                  45

Pro Arg Glu Thr Glu Lys Glu Val Gln Ser Glu Arg Gly Arg Glu Arg
 50                  55                  60

Thr Gln Lys Gly Ala Gly Glu Lys Glu Thr Gly Val Asp Gly Val Thr
 65                  70                  75                  80

Gly Glu Gln Leu Leu Ala Leu Thr Lys Gly Glu Pro Glu Ala Ala Glu
 85                  90                  95

Glu Ala Arg Glu Glu Asp Glu Gly Lys Gly Glu Asp Arg Trp Asn Glu
100                 105                 110

Glu Gly Ala Arg Arg Glu Lys Glu Ala Ala Arg Val Met Ser Thr Pro
115                 120                 125
```

```
Gln Thr Tyr Ala Glu Ala Thr Asp Thr Thr Ala
130             135
```

<210> SEQ ID NO 65
<211> LENGTH: 416
<212> TYPE: DNA
<213> ORGANISM: Toxoplasma gondii
<220> FEATURE:
<221> NAME/KEY: CDS
<222> LOCATION: (1)..(414)
<223> OTHER INFORMATION:
<220> FEATURE:
<221> NAME/KEY: misc_feature
<222> LOCATION: (174)..(174)
<223> OTHER INFORMATION: At nucleotide 174, n = unknown
    At amino acid residue 58, Xaa = Arg
<220> FEATURE:
<221> NAME/KEY: misc_feature
<222> LOCATION: (207)..(207)
<223> OTHER INFORMATION: At nucleotide 207, n = unknown
    At amino acid residue 69, Xaa = Ala

<400> SEQUENCE: 65

```
ccg gat cgc ggg aga gaa gaa cgt gag gga gaa gaa gag agt gcc gag      48
Pro Asp Arg Gly Arg Glu Glu Arg Glu Gly Glu Glu Glu Ser Ala Glu
1               5                   10                  15 gct ttg cca gac cat aag cgg ggg cca gga aaa gag ctg gag gaa ggc      96
Ala Leu Pro Asp His Lys Arg Gly Pro Gly Lys Glu Leu Glu Glu Gly
        20                  25                  30 cga gac tcg cag gtc cgt ggt gag gag agc ggg cgc agc tcg ctt tcg     144
Arg Asp Ser Gln Val Arg Gly Glu Glu Ser Gly Arg Ser Ser Leu Ser
35                  40                  45 cag gag agg gaa agt ttt cgt tct cag cgn gtc tcg gct gag ggt cag     192
Gln Glu Arg Glu Ser Phe Arg Ser Gln Arg Val Ser Ala Glu Gly Gln
50                  55                  60 gag gtg gag gca gcn tct gtc aag gcg ctt gaa gag gca aag tcg aac     240
Glu Val Glu Ala Ala Ser Val Lys Ala Leu Glu Glu Ala Lys Ser Asn
65                  70                  75                  80 gac aga ccc gac ggc gag agc aac gag ctg cgt cgc ttg tca ccc acc     288
Asp Arg Pro Asp Gly Glu Ser Asn Glu Leu Arg Arg Leu Ser Pro Thr
            85                  90                  95 agc cag aca gag caa gaa ggc tcc gtc gag aaa gaa ggg aca tca gag     336
Ser Gln Thr Glu Gln Glu Gly Ser Val Glu Lys Glu Gly Thr Ser Glu
100                 105                 110 gcg acg atg aac gac caa gac gag aca ggg aag gaa aaa caa gac caa     384
Ala Thr Met Asn Asp Gln Asp Glu Thr Gly Lys Glu Lys Gln Asp Gln
115                 120                 125 cga gag gtg cct gtg ccc cgc gct ctt cgc tt                          416
Arg Glu Val Pro Val Pro Arg Ala Leu Arg
130                 135
```

<210> SEQ ID NO 66
<211> LENGTH: 138
<212> TYPE: PRT
<213> ORGANISM: Toxoplasma gondii
<220> FEATURE:
<221> NAME/KEY: misc_feature
<222> LOCATION: (174)..(174)
<223> OTHER INFORMATION: At nucleotide 174, n = unknown
    At amino acid residue 58, Xaa = Arg
<220> FEATURE:
<221> NAME/KEY: misc_feature
<222> LOCATION: (207)..(207)
<223> OTHER INFORMATION: At nucleotide 207, n = unknown
    At amino acid residue 69, Xaa = Ala

<400> SEQUENCE: 66

Pro Asp Arg Gly Arg Glu Glu Arg Glu Gly Glu Glu Ser Ala Glu
1               5                   10                  15

Ala Leu Pro Asp His Lys Arg Gly Pro Gly Lys Glu Leu Glu Glu Gly
20                  25                  30

Arg Asp Ser Gln Val Arg Gly Glu Ser Gly Arg Ser Ser Leu Ser
35                  40                  45

Gln Glu Arg Glu Ser Phe Arg Ser Gln Arg Val Ser Ala Glu Gly Gln
50                  55                  60

Glu Val Glu Ala Ala Ser Val Lys Ala Leu Glu Glu Ala Lys Ser Asn
65                  70                  75                  80

Asp Arg Pro Asp Gly Glu Ser Asn Glu Leu Arg Arg Leu Ser Pro Thr
85                  90                  95

Ser Gln Thr Glu Gln Glu Gly Ser Val Glu Lys Gly Thr Ser Glu
100                 105                 110

Ala Thr Met Asn Asp Gln Asp Glu Thr Gly Lys Glu Lys Gln Asp Gln
115                 120                 125

Arg Glu Val Pro Val Pro Arg Ala Leu Arg
130                 135

<210> SEQ ID NO 67
<211> LENGTH: 500
<212> TYPE: DNA
<213> ORGANISM: Toxoplasma gondii

<400> SEQUENCE: 67
ccgagaatca tgttacgcca tgtagacagc gtttagggag tgcagacatt ttaatctgga      60
cggagtccaa gtggacgcgg atgtagatat ctgtcgcagc acctccgcag ttgcgctagg     120
gattctgatg ctgctagttt taacatccaa aactctgact tcgcttggtg atctccaggt     180
gcatatacat gcgaaggcaa tcgtgtttgt gagaggcgaa tgtacgaatt tcagtgtctt     240
tgtgtggaag tcaagttccc ctgaaccagc tgcttgtttt attctaccgc taatgtatga     300
agcttagcct cgtgtcctct tcgcccgtac acgagacacg atccaagagt catacaaatt     360
cttgcggcgg tgaggtaatt gtcaacagaa acaaaagtcg cgggtatctg tggtgtctct     420
gcttctgcac ttccaaggac cgccgcaagt tcggcccgat cggctggaac attcagtacg     480
agttcacgac ggaggatccg                                                 500

<210> SEQ ID NO 68
<211> LENGTH: 321
<212> TYPE: DNA
<213> ORGANISM: Toxoplasma gondii
<220> FEATURE:
<221> NAME/KEY: CDS
<222> LOCATION: (1)..(219)
<223> OTHER INFORMATION:

<400> SEQUENCE: 68 cgg cgg gac ttg cgg act tcg gtc tgg gac gct cgg gtg tac gta cac      48
Arg Arg Asp Leu Arg Thr Ser Val Trp Asp Ala Arg Val Tyr Val His
1               5                   10                  15 ctg gcg ggg ggc cag agg cgc tgc aac gag tcg cgg ggg atg gag gaa      96
Leu Ala Gly Gly Gln Arg Arg Cys Asn Glu Ser Arg Gly Met Glu Glu
20                  25                  30 gcg agg aaa agg agg tgt ctc gcg atg cgg tgc cag tgg act tcg tct     144
Ala Arg Lys Arg Arg Cys Leu Ala Met Arg Cys Gln Trp Thr Ser Ser
35                  40                  45 gcg cta gat tgg agg gag agc tgg aaa aat gcc gag aca gct tcg cac     192
Ala Leu Asp Trp Arg Glu Ser Trp Lys Asn Ala Glu Thr Ala Ser His -continued

```
Ala Leu Asp Trp Arg Glu Ser Trp Lys Asn Ala Glu Thr Ala Ser His
 50                  55                  60 gtc aca ttc ccg acg aaa cgc ccg cca tgaaggaaat cacagacatc              239
Val Thr Phe Pro Thr Lys Arg Pro Pro
 65                  70 accaaccttc cgccgtggc taaaggaccg tcctgtgtat gtacagtttt tccaggcgaa       299
agccgagaga cagcgaaacc gg                                               321

<210> SEQ ID NO 69
<211> LENGTH: 73
<212> TYPE: PRT
<213> ORGANISM: Toxoplasma gondii

<400> SEQUENCE: 69

Arg Arg Asp Leu Arg Thr Ser Val Trp Asp Ala Arg Val Tyr Val His
 1               5                  10                  15

Leu Ala Gly Gly Gln Arg Arg Cys Asn Glu Ser Arg Gly Met Glu Glu
         20                  25                  30

Ala Arg Lys Arg Arg Cys Leu Ala Met Arg Cys Gln Trp Thr Ser Ser
     35                  40                  45

Ala Leu Asp Trp Arg Glu Ser Trp Lys Asn Ala Glu Thr Ala Ser His
 50                  55                  60

Val Thr Phe Pro Thr Lys Arg Pro Pro
 65                  70

<210> SEQ ID NO 70
<211> LENGTH: 513
<212> TYPE: DNA
<213> ORGANISM: Toxoplasma gondii
<220> FEATURE:
<221> NAME/KEY: CDS
<222> LOCATION: (1)..(513)
<223> OTHER INFORMATION:

<400> SEQUENCE: 70 cgg gat cag gct tct atg cca ctg ccc ccg gcc ccc gaa gac ttt gac        48
Arg Asp Gln Ala Ser Met Pro Leu Pro Pro Ala Pro Glu Asp Phe Asp
 1               5                  10                  15 ctg cct cct atg cca ctg ccc gaa gca ccc gaa gac ttt gac cag gct        96
Leu Pro Pro Met Pro Leu Pro Glu Ala Pro Glu Asp Phe Asp Gln Ala
         20                  25                  30 cct atg cca ctg ccc gag gca ccc gaa gac ttt gac cag gct cct atg       144
Pro Met Pro Leu Pro Glu Ala Pro Glu Asp Phe Asp Gln Ala Pro Met
     35                  40                  45 cca ctg ccc gag gca ccc gaa gac ttt gac cag cct cct atg cca ctg       192
Pro Leu Pro Glu Ala Pro Glu Asp Phe Asp Gln Pro Pro Met Pro Leu
 50                  55                  60 ccc gaa gca ccc gaa gac ttt gac cag gct cct atg cca ctg ccc gaa       240
Pro Glu Ala Pro Glu Asp Phe Asp Gln Ala Pro Met Pro Leu Pro Glu
 65                  70                  75                  80 gca ccc gaa gtc ttt gac cag gct cct atg cca ctg ccc gag gca ccc       288
Ala Pro Glu Val Phe Asp Gln Ala Pro Met Pro Leu Pro Glu Ala Pro
             85                  90                  95 gaa gtc ttt gac cag gct cct atg cca ctg ccc gaa gca ccc gaa gac       336
Glu Val Phe Asp Gln Ala Pro Met Pro Leu Pro Glu Ala Pro Glu Asp
        100                 105                 110 ttt gac cag gct cct atg cca ctg ccc gaa gca ccc gaa gtc ttt gac       384
Phe Asp Gln Ala Pro Met Pro Leu Pro Glu Ala Pro Glu Val Phe Asp
    115                 120                 125 cag gct cct atg cca ctg ccc gag gca ccc gaa gac ttt gac cag gct       432
```

```
                          Gln Ala Pro Met Pro Leu Pro Glu Ala Pro Glu Asp Phe Asp Gln Ala
                          130                 135                 140 cct atg cca gtg ccc gag gca ccc gaa gac ttt gac cag gct cct gag          480
Pro Met Pro Val Pro Glu Ala Pro Glu Asp Phe Asp Gln Ala Pro Glu
145                 150                 155                 160 cca ctg ccc gag gca gcc gaa gaa ttt gat ccc                              513
Pro Leu Pro Glu Ala Ala Glu Glu Phe Asp Pro
165                 170

<210> SEQ ID NO 71
<211> LENGTH: 171
<212> TYPE: PRT
<213> ORGANISM: Toxoplasma gondii

<400> SEQUENCE: 71

Arg Asp Gln Ala Ser Met Pro Leu Pro Ala Pro Glu Asp Phe Asp
1               5                   10                  15

Leu Pro Pro Met Pro Leu Pro Glu Ala Pro Glu Asp Phe Asp Gln Ala
20                  25                  30

Pro Met Pro Leu Pro Glu Ala Pro Glu Asp Phe Asp Gln Ala Pro Met
35                  40                  45

Pro Leu Pro Glu Ala Pro Glu Asp Phe Asp Gln Pro Pro Met Pro Leu
50                  55                  60

Pro Glu Ala Pro Glu Asp Phe Asp Gln Ala Pro Met Pro Leu Pro Glu
65                  70                  75                  80

Ala Pro Glu Val Phe Asp Gln Ala Pro Met Pro Leu Pro Glu Ala Pro
85                  90                  95

Glu Val Phe Asp Gln Ala Pro Met Pro Leu Pro Glu Ala Pro Glu Asp
100                 105                 110

Phe Asp Gln Ala Pro Met Pro Leu Pro Glu Ala Pro Glu Val Phe Asp
115                 120                 125

Gln Ala Pro Met Pro Leu Pro Glu Ala Pro Glu Asp Phe Asp Gln Ala
130                 135                 140

Pro Met Pro Val Pro Glu Ala Pro Glu Asp Phe Asp Gln Ala Pro Glu
145                 150                 155                 160

Pro Leu Pro Glu Ala Ala Glu Glu Phe Asp Pro
165                 170

<210> SEQ ID NO 72
<211> LENGTH: 528
<212> TYPE: DNA
<213> ORGANISM: Toxoplasma gondii
<220> FEATURE:
<221> NAME/KEY: CDS
<222> LOCATION: (1)..(528)
<223> OTHER INFORMATION:

<400> SEQUENCE: 72 cga tct gaa cgt tgt gca acc gtt ggg gac cca ggt aca ggc gtc tcc          48
Arg Ser Glu Arg Cys Ala Thr Val Gly Asp Pro Gly Thr Gly Val Ser
1               5                   10                  15 aac act gag gcg ggg gga aag cgc cca cac tgg cgt ctc agg cac ctt          96
Asn Thr Glu Ala Gly Gly Lys Arg Pro His Trp Arg Leu Arg His Leu
20                  25                  30 caa tgc cac agg tat ccg gca tcc ttg gag aca gag ctt gag acg gag          144
Gln Cys His Arg Tyr Pro Ala Ser Leu Glu Thr Glu Leu Glu Thr Glu
35                  40                  45 aca ctc gca cac aca ccc aga gag ctt gtg gtg aca aat cga agc ttg          192
Thr Leu Ala His Thr Pro Arg Glu Leu Val Val Thr Asn Arg Ser Leu
50                  55                  60
```

```
ggg ttt gtc tcg ctt ctt cgc cag tcg ttc gcg tcg cag tca gaa gca    240
Gly Phe Val Ser Leu Leu Arg Gln Ser Phe Ala Ser Gln Ser Glu Ala
 65                  70                  75                  80 gtc aag gcg acc gcg gag acg ccg aca gag aca gag aca gtc ctt gtg    288
Val Lys Ala Thr Ala Glu Thr Pro Thr Glu Thr Glu Thr Val Leu Val
             85                  90                  95 gcg ggc gag cgc aac acc gcg aaa gaa aga gag aga aaa ggg cag gac    336
Ala Gly Glu Arg Asn Thr Ala Lys Glu Arg Glu Arg Lys Gly Gln Asp
100                 105                 110 gaa gag gtt tcg cag aga gca gcg gag aac aag aga gga cga gtg gag    384
Glu Glu Val Ser Gln Arg Ala Ala Glu Asn Lys Arg Gly Arg Val Glu
    115                 120                 125 gac aca gac tac cgg gag acg gat aag aaa gcc gag aaa gat gag cga    432
Asp Thr Asp Tyr Arg Glu Thr Asp Lys Lys Ala Glu Lys Asp Glu Arg
130                 135                 140 gaa gag aac ccc cga gga gac aca ggg gag cag aga agc gag aag cac    480
Glu Glu Asn Pro Arg Gly Asp Thr Gly Glu Gln Arg Ser Glu Lys His
    145                 150                 155                 160 acg aga gat tta ttg gga cag gag aga gag aac gca tgg gag atc ccg    528
Thr Arg Asp Leu Leu Gly Gln Glu Arg Glu Asn Ala Trp Glu Ile Pro
        165                 170                 175

<210> SEQ ID NO 73
<211> LENGTH: 176
<212> TYPE: PRT
<213> ORGANISM: Toxoplasma gondii

<400> SEQUENCE: 73

Arg Ser Glu Arg Cys Ala Thr Val Gly Asp Pro Gly Thr Gly Val Ser
  1               5                  10                  15

Asn Thr Glu Ala Gly Gly Lys Arg Pro His Trp Arg Leu Arg His Leu
         20                  25                  30

Gln Cys His Arg Tyr Pro Ala Ser Leu Glu Thr Glu Leu Glu Thr Glu
     35                  40                  45

Thr Leu Ala His Thr Pro Arg Glu Leu Val Val Thr Asn Arg Ser Leu
 50                  55                  60

Gly Phe Val Ser Leu Leu Arg Gln Ser Phe Ala Ser Gln Ser Glu Ala
 65                  70                  75                  80

Val Lys Ala Thr Ala Glu Thr Pro Thr Glu Thr Glu Thr Val Leu Val
             85                  90                  95

Ala Gly Glu Arg Asn Thr Ala Lys Glu Arg Glu Arg Lys Gly Gln Asp
100                 105                 110

Glu Glu Val Ser Gln Arg Ala Ala Glu Asn Lys Arg Gly Arg Val Glu
    115                 120                 125

Asp Thr Asp Tyr Arg Glu Thr Asp Lys Lys Ala Glu Lys Asp Glu Arg
130                 135                 140

Glu Glu Asn Pro Arg Gly Asp Thr Gly Glu Gln Arg Ser Glu Lys His
    145                 150                 155                 160

Thr Arg Asp Leu Leu Gly Gln Glu Arg Glu Asn Ala Trp Glu Ile Pro
        165                 170                 175

<210> SEQ ID NO 74
<211> LENGTH: 375
<212> TYPE: DNA
<213> ORGANISM: Toxoplasma gondii
<220> FEATURE:
<221> NAME/KEY: CDS
<222> LOCATION: (1)..(375)
<223> OTHER INFORMATION:
```

<400> SEQUENCE: 74

```
ccg gag gag tac aag tgc agc aaa acc acg tac gaa gac agc tgc acc        48
Pro Glu Glu Tyr Lys Cys Ser Lys Thr Thr Tyr Glu Asp Ser Cys Thr
1               5                   10                  15 gat gtc gct gtc cag gtc ccc gac acc tgc tac cgc act gtc gat cag        96
Asp Val Ala Val Gln Val Pro Asp Thr Cys Tyr Arg Thr Val Asp Gln
 20                  25                  30 aag aag gct tac aag tgc aag aaa acg ctg acg aaa aac caa tgc acg       144
Lys Lys Ala Tyr Lys Cys Lys Lys Thr Leu Thr Lys Asn Gln Cys Thr
 35                  40                  45 aag gtt cca gtc cag gtt cca agc aca tgc acg aag acg gcg atg tca       192
Lys Val Pro Val Gln Val Pro Ser Thr Cys Thr Lys Thr Ala Met Ser
 50                  55                  60 aag gag gcg tac gac tgc tcg aag acc gag ttc cgc acc gag tgc acc       240
Lys Glu Ala Tyr Asp Cys Ser Lys Thr Glu Phe Arg Thr Glu Cys Thr
 65                  70                  75                  80 gac gaa gtc gag caa gtc ccg tgc atg ggc aaa gag tgc aag ctg cgc       288
Asp Glu Val Glu Gln Val Pro Cys Met Gly Lys Glu Cys Lys Leu Arg
 85                  90                  95 cag ctg aag aag aag cgc gtc tgc agg cag gtc ccg ttc acc agc aag       336
Gln Leu Lys Lys Lys Arg Val Cys Arg Gln Val Pro Phe Thr Ser Lys
100                 105                 110 aac gtc tgc tac aaa aat gtg ccc acg gag cag acg tcg                   375
Asn Val Cys Tyr Lys Asn Val Pro Thr Glu Gln Thr Ser
115                 120                 125
```

<210> SEQ ID NO 75
<211> LENGTH: 125
<212> TYPE: PRT
<213> ORGANISM: Toxoplasma gondii

<400> SEQUENCE: 75

```
Pro Glu Glu Tyr Lys Cys Ser Lys Thr Thr Tyr Glu Asp Ser Cys Thr
1               5                   10                  15

Asp Val Ala Val Gln Val Pro Asp Thr Cys Tyr Arg Thr Val Asp Gln
 20                  25                  30

Lys Lys Ala Tyr Lys Cys Lys Lys Thr Leu Thr Lys Asn Gln Cys Thr
 35                  40                  45

Lys Val Pro Val Gln Val Pro Ser Thr Cys Thr Lys Thr Ala Met Ser
 50                  55                  60

Lys Glu Ala Tyr Asp Cys Ser Lys Thr Glu Phe Arg Thr Glu Cys Thr
 65                  70                  75                  80

Asp Glu Val Glu Gln Val Pro Cys Met Gly Lys Glu Cys Lys Leu Arg
 85                  90                  95

Gln Leu Lys Lys Lys Arg Val Cys Arg Gln Val Pro Phe Thr Ser Lys
100                 105                 110

Asn Val Cys Tyr Lys Asn Val Pro Thr Glu Gln Thr Ser
115                 120                 125
```

<210> SEQ ID NO 76
<211> LENGTH: 543
<212> TYPE: DNA
<213> ORGANISM: Toxoplasma gondii
<220> FEATURE:
<221> NAME/KEY: CDS
<222> LOCATION: (1)..(267)
<223> OTHER INFORMATION:

<400> SEQUENCE: 76

```
cga tcc aac agt tta cga ggt aca agg caa cag ccg aac ctc tac gag     48
Arg Ser Asn Ser Leu Arg Gly Thr Arg Gln Gln Pro Asn Leu Tyr Glu
1               5                   10                  15 cac gtg tcc cca cgg ttc acg ctc tcc cat gga aaa gca aag cga ttc     96
His Val Ser Pro Arg Phe Thr Leu Ser His Gly Lys Ala Lys Arg Phe
        20                  25                  30 ctc cat tat cac cac tgc cac tgc cat tcc agc cta aga atc cta cac    144
Leu His Tyr His His Cys His Cys His Ser Ser Leu Arg Ile Leu His
35                  40                  45 ttc aaa gac gaa ctt ttg cat cgt ccg tgc gtc tcc cgt ggc caa cac    192
Phe Lys Asp Glu Leu Leu His Arg Pro Cys Val Ser Arg Gly Gln His
    50                  55                  60 cct caa gcc aaa aga gag ggc acc ttc tac act gcc cac gca atc acc    240
Pro Gln Ala Lys Arg Glu Gly Thr Phe Tyr Thr Ala His Ala Ile Thr
65                  70                  75                  80 ctg tgc ggc ggc aca caa aag cga aac tgacacacgc tactgccgtt          287
Leu Cys Gly Gly Thr Gln Lys Arg Asn
            85 ccggaaagtg gtctgaaaga aactgacaac agccgcaaag agacatttac ccggtgcctg  347 gcgtggtcaa aaatccggca taatggtttc tgcgcatcct ccattcagcc gcccaacatc  407 tgcggtcgtt cttccgtcga actatgaca caacgagcct tgtggaacaa acggttcgt    467 actgacgaca ttgcctgggt cggattcact gcatgtttgc cagggtgcat ttccacggtg  527 ctctgcgtcg atcccg                                                  543

<210> SEQ ID NO 77
<211> LENGTH: 89
<212> TYPE: PRT
<213> ORGANISM: Toxoplasma gondii

<400> SEQUENCE: 77

Arg Ser Asn Ser Leu Arg Gly Thr Arg Gln Gln Pro Asn Leu Tyr Glu
1               5                   10                  15

His Val Ser Pro Arg Phe Thr Leu Ser His Gly Lys Ala Lys Arg Phe
        20                  25                  30

Leu His Tyr His His Cys His Cys His Ser Ser Leu Arg Ile Leu His
35                  40                  45

Phe Lys Asp Glu Leu Leu His Arg Pro Cys Val Ser Arg Gly Gln His
    50                  55                  60

Pro Gln Ala Lys Arg Glu Gly Thr Phe Tyr Thr Ala His Ala Ile Thr
65                  70                  75                  80

Leu Cys Gly Gly Thr Gln Lys Arg Asn
            85

<210> SEQ ID NO 78
<211> LENGTH: 573
<212> TYPE: DNA
<213> ORGANISM: Toxoplasma gondii
<220> FEATURE:
<221> NAME/KEY: CDS
<222> LOCATION: (1)..(573)
<223> OTHER INFORMATION:

<400> SEQUENCE: 78 ccg gcg tcg tcg agc tcg agg ctg ggc aag ctg gct tac gac gat gca     48
Pro Ala Ser Ser Ser Ser Arg Leu Gly Lys Leu Ala Tyr Asp Asp Ala
1               5                   10                  15 gga ggt gga cga gga gcg agc tcg cca cca tct tct aag ttg ttt gtt     96
Gly Gly Gly Arg Gly Ala Ser Ser Pro Pro Ser Ser Lys Leu Phe Val
        20                  25                  30
```

|  |  |  |  |  |  |  |  |  |  |  |  |  |  |  |  |
|---|---|---|---|---|---|---|---|---|---|---|---|---|---|---|---|
| tcc | cca | gtc | aac | gac | agg | tca | cgg | atg | gca | gat | caa | cga | aaa | cct | gca | 144 |
| Ser | Pro | Val | Asn | Asp | Arg | Ser | Arg | Met | Ala | Asp | Gln | Arg | Lys | Pro | Ala |
| 35 |  |  |  | 40 |  |  |  |  | 45 |  |  |  |  |  |  |

```
tcc cca gtc aac gac agg tca cgg atg gca gat caa cga aaa cct gca    144
Ser Pro Val Asn Asp Arg Ser Arg Met Ala Asp Gln Arg Lys Pro Ala
 35                  40                  45 ccc gaa caa tcg tcc aat cac gat tcg gaa tgc tgt tgc cta cgc tgt    192
Pro Glu Gln Ser Ser Asn His Asp Ser Glu Cys Cys Cys Leu Arg Cys
 50                  55                  60 ctg agt gag aag acg ctg atg atg gca cag ctc tgc agg cct gca cct    240
Leu Ser Glu Lys Thr Leu Met Met Ala Gln Leu Cys Arg Pro Ala Pro
 65                  70                  75                  80 gta acc ctg tct gta aca gag agg aac cta ttt gga gat aat ggc aga    288
Val Thr Leu Ser Val Thr Glu Arg Asn Leu Phe Gly Asp Asn Gly Arg
 85                  90                  95 gac gtc gtt gaa tgg gag ggt tca tgc gga ttt ttt tct gga aat gca    336
Asp Val Val Glu Trp Glu Gly Ser Cys Gly Phe Phe Ser Gly Asn Ala
100                 105                 110 tcg act agg cca tct ctg cag ttc tcc cct cac cgt gtc atc gat gcc    384
Ser Thr Arg Pro Ser Leu Gln Phe Ser Pro His Arg Val Ile Asp Ala
115                 120                 125 cca aca gcc aat gac gat atg aga gat tgc aga gca gcc cct gaa gac    432
Pro Thr Ala Asn Asp Asp Met Arg Asp Cys Arg Ala Ala Pro Glu Asp
130                 135                 140 ggg aca ggt acc tca aag gca aat att cac cgc agt agc aac ata aca    480
Gly Thr Gly Thr Ser Lys Ala Asn Ile His Arg Ser Ser Asn Ile Thr
145                 150                 155                 160 aaa acg aag gaa gag aat ggt aga gat gtg tgt gag gga ctc agg aaa    528
Lys Thr Lys Glu Glu Asn Gly Arg Asp Val Cys Glu Gly Leu Arg Lys
165                 170                 175 ccg ttg cag gac gat tct gaa gga gtc caa caa cct ctt ccg ccg        573
Pro Leu Gln Asp Asp Ser Glu Gly Val Gln Gln Pro Leu Pro Pro
180                 185                 190

<210> SEQ ID NO 79
<211> LENGTH: 191
<212> TYPE: PRT
<213> ORGANISM: Toxoplasma gondii

<400> SEQUENCE: 79

Pro Ala Ser Ser Ser Arg Leu Gly Lys Leu Ala Tyr Asp Asp Ala
  1               5                  10                  15

Gly Gly Gly Arg Gly Ala Ser Ser Pro Ser Ser Lys Leu Phe Val
 20                  25                  30

Ser Pro Val Asn Asp Arg Ser Arg Met Ala Asp Gln Arg Lys Pro Ala
 35                  40                  45

Pro Glu Gln Ser Ser Asn His Asp Ser Glu Cys Cys Cys Leu Arg Cys
 50                  55                  60

Leu Ser Glu Lys Thr Leu Met Met Ala Gln Leu Cys Arg Pro Ala Pro
 65                  70                  75                  80

Val Thr Leu Ser Val Thr Glu Arg Asn Leu Phe Gly Asp Asn Gly Arg
 85                  90                  95

Asp Val Val Glu Trp Glu Gly Ser Cys Gly Phe Phe Ser Gly Asn Ala
100                 105                 110

Ser Thr Arg Pro Ser Leu Gln Phe Ser Pro His Arg Val Ile Asp Ala
115                 120                 125

Pro Thr Ala Asn Asp Asp Met Arg Asp Cys Arg Ala Ala Pro Glu Asp
130                 135                 140

Gly Thr Gly Thr Ser Lys Ala Asn Ile His Arg Ser Ser Asn Ile Thr
145                 150                 155                 160
```

-continued

```
Lys Thr Lys Glu Glu Asn Gly Arg Asp Val Cys Glu Gly Leu Arg Lys
165                 170                 175

Pro Leu Gln Asp Asp Ser Glu Gly Val Gln Gln Pro Leu Pro Pro
180                 185                 190

<210> SEQ ID NO 80
<211> LENGTH: 1835
<212> TYPE: DNA
<213> ORGANISM: Toxoplasma gondii
<220> FEATURE:
<221> NAME/KEY: CDS
<222> LOCATION: (1)..(1833)
<223> OTHER INFORMATION:

<400> SEQUENCE: 80 cgg atc agt ggg gac cag tac tct tgt ctt caa cga gga gcg gga gga      48
Arg Ile Ser Gly Asp Gln Tyr Ser Cys Leu Gln Arg Gly Ala Gly Gly
1               5                   10                  15 gac aag gag aca gca acc gag aga gaa gag agg aac aga gaa gat gcg      96
Asp Lys Glu Thr Ala Thr Glu Arg Glu Glu Arg Asn Arg Glu Asp Ala
            20                  25                  30 ccc tcc ttt ctt gaa gga gga ctc gga gat gac gag aca gag aga gcg     144
Pro Ser Phe Leu Glu Gly Gly Leu Gly Asp Asp Glu Thr Glu Arg Ala
        35                  40                  45 aag caa gcg agt gag ttg ccc gcg tct ctt tgc tct ttc gcc gca gca     192
Lys Gln Ala Ser Glu Leu Pro Ala Ser Leu Cys Ser Phe Ala Ala Ala
    50                  55                  60 cgc agg ggc gcg agc cgc gca gag aag aca ggc gca aag ggg gag gaa     240
Arg Arg Gly Ala Ser Arg Ala Glu Lys Thr Gly Ala Lys Gly Glu Glu
65                  70                  75                  80 gcc aga gag aaa gaa gtc agt ttc ggt gaa gac agt ggg cta tcc aga     288
Ala Arg Glu Lys Glu Val Ser Phe Gly Glu Asp Ser Gly Leu Ser Arg
                85                  90                  95 cag gtg gac atg gac agt tcg cag gaa tct gtc aac gaa gga gag ccg     336
Gln Val Asp Met Asp Ser Ser Gln Glu Ser Val Asn Glu Gly Glu Pro
            100                 105                 110 cta cac gac aga gcc gca ggg gag gac gca gaa ggc ggg gga gca gag     384
Leu His Asp Arg Ala Ala Gly Glu Asp Ala Glu Gly Gly Gly Ala Glu
        115                 120                 125 gcg aac gac gga gac aga gag gga gac gag aag gag act cga gac gtc     432
Ala Asn Asp Gly Asp Arg Glu Gly Asp Glu Lys Glu Thr Arg Asp Val
    130                 135                 140 gag gac gaa gga gag acg cgt cgt tct tcc tct ttc gct gaa caa act     480
Glu Asp Glu Gly Glu Thr Arg Arg Ser Ser Ser Phe Ala Glu Gln Thr
145                 150                 155                 160 gga aat gaa aga acc gag atg aga acc aga cat ggg ggt gac gag ggc     528
Gly Asn Glu Arg Thr Glu Met Arg Thr Arg His Gly Gly Asp Glu Gly
                165                 170                 175 tgg acc tcg aag tcg aat cgg ttc gct ttt gcc tgc cct cgg ttt tcc     576
Trp Thr Ser Lys Ser Asn Arg Phe Ala Phe Ala Cys Pro Arg Phe Ser
            180                 185                 190 aaa tct gat gtc tgc tgt tct ccc cag gct cgg ctg tct ttg cct gaa     624
Lys Ser Asp Val Cys Cys Ser Pro Gln Ala Arg Leu Ser Leu Pro Glu
        195                 200                 205 cag tcc cta ggc tcc tct ccg tcg tcg ccc att tct gtc aca aat gat     672
Gln Ser Leu Gly Ser Ser Pro Ser Ser Pro Ile Ser Val Thr Asn Asp
    210                 215                 220 gtc tat gct ctc ttc gat tcg tct gca tct cct ctg cat gcg gga gag     720
Val Tyr Ala Leu Phe Asp Ser Ser Ala Ser Pro Leu His Ala Gly Glu
225                 230                 235                 240 tta tct tct ctt ccc ggc gcg gtc tcg gcc tca gag cgc cta ttg act     768
```

```
                                                                -continued

Leu Ser Ser Leu Pro Gly Ala Val Ser Ala Ser Glu Arg Leu Leu Thr
245                 250                 255 gct ccg gca gaa ata ggt ccc tcg gcc tcc tca gcc tgc ctc tcc gtt         816
Ala Pro Ala Glu Ile Gly Pro Ser Ala Ser Ser Ala Cys Leu Ser Val
260                 265                 270 tct tgt ggt cca ggc gaa atg tct ccg aca gcg gat acg acg aga cac         864
Ser Cys Gly Pro Gly Glu Met Ser Pro Thr Ala Asp Thr Thr Arg His
275                 280                 285 gac gcg gaa gag aga gaa cgc agg aga gcg gag gaa gag aag gag aga         912
Asp Ala Glu Glu Arg Glu Arg Arg Ala Glu Glu Glu Lys Glu Arg
290                 295                 300 gag aga cag gaa gaa gaa gag aga gaa cgc agg aga gtg gag gaa gag         960
Glu Arg Gln Glu Glu Glu Glu Arg Glu Arg Arg Arg Val Glu Glu Glu
305                 310                 315                 320 aag gag aga gag aga cag gaa gaa gaa gag aga gaa cgc agg aga gtg        1008
Lys Glu Arg Glu Arg Gln Glu Glu Glu Glu Arg Glu Arg Arg Arg Val
325                 330                 335 gag gaa gag aag gcg aga cag aga gag gaa gat gag aga gaa cgc agg        1056
Glu Glu Glu Lys Ala Arg Gln Arg Glu Glu Asp Glu Arg Glu Arg Arg
340                 345                 350 aga gtg gag gaa gag aag gcg aga cag aga gag gaa gaa gag aga gaa        1104
Arg Val Glu Glu Glu Lys Ala Arg Gln Arg Glu Glu Glu Glu Arg Glu
355                 360                 365 cgc agg aga gtg gag gaa gag aag gcg aga cag aga gag gaa gaa gaa        1152
Arg Arg Arg Val Glu Glu Glu Lys Ala Arg Gln Arg Glu Glu Glu Glu
370                 375                 380 gag aga gaa cgc agg aga gtg gag gaa gag aag gcg aga cag aga gag        1200
Glu Arg Glu Arg Arg Arg Val Glu Glu Glu Lys Ala Arg Gln Arg Glu
385                 390                 395                 400 gaa gaa gaa gag aga gaa cgc agg aga gtg gag gaa gag aag gcg aga        1248
Glu Glu Glu Glu Arg Glu Arg Arg Arg Val Glu Glu Glu Lys Ala Arg
405                 410                 415 cag aga gag gaa gaa gaa gag aga gaa ggc agg aga gtg gag gaa gag        1296
Gln Arg Glu Glu Glu Glu Arg Glu Gly Arg Arg Val Glu Glu Glu
420                 425                 430 aag gcg aga cag aga gag gaa gaa gaa gag aga gaa ggc agg aga gtg        1344
Lys Ala Arg Gln Arg Glu Glu Glu Glu Arg Glu Gly Arg Arg Val
435                 440                 445 gag gaa gag aag gcg aga cag aga gag gaa gaa gag aga gaa cgc agg        1392
Glu Glu Glu Lys Ala Arg Gln Arg Glu Glu Glu Arg Glu Arg Arg
450                 455                 460 aga gta gag gaa gag aag gag aga gag aga cag gag gaa gag aga gaa        1440
Arg Val Glu Glu Glu Lys Glu Arg Glu Arg Gln Glu Glu Glu Arg Glu
465                 470                 475                 480 cgc agg aga gta gag gaa gag aag gag aga gag aga cag gag gaa gaa        1488
Arg Arg Arg Val Glu Glu Glu Lys Glu Arg Glu Arg Gln Glu Glu Glu
485                 490                 495 gag aga gaa cgc agg aga gtg gag gaa gag aag gag aga gag aga cag        1536
Glu Arg Glu Arg Arg Arg Val Glu Glu Glu Lys Glu Arg Glu Arg Gln
500                 505                 510 gaa gaa gaa aag aga gaa cgc agg aga gtg gag gaa gag aag gcg aga        1584
Glu Glu Glu Lys Arg Glu Arg Arg Arg Val Glu Glu Glu Lys Ala Arg
515                 520                 525 cag aga cag gaa gaa gaa ggg aga gaa aga caa aga gga gag gag aga        1632
Gln Arg Gln Glu Glu Glu Gly Arg Glu Arg Gln Arg Gly Glu Glu Arg
530                 535                 540 gaa gag aga gag aga gaa ttt caa cag cgc gag cgg gag ctg aag aca        1680
Glu Glu Arg Glu Arg Glu Phe Gln Gln Arg Glu Arg Glu Leu Lys Thr
545                 550                 555                 560
```

```
cgg cta gta gag ctt cag aga gag cac gca gag tct gtt gaa acg tgg      1728
Arg Leu Val Glu Leu Gln Arg Glu His Ala Glu Ser Val Glu Thr Trp
565                 570                 575 atg aag gag caa gga gaa cga gaa agg cac ttg act cag gat tgg gag      1776
Met Lys Glu Gln Gly Glu Arg Glu Arg His Leu Thr Gln Asp Trp Glu
    580                 585                 590 agg aaa ttg cat gcg ttt gaa gag cag agt cgg act gtg ttg ctc caa      1824
Arg Lys Leu His Ala Phe Glu Glu Gln Ser Arg Thr Val Leu Leu Gln
595                 600                 605 gag aga tcc cg                                                       1835
Glu Arg Ser
610

<210> SEQ ID NO 81
<211> LENGTH: 611
<212> TYPE: PRT
<213> ORGANISM: Toxoplasma gondii

<400> SEQUENCE: 81

Arg Ile Ser Gly Asp Gln Tyr Ser Cys Leu Gln Arg Gly Ala Gly Gly
1               5                   10                  15

Asp Lys Glu Thr Ala Thr Glu Arg Glu Arg Asn Arg Glu Asp Ala
        20                  25                  30

Pro Ser Phe Leu Glu Gly Gly Leu Gly Asp Glu Thr Glu Arg Ala
35                  40                  45

Lys Gln Ala Ser Glu Leu Pro Ala Ser Leu Cys Ser Phe Ala Ala Ala
50                  55                  60

Arg Arg Gly Ala Ser Arg Ala Glu Lys Thr Gly Ala Lys Gly Glu Glu
65                  70                  75                  80

Ala Arg Glu Lys Glu Val Ser Phe Gly Glu Asp Ser Gly Leu Ser Arg
                85                  90                  95

Gln Val Asp Met Asp Ser Ser Gln Glu Ser Val Asn Glu Gly Glu Pro
            100                 105                 110

Leu His Asp Arg Ala Ala Gly Glu Asp Ala Glu Gly Gly Gly Ala Glu
115                 120                 125

Ala Asn Asp Gly Asp Arg Glu Gly Asp Glu Lys Glu Thr Arg Asp Val
130                 135                 140

Glu Asp Glu Gly Glu Thr Arg Arg Ser Ser Phe Ala Glu Gln Thr
145                 150                 155                 160

Gly Asn Glu Arg Thr Glu Met Arg Thr Arg His Gly Gly Asp Glu Gly
            165                 170                 175

Trp Thr Ser Lys Ser Asn Arg Phe Ala Phe Ala Cys Pro Arg Phe Ser
180                 185                 190

Lys Ser Asp Val Cys Cys Ser Pro Gln Ala Arg Leu Ser Leu Pro Glu
195                 200                 205

Gln Ser Leu Gly Ser Ser Pro Ser Ser Pro Ile Ser Val Thr Asn Asp
210                 215                 220

Val Tyr Ala Leu Phe Asp Ser Ser Ala Ser Pro Leu His Ala Gly Glu
225                 230                 235                 240

Leu Ser Ser Leu Pro Gly Ala Val Ser Ala Ser Glu Arg Leu Leu Thr
                245                 250                 255

Ala Pro Ala Glu Ile Gly Pro Ser Ala Ser Ser Ala Cys Leu Ser Val
            260                 265                 270

Ser Cys Gly Pro Gly Glu Met Ser Pro Thr Ala Asp Thr Thr Arg His
275                 280                 285

Asp Ala Glu Glu Arg Glu Arg Arg Arg Ala Glu Glu Glu Lys Glu Arg
```

-continued

```
                290                 295                 300
Glu Arg Gln Glu Glu Glu Arg Glu Arg Arg Val Glu Glu Glu
305                 310                 315                 320

Lys Glu Arg Glu Arg Gln Glu Glu Glu Arg Glu Arg Arg Val
325                 330                 335

Glu Glu Glu Lys Ala Arg Gln Arg Glu Asp Glu Arg Glu Arg
340                 345                 350

Arg Val Glu Glu Lys Ala Arg Gln Arg Glu Glu Glu Arg Glu
355                 360                 365

Arg Arg Arg Val Glu Glu Lys Ala Arg Gln Arg Glu Glu Glu
370                 375                 380

Glu Arg Glu Arg Arg Val Glu Glu Glu Lys Ala Arg Gln Arg Glu
385                 390                 395                 400

Glu Glu Glu Arg Glu Arg Arg Val Glu Glu Lys Ala Arg
405                 410                 415

Gln Arg Glu Glu Glu Glu Arg Glu Gly Arg Arg Val Glu Glu Glu
420                 425                 430

Lys Ala Arg Gln Arg Glu Glu Glu Glu Arg Glu Gly Arg Arg Val
435                 440                 445

Glu Glu Glu Lys Ala Arg Gln Arg Glu Glu Glu Arg Glu Arg Arg
450                 455                 460

Arg Val Glu Glu Glu Lys Glu Arg Glu Arg Gln Glu Glu Glu Arg Glu
465                 470                 475                 480

Arg Arg Arg Val Glu Glu Glu Lys Glu Arg Glu Arg Gln Glu Glu Glu
485                 490                 495

Glu Arg Glu Arg Arg Val Glu Glu Glu Lys Glu Arg Glu Arg Gln
500                 505                 510

Glu Glu Glu Lys Arg Glu Arg Arg Val Glu Glu Lys Ala Arg
515                 520                 525

Gln Arg Gln Glu Glu Gly Arg Glu Arg Gln Gly Glu Glu Arg
530                 535                 540

Glu Glu Arg Glu Arg Glu Phe Gln Gln Arg Glu Arg Glu Leu Lys Thr
545                 550                 555                 560

Arg Leu Val Glu Leu Gln Arg Glu His Ala Glu Ser Val Glu Thr Trp
565                 570                 575

Met Lys Glu Gln Gly Glu Arg Glu Arg His Leu Thr Gln Asp Trp Glu
580                 585                 590

Arg Lys Leu His Ala Phe Glu Gln Ser Arg Thr Val Leu Leu Gln
595                 600                 605

Glu Arg Ser
610

<210> SEQ ID NO 82
<211> LENGTH: 604
<212> TYPE: DNA
<213> ORGANISM: Toxoplasma gondii
<220> FEATURE:
<221> NAME/KEY: CDS
<222> LOCATION: (1)..(336)
<223> OTHER INFORMATION:

<400> SEQUENCE: 82 ccg atg caa ttt gtc tct cct tcc cct ttt gtg caa tcc gac tcc ccc    48
Pro Met Gln Phe Val Ser Pro Ser Pro Phe Val Gln Ser Asp Ser Pro
1               5                   10                  15 tct tcg ccc ttc gca caa tcg gct tca cct cct cct tcc gag tac caa    96
```

```
Ser Ser Pro Phe Ala Gln Ser Ala Ser Pro Pro Ser Glu Tyr Gln
 20                  25                  30 gac tct ctt tcc ctt cct ttg gca gaa tcc gtc tcg tcg ctt cct ttg      144
Asp Ser Leu Ser Leu Pro Leu Ala Glu Ser Val Ser Ser Leu Pro Leu
 35                  40                  45 gcg aaa cag gct tct cct ctt cac ttg aca caa cac cct tct ccc ctt      192
Ala Lys Gln Ala Ser Pro Leu His Leu Thr Gln His Pro Ser Pro Leu
 50                  55                  60 cta tgg aca cag cgg gcc tct cca tct cct ttc ttg gtt caa cgg gat      240
Leu Trp Thr Gln Arg Ala Ser Pro Ser Pro Phe Leu Val Gln Arg Asp
 65                  70                  75                  80 tcg tca cct cct tct gcg tca atg cgg ctt tct gct cgt cct ttg gca      288
Ser Ser Pro Pro Ser Ala Ser Met Arg Leu Ser Ala Arg Pro Leu Ala
 85                  90                  95 aaa cat gtc tct ccc ctt ctc cgg gca aaa cag gct tct cct ttt cca      336
Lys His Val Ser Pro Leu Leu Arg Ala Lys Gln Ala Ser Pro Phe Pro
100                 105                 110 tagaaccagc agcgggcctc tccatctcct ttcttggtcc accgggtttc gttctccttt    396
catccgtcaa tgcaggtttc atctcgtcct tggggaaac atgtccctcc ccttctccgg     456
gcaaaacagg cttctccttt tccatagaac cagcagcggg cctctccatc tccgttggtg    516
gtccaccggg tttcgttctc ttttcatctg tcaatgcagg tttcgtctcg tgctttggca    576
aaacatgtcc ctccccttct ccggggtg                                       604

<210> SEQ ID NO 83
<211> LENGTH: 112
<212> TYPE: PRT
<213> ORGANISM: Toxoplasma gondii

<400> SEQUENCE: 83

Pro Met Gln Phe Val Ser Pro Ser Pro Phe Val Gln Ser Asp Ser Pro
  1               5                  10                  15

Ser Ser Pro Phe Ala Gln Ser Ala Ser Pro Pro Ser Glu Tyr Gln
 20                  25                  30

Asp Ser Leu Ser Leu Pro Leu Ala Glu Ser Val Ser Ser Leu Pro Leu
 35                  40                  45

Ala Lys Gln Ala Ser Pro Leu His Leu Thr Gln His Pro Ser Pro Leu
 50                  55                  60

Leu Trp Thr Gln Arg Ala Ser Pro Ser Pro Phe Leu Val Gln Arg Asp
 65                  70                  75                  80

Ser Ser Pro Pro Ser Ala Ser Met Arg Leu Ser Ala Arg Pro Leu Ala
 85                  90                  95

Lys His Val Ser Pro Leu Leu Arg Ala Lys Gln Ala Ser Pro Phe Pro
100                 105                 110

<210> SEQ ID NO 84
<211> LENGTH: 549
<212> TYPE: DNA
<213> ORGANISM: Toxoplasma gondii

<400> SEQUENCE: 84
ggcctttcca tcgccattct tggtccaccg ggttccgtca tctcttcctc cgtcaaggca     60
ggtttgtctc ggccttgggc aaaaaatgtc cttcccttc tccgggcaac acaagcttgt    120
ccttttccat agaaccagca gcgggctttt catctcccgt tggtggtcca ccgggtttcg    180
ttctcttttc atccgtcaat gcaggtttcg tctcgtcctt aggcaaaaca tgtctctccc    240
cttctccggg caaaacaagc ttgtcctttc ccatagaacc agcagcgggc ctctccatcg    300
```

-continued

```
ccattcttgg tccaccgggt ttcgttctct tttcatccgt caatgcaggt ttcgtctcgt      360
cctttggcaa acatgtctc tccccttctc cgggcaaaac aggcttctcc ttttccatag       420
aaccagcagc gggcctctcc atctccttc ttggtccacc gggtttcgtt ctctttcat        480 ccgtcaatgc aggtttcgtc tcgtccttag gcaaaacatg tctctcccct tctccgggca     540
acacaagcg                                                              549

<210> SEQ ID NO 85
<211> LENGTH: 270
<212> TYPE: DNA
<213> ORGANISM: Toxoplasma gondii
<220> FEATURE:
<221> NAME/KEY: CDS
<222> LOCATION: (1)..(270)
<223> OTHER INFORMATION:

<400> SEQUENCE: 85 cgg acg gat gaa cac tgg tgc atc atg aag gat att ggc tac aag ggc       48
Arg Thr Asp Glu His Trp Cys Ile Met Lys Asp Ile Gly Tyr Lys Gly
1               5                   10                  15 aca gac tcg aag tca aca aaa gca aac tca gcg gca gag tgc cag cag       96
Thr Asp Ser Lys Ser Thr Lys Ala Asn Ser Ala Ala Glu Cys Gln Gln
            20                  25                  30 atg tgc ctc aac gat gag agg tgt gac ttt ttc acg tgg caa cag gcg      144
Met Cys Leu Asn Asp Glu Arg Cys Asp Phe Phe Thr Trp Gln Gln Ala
35                  40                  45 ggc aag cat tgt tgg ttt aag gct ggg gcg tcc act gcc tca aca aaa      192
Gly Lys His Cys Trp Phe Lys Ala Gly Ala Ser Thr Ala Ser Thr Lys
    50                  55                  60 tac aat cgg gct ggc gac tat tct gca cca aaa cac tgc ggc ctg ccg      240
Tyr Asn Arg Ala Gly Asp Tyr Ser Ala Pro Lys His Cys Gly Leu Pro
65                  70                  75                  80 acc aca tgt gtc aag gag cgg acc aag tcg                              270
Thr Thr Cys Val Lys Glu Arg Thr Lys Ser
                85                  90

<210> SEQ ID NO 86
<211> LENGTH: 90
<212> TYPE: PRT
<213> ORGANISM: Toxoplasma gondii

<400> SEQUENCE: 86

Arg Thr Asp Glu His Trp Cys Ile Met Lys Asp Ile Gly Tyr Lys Gly
1               5                   10                  15

Thr Asp Ser Lys Ser Thr Lys Ala Asn Ser Ala Ala Glu Cys Gln Gln
            20                  25                  30

Met Cys Leu Asn Asp Glu Arg Cys Asp Phe Phe Thr Trp Gln Gln Ala
35                  40                  45

Gly Lys His Cys Trp Phe Lys Ala Gly Ala Ser Thr Ala Ser Thr Lys
    50                  55                  60

Tyr Asn Arg Ala Gly Asp Tyr Ser Ala Pro Lys His Cys Gly Leu Pro
65                  70                  75                  80

Thr Thr Cys Val Lys Glu Arg Thr Lys Ser
                85                  90

<210> SEQ ID NO 87
<211> LENGTH: 306
<212> TYPE: DNA
<213> ORGANISM: Toxoplasma gondii
<220> FEATURE:
```

```
<221> NAME/KEY: CDS
<222> LOCATION: (1)..(306)
<223> OTHER INFORMATION:

<400> SEQUENCE: 87 cgg cgg caa caa atg ggc cct gtt cga gcc cct gac ctc caa ttc aac      48
Arg Arg Gln Gln Met Gly Pro Val Arg Ala Pro Asp Leu Gln Phe Asn
1               5                   10                  15 cag tcg cca ctg ctc ccc cac aac ctc ggc cct gcc cac gtt ccc atg      96
Gln Ser Pro Leu Leu Pro His Asn Leu Gly Pro Ala His Val Pro Met
            20                  25                  30 gga ggt ctc ccg tcg cat cct cat atc tcg gac ttt cat aac tca tcg     144
Gly Gly Leu Pro Ser His Pro His Ile Ser Asp Phe His Asn Ser Ser
35                  40                  45 gag tcg cgc ccg caa cat ccg ctg ctt gcc agc ggg ctc gca tcg aga     192
Glu Ser Arg Pro Gln His Pro Leu Leu Ala Ser Gly Leu Ala Ser Arg
    50                  55                  60 ctc gga cag ggc ctg acg ccc cag gag aga cag ttc gtg ctc tct caa     240
Leu Gly Gln Gly Leu Thr Pro Gln Glu Arg Gln Phe Val Leu Ser Gln
65                  70                  75                  80 cag tct ggc gga tcg acc tcg ttc ctg ctg cct gcg ttg ccg tct ctc     288
Gln Ser Gly Gly Ser Thr Ser Phe Leu Leu Pro Ala Leu Pro Ser Leu
            85                  90                  95 tca gag aac ctc tcc gcg                                             306
Ser Glu Asn Leu Ser Ala
100

<210> SEQ ID NO 88
<211> LENGTH: 102
<212> TYPE: PRT
<213> ORGANISM: Toxoplasma gondii

<400> SEQUENCE: 88

Arg Arg Gln Gln Met Gly Pro Val Arg Ala Pro Asp Leu Gln Phe Asn
1               5                   10                  15

Gln Ser Pro Leu Leu Pro His Asn Leu Gly Pro Ala His Val Pro Met
            20                  25                  30

Gly Gly Leu Pro Ser His Pro His Ile Ser Asp Phe His Asn Ser Ser
35                  40                  45

Glu Ser Arg Pro Gln His Pro Leu Leu Ala Ser Gly Leu Ala Ser Arg
    50                  55                  60

Leu Gly Gln Gly Leu Thr Pro Gln Glu Arg Gln Phe Val Leu Ser Gln
65                  70                  75                  80

Gln Ser Gly Gly Ser Thr Ser Phe Leu Leu Pro Ala Leu Pro Ser Leu
            85                  90                  95

Ser Glu Asn Leu Ser Ala
100

<210> SEQ ID NO 89
<211> LENGTH: 804
<212> TYPE: DNA
<213> ORGANISM: Toxoplasma gondii
<220> FEATURE:
<221> NAME/KEY: CDS
<222> LOCATION: (1)..(804)
<223> OTHER INFORMATION:

<400> SEQUENCE: 89 cgc gga ggc att tca gtt ccc aca ctt tcc atc atg aat cag agc acc      48
Arg Gly Gly Ile Ser Val Pro Thr Leu Ser Ile Met Asn Gln Ser Thr
1               5                   10                  15
```

| | | |
|---|---|---|
| att gtt gcg acg tct gtg gtc gct ccg cag agc gca gtc tca ctt tcg<br>Ile Val Ala Thr Ser Val Val Ala Pro Gln Ser Ala Val Ser Leu Ser<br>20                      25                        30 | | 96 |
| agg gcc cct agc cga cca ggg cct agc gag agt ttc ggt aaa cag caa<br>Arg Ala Pro Ser Arg Pro Gly Pro Ser Glu Ser Phe Gly Lys Gln Gln<br>35                      40                        45 | | 144 |
| gaa agt cgt cca ggt gtt tcg ggt gct ggc ctc gct gaa agc aaa cgc<br>Glu Ser Arg Pro Gly Val Ser Gly Ala Gly Leu Ala Glu Ser Lys Arg<br>50                      55                        60 | | 192 |
| gtg ccc agc ctt act cag ccg tct ctg gaa cgg tcc gta acc ata tca<br>Val Pro Ser Leu Thr Gln Pro Ser Leu Glu Arg Ser Val Thr Ile Ser<br>65                      70                        75                        80 | | 240 |
| cga cgc aaa att gat gcg gtg ggc atg tca ctc gtg ccg aag tta gac<br>Arg Arg Lys Ile Asp Ala Val Gly Met Ser Leu Val Pro Lys Leu Asp<br>85                      90                        95 | | 288 |
| agg aca acg act tct ctt gca gcg aag gag gag aaa ttc agt tct atc<br>Arg Thr Thr Thr Ser Leu Ala Ala Lys Glu Glu Lys Phe Ser Ser Ile<br>100                     105                     110 | | 336 |
| gac aag ata gtc tca aag cca acc cat tct ttt ggg gag agt tcc aaa<br>Asp Lys Ile Val Ser Lys Pro Thr His Ser Phe Gly Glu Ser Ser Lys<br>115                     120                     125 | | 384 |
| tta cca gcg ggt ata atg aaa gcg aaa tca atg ttt ccg tca caa acc<br>Leu Pro Ala Gly Ile Met Lys Ala Lys Ser Met Phe Pro Ser Gln Thr<br>130                     135                     140 | | 432 |
| ctt tcc gca ccg tgg aac gct cct gct cgt tgc gct cgg aaa gac agc<br>Leu Ser Ala Pro Trp Asn Ala Pro Ala Arg Cys Ala Arg Lys Asp Ser<br>145                     150                     155                     160 | | 480 |
| ttc ggg acg aag gcc tgg atc gaa aaa ctg caa aga gaa acc aca gac<br>Phe Gly Thr Lys Ala Trp Ile Glu Lys Leu Gln Arg Glu Thr Thr Asp<br>165                     170                     175 | | 528 |
| acc tcg cag cct cca ctt gag cgt caa aag tcg cag cgc ctc gcg caa<br>Thr Ser Gln Pro Pro Leu Glu Arg Gln Lys Ser Gln Arg Leu Ala Gln<br>180                     185                     190 | | 576 |
| acc gag cct gtg cag aaa ctc aag aca tcc tgg ttg gag cct cct caa<br>Thr Glu Pro Val Gln Lys Leu Lys Thr Ser Trp Leu Glu Pro Pro Gln<br>195                     200                     205 | | 624 |
| gag gtc gaa agt gga cat gga gtc gct gaa ggc gac gat ctc agc gtt<br>Glu Val Glu Ser Gly His Gly Val Ala Glu Gly Asp Asp Leu Ser Val<br>210                     215                     220 | | 672 |
| gca gca gcc gag tat cac gtc cca gaa acg gaa gat gga aaa ccc agc<br>Ala Ala Ala Glu Tyr His Val Pro Glu Thr Glu Asp Gly Lys Pro Ser<br>225                     230                     235                     240 | | 720 |
| ttc aaa cct agc gac ccc cgc gtg tgg aat cgc gag tgg atc cac cga<br>Phe Lys Pro Ser Asp Pro Arg Val Trp Asn Arg Glu Trp Ile His Arg<br>245                     250                     255 | | 768 |
| agg ata cat aac ccc gtc ctc agt cgc tcg aac cgg<br>Arg Ile His Asn Pro Val Leu Ser Arg Ser Asn Arg<br>260                     265 | | 804 |

<210> SEQ ID NO 90
<211> LENGTH: 268
<212> TYPE: PRT
<213> ORGANISM: Toxoplasma gondii

<400> SEQUENCE: 90

Arg Gly Gly Ile Ser Val Pro Thr Leu Ser Ile Met Asn Gln Ser Thr
1               5                    10                   15

Ile Val Ala Thr Ser Val Val Ala Pro Gln Ser Ala Val Ser Leu Ser
20                      25                        30

Arg Ala Pro Ser Arg Pro Gly Pro Ser Glu Ser Phe Gly Lys Gln Gln

```
                 35                  40                  45
Glu Ser Arg Pro Gly Val Ser Gly Ala Gly Leu Ala Glu Ser Lys Arg
 50                  55                  60

Val Pro Ser Leu Thr Gln Pro Ser Leu Glu Arg Ser Val Thr Ile Ser
 65                  70                  75                  80

Arg Arg Lys Ile Asp Ala Val Gly Met Ser Leu Val Pro Lys Leu Asp
             85                  90                  95

Arg Thr Thr Thr Ser Leu Ala Ala Lys Glu Glu Lys Phe Ser Ser Ile
        100                 105                 110

Asp Lys Ile Val Ser Lys Pro Thr His Ser Phe Gly Glu Ser Ser Lys
    115                 120                 125

Leu Pro Ala Gly Ile Met Lys Ala Lys Ser Met Phe Pro Ser Gln Thr
130                 135                 140

Leu Ser Ala Pro Trp Asn Ala Pro Ala Arg Cys Ala Arg Lys Asp Ser
145                 150                 155                 160

Phe Gly Thr Lys Ala Trp Ile Glu Lys Leu Gln Arg Glu Thr Thr Asp
            165                 170                 175

Thr Ser Gln Pro Pro Leu Glu Arg Gln Lys Ser Gln Arg Leu Ala Gln
        180                 185                 190

Thr Glu Pro Val Gln Lys Leu Lys Thr Ser Trp Leu Glu Pro Pro Gln
    195                 200                 205

Glu Val Glu Ser Gly His Gly Val Ala Glu Gly Asp Asp Leu Ser Val
210                 215                 220

Ala Ala Ala Glu Tyr His Val Pro Glu Thr Glu Asp Gly Lys Pro Ser
225                 230                 235                 240

Phe Lys Pro Ser Asp Pro Arg Val Trp Asn Arg Glu Trp Ile His Arg
            245                 250                 255

Arg Ile His Asn Pro Val Leu Ser Arg Ser Asn Arg
        260                 265

<210> SEQ ID NO 91
<211> LENGTH: 867
<212> TYPE: DNA
<213> ORGANISM: Toxoplasma gondii
<220> FEATURE:
<221> NAME/KEY: CDS
<222> LOCATION: (1)..(867)
<223> OTHER INFORMATION:

<400> SEQUENCE: 91 cgg gat cca gct ggc aag gca gta aag aag gca gcc aca ggg ata cca        48
Arg Asp Pro Ala Gly Lys Ala Val Lys Lys Ala Ala Thr Gly Ile Pro
1               5                  10                  15 aag cct gca gct cca ggt ggc aag gca gtc aag gtg act cct gtc gcg       96
Lys Pro Ala Ala Pro Gly Gly Lys Ala Val Lys Val Thr Pro Val Ala
            20                  25                  30 cga aaa cct gtt gca cca aag gca gca gct cca gac ggc aag gcg gtc      144
Arg Lys Pro Val Ala Pro Lys Ala Ala Ala Pro Asp Gly Lys Ala Val
        35                  40                  45 aag aag gca acc gta gtc gtg cca aag cct gca gct ccc agt ggc aag      192
Lys Lys Ala Thr Val Val Val Pro Lys Pro Ala Ala Pro Ser Gly Lys
    50                  55                  60 gca gtg aag aag ccg gtt gtc agc gtg cca aag cct gca aca ctc ggt      240
Ala Val Lys Lys Pro Val Val Ser Val Pro Lys Pro Ala Thr Leu Gly
65                  70                  75                  80 ggc aag gca gtg aag aag cca gct gcc ggc gtg cca aag ccc gca gct      288
Gly Lys Ala Val Lys Lys Pro Ala Ala Gly Val Pro Lys Pro Ala Ala
            85                  90                  95
```

```
ccc gat ggc aag gcg gtg aga aag cca gtt gtc ggc gtg cca aag ccc        336
Pro Asp Gly Lys Ala Val Arg Lys Pro Val Val Gly Val Pro Lys Pro
100                 105                 110 gca gct ccc gat ggt aag gcg gcg aaa aag cca gcg tcc ggc gtg cca        384
Ala Ala Pro Asp Gly Lys Ala Lys Lys Pro Ala Ser Gly Val Pro
115                 120                 125 aag cct gcg gat cca gct ggc aag gca gta aag aag gca gcc aca ggg        432
Lys Pro Ala Asp Pro Ala Gly Lys Ala Val Lys Lys Ala Ala Thr Gly
130                 135                 140 ata cca aag cct gca gct cca ggt ggc aag gca atc aag gtg act cct        480
Ile Pro Lys Pro Ala Ala Pro Gly Gly Lys Ala Ile Lys Val Thr Pro
145                 150                 155                 160 gtc gcg cga aaa cct gtt gca cca aag gca gca gct cca gac ggc aag        528
Val Ala Arg Lys Pro Val Ala Pro Lys Ala Ala Ala Pro Asp Gly Lys
165                 170                 175 gca gtc aag aag gca acc gta gtc gtg cca aag cct gca gct ccc agt        576
Ala Val Lys Lys Ala Thr Val Val Val Pro Lys Pro Ala Ala Pro Ser
180                 185                 190 ggc aag gca gtg aag aag cca gtt gtc agc gtg cca aag cct gca acg        624
Gly Lys Ala Val Lys Lys Pro Val Val Ser Val Pro Lys Pro Ala Thr
195                 200                 205 ctc gat ggc aag gcg gtg aga aag cca gtt gtc ggc gtg cca aag ccc        672
Leu Asp Gly Lys Ala Val Arg Lys Pro Val Val Gly Val Pro Lys Pro
210                 215                 220 gca gct ccc gat ggt aag gcg gtg aaa aag cca gtt gtc ggc gtg cca        720
Ala Ala Pro Asp Gly Lys Ala Val Lys Lys Pro Val Val Gly Val Pro
225                 230                 235                 240 aag cct gca gct cca gat gac acg gga atc aac aag gcg acc ctt gtc        768
Lys Pro Ala Ala Pro Asp Asp Thr Gly Ile Asn Lys Ala Thr Leu Val
245                 250                 255 acg cgg aaa cct gag gct cca gac gtg aag gta gtc aag aag gca acc        816
Thr Arg Lys Pro Glu Ala Pro Asp Val Lys Val Val Lys Lys Ala Thr
260                 265                 270 gta gtt gtg cca aaa cct gaa gcg cca gat ata aag gta atg acg gat        864
Val Val Val Pro Lys Pro Glu Ala Pro Asp Ile Lys Val Met Thr Asp
275                 280                 285 ccg                                                                    867
Pro

<210> SEQ ID NO 92
<211> LENGTH: 289
<212> TYPE: PRT
<213> ORGANISM: Toxoplasma gondii

<400> SEQUENCE: 92

Arg Asp Pro Ala Gly Lys Ala Val Lys Lys Ala Thr Gly Ile Pro
1               5                   10                  15

Lys Pro Ala Ala Pro Gly Gly Lys Ala Val Lys Val Thr Pro Val Ala
20                  25                  30

Arg Lys Pro Val Ala Pro Lys Ala Ala Ala Pro Asp Gly Lys Ala Val
35                  40                  45

Lys Lys Ala Thr Val Val Val Pro Lys Pro Ala Ala Pro Ser Gly Lys
50                  55                  60

Ala Val Lys Lys Pro Val Val Ser Val Pro Lys Pro Ala Thr Leu Gly
65                  70                  75                  80

Gly Lys Ala Val Lys Lys Pro Ala Ala Gly Val Pro Lys Pro Ala Ala
85                  90                  95

Pro Asp Gly Lys Ala Val Arg Lys Pro Val Val Gly Val Pro Lys Pro
```

```
                100                 105                 110
Ala Ala Pro Asp Gly Lys Ala Ala Lys Lys Pro Ala Ser Gly Val Pro
115                 120                 125

Lys Pro Ala Asp Pro Ala Gly Lys Ala Val Lys Lys Ala Ala Thr Gly
130                 135                 140

Ile Pro Lys Pro Ala Ala Pro Gly Gly Lys Ala Ile Lys Val Thr Pro
145                 150                 155                 160

Val Ala Arg Lys Pro Val Ala Pro Lys Ala Ala Ala Pro Asp Gly Lys
165                 170                 175

Ala Val Lys Lys Ala Thr Val Val Pro Lys Pro Ala Ala Pro Ser
180                 185                 190

Gly Lys Ala Val Lys Lys Pro Val Val Ser Val Pro Lys Pro Ala Thr
195                 200                 205

Leu Asp Gly Lys Ala Val Arg Lys Pro Val Val Gly Val Pro Lys Pro
210                 215                 220

Ala Ala Pro Asp Gly Lys Ala Val Lys Lys Pro Val Val Gly Val Pro
225                 230                 235                 240

Lys Pro Ala Ala Pro Asp Asp Thr Gly Ile Asn Lys Ala Thr Leu Val
245                 250                 255

Thr Arg Lys Pro Glu Ala Pro Asp Val Lys Val Val Lys Lys Ala Thr
260                 265                 270

Val Val Pro Lys Pro Glu Ala Pro Asp Ile Lys Val Met Thr Asp
275                 280                 285

Pro

<210> SEQ ID NO 93
<211> LENGTH: 1434
<212> TYPE: DNA
<213> ORGANISM: Toxoplasma gondii
<220> FEATURE:
<221> NAME/KEY: CDS
<222> LOCATION: (1)..(492)
<223> OTHER INFORMATION:

<400> SEQUENCE: 93 cgg ctt gtg ttg ccc gga gaa ggg gag aga cat gtt ttg cca aag gac        48
Arg Leu Val Leu Pro Gly Glu Gly Glu Arg His Val Leu Pro Lys Asp
1               5                   10                  15 gag acg aaa cct gca ttg acg gat gaa aag aga acg aaa ccc ggt gga        96
Glu Thr Lys Pro Ala Leu Thr Asp Glu Lys Arg Thr Lys Pro Gly Gly
        20                  25                  30 cca agg aag gag atg gag agg ccc gct gct ggt tct atg gaa aag gac       144
Pro Arg Lys Glu Met Glu Arg Pro Ala Ala Gly Ser Met Glu Lys Asp
    35                  40                  45 aag ctt gtt ttg ccc gga gaa ggg gag aga cat gtt ttg cca aag gac       192
Lys Leu Val Leu Pro Gly Gly Glu Arg His Val Leu Pro Lys Asp
50                  55                  60 gag acg aaa cct gca ttg acg gag gaa aag aga acg aaa ccc ggt gga       240
Glu Thr Lys Pro Ala Leu Thr Glu Glu Lys Arg Thr Lys Pro Gly Gly
65                  70                  75                  80 cca cga acg gag atg gag agg ccc gct gct ggt tct atg gaa aag gac       288
Pro Arg Thr Glu Met Glu Arg Pro Ala Ala Gly Ser Met Glu Lys Asp
            85                  90                  95 aag cct ggt ttg ccc gga gaa ggg gag aga cat gtt ttg cca aag gac       336
Lys Pro Gly Leu Pro Gly Glu Gly Glu Arg His Val Leu Pro Lys Asp
        100                 105                 110 gag acg aaa cct gca ttg acg gag gaa aag aga acg aac ctg gcg gac       384
Glu Thr Lys Pro Ala Leu Thr Glu Glu Lys Arg Thr Asn Leu Ala Asp
```

```
                115                 120                 125
caa gaa agg aga tgg aga gcc cgc tgc tgg ttc ttg gaa aag gag aac        432
Gln Glu Arg Arg Trp Arg Ala Arg Cys Trp Phe Leu Glu Lys Glu Asn
130                 135                 140 ctg ttt ggc ccg gag aag ggg aga gac acg ctt cgc caa agg acg aga        480
Leu Phe Gly Pro Glu Lys Gly Arg Asp Thr Leu Arg Gln Arg Thr Arg
145                 150                 155                 160 cga aag ccg cat tgacgcaaaa ggaggtgacg aatcccgttg aaccaagaaa            532
Arg Lys Pro His ggcgatggag aggcccgctg ctggttctat ggaaaaggaa aacctgtttc cccggagaag      592
gggagggaca tgttttgcca agcacagac gaaacctgca ttgacagatg aaagagaac        652 gaaacccggt ggaccaccaa cggagatgga gaggcccgct gctggtttta tggaaaagga     712
gaagcctgtt ttgcccggag aaggggaggg acatgtttcc ccaaaggacg agatgaaacc     772
tgcattgacg gatgaaaaga gaacgaaacc cggtggacca agaaggaga tggagaggcc      832 cgctgctggt tttatggaaa aggagaagcc tgttttgccc ggagaagggg agagacatgt     892
tttgccaaag gacgagcaga aagccgcatt gacgcagaag gaggtgacga atcccgttga     952
accaagaaag gagatggaga ggcccgctgt gcccatagaa ggggagaagg gtgttgtgtc    1012
aagtgaagag gagaagcctg tttcgccaaa ggaagcgacg agacggattt tgccaaagga    1072
agggaaagag atttggtact cggaaggagg aggtgaagcc gattgtgcga agggcaaaga    1132
gggggagacg gattgcacaa aaggggaagg agaaacaaat tgcatcgaag gaggggaaga    1192
aacccgctgt accaaaggaa ggtgaggaaa gacccgctga accaacggaa ggcgaggaaa    1252
ggcccgttgg gccaaaggaa ggcgaggaaa gacccgttgt gccggacgta gacaaggaga    1312
aacctgttgt gcctgaagga gacaaggaga aacctgttgt gccggaagga gacaaggatc    1372
accctgcttc tgccagagca ggatgaggag aaacacgcta catgggagaa agaaatgatc    1432
cg                                                                    1434

<210> SEQ ID NO 94
<211> LENGTH: 164
<212> TYPE: PRT
<213> ORGANISM: Toxoplasma gondii

<400> SEQUENCE: 94

Arg Leu Val Leu Pro Gly Glu Gly Glu Arg His Val Leu Pro Lys Asp
1               5                   10                  15

Glu Thr Lys Pro Ala Leu Thr Asp Glu Lys Arg Thr Lys Pro Gly Gly
            20                  25                  30

Pro Arg Lys Glu Met Glu Arg Pro Ala Ala Gly Ser Met Glu Lys Asp
        35                  40                  45

Lys Leu Val Leu Pro Gly Glu Gly Glu Arg His Val Leu Pro Lys Asp
    50                  55                  60

Glu Thr Lys Pro Ala Leu Thr Glu Glu Lys Arg Thr Lys Pro Gly Gly
65                  70                  75                  80

Pro Arg Thr Glu Met Glu Arg Pro Ala Ala Gly Ser Met Glu Lys Asp
                85                  90                  95

Lys Pro Gly Leu Pro Gly Glu Gly Glu Arg His Val Leu Pro Lys Asp
            100                 105                 110

Glu Thr Lys Pro Ala Leu Thr Glu Glu Lys Arg Thr Asn Leu Ala Asp
        115                 120                 125

Gln Glu Arg Arg Trp Arg Ala Arg Cys Trp Phe Leu Glu Lys Glu Asn
    130                 135                 140
```

```
Leu Phe Gly Pro Glu Lys Gly Arg Asp Thr Leu Arg Gln Arg Thr Arg
145                 150                 155                 160

Arg Lys Pro His

<210> SEQ ID NO 95
<211> LENGTH: 680
<212> TYPE: DNA
<213> ORGANISM: Toxoplasma gondii
<220> FEATURE:
<221> NAME/KEY: CDS
<222> LOCATION: (1)..(678)
<223> OTHER INFORMATION:

<400> SEQUENCE: 95 cga cca aga gca ggg agg gag cag cct gct gtt ccg cgg cag gaa gaa       48
Arg Pro Arg Ala Gly Arg Glu Gln Pro Ala Val Pro Arg Gln Glu Glu
1               5                   10                  15 cag aaa ctt gtt ttg caa aag aca gag agg aaa cca gtt ttg cca gag       96
Gln Lys Leu Val Leu Gln Lys Thr Glu Arg Lys Pro Val Leu Pro Glu
            20                  25                  30 gaa gac cag aaa ccg gtt tta cca gaa aca ggg gcg aaa cat gtt tta      144
Glu Asp Gln Lys Pro Val Leu Pro Glu Thr Gly Ala Lys His Val Leu
35                  40                  45 ccg gaa ata gcg acc gaa tcc act ttg acg cag aaa gag ctg aca aaa      192
Pro Glu Ile Ala Thr Glu Ser Thr Leu Thr Gln Lys Glu Leu Thr Lys
50                  55                  60 ccc gtt gaa aca aga cag gac atg agg ggg acc gct ggt tct atg gac      240
Pro Val Glu Thr Arg Gln Asp Met Arg Gly Thr Ala Gly Ser Met Asp
65                  70                  75                  80 gag aag aag cct gtt ttg ccc gga gaa tgg gag aga cat gtc ttg cca      288
Glu Lys Lys Pro Val Leu Pro Gly Glu Trp Glu Arg His Val Leu Pro
                85                  90                  95 aaa gac gag acg aaa cct gca ttg acg gag gaa aag aga acg aaa ccc      336
Lys Asp Glu Thr Lys Pro Ala Leu Thr Glu Glu Lys Arg Thr Lys Pro
            100                 105                 110 gtt gaa cca aga aag gag atg gag agg ccc gct cgc ccc atg gaa gag      384
Val Glu Pro Arg Lys Glu Met Glu Arg Pro Ala Arg Pro Met Glu Glu
115                 120                 125 gag aag cct gtt tta ccc gga gaa ggg gag aga cat gtt ttg cca aag      432
Glu Lys Pro Val Leu Pro Gly Glu Gly Glu Arg His Val Leu Pro Lys
130                 135                 140 gac ggg atg aaa cct gca ttg acg gat gaa aag aga acg aaa ccc ggt      480
Asp Gly Met Lys Pro Ala Leu Thr Asp Glu Lys Arg Thr Lys Pro Gly
145                 150                 155                 160 gga cca agg aag gag atg gag agg ccc gct gct ggt tct atg gaa aag      528
Gly Pro Arg Lys Glu Met Glu Arg Pro Ala Ala Gly Ser Met Glu Lys
                165                 170                 175 gac aag ctt gtg ttg ccc gga gaa ggg gag aga cat gtt ttg cct aag      576
Asp Lys Leu Val Leu Pro Gly Glu Gly Glu Arg His Val Leu Pro Lys
            180                 185                 190 gac gag acg aaa cct gca ttg acg gat gaa aag aga acg aaa ccc ggt      624
Asp Glu Thr Lys Pro Ala Leu Thr Asp Glu Lys Arg Thr Lys Pro Gly
195                 200                 205 gga cca aga aag gcg atg gag agg ccc gct gct ggt tct atg gaa aag      672
Gly Pro Arg Lys Ala Met Glu Arg Pro Ala Ala Gly Ser Met Glu Lys
210                 215                 220 gac aag cg                                                            680
Asp Lys
225
```

<210> SEQ ID NO 96
<211> LENGTH: 226
<212> TYPE: PRT
<213> ORGANISM: Toxoplasma gondii

<400> SEQUENCE: 96

Arg Pro Arg Ala Gly Arg Glu Gln Pro Ala Val Pro Arg Gln Glu Glu
1               5                   10                  15

Gln Lys Leu Val Leu Gln Lys Thr Glu Arg Lys Pro Val Leu Pro Glu
            20                  25                  30

Glu Asp Gln Lys Pro Val Leu Pro Glu Thr Gly Ala Lys His Val Leu
        35                  40                  45

Pro Glu Ile Ala Thr Glu Ser Thr Leu Thr Gln Lys Glu Leu Thr Lys
    50                  55                  60

Pro Val Glu Thr Arg Gln Asp Met Arg Gly Thr Ala Gly Ser Met Asp
65                  70                  75                  80

Glu Lys Lys Pro Val Leu Pro Gly Glu Trp Glu Arg His Val Leu Pro
                85                  90                  95

Lys Asp Glu Thr Lys Pro Ala Leu Thr Glu Glu Lys Arg Thr Lys Pro
            100                 105                 110

Val Glu Pro Arg Lys Glu Met Glu Arg Pro Ala Arg Pro Met Glu Glu
        115                 120                 125

Glu Lys Pro Val Leu Pro Gly Glu Gly Glu Arg His Val Leu Pro Lys
    130                 135                 140

Asp Gly Met Lys Pro Ala Leu Thr Asp Glu Lys Arg Thr Lys Pro Gly
145                 150                 155                 160

Gly Pro Arg Lys Glu Met Glu Arg Pro Ala Ala Gly Ser Met Glu Lys
                165                 170                 175

Asp Lys Leu Val Leu Pro Gly Glu Gly Glu Arg His Val Leu Pro Lys
            180                 185                 190

Asp Glu Thr Lys Pro Ala Leu Thr Asp Glu Lys Arg Thr Lys Pro Gly
        195                 200                 205

Gly Pro Arg Lys Ala Met Glu Arg Pro Ala Ala Gly Ser Met Glu Lys
    210                 215                 220

Asp Lys
225

<210> SEQ ID NO 97
<211> LENGTH: 296
<212> TYPE: DNA
<213> ORGANISM: Toxoplasma gondii
<220> FEATURE:
<221> NAME/KEY: CDS
<222> LOCATION: (1)..(294)
<223> OTHER INFORMATION:

<400> SEQUENCE: 97 ccg gtc gac gtg gac gac ccc cgt ggc tgt tcg cag caa agc gga gac      48
Pro Val Asp Val Asp Asp Pro Arg Gly Cys Ser Gln Gln Ser Gly Asp
1               5                   10                  15 acc aga gac agc agc agt ccc gcc aca cct ggt ggt cgg ccg gct ggt      96
Thr Arg Asp Ser Ser Ser Pro Ala Thr Pro Gly Gly Arg Pro Ala Gly
            20                  25                  30 ggg gca gga ggt gca gcg aca agc ccg aag gga cag gcc ttt gcc ccg     144
Gly Ala Gly Gly Ala Ala Thr Ser Pro Lys Gly Gln Ala Phe Ala Pro
        35                  40                  45 cgg ggc ggt gaa ggg gag ata aag ccc cag gag aca gga aac agt gga     192
Arg Gly Gly Glu Gly Glu Ile Lys Pro Gln Glu Thr Gly Asn Ser Gly
    50                  55                  60

```
gac agc aag gcg gag gga aag gaa gca agt gga gac gcg aac act tcg        240
Asp Ser Lys Ala Glu Gly Lys Glu Ala Ser Gly Asp Ala Asn Thr Ser
65                  70                  75                  80 gaa gga aag cga ttg tcg ggc gaa gtg gac aag aca gcc gag gtg gag        288
Glu Gly Lys Arg Leu Ser Gly Glu Val Asp Lys Thr Ala Glu Val Glu
            85                  90                  95 aca gcc gg                                                             296
Thr Ala <210> SEQ ID NO 98
<211> LENGTH: 98
<212> TYPE: PRT
<213> ORGANISM: Toxoplasma gondii

<400> SEQUENCE: 98

Pro Val Asp Val Asp Pro Arg Gly Cys Ser Gln Gln Ser Gly Asp
1               5                   10                  15

Thr Arg Asp Ser Ser Pro Ala Thr Pro Gly Gly Arg Pro Ala Gly
    20                  25                  30

Gly Ala Gly Gly Ala Ala Thr Ser Pro Lys Gly Gln Ala Phe Ala Pro
35                  40                  45

Arg Gly Gly Glu Gly Glu Ile Lys Pro Gln Glu Thr Gly Asn Ser Gly
50                  55                  60

Asp Ser Lys Ala Glu Gly Lys Glu Ala Ser Gly Asp Ala Asn Thr Ser
65                  70                  75                  80

Glu Gly Lys Arg Leu Ser Gly Glu Val Asp Lys Thr Ala Glu Val Glu
            85                  90                  95

Thr Ala

<210> SEQ ID NO 99
<211> LENGTH: 723
<212> TYPE: DNA
<213> ORGANISM: Toxoplasma gondii
<220> FEATURE:
<221> NAME/KEY: CDS
<222> LOCATION: (1)..(159)
<223> OTHER INFORMATION:

<400> SEQUENCE: 99 cga tcc tcc cga ggg acc gca gga agg ctc gcg tcc gaa gaa gac gac        48
Arg Ser Ser Arg Gly Thr Ala Gly Arg Leu Ala Ser Glu Glu Asp Asp
1               5                   10                  15 gga gac aac gaa gaa gag gaa cga gaa gaa gaa agg gag aga cgc gaa        96
Gly Asp Asn Glu Glu Glu Glu Arg Glu Glu Glu Arg Glu Arg Arg Glu
            20                  25                  30 aga gaa gac ggg gaa gac gca ggc tct agg cgt cga gag aag gac ttc        144
Arg Glu Asp Gly Glu Asp Ala Gly Ser Arg Arg Arg Glu Lys Asp Phe
35                  40                  45 ttc cca gac acg act tgaatgcgta aggcgtatt tttgtttccg atgaaaactc         199
Phe Pro Asp Thr Thr
50 gccaggggag cgacttctc gcctctgagg aatccgacag tgacgagagg aagagggaag       259 gagacgcaga aaggacgcg tcaggaggat ccggaattcc ggatcgggcg atggccccgg       319 agcgcgtgag gcggtacac tgaagaacca acggaagaac actggggtc gaaaatgtgt       379 ttccttttccg atgtggtctt cccagctttc ctgcagacat gtgtacagaa cagctgagaa    439 aaaacgacga aagctccaat tgtctcttcg ttctcgagca gagaaaaccc ccgaggcct     499 tcgcttggtc agggcgaaac ctcaagggtg catgcagagt cggccgtgcc cagagtagcc    559
```

```
tagtcatgca gcccatcagt agcttaattt gacgcaatgg ctattttttac attgtgaaga    619 gggttttcca atcaacaaac gccagagaag cctgtgttct ggaaaacctg aacgacggcc    679
gtcgttcccc tgtctgcttt accccctgac agtgcgtggt gagg                     723
```

```
<210> SEQ ID NO 100
<211> LENGTH: 53
<212> TYPE: PRT
<213> ORGANISM: Toxoplasma gondii

<400> SEQUENCE: 100

Arg Ser Ser Arg Gly Thr Ala Gly Arg Leu Ala Ser Glu Glu Asp Asp
1               5                  10                  15
Gly Asp Asn Glu Glu Glu Arg Glu Glu Arg Glu Arg Arg Glu
        20                  25                  30
Arg Glu Asp Gly Glu Asp Ala Gly Ser Arg Arg Glu Lys Asp Phe
35                  40                  45
Phe Pro Asp Thr Thr
50

<210> SEQ ID NO 101
<211> LENGTH: 270
<212> TYPE: DNA
<213> ORGANISM: Toxoplasma gondii
<220> FEATURE:
<221> NAME/KEY: CDS
<222> LOCATION: (1)..(270)
<223> OTHER INFORMATION:

<400> SEQUENCE: 101 cgg aag ccg att gtg cga agg gca aag agg ggg aga cgg att gca caa   48
Arg Lys Pro Ile Val Arg Arg Ala Lys Arg Gly Arg Arg Ile Ala Gln
1               5                  10                  15 aag ggg aag gag aaa caa att gca tcg aag gag ggg aag aaa ccc gct   96
Lys Gly Lys Glu Lys Gln Ile Ala Ser Lys Glu Gly Lys Lys Pro Ala
        20                  25                  30 gta cca aag gaa ggt gag gaa aga ccc gct gaa cca acg gaa ggc gag  144
Val Pro Lys Glu Gly Glu Glu Arg Pro Ala Glu Pro Thr Glu Gly Glu
35                  40                  45 gaa agg ccc gtt ggg cca aag gaa ggc gag gaa aga ccc gtt gtg ccg  192
Glu Arg Pro Val Gly Pro Lys Glu Gly Glu Glu Arg Pro Val Val Pro
50                  55                  60 gac gta gac aag gag aaa cct gtt gtg cct gaa gga gac aag gag aaa  240
Asp Val Asp Lys Glu Lys Pro Val Val Pro Glu Gly Asp Lys Glu Lys
65                  70                  75                  80 cct gtt gtg ccg gaa gga gac aag gat ccg                           270
Pro Val Val Pro Glu Gly Asp Lys Asp Pro
85                  90

<210> SEQ ID NO 102
<211> LENGTH: 90
<212> TYPE: PRT
<213> ORGANISM: Toxoplasma gondii

<400> SEQUENCE: 102

Arg Lys Pro Ile Val Arg Arg Ala Lys Arg Gly Arg Arg Ile Ala Gln
1               5                  10                  15
Lys Gly Lys Glu Lys Gln Ile Ala Ser Lys Glu Gly Lys Lys Pro Ala
        20                  25                  30
Val Pro Lys Glu Gly Glu Glu Arg Pro Ala Glu Pro Thr Glu Gly Glu
35                  40                  45
```

Glu Arg Pro Val Gly Pro Lys Glu Gly Glu Arg Pro Val Val Pro
50                  55                  60

Asp Val Asp Lys Glu Lys Pro Val Val Pro Glu Gly Asp Lys Glu Lys
65                  70                  75                  80

Pro Val Val Pro Glu Gly Asp Lys Asp Pro
                85                  90

<210> SEQ ID NO 103
<211> LENGTH: 503
<212> TYPE: DNA
<213> ORGANISM: Toxoplasma gondii
<220> FEATURE:
<221> NAME/KEY: CDS
<222> LOCATION: (1)..(186)
<223> OTHER INFORMATION:
<220> FEATURE:
<221> NAME/KEY: misc_feature
<222> LOCATION: (433)..(433)
<223> OTHER INFORMATION: n = unknown
<220> FEATURE:
<221> NAME/KEY: misc_feature
<222> LOCATION: (489)..(489)
<223> OTHER INFORMATION: n = unknown

<400> SEQUENCE: 103 cgg cat ctc tgg tgc gtg cgc gag aga tcc ccg caa cga gaa aga tgg       48
Arg His Leu Trp Cys Val Arg Glu Arg Ser Pro Gln Arg Glu Arg Trp
1               5                   10                  15 agc ttc gtc tcg ttc tcg ctt ttc ttc tct ttc cag ttc ttt ttc agc       96
Ser Phe Val Ser Phe Ser Leu Phe Phe Ser Phe Gln Phe Phe Phe Ser
            20                  25                  30 aag caa gtc tcg cgc ctc cct cgt ccg agc agc gtc act gca ctg tgg      144
Lys Gln Val Ser Arg Leu Pro Arg Pro Ser Ser Val Thr Ala Leu Trp
35                  40                  45 gcc atc agc aga aag aag gcg aag aaa aga gac gac ggc aga              186
Ala Ile Ser Arg Lys Lys Ala Lys Lys Arg Asp Asp Gly Arg
            50                  55                  60 taatggcgcg aaaatctatc ccaaaaacac atatatgcct tatggcagtg agcgaagaga    246
gggaactgcc aacgccttgg cggaagcccg ttctccaaac gaggttgagg taccaaacct    306
gcatgcggag agaccaaggc aggttttgtc ttccgtcgct tccgtggatg cttttcgcac    366
gtatgcaaaa gagagaacgg gaccaagtgc aagaagttat agagcagtcc cgacgacaga    426
gacgcancta gaggccgagc aagaatcgtt tttttcttct cgtaagggaa acgcagtgca    486
tanaagcaaa agaccgg                                                  503

<210> SEQ ID NO 104
<211> LENGTH: 62
<212> TYPE: PRT
<213> ORGANISM: Toxoplasma gondii
<220> FEATURE:
<221> NAME/KEY: misc_feature
<222> LOCATION: (433)..(433)
<223> OTHER INFORMATION: n = unknown
<220> FEATURE:
<221> NAME/KEY: misc_feature
<222> LOCATION: (489)..(489)
<223> OTHER INFORMATION: n = unknown

<400> SEQUENCE: 104

Arg His Leu Trp Cys Val Arg Glu Arg Ser Pro Gln Arg Glu Arg Trp
1               5                   10                  15

Ser Phe Val Ser Phe Ser Leu Phe Phe Ser Phe Gln Phe Phe Phe Ser
            20                  25                  30

```
Lys Gln Val Ser Arg Leu Pro Arg Pro Ser Ser Val Thr Ala Leu Trp
 35                  40                  45

Ala Ile Ser Arg Lys Lys Ala Lys Lys Arg Asp Asp Gly Arg
 50                  55                  60

<210> SEQ ID NO 105
<211> LENGTH: 322
<212> TYPE: DNA
<213> ORGANISM: Toxoplasma gondii
<220> FEATURE:
<221> NAME/KEY: CDS
<222> LOCATION: (1)..(219)
<223> OTHER INFORMATION:
<220> FEATURE:
<221> NAME/KEY: misc_feature
<222> LOCATION: (141)..(141)
<223> OTHER INFORMATION: At nucleotide 141, n = unknown
      At amino acid residue 47, Xaa = Ser

<400> SEQUENCE: 105 cgg cgg gac ttg cgg act tcg gtc tgg gac gct cgg gtg tac gta cac        48
Arg Arg Asp Leu Arg Thr Ser Val Trp Asp Ala Arg Val Tyr Val His
 1               5                  10                  15 ctg gcg ggg ggc cag agg cgc tgc aac gag tcg cgg ggg atg gag gaa        96
Leu Ala Gly Gly Gln Arg Arg Cys Asn Glu Ser Arg Gly Met Glu Glu
         20                  25                  30 gcg agg aaa agg agg tgt ctc gcg atg cgg tgc cag tgg act tcn tct       144
Ala Arg Lys Arg Arg Cys Leu Ala Met Arg Cys Gln Trp Thr Xaa Ser
 35                  40                  45 gcg cta gat tgg agg gag agc tgg aaa aat gcc gag aca gct tcg cac       192
Ala Leu Asp Trp Arg Glu Ser Trp Lys Asn Ala Glu Thr Ala Ser His
 50                  55                  60 gtc aca ttc ccg acg aaa cgc ccg cca tgaaggaaat cacagacatc             239
Val Thr Phe Pro Thr Lys Arg Pro Pro
 65                  70 accaaccttc ccgccgtggc taaaggaccg tcctgtgtat gtacagtttt tccaggcgaa     299
agccgaagag acagcgaaac cgg                                             322

<210> SEQ ID NO 106
<211> LENGTH: 73
<212> TYPE: PRT
<213> ORGANISM: Toxoplasma gondii
<220> FEATURE:
<221> NAME/KEY: misc_feature
<222> LOCATION: (47)..(47)
<223> OTHER INFORMATION: The 'Xaa' at location 47 stands for Ser.
<220> FEATURE:
<221> NAME/KEY: misc_feature
<222> LOCATION: (141)..(141)
<223> OTHER INFORMATION: At nucleotide 141, n = unknown
      At amino acid residue 47, Xaa = Ser

<400> SEQUENCE: 106

Arg Arg Asp Leu Arg Thr Ser Val Trp Asp Ala Arg Val Tyr Val His
 1               5                  10                  15

Leu Ala Gly Gly Gln Arg Arg Cys Asn Glu Ser Arg Gly Met Glu Glu
         20                  25                  30

Ala Arg Lys Arg Arg Cys Leu Ala Met Arg Cys Gln Trp Thr Xaa Ser
 35                  40                  45

Ala Leu Asp Trp Arg Glu Ser Trp Lys Asn Ala Glu Thr Ala Ser His
 50                  55                  60

Val Thr Phe Pro Thr Lys Arg Pro Pro
 65                  70
```

```
<210> SEQ ID NO 107
<211> LENGTH: 390
<212> TYPE: DNA
<213> ORGANISM: Toxoplasma gondii
<220> FEATURE:
<221> NAME/KEY: CDS
<222> LOCATION: (1)..(201)
<223> OTHER INFORMATION:
<220> FEATURE:
<221> NAME/KEY: misc_feature
<222> LOCATION: (104)..(104)
<223> OTHER INFORMATION: At nucleotide 104, n = unknown
      At amino acid residue 35, Xaa = Lys, Arg, Thr or Ile

<400> SEQUENCE: 107 cgg cga atc ccc cag gaa ttg ttg aaa cag agt ctc aga ttc tac gga      48
Arg Arg Ile Pro Gln Glu Leu Leu Lys Gln Ser Leu Arg Phe Tyr Gly
1               5                   10                  15 ctc cga ggg cct ctg ctt gcc cgc cct gtg cac agg cgt cag cac gtg      96
Leu Arg Gly Pro Leu Leu Ala Arg Pro Val His Arg Arg Gln His Val
            20                  25                  30 gtt ctc ana gaa aaa gtt ggt aag tgg aag tgg tgg agc caa gaa aaa     144
Val Leu Xaa Glu Lys Val Gly Lys Trp Lys Trp Trp Ser Gln Glu Lys
35                  40                  45 ctc aac tct tct tgt ttt ccg gag aat ttt cct ggt gtt caa ttc cac     192
Leu Asn Ser Ser Cys Phe Pro Glu Asn Phe Pro Gly Val Gln Phe His
50                  55                  60 ggt tct gga tagtctttgt tgtattaaaa cacatctaga aggactgaga             241
Gly Ser Gly
65 cgttgtcggt agttgaatta cagacacttc gttttccagc gtcagcttgc atgcccgtcc   301 cctgtttctg gaacacaagc tttgagaagg aaacgagaca gagaacgacg aaggaagtga   361 agcaaatcct ctgacggatt tccattcgg                                     390

<210> SEQ ID NO 108
<211> LENGTH: 67
<212> TYPE: PRT
<213> ORGANISM: Toxoplasma gondii
<220> FEATURE:
<221> NAME/KEY: misc_feature
<222> LOCATION: (35)..(35)
<223> OTHER INFORMATION: The 'Xaa' at location 35 stands for Lys, Arg,
      Thr, or Ile.
<220> FEATURE:
<221> NAME/KEY: misc_feature
<222> LOCATION: (104)..(104)
<223> OTHER INFORMATION: At nucleotide 104, n = unknown
      At amino acid residue 35, Xaa = Lys, Arg, Thr or Ile

<400> SEQUENCE: 108

Arg Arg Ile Pro Gln Glu Leu Leu Lys Gln Ser Leu Arg Phe Tyr Gly
1               5                   10                  15

Leu Arg Gly Pro Leu Leu Ala Arg Pro Val His Arg Arg Gln His Val
            20                  25                  30

Val Leu Xaa Glu Lys Val Gly Lys Trp Lys Trp Trp Ser Gln Glu Lys
35                  40                  45

Leu Asn Ser Ser Cys Phe Pro Glu Asn Phe Pro Gly Val Gln Phe His
50                  55                  60

Gly Ser Gly
65

<210> SEQ ID NO 109
```

<211> LENGTH: 699
<212> TYPE: DNA
<213> ORGANISM: Toxoplasma gondii
<220> FEATURE:
<221> NAME/KEY: CDS
<222> LOCATION: (1)..(699)
<223> OTHER INFORMATION:

<400> SEQUENCE: 109

| | | | | | | | | | | | | | | | | |
|---|---|---|---|---|---|---|---|---|---|---|---|---|---|---|---|---|
| ccg | tgc | gtc | tgt | gag | gaa | aag | tgc | aag | aca | ggg | ccg | aac | tgt | gac | cag | 48 |
| Pro | Cys | Val | Cys | Glu | Glu | Lys | Cys | Lys | Thr | Gly | Pro | Asn | Cys | Asp | Gln | |
| 1 | | | | 5 | | | | | 10 | | | | | 15 | | |

| cat | aaa | ccg | gag | tgc | tgt | ggg | tcg | aac | gac | gac | tgc | cat | cag | cct | cag | 96 |
|---|---|---|---|---|---|---|---|---|---|---|---|---|---|---|---|---|
| His | Lys | Pro | Glu | Cys | Cys | Gly | Ser | Asn | Asp | Asp | Cys | His | Gln | Pro | Gln | |
| | 20 | | | | 25 | | | | | 30 | | | | | | |

| ggg | tac | tgc | aag | atg | gac | atg | tcc | aca | tgc | atc | tgc | cgt | cca | ggc | ttc | 144 |
|---|---|---|---|---|---|---|---|---|---|---|---|---|---|---|---|---|
| Gly | Tyr | Cys | Lys | Met | Asp | Met | Ser | Thr | Cys | Ile | Cys | Arg | Pro | Gly | Phe | |
| 35 | | | | | 40 | | | | | 45 | | | | | | |

| acg | ggc | gag | aac | tgc | gga | aca | cgg | gaa | gat | ctg | tgc | gca | ggt | gtg | acg | 192 |
|---|---|---|---|---|---|---|---|---|---|---|---|---|---|---|---|---|
| Thr | Gly | Glu | Asn | Cys | Gly | Thr | Arg | Glu | Asp | Leu | Cys | Ala | Gly | Val | Thr | |
| 50 | | | | | 55 | | | | | 60 | | | | | | |

| tgc | aag | aac | ggc | ggg | aca | tgc | gac | tcc | gtc | act | ggc | ctg | tgc | cag | tgc | 240 |
|---|---|---|---|---|---|---|---|---|---|---|---|---|---|---|---|---|
| Cys | Lys | Asn | Gly | Gly | Thr | Cys | Asp | Ser | Val | Thr | Gly | Leu | Cys | Gln | Cys | |
| 65 | | | | 70 | | | | | 75 | | | | | 80 | | |

| gat | gcc | tgc | cac | ggc | ggg | aag | acc | tgc | gag | att | acg | aag | gaa | cac | tgc | 288 |
|---|---|---|---|---|---|---|---|---|---|---|---|---|---|---|---|---|
| Asp | Ala | Cys | His | Gly | Gly | Lys | Thr | Cys | Glu | Ile | Thr | Lys | Glu | His | Cys | |
| 85 | | | | | 90 | | | | | 95 | | | | | | |

| tgc | atc | aat | gac | agt | gac | tgc | aac | ggc | cac | ggc | acc | tgc | aac | acg | agc | 336 |
|---|---|---|---|---|---|---|---|---|---|---|---|---|---|---|---|---|
| Cys | Ile | Asn | Asp | Ser | Asp | Cys | Asn | Gly | His | Gly | Thr | Cys | Asn | Thr | Ser | |
| 100 | | | | 105 | | | | | 110 | | | | | | | |

| aac | aat | acc | tgc | aac | tgc | gag | gca | ggc | ttc | gct | ggc | acc | aac | tgc | tcg | 384 |
|---|---|---|---|---|---|---|---|---|---|---|---|---|---|---|---|---|
| Asn | Asn | Thr | Cys | Asn | Cys | Glu | Ala | Gly | Phe | Ala | Gly | Thr | Asn | Cys | Ser | |
| 115 | | | | | 120 | | | | | 125 | | | | | | |

| agc | agc | gaa | ggc | aag | tgc | agc | ggc | aag | acc | tgc | ttg | agt | gga | cac | tgc | 432 |
|---|---|---|---|---|---|---|---|---|---|---|---|---|---|---|---|---|
| Ser | Ser | Glu | Gly | Lys | Cys | Ser | Gly | Lys | Thr | Cys | Leu | Ser | Gly | His | Cys | |
| 130 | | | | | 135 | | | | | 140 | | | | | | |

| aat | ccg | gcg | act | ggc | gca | tgc | gtc | tgc | gac | ccg | tgc | cac | acc | ggc | gag | 480 |
|---|---|---|---|---|---|---|---|---|---|---|---|---|---|---|---|---|
| Asn | Pro | Ala | Thr | Gly | Ala | Cys | Val | Cys | Asp | Pro | Cys | His | Thr | Gly | Glu | |
| 145 | | | | 150 | | | | | 155 | | | | | 160 | | |

| aga | tgc | gaa | acg | ctc | gtc | aag | gac | tgc | tgt | gtt | gtg | aac | gac | acg | tgc | 528 |
|---|---|---|---|---|---|---|---|---|---|---|---|---|---|---|---|---|
| Arg | Cys | Glu | Thr | Leu | Val | Lys | Asp | Cys | Cys | Val | Val | Asn | Asp | Thr | Cys | |
| 165 | | | | 170 | | | | | 175 | | | | | | | |

| aag | ttc | ccc | aac | ggc | gtc | tgc | act | gac | agc | aac | agg | tgt | gag | tgc | cag | 576 |
|---|---|---|---|---|---|---|---|---|---|---|---|---|---|---|---|---|
| Lys | Phe | Pro | Asn | Gly | Val | Cys | Thr | Asp | Ser | Asn | Arg | Cys | Glu | Cys | Gln | |
| 180 | | | | | 185 | | | | | 190 | | | | | | |

| agc | ggc | tgg | ggc | cag | ggc | gac | tgc | agc | aaa | cca | gtc | gac | aag | tgc | gaa | 624 |
|---|---|---|---|---|---|---|---|---|---|---|---|---|---|---|---|---|
| Ser | Gly | Trp | Gly | Gln | Gly | Asp | Cys | Ser | Lys | Pro | Val | Asp | Lys | Cys | Glu | |
| 195 | | | | | 200 | | | | | 205 | | | | | | |

| gac | gtc | agt | tgc | aac | aac | ggt | tca | tca | tgc | gac | gcg | gac | tcc | ggc | aca | 672 |
|---|---|---|---|---|---|---|---|---|---|---|---|---|---|---|---|---|
| Asp | Val | Ser | Cys | Asn | Asn | Gly | Ser | Ser | Cys | Asp | Ala | Asp | Ser | Gly | Thr | |
| 210 | | | | 215 | | | | | 220 | | | | | | | |

| tgc | att | tgc | ccc | cca | ggc | ttt | gga | gac | | | | | | | | 699 |
|---|---|---|---|---|---|---|---|---|---|---|---|---|---|---|---|---|
| Cys | Ile | Cys | Pro | Pro | Gly | Phe | Gly | Asp | | | | | | | | |
| 225 | | | | 230 | | | | | | | | | | | | |

<210> SEQ ID NO 110
<211> LENGTH: 233
<212> TYPE: PRT
<213> ORGANISM: Toxoplasma gondii

<400> SEQUENCE: 110

Pro Cys Val Cys Glu Glu Lys Cys Lys Thr Gly Pro Asn Cys Asp Gln

```
              1               5                  10                 15
His Lys Pro Glu Cys Cys Gly Ser Asn Asp Cys His Gln Pro Gln
 20                  25                30

Gly Tyr Cys Lys Met Asp Met Ser Thr Cys Ile Cys Arg Pro Gly Phe
 35                  40                 45

Thr Gly Glu Asn Cys Gly Thr Arg Glu Asp Leu Cys Ala Gly Val Thr
 50                  55                 60

Cys Lys Asn Gly Gly Thr Cys Asp Ser Val Thr Gly Leu Cys Gln Cys
 65                   70                75                  80

Asp Ala Cys His Gly Gly Lys Thr Cys Glu Ile Thr Lys Glu His Cys
 85                   90                95

Cys Ile Asn Asp Ser Asp Cys Asn Gly His Gly Thr Cys Asn Thr Ser
100                  105               110

Asn Asn Thr Cys Asn Cys Glu Ala Gly Phe Ala Gly Thr Asn Cys Ser
115                  120               125

Ser Ser Glu Gly Lys Cys Ser Gly Lys Thr Cys Leu Ser Gly His Cys
130                  135               140

Asn Pro Ala Thr Gly Ala Cys Val Cys Asp Pro Cys His Thr Gly Glu
145                  150               155                 160

Arg Cys Glu Thr Leu Val Lys Asp Cys Cys Val Val Asn Asp Thr Cys
165                  170               175

Lys Phe Pro Asn Gly Val Cys Thr Asp Ser Asn Arg Cys Glu Cys Gln
180                  185               190

Ser Gly Trp Gly Gln Gly Asp Cys Ser Lys Pro Val Asp Lys Cys Glu
195                  200               205

Asp Val Ser Cys Asn Asn Gly Ser Ser Cys Asp Ala Asp Ser Gly Thr
210                  215               220

Cys Ile Cys Pro Pro Gly Phe Gly Asp
225                  230

<210> SEQ ID NO 111
<211> LENGTH: 419
<212> TYPE: DNA
<213> ORGANISM: Toxoplasma gondii
<220> FEATURE:
<221> NAME/KEY: CDS
<222> LOCATION: (1)..(417)
<223> OTHER INFORMATION:

<400> SEQUENCE: 111 gag atg agc gcc cca gat agg caa aca gga aag ctt tcc gat tta ccg      48
Glu Met Ser Ala Pro Asp Arg Gln Thr Gly Lys Leu Ser Asp Leu Pro
 1               5                  10                 15 cca ttt gct gag ctg cca cag ctg gca gaa ata cca aag ctc tcc gaa     96
Pro Phe Ala Glu Leu Pro Gln Leu Ala Glu Ile Pro Lys Leu Ser Glu
 20                  25                 30 ctt ccg aaa atc gcg gac atg ccg aaa ttt tcg gat atg ccc aag atg    144
Leu Pro Lys Ile Ala Asp Met Pro Lys Phe Ser Asp Met Pro Lys Met
 35                  40                 45 gcc gag atg ccc aag tta tca gat ata ccc aag atg gct gag atg ccc    192
Ala Glu Met Pro Lys Leu Ser Asp Ile Pro Lys Met Ala Glu Met Pro
 50                  55                 60 aag tta tca gat ata ccc aag atg gct gag atg ccc aag tta tca gat    240
Lys Leu Ser Asp Ile Pro Lys Met Ala Glu Met Pro Lys Leu Ser Asp
 65                   70                75                  80 ata ccc aag atg gct gag atg ccc aag ttt tca gat ata ccc aag atg    288
Ile Pro Lys Met Ala Glu Met Pro Lys Phe Ser Asp Ile Pro Lys Met
 85                   90                95
```

```
gct gag atg cca aag tta tca gat atg ccc aga atg gct gac att cca      336
Ala Glu Met Pro Lys Leu Ser Asp Met Pro Arg Met Ala Asp Ile Pro
100                 105                 110 cag ttt cca gag atg cct agg atg gtt gac atg cct cag ttt cca gaa      384
Gln Phe Pro Glu Met Pro Arg Met Val Asp Met Pro Gln Phe Pro Glu
115                 120                 125 atc ccc agg atg gct gat atg ccg caa ttt ccg cg                       419
Ile Pro Arg Met Ala Asp Met Pro Gln Phe Pro
130                 135
```

```
<210> SEQ ID NO 112
<211> LENGTH: 139
<212> TYPE: PRT
<213> ORGANISM: Toxoplasma gondii

<400> SEQUENCE: 112

Glu Met Ser Ala Pro Asp Arg Gln Thr Gly Lys Leu Ser Asp Leu Pro
1               5                   10                  15

Pro Phe Ala Glu Leu Pro Gln Leu Ala Glu Ile Pro Lys Leu Ser Glu
            20                  25                  30

Leu Pro Lys Ile Ala Asp Met Pro Lys Phe Ser Asp Met Pro Lys Met
35                  40                  45

Ala Glu Met Pro Lys Leu Ser Asp Ile Pro Lys Met Ala Glu Met Pro
50                  55                  60

Lys Leu Ser Asp Ile Pro Lys Met Ala Glu Met Pro Lys Leu Ser Asp
65                  70                  75                  80

Ile Pro Lys Met Ala Glu Met Pro Lys Phe Ser Asp Ile Pro Lys Met
                85                  90                  95

Ala Glu Met Pro Lys Leu Ser Asp Met Pro Arg Met Ala Asp Ile Pro
100                 105                 110

Gln Phe Pro Glu Met Pro Arg Met Val Asp Met Pro Gln Phe Pro Glu
115                 120                 125

Ile Pro Arg Met Ala Asp Met Pro Gln Phe Pro
130                 135
```

```
<210> SEQ ID NO 113
<211> LENGTH: 303
<212> TYPE: DNA
<213> ORGANISM: Toxoplasma gondii
<220> FEATURE:
<221> NAME/KEY: CDS
<222> LOCATION: (1)..(303)
<223> OTHER INFORMATION:

<400> SEQUENCE: 113 gac gaa gct ctt cct ctc ttt gga gca aac ggt gga acc tca gtt cgg      48
Asp Glu Ala Leu Pro Leu Phe Gly Ala Asn Gly Gly Thr Ser Val Arg
1               5                   10                  15 ctc tcc ctc gac cgc agc gtc ctg ctt gtt ctc gaa ccc gca gag ccc      96
Leu Ser Leu Asp Arg Ser Val Leu Leu Val Leu Glu Pro Ala Glu Pro
            20                  25                  30 ctg cta tcc tct tgg ccc cac ccg ggg aga aga gac act ttt ctt gaa      144
Leu Leu Ser Ser Trp Pro His Pro Gly Arg Arg Asp Thr Phe Leu Glu
35                  40                  45 ggc gat ggc gcg ggc atc ccg tct cct tca tct cgg ccg agt cgc gcg      192
Gly Asp Gly Ala Gly Ile Pro Ser Pro Ser Ser Arg Pro Ser Arg Ala
50                  55                  60 gcc gac cat tac acg aga ctc tcc acg att cgg tct ctt gcc agg gat      240
Ala Asp His Tyr Thr Arg Leu Ser Thr Ile Arg Ser Leu Ala Arg Asp
65                  70                  75                  80
```

```
gga gag gtc gac tcc gag ctg gcg ggg gga ccg cag gaa aga gaa agt     288
Gly Glu Val Asp Ser Glu Leu Ala Gly Gly Pro Gln Glu Arg Glu Ser
85                  90                  95 gtc aga gtg gat ccg                                                 303
Val Arg Val Asp Pro
100

<210> SEQ ID NO 114
<211> LENGTH: 101
<212> TYPE: PRT
<213> ORGANISM: Toxoplasma gondii

<400> SEQUENCE: 114

Asp Glu Ala Leu Pro Leu Phe Gly Ala Asn Gly Gly Thr Ser Val Arg
1               5                   10                  15

Leu Ser Leu Asp Arg Ser Val Leu Leu Val Leu Glu Pro Ala Glu Pro
            20                  25                  30

Leu Leu Ser Ser Trp Pro His Pro Gly Arg Arg Asp Thr Phe Leu Glu
        35                  40                  45

Gly Asp Gly Ala Gly Ile Pro Ser Pro Ser Ser Arg Pro Ser Arg Ala
    50                  55                  60

Ala Asp His Tyr Thr Arg Leu Ser Thr Ile Arg Ser Leu Ala Arg Asp
65                  70                  75                  80

Gly Glu Val Asp Ser Glu Leu Ala Gly Gly Pro Gln Glu Arg Glu Ser
                85                  90                  95

Val Arg Val Asp Pro
            100

<210> SEQ ID NO 115
<211> LENGTH: 696
<212> TYPE: DNA
<213> ORGANISM: Toxoplasma gondii
<220> FEATURE:
<221> NAME/KEY: CDS
<222> LOCATION: (1)..(696)
<223> OTHER INFORMATION:

<400> SEQUENCE: 115 cgc ggt aac gaa aaa aca tgc tca gat gcc aag cat cca gtg tac atc     48
Arg Gly Asn Glu Lys Thr Cys Ser Asp Ala Lys His Pro Val Tyr Ile
1               5                   10                  15 aaa ctt ggc aaa ggg gaa cgc gag gcc gta ttc aag tgt ggc gac ggc     96
Lys Leu Gly Lys Gly Glu Arg Glu Ala Val Phe Lys Cys Gly Asp Gly
            20                  25                  30 ctc act act ctt gag cca tcg cag aac aca gat aaa cca aaa ttc tgt    144
Leu Thr Thr Leu Glu Pro Ser Gln Asn Thr Asp Lys Pro Lys Phe Cys
        35                  40                  45 gaa tcg ata gac tgc aac gat act gca gaa ctt gaa aca acg ttc cca    192
Glu Ser Ile Asp Cys Asn Asp Thr Ala Glu Leu Glu Thr Thr Phe Pro
    50                  55                  60 ggg gcg tac tgg gac gag aga aac aaa aaa gcg aat ata tac aga ctg    240
Gly Ala Tyr Trp Asp Glu Arg Asn Lys Lys Ala Asn Ile Tyr Arg Leu
65                  70                  75                  80 gtc att cct acc gtg agc aga aaa gac act cgg atg tat tat aaa tgt    288
Val Ile Pro Thr Val Ser Arg Lys Asp Thr Arg Met Tyr Tyr Lys Cys
                85                  90                  95 aaa ggc act tcg gat tcc gcc gac cca tgc aca gta ctg ata aac gtg    336
Lys Gly Thr Ser Asp Ser Ala Asp Pro Cys Thr Val Leu Ile Asn Val
            100                 105                 110 aaa tct aca gag act gat gat gat gag gaa gag gac gtg cag gag tgc    384
```

```
Lys Ser Thr Glu Thr Asp Asp Glu Glu Glu Asp Val Gln Glu Cys
115                 120                 125 acg gtg ggc acc gag aag aaa gtc aca ctg tcc ccc acc gat acc gtg    432
Thr Val Gly Thr Glu Lys Lys Val Thr Leu Ser Pro Thr Asp Thr Val
130                 135                 140 aaa ttc aag tgc aat ctc gga aca gtt gtg cag cca tca ttc tcc aca    480
Lys Phe Lys Cys Asn Leu Gly Thr Val Val Gln Pro Ser Phe Ser Thr
145                 150                 155                 160 gca act ccg aaa gtc ttt gac gac tcc gat ggc tcc tgc agt gca cag    528
Ala Thr Pro Lys Val Phe Asp Asp Ser Asp Gly Ser Cys Ser Ala Gln
165                 170                 175 gct agc ctg acg tct ctg gta gat gcc tcg ctc acg gaa gac agt tca    576
Ala Ser Leu Thr Ser Leu Val Asp Ala Ser Leu Thr Glu Asp Ser Ser
180                 185                 190 cat ggc aag tac aca atg tat acc atg aac ctg aac gca cgc cca gct    624
His Gly Lys Tyr Thr Met Tyr Thr Met Asn Leu Asn Ala Arg Pro Ala
195                 200                 205 gag aca aag aat ctc tgt ctc caa tgt tcc tct gga aag cag aac tgc    672
Glu Thr Lys Asn Leu Cys Leu Gln Cys Ser Ser Gly Lys Gln Asn Cys
210                 215                 220 aaa atg cgc atc cat gta ccc gcg                                     696
Lys Met Arg Ile His Val Pro Ala
225                 230

<210> SEQ ID NO 116
<211> LENGTH: 232
<212> TYPE: PRT
<213> ORGANISM: Toxoplasma gondii

<400> SEQUENCE: 116

Arg Gly Asn Glu Lys Thr Cys Ser Asp Ala Lys His Pro Val Tyr Ile
1               5                   10                  15

Lys Leu Gly Lys Gly Glu Arg Glu Ala Val Phe Lys Cys Gly Asp Gly
            20                  25                  30

Leu Thr Thr Leu Glu Pro Ser Gln Asn Thr Asp Lys Pro Lys Phe Cys
35                  40                  45

Glu Ser Ile Asp Cys Asn Asp Thr Ala Glu Leu Glu Thr Thr Phe Pro
50                  55                  60

Gly Ala Tyr Trp Asp Glu Arg Asn Lys Lys Ala Asn Ile Tyr Arg Leu
65                  70                  75                  80

Val Ile Pro Thr Val Ser Arg Lys Asp Thr Arg Met Tyr Tyr Lys Cys
            85                  90                  95

Lys Gly Thr Ser Asp Ser Ala Asp Pro Cys Thr Val Leu Ile Asn Val
100                 105                 110

Lys Ser Thr Glu Thr Asp Asp Glu Glu Glu Asp Val Gln Glu Cys
115                 120                 125

Thr Val Gly Thr Glu Lys Lys Val Thr Leu Ser Pro Thr Asp Thr Val
130                 135                 140

Lys Phe Lys Cys Asn Leu Gly Thr Val Val Gln Pro Ser Phe Ser Thr
145                 150                 155                 160

Ala Thr Pro Lys Val Phe Asp Asp Ser Asp Gly Ser Cys Ser Ala Gln
165                 170                 175

Ala Ser Leu Thr Ser Leu Val Asp Ala Ser Leu Thr Glu Asp Ser Ser
180                 185                 190

His Gly Lys Tyr Thr Met Tyr Thr Met Asn Leu Asn Ala Arg Pro Ala
195                 200                 205

Glu Thr Lys Asn Leu Cys Leu Gln Cys Ser Ser Gly Lys Gln Asn Cys
```

Lys Met Arg Ile His Val Pro Ala
225                230

<210> SEQ ID NO 117
<211> LENGTH: 173
<212> TYPE: DNA
<213> ORGANISM: Toxoplasma gondii
<220> FEATURE:
<221> NAME/KEY: CDS
<222> LOCATION: (1)..(171)
<223> OTHER INFORMATION:

<400> SEQUENCE: 117

```
act tgt gcg ggg gac ccc tcg gcc ttt ccg acg aag ctg ccg tcg aca      48
Thr Cys Ala Gly Asp Pro Ser Ala Phe Pro Thr Lys Leu Pro Ser Thr
1               5                   10                  15 cca ccc gct gct gtg ccg tct gac ggg ttg ctc gct ttg ccc tca gaa      96
Pro Pro Ala Ala Val Pro Ser Asp Gly Leu Leu Ala Leu Pro Ser Glu
            20                  25                  30 ctt gag gcg ccg gtg gag gac ggc gac cgc gag gct ttc gtt gga gtc     144
Leu Glu Ala Pro Val Glu Asp Gly Asp Arg Glu Ala Phe Val Gly Val
35                  40                  45 gac ggc gcg gtc agc ggc tgg gac gag cg                              173
Asp Gly Ala Val Ser Gly Trp Asp Glu
50                  55
```

<210> SEQ ID NO 118
<211> LENGTH: 57
<212> TYPE: PRT
<213> ORGANISM: Toxoplasma gondii

<400> SEQUENCE: 118

Thr Cys Ala Gly Asp Pro Ser Ala Phe Pro Thr Lys Leu Pro Ser Thr
1               5                   10                  15

Pro Pro Ala Ala Val Pro Ser Asp Gly Leu Leu Ala Leu Pro Ser Glu
            20                  25                  30

Leu Glu Ala Pro Val Glu Asp Gly Asp Arg Glu Ala Phe Val Gly Val
35                  40                  45

Asp Gly Ala Val Ser Gly Trp Asp Glu
50                  55

<210> SEQ ID NO 119
<211> LENGTH: 369
<212> TYPE: DNA
<213> ORGANISM: Toxoplasma gondii
<220> FEATURE:
<221> NAME/KEY: CDS
<222> LOCATION: (1)..(369)
<223> OTHER INFORMATION:

<400> SEQUENCE: 119

```
cgc tct gtg ttt cag gtc gcg agc gac gcg aga aac gcc cga cag gcg      48
Arg Ser Val Phe Gln Val Ala Ser Asp Ala Arg Asn Ala Arg Gln Ala
1               5                   10                  15 acc tcg ggc gtg ccg cgg cag agg gga aag aag gcc gtc acg gcg cga      96
Thr Ser Gly Val Pro Arg Gln Arg Gly Lys Lys Ala Val Thr Ala Arg
            20                  25                  30 gtc tct ttc ggc gct cta gag gag aga gac agt tcg agt tcg gac gtt     144
Val Ser Phe Gly Ala Leu Glu Glu Arg Asp Ser Ser Ser Ser Asp Val
35                  40                  45 ccc gag gaa agg gat aaa gac gcc gaa aac ggc tct gcg cct cgc atc     192
Pro Glu Glu Arg Asp Lys Asp Ala Glu Asn Gly Ser Ala Pro Arg Ile
```

```
                50                  55                  60
ttc gcg tct tct tcc ctg acg cgg ctt tcg cct cct tct ctc tct ccg      240
Phe Ala Ser Ser Ser Leu Thr Arg Leu Ser Pro Pro Ser Leu Ser Pro
 65                  70                  75                  80 ctc tca agt tcg ggg cca tct tca ccg tct tct tcc gtt tcg cgg ttt      288
Leu Ser Ser Ser Gly Pro Ser Ser Pro Ser Ser Ser Val Ser Arg Phe
 85                  90                  95 acc gac tcc ctg ccg cag tcg acg gct tcg tct cgt ctc tcc tct gct      336
Thr Asp Ser Leu Pro Gln Ser Thr Ala Ser Ser Arg Leu Ser Ser Ala
100                 105                 110 tat tcg ctt gag tcg cgt cgg cct ctg gag ccg                          369
Tyr Ser Leu Glu Ser Arg Arg Pro Leu Glu Pro
115                 120

<210> SEQ ID NO 120
<211> LENGTH: 123
<212> TYPE: PRT
<213> ORGANISM: Toxoplasma gondii

<400> SEQUENCE: 120

Arg Ser Val Phe Gln Val Ala Ser Asp Ala Arg Asn Ala Arg Gln Ala
  1               5                  10                  15

Thr Ser Gly Val Pro Arg Gln Arg Gly Lys Lys Ala Val Thr Ala Arg
 20                  25                  30

Val Ser Phe Gly Ala Leu Glu Glu Arg Asp Ser Ser Ser Ser Asp Val
 35                  40                  45

Pro Glu Glu Arg Asp Lys Asp Ala Glu Asn Gly Ser Ala Pro Arg Ile
 50                  55                  60

Phe Ala Ser Ser Ser Leu Thr Arg Leu Ser Pro Pro Ser Leu Ser Pro
 65                  70                  75                  80

Leu Ser Ser Ser Gly Pro Ser Ser Pro Ser Ser Ser Val Ser Arg Phe
 85                  90                  95

Thr Asp Ser Leu Pro Gln Ser Thr Ala Ser Ser Arg Leu Ser Ser Ala
100                 105                 110

Tyr Ser Leu Glu Ser Arg Arg Pro Leu Glu Pro
115                 120

<210> SEQ ID NO 121
<211> LENGTH: 566
<212> TYPE: DNA
<213> ORGANISM: Toxoplasma gondii
<220> FEATURE:
<221> NAME/KEY: CDS
<222> LOCATION: (1)..(183)
<223> OTHER INFORMATION:

<400> SEQUENCE: 121 cgg cgg tgg atg acg ggt gct aat tac gag ggc cac cag gga caa tat       48
Arg Arg Trp Met Thr Gly Ala Asn Tyr Glu Gly His Gln Gly Gln Tyr
  1               5                  10                  15 ttg aac tac tgc acc att tct cac ttc ttg tgt tgc cct aat ggg atc       96
Leu Asn Tyr Cys Thr Ile Ser His Phe Leu Cys Cys Pro Asn Gly Ile
 20                  25                  30 tgt cgt ttt caa tgg gac aat cag ccc agt ctc gat agg gag gac tca      144
Cys Arg Phe Gln Trp Asp Asn Gln Pro Ser Leu Asp Arg Glu Asp Ser
 35                  40                  45 atc tgg tgc tct gaa tcg att tct cgt ttt cgc ctg agc taagataact      193
Ile Trp Cys Ser Glu Ser Ile Ser Arg Phe Arg Leu Ser
 50                  55                  60 gctgaagaca tttgtagacg ctttctacaa acccacgtgg caaaatctta cggaaggaca    253
```

```
aatgcctctt tcaacactct tctttcatcg ctgcttgtta cactcctgag aggccccaag    313
agccacggtg ccactttgct tccccagccg ctactgtgca aattctttat agaagagcac    373
aaatgttccc cgaagaagca gcagcaccct tgaggagcc tgaagagcga ccctacgaat     433
cacagcgttc agaaatagcc tactgtagta ttaaggagac taccaaagtg aaaatcgtga    493
tatgtctaca ggtggtatgc aagtgttggt tttccagata tacgctgcaa ctaaaacacc    553
aaaatgatag aat                                                       566
```

<210> SEQ ID NO 122
<211> LENGTH: 61
<212> TYPE: PRT
<213> ORGANISM: Toxoplasma gondii

<400> SEQUENCE: 122

```
Arg Arg Trp Met Thr Gly Ala Asn Tyr Glu Gly His Gln Gly Gln Tyr
1               5                   10                  15

Leu Asn Tyr Cys Thr Ile Ser His Phe Leu Cys Cys Pro Asn Gly Ile
            20                  25                  30

Cys Arg Phe Gln Trp Asp Asn Gln Pro Ser Leu Asp Arg Glu Asp Ser
        35                  40                  45

Ile Trp Cys Ser Glu Ser Ile Ser Arg Phe Arg Leu Ser
    50                  55                  60
```

<210> SEQ ID NO 123
<211> LENGTH: 616
<212> TYPE: DNA
<213> ORGANISM: Toxoplasma gondii
<220> FEATURE:
<221> NAME/KEY: CDS
<222> LOCATION: (1)..(615)
<223> OTHER INFORMATION:

<400> SEQUENCE: 123

```
cac gag cgc cgt gtg gca gag caa aag gct cgt gaa gaa cgc gag aga        48
His Glu Arg Arg Val Ala Glu Gln Lys Ala Arg Glu Glu Arg Glu Arg
1               5                   10                  15 cag gca gca tct cag cga aac gga tcg aca gaa ccc gct gtt gct ccc        96
Gln Ala Ala Ser Gln Arg Asn Gly Ser Thr Glu Pro Ala Val Ala Pro
            20                  25                  30 tcc tct tgt tcc tcc agc aac tca cag aac cct ccg caa gat tcc tcg       144
Ser Ser Cys Ser Ser Ser Asn Ser Gln Asn Pro Pro Gln Asp Ser Ser
        35                  40                  45 cac gtc tgc tgt ccc tcc tcc tct gcc ttc tcc cag ccg cgc tct tct       192
His Val Cys Cys Pro Ser Ser Ser Ala Phe Ser Gln Pro Arg Ser Ser
    50                  55                  60 ctg tcc tca tcc tca ccc tct tcg tct gcc gcg tta cca tcg ggg tct       240
Leu Ser Ser Ser Ser Pro Ser Ser Ala Ala Leu Pro Ser Gly Ser
65                  70                  75                  80 tct ccc tcg gct gcg tct tcg tct cat gca ctt ggg gtg gtg gac tcg       288
Ser Pro Ser Ala Ala Ser Ser Ser His Ala Leu Gly Val Val Asp Ser
                85                  90                  95 gac cgg att tct gcg gag gag gcg gcg tcc ctc gag gag gcc cgg cgg       336
Asp Arg Ile Ser Ala Glu Glu Ala Ala Ser Leu Glu Glu Ala Arg Arg
            100                 105                 110 ctg cag aga cag ttc gag gcg gaa atg gtg ggc att cga ccg cca gac       384
Leu Gln Arg Gln Phe Glu Ala Glu Met Val Gly Ile Arg Pro Pro Asp
        115                 120                 125 gac acc tac gag gaa acg ctg att tct gag gac atc cat cct tcc cac       432
Asp Thr Tyr Glu Glu Thr Leu Ile Ser Glu Asp Ile His Pro Ser His
```

```
                                                                    130                     135                     140
cga gcc tgg tgg gaa aga cct agc gcc tcg ccg att cgt ctg tcg cgc        480
Arg Ala Trp Trp Glu Arg Pro Ser Ala Ser Pro Ile Arg Leu Ser Arg
145                 150                 155                 160 gcg gcg tcg atg aga agt gac ggt cgc aga ggt caa cag ccc ccg agt        528
Ala Ala Ser Met Arg Ser Asp Gly Arg Arg Gly Gln Gln Pro Pro Ser
165                 170                 175 cga cag tct cct cag gac ggg gag gaa gac gac gcc gct ctc gcc aga        576
Arg Gln Ser Pro Gln Asp Gly Glu Glu Asp Asp Ala Ala Leu Ala Arg
180                 185                 190 cga ctt cag gaa gaa gaa tac agc cga cat cga gag gtc g                  616
Arg Leu Gln Glu Glu Glu Tyr Ser Arg His Arg Glu Val
195                 200                 205

<210> SEQ ID NO 124
<211> LENGTH: 205
<212> TYPE: PRT
<213> ORGANISM: Toxoplasma gondii

<400> SEQUENCE: 124

His Glu Arg Arg Val Ala Glu Gln Lys Ala Arg Glu Glu Arg Glu Arg
1               5                   10                  15

Gln Ala Ala Ser Gln Arg Asn Gly Ser Thr Glu Pro Ala Val Ala Pro
            20                  25                  30

Ser Ser Cys Ser Ser Ser Asn Ser Gln Asn Pro Pro Gln Asp Ser Ser
        35                  40                  45

His Val Cys Cys Pro Ser Ser Ser Ala Phe Ser Gln Pro Arg Ser Ser
    50                  55                  60

Leu Ser Ser Ser Ser Pro Ser Ser Ser Ala Ala Leu Pro Ser Gly Ser
65                  70                  75                  80

Ser Pro Ser Ala Ala Ser Ser Ser His Ala Leu Gly Val Val Asp Ser
                85                  90                  95

Asp Arg Ile Ser Ala Glu Ala Ala Ser Leu Glu Glu Ala Arg Arg
            100                 105                 110

Leu Gln Arg Gln Phe Glu Ala Glu Met Val Gly Ile Arg Pro Pro Asp
        115                 120                 125

Asp Thr Tyr Glu Glu Thr Leu Ile Ser Glu Asp Ile His Pro Ser His
    130                 135                 140

Arg Ala Trp Trp Glu Arg Pro Ser Ala Ser Pro Ile Arg Leu Ser Arg
145                 150                 155                 160

Ala Ala Ser Met Arg Ser Asp Gly Arg Arg Gly Gln Gln Pro Pro Ser
                165                 170                 175

Arg Gln Ser Pro Gln Asp Gly Glu Glu Asp Asp Ala Ala Leu Ala Arg
            180                 185                 190

Arg Leu Gln Glu Glu Glu Tyr Ser Arg His Arg Glu Val
        195                 200                 205

<210> SEQ ID NO 125
<211> LENGTH: 762
<212> TYPE: DNA
<213> ORGANISM: Toxoplasma gondii
<220> FEATURE:
<221> NAME/KEY: CDS
<222> LOCATION: (1)..(762)
<223> OTHER INFORMATION:

<400> SEQUENCE: 125 cgg gat cag gct cct aag cca gtg ccc gag gca gcc gac gaa ttt gac         48
Arg Asp Gln Ala Pro Lys Pro Val Pro Glu Ala Ala Asp Glu Phe Asp
```

```
                1               5                   10                  15 cag gct cct atg cca ctg ccc gaa gca ccc gaa gac ttt gac cag gct      96
Gln Ala Pro Met Pro Leu Pro Glu Ala Pro Glu Asp Phe Asp Gln Ala
 20                  25                  30 cct gag cca ctg cgc gag gca gcc gaa gaa ttt gac cag gct cct atg     144
Pro Glu Pro Leu Arg Glu Ala Ala Glu Glu Phe Asp Gln Ala Pro Met
 35                  40                  45 cca gtg ccc gag gca ccc gaa gac ttt gac cag att cct aag cca gtg     192
Pro Val Pro Glu Ala Pro Glu Asp Phe Asp Gln Ile Pro Lys Pro Val
 50                  55                  60 ccc gag gca ccc gaa gaa ttt gac cag gct cct atg cca gtg ccc gag     240
Pro Glu Ala Pro Glu Glu Phe Asp Gln Ala Pro Met Pro Val Pro Glu
 65                  70                  75                  80 gca ccc gaa gac ttt gac cag att cct aag cca gtg ccc gag gca ccc     288
Ala Pro Glu Asp Phe Asp Gln Ile Pro Lys Pro Val Pro Glu Ala Pro
 85                  90                  95 gaa gaa ttt gac cag gct cct atg cca ctc ccc gaa gca ccc gaa gaa     336
Glu Glu Phe Asp Gln Ala Pro Met Pro Leu Pro Glu Ala Pro Glu Glu
100                 105                 110 tcc gag cag gct cct gag cca ctg ccc gag gca ccc gaa gaa tcc gag     384
Ser Glu Gln Ala Pro Glu Pro Leu Pro Glu Ala Pro Glu Glu Ser Glu
115                 120                 125 cag gct cct gag cca ctg ccc gag gca ccc gaa gaa tcc gag cag gct     432
Gln Ala Pro Glu Pro Leu Pro Glu Ala Pro Glu Glu Ser Glu Gln Ala
130                 135                 140 cct gag cca ctg ccc gag gca ccc gaa gaa tcc gag cag gct cct gag     480
Pro Glu Pro Leu Pro Glu Ala Pro Glu Glu Ser Glu Gln Ala Pro Glu
145                 150                 155                 160 cca ctg ccc gag gca ccc gaa gaa tcc gag cag gct cct gag cca ctg     528
Pro Leu Pro Glu Ala Pro Glu Glu Ser Glu Gln Ala Pro Glu Pro Leu
165                 170                 175 ccc gag gca ccc gaa gaa ttt gac cag gct cct atg cca ctg ccc gcg     576
Pro Glu Ala Pro Glu Glu Phe Asp Gln Ala Pro Met Pro Leu Pro Ala
180                 185                 190 gcc ccc gaa gac ttt gac cag cct gct atg cca ctg ccc ccg gcc ccc     624
Ala Pro Glu Asp Phe Asp Gln Pro Ala Met Pro Leu Pro Pro Ala Pro
195                 200                 205 gaa gac ttt gac cag gct ccc atg cca ctg ccg cag gca ccc gaa gaa     672
Glu Asp Phe Asp Gln Ala Pro Met Pro Leu Pro Gln Ala Pro Glu Glu
210                 215                 220 ctc gag cag gct ccc gct tcc acc ccg agg agg cgg agc agg agg tgc     720
Leu Glu Gln Ala Pro Ala Ser Thr Pro Arg Arg Arg Ser Arg Arg Cys
225                 230                 235                 240 ctg aga gaa aaa ctg acg cag gaa gtg aac ctg aga agg atc             762
Leu Arg Glu Lys Leu Thr Gln Glu Val Asn Leu Arg Arg Ile
245                 250

<210> SEQ ID NO 126
<211> LENGTH: 254
<212> TYPE: PRT
<213> ORGANISM: Toxoplasma gondii

<400> SEQUENCE: 126

Arg Asp Gln Ala Pro Lys Pro Val Pro Glu Ala Ala Asp Glu Phe Asp
  1               5                  10                  15

Gln Ala Pro Met Pro Leu Pro Glu Ala Pro Glu Asp Phe Asp Gln Ala
 20                  25                  30

Pro Glu Pro Leu Arg Glu Ala Ala Glu Glu Phe Asp Gln Ala Pro Met
 35                  40                  45
```

```
Pro Val Pro Glu Ala Pro Glu Asp Phe Asp Gln Ile Pro Lys Pro Val
 50                  55                  60
Pro Glu Ala Pro Glu Glu Phe Asp Gln Ala Pro Met Pro Val Pro Glu
 65                  70                  75                  80
Ala Pro Glu Asp Phe Asp Gln Ile Pro Lys Pro Val Pro Glu Ala Pro
             85                  90                  95
Glu Glu Phe Asp Gln Ala Pro Met Pro Leu Pro Glu Ala Pro Glu Glu
100                 105                 110
Ser Glu Gln Ala Pro Glu Pro Leu Pro Glu Ala Pro Glu Glu Ser Glu
115                 120                 125
Gln Ala Pro Glu Pro Leu Pro Glu Ala Pro Glu Ser Glu Gln Ala
130                 135                 140
Pro Glu Pro Leu Pro Glu Ala Pro Glu Glu Ser Glu Gln Ala Pro Glu
145                 150                 155                 160
Pro Leu Pro Glu Ala Pro Glu Glu Ser Glu Gln Ala Pro Glu Pro Leu
            165                 170                 175
Pro Glu Ala Pro Glu Glu Phe Asp Gln Ala Pro Met Pro Leu Pro Ala
180                 185                 190
Ala Pro Glu Asp Phe Asp Gln Pro Ala Met Pro Leu Pro Pro Ala Pro
195                 200                 205
Glu Asp Phe Asp Gln Ala Pro Met Pro Leu Pro Gln Ala Pro Glu Glu
210                 215                 220
Leu Glu Gln Ala Pro Ala Ser Thr Pro Arg Arg Ser Arg Arg Cys
225                 230                 235                 240
Leu Arg Glu Lys Leu Thr Gln Glu Val Asn Leu Arg Arg Ile
245                 250

<210> SEQ ID NO 127
<211> LENGTH: 236
<212> TYPE: DNA
<213> ORGANISM: Toxoplasma gondii
<220> FEATURE:
<221> NAME/KEY: CDS
<222> LOCATION: (1)..(234)
<223> OTHER INFORMATION:

<400> SEQUENCE: 127 cgc gga gag ggg gag act gag aga ggg cag aat gag gag act cac gca    48
Arg Gly Glu Gly Glu Thr Glu Arg Gly Gln Asn Glu Glu Thr His Ala
 1               5                  10                  15 acg aac aag tcc tca ggc gtc gcc agt ttg gag gca cca gcg tcg ttc    96
Thr Asn Lys Ser Ser Gly Val Ala Ser Leu Glu Ala Pro Ala Ser Phe
            20                  25                  30 gcg cag gag ggc gac gga ggg cgg aga gaa gaa gca agc caa gca aaa   144
Ala Gln Glu Gly Asp Gly Gly Arg Arg Glu Glu Ala Ser Gln Ala Lys
35                  40                  45 atg ggg acg tct ccc ccg tcg aat cag gtg atc aac gtt gta gac gaa   192
Met Gly Thr Ser Pro Pro Ser Asn Gln Val Ile Asn Val Val Asp Glu
 50                  55                  60 gac gag gag gac gac gag gaa gca gag gcg cta gag gct ccc gg        236
Asp Glu Glu Asp Asp Glu Glu Ala Glu Ala Leu Glu Ala Pro
 65                  70                  75

<210> SEQ ID NO 128
<211> LENGTH: 78
<212> TYPE: PRT
<213> ORGANISM: Toxoplasma gondii

<400> SEQUENCE: 128
```

```
Arg Gly Glu Gly Glu Thr Glu Arg Gly Gln Asn Glu Thr His Ala
1               5                   10                  15

Thr Asn Lys Ser Ser Gly Val Ala Ser Leu Glu Ala Pro Ala Ser Phe
20              25                  30

Ala Gln Glu Gly Asp Gly Gly Arg Arg Glu Ala Ser Gln Ala Lys
35              40                  45

Met Gly Thr Ser Pro Pro Ser Asn Gln Val Ile Asn Val Val Asp Glu
50              55                  60

Asp Glu Glu Asp Asp Glu Ala Glu Ala Leu Glu Ala Pro
65              70                  75

<210> SEQ ID NO 129
<211> LENGTH: 569
<212> TYPE: DNA
<213> ORGANISM: Toxoplasma gondii
<220> FEATURE:
<221> NAME/KEY: CDS
<222> LOCATION: (1)..(567)
<223> OTHER INFORMATION:

<400> SEQUENCE: 129 cga tct cgt ttt ggt cct gag caa ttc gct att tcg gat gtc tca ggc      48
Arg Ser Arg Phe Gly Pro Glu Gln Phe Ala Ile Ser Asp Val Ser Gly
1               5                   10                  15 aca ctt gtt aat gca agc tgg ctt ggt gcc tct gca ggg gag act atc      96
Thr Leu Val Asn Ala Ser Trp Leu Gly Ala Ser Ala Gly Glu Thr Ile
        20                  25                  30 gct gat tca agg gct tta agg cgt gac cta tca ttc cca ctg tct agt     144
Ala Asp Ser Arg Ala Leu Arg Arg Asp Leu Ser Phe Pro Leu Ser Ser
    35                  40                  45 cgt caa ctg cga gaa cgt ggc ctt gct tct caa gat tcc tca ctt tca     192
Arg Gln Leu Arg Glu Arg Gly Leu Ala Ser Gln Asp Ser Ser Leu Ser
50                  55                  60 agc act cca aaa ttg tcc ctg caa cac gac cac ttt gca aag act ctg     240
Ser Thr Pro Lys Leu Ser Leu Gln His Asp His Phe Ala Lys Thr Leu
65                  70                  75                  80 gta aaa cga aga gcg ctg tct gca acg aac tcc aca gaa cgc agc ggc     288
Val Lys Arg Arg Ala Leu Ser Ala Thr Asn Ser Thr Glu Arg Ser Gly
            85                  90                  95 aaa cca gtt cgt tgc ttt act gaa acc agc gtg agg tta ggt gca cct     336
Lys Pro Val Arg Cys Phe Thr Glu Thr Ser Val Arg Leu Gly Ala Pro
        100                 105                 110 act caa ccg gta atg gag gaa atg cct ttg gga gaa gga gag gta aat     384
Thr Gln Pro Val Met Glu Glu Met Pro Leu Gly Glu Gly Glu Val Asn
    115                 120                 125 ctg gtc tcc gaa cac gac gat tat gca gaa tcc acc agt cat ctg gat     432
Leu Val Ser Glu His Asp Asp Tyr Ala Glu Ser Thr Ser His Leu Asp
130                 135                 140 acg gtg aat ggg aga gaa aga aga gag gaa agg cat tac gcg gag acg     480
Thr Val Asn Gly Arg Glu Arg Arg Glu Glu Arg His Tyr Ala Glu Thr
145                 150                 155                 160 gag gcg aca gac gaa ttc aaa tcc gca atg cac cac gtg acg tcg ccc     528
Glu Ala Thr Asp Glu Phe Lys Ser Ala Met His His Val Thr Ser Pro
            165                 170                 175 gga ggg gta ccc gca acg aaa aag gtg gtg tgg aag atc cg              569
Gly Gly Val Pro Ala Thr Lys Lys Val Val Trp Lys Ile
        180                 185

<210> SEQ ID NO 130
<211> LENGTH: 189
<212> TYPE: PRT
```

<213> ORGANISM: Toxoplasma gondii

<400> SEQUENCE: 130

```
Arg Ser Arg Phe Gly Pro Glu Gln Phe Ala Ile Ser Asp Val Ser Gly
1               5                   10                  15

Thr Leu Val Asn Ala Ser Trp Leu Gly Ala Ser Ala Gly Glu Thr Ile
            20                  25                  30

Ala Asp Ser Arg Ala Leu Arg Arg Asp Leu Ser Phe Pro Leu Ser Ser
        35                  40                  45

Arg Gln Leu Arg Glu Arg Gly Leu Ala Ser Gln Asp Ser Ser Leu Ser
    50                  55                  60

Ser Thr Pro Lys Leu Ser Leu Gln His Asp His Phe Ala Lys Thr Leu
65                  70                  75                  80

Val Lys Arg Arg Ala Leu Ser Ala Thr Asn Ser Thr Glu Arg Ser Gly
                85                  90                  95

Lys Pro Val Arg Cys Phe Thr Glu Thr Ser Val Arg Leu Gly Ala Pro
            100                 105                 110

Thr Gln Pro Val Met Glu Glu Met Pro Leu Gly Glu Gly Glu Val Asn
        115                 120                 125

Leu Val Ser Glu His Asp Asp Tyr Ala Glu Ser Thr Ser His Leu Asp
    130                 135                 140

Thr Val Asn Gly Arg Glu Arg Arg Glu Glu Arg His Tyr Ala Glu Thr
145                 150                 155                 160

Glu Ala Thr Asp Glu Phe Lys Ser Ala Met His His Val Thr Ser Pro
                165                 170                 175

Gly Gly Val Pro Ala Thr Lys Lys Val Val Trp Lys Ile
            180                 185
```

<210> SEQ ID NO 131
<211> LENGTH: 232
<212> TYPE: DNA
<213> ORGANISM: Toxoplasma gondii

<400> SEQUENCE: 131

```
cggcgactca gatgggagtg agaaagatgc aaacaggtgc tgaaaaaaca ccacttaata    60
gaggagacaa accccggtgg agaaagcgaa acgagactgg aacggcaacg aaatagagaa   120
gacacagccc caaactcccg acagcgtgtt gctctgtcgg gcaggcaggc caagctggca   180
agccgctagc atgccacgtg ctgtactgct ggcccgaaac tacagtgcgc ac           232
```

<210> SEQ ID NO 132
<211> LENGTH: 276
<212> TYPE: DNA
<213> ORGANISM: Toxoplasma gondii
<220> FEATURE:
<221> NAME/KEY: CDS
<222> LOCATION: (1)..(276)
<223> OTHER INFORMATION:

<400> SEQUENCE: 132

```
ccc gga att ccg gct ccg ggt cgc aaa gcg atc cat ttg ata aaa gac     48
Pro Gly Ile Pro Ala Pro Gly Arg Lys Ala Ile His Leu Ile Lys Asp
1               5                   10                  15 tgc gtt ttc tgc ctt ggg gaa ctc ttc ttg aat ggc acg aga ggc cac     96
Cys Val Phe Cys Leu Gly Glu Leu Phe Leu Asn Gly Thr Arg Gly His
            20                  25                  30 aga cag aga gag agg gag gga aag cca aag aag caa aca ggc tcg gaa    144
Arg Gln Arg Glu Arg Glu Gly Lys Pro Lys Lys Gln Thr Gly Ser Glu
        35                  40                  45
```

```
gcg ccc aga ata cag gca gcc tct ccg aag tca ctc acc ttg tac gat         192
Ala Pro Arg Ile Gln Ala Ala Ser Pro Lys Ser Leu Thr Leu Tyr Asp
50                  55                  60 ctt gtg cac agt gat gta ggg cgc atg cag aac gac gcc tcc aac atg         240
Leu Val His Ser Asp Val Gly Arg Met Gln Asn Asp Ala Ser Asn Met
65                  70                  75                  80 aat att ctc ctc ggc caa ggc cgc cgc caa gta gcg                         276
Asn Ile Leu Leu Gly Gln Gly Arg Arg Gln Val Ala
85                  90
```

<210> SEQ ID NO 133
<211> LENGTH: 92
<212> TYPE: PRT
<213> ORGANISM: Toxoplasma gondii

<400> SEQUENCE: 133

```
Pro Gly Ile Pro Ala Pro Gly Arg Lys Ala Ile His Leu Ile Lys Asp
1               5                   10                  15

Cys Val Phe Cys Leu Gly Glu Leu Phe Leu Asn Gly Thr Arg Gly His
                20                  25                  30

Arg Gln Arg Glu Arg Gly Lys Pro Lys Lys Gln Thr Gly Ser Glu
35                  40                  45

Ala Pro Arg Ile Gln Ala Ala Ser Pro Lys Ser Leu Thr Leu Tyr Asp
50                  55                  60

Leu Val His Ser Asp Val Gly Arg Met Gln Asn Asp Ala Ser Asn Met
65                  70                  75                  80

Asn Ile Leu Leu Gly Gln Gly Arg Arg Gln Val Ala
85                  90
```

<210> SEQ ID NO 134
<211> LENGTH: 309
<212> TYPE: DNA
<213> ORGANISM: Toxoplasma gondii
<220> FEATURE:
<221> NAME/KEY: CDS
<222> LOCATION: (1)..(309)
<223> OTHER INFORMATION:

<400> SEQUENCE: 134

```
cgc gga cac act gga gag agg tgg tcg gac agg gag gga gaa tcc gag         48
Arg Gly His Thr Gly Glu Arg Trp Ser Asp Arg Glu Gly Glu Ser Glu
1               5                   10                  15 atg tgc agt gga gga caa atg gaa aag aga gag agc cga cgc gtt tct         96
Met Cys Ser Gly Gly Gln Met Glu Lys Arg Glu Ser Arg Arg Val Ser
            20                  25                  30 ttt gcg gat gaa gag atg cgg aat ccg aca gaa aac ctg aag gta gat         144
Phe Ala Asp Glu Glu Met Arg Asn Pro Thr Glu Asn Leu Lys Val Asp
35                  40                  45 gcc aac tgt gtg ctc gaa ggt ctg tcc acc tca gtg tgt gcg agg cgg         192
Ala Asn Cys Val Leu Glu Gly Leu Ser Thr Ser Val Cys Ala Arg Arg
50                  55                  60 ctg aag agg caa aag cga act gca ggt cag tct ggc ttc ctc gca ata         240
Leu Lys Arg Gln Lys Arg Thr Ala Gly Gln Ser Gly Phe Leu Ala Ile
65                  70                  75                  80 cga aac gtc caa ggc acc gcg acc gcc cta aaa cac cct gat tcc aca         288
Arg Asn Val Gln Gly Thr Ala Thr Ala Leu Lys His Pro Asp Ser Thr
85                  90                  95 gga cga cgg tct tgg gat ccg                                             309
Gly Arg Arg Ser Trp Asp Pro
100
```

<210> SEQ ID NO 135
<211> LENGTH: 103
<212> TYPE: PRT
<213> ORGANISM: Toxoplasma gondii

<400> SEQUENCE: 135

```
Arg Gly His Thr Gly Glu Arg Trp Ser Asp Arg Glu Gly Glu Ser Glu
1               5                   10                  15

Met Cys Ser Gly Gly Gln Met Glu Lys Arg Glu Ser Arg Arg Val Ser
            20                  25                  30

Phe Ala Asp Glu Glu Met Arg Asn Pro Thr Glu Asn Leu Lys Val Asp
        35                  40                  45

Ala Asn Cys Val Leu Glu Gly Leu Ser Thr Ser Val Cys Ala Arg Arg
    50                  55                  60

Leu Lys Arg Gln Lys Arg Thr Ala Gly Gln Ser Gly Phe Leu Ala Ile
65                  70                  75                  80

Arg Asn Val Gln Gly Thr Ala Thr Ala Leu Lys His Pro Asp Ser Thr
                85                  90                  95

Gly Arg Arg Ser Trp Asp Pro
            100
```

<210> SEQ ID NO 136
<211> LENGTH: 534
<212> TYPE: DNA
<213> ORGANISM: Toxoplasma gondii
<220> FEATURE:
<221> NAME/KEY: CDS
<222> LOCATION: (1)..(534)
<223> OTHER INFORMATION:

<400> SEQUENCE: 136

| | |
|---|---:|
| cgg atc gag gct gaa atc gct agg cag aag gag cgg gaa gcc aaa ctg<br>Arg Ile Glu Ala Glu Ile Ala Arg Gln Lys Glu Arg Glu Ala Lys Leu<br>1               5                   10                 15 | 48 |
| cgt cgc agg ctt gct gcg gtc gtg gcc tca atg ctg gta gca gcg agc<br>Arg Arg Arg Leu Ala Ala Val Val Ala Ser Met Leu Val Ala Ala Ser<br>            20                   25                   30 | 96 |
| ctc tac ggc ttg aac tcg ttc ctc cac ggt tct gac aag gag att tct<br>Leu Tyr Gly Leu Asn Ser Phe Leu His Gly Ser Asp Lys Glu Ile Ser<br>35                  40                   45 | 144 |
| tcg atg cca tcc tct atc gac aaa aaa cca gat tcc ccc ttt gcc gca<br>Ser Met Pro Ser Ser Ile Asp Lys Lys Pro Asp Ser Pro Phe Ala Ala<br>50                  55                  60 | 192 |
| cag ctg ggc acc tcg ctc gag tca gaa att ggt ata ccc gaa gaa aaa<br>Gln Leu Gly Thr Ser Leu Glu Ser Glu Ile Gly Ile Pro Glu Glu Lys<br>65                  70                  75               80 | 240 |
| gca att cct gag gcg gcc gac ata agc agt ttt att gag aat ctt tcc<br>Ala Ile Pro Glu Ala Ala Asp Ile Ser Ser Phe Ile Glu Asn Leu Ser<br>85                  90                  95 | 288 |
| gcg acg gtg gca ggc aat tct gtg caa gcc cag agc atc ggc ttt gtg<br>Ala Thr Val Ala Gly Asn Ser Val Gln Ala Gln Ser Ile Gly Phe Val<br>100                 105               110 | 336 |
| ttg aca gtt gtt gta ctt ggt ctt gtc gcc ttc tca ctc aag gct gct<br>Leu Thr Val Val Val Leu Gly Leu Val Ala Phe Ser Leu Lys Ala Ala<br>115                 120               125 | 384 |
| cga cgt tcc tcg cca aga gag gag cag gca ttc agc ctg ccg gca cac<br>Arg Arg Ser Ser Pro Arg Glu Glu Gln Ala Phe Ser Leu Pro Ala His<br>130                 135               140 | 432 |
| ccg cct cgc gag gaa aaa tca aaa tac ctg ctg aag ccg ccc cag cag<br>Pro Pro Arg Glu Glu Lys Ser Lys Tyr Leu Leu Lys Pro Pro Gln Gln | 480 |

```
                145                 150                 155                 160
ccc aag ccc agg cgg ctc aaa agg cag ctc cgc aag tac cga caa agg    528
Pro Lys Pro Arg Arg Leu Lys Arg Gln Leu Arg Lys Tyr Arg Gln Arg
165                 170                 175 gtg ctg                                                             534
Val Leu
```

<210> SEQ ID NO 137
<211> LENGTH: 178
<212> TYPE: PRT
<213> ORGANISM: Toxoplasma gondii

<400> SEQUENCE: 137

```
Arg Ile Glu Ala Glu Ile Ala Arg Gln Lys Glu Arg Glu Ala Lys Leu
1               5                   10                  15

Arg Arg Arg Leu Ala Ala Val Val Ala Ser Met Leu Val Ala Ala Ser
            20                  25                  30

Leu Tyr Gly Leu Asn Ser Phe Leu His Gly Ser Asp Lys Glu Ile Ser
        35                  40                  45

Ser Met Pro Ser Ser Ile Asp Lys Lys Pro Asp Ser Pro Phe Ala Ala
    50                  55                  60

Gln Leu Gly Thr Ser Leu Glu Ser Glu Ile Gly Ile Pro Glu Glu Lys
65                  70                  75                  80

Ala Ile Pro Glu Ala Ala Asp Ile Ser Ser Phe Ile Glu Asn Leu Ser
                85                  90                  95

Ala Thr Val Ala Gly Asn Ser Val Gln Ala Gln Ser Ile Gly Phe Val
            100                 105                 110

Leu Thr Val Val Leu Gly Leu Val Ala Phe Ser Leu Lys Ala Ala
        115                 120                 125

Arg Arg Ser Ser Pro Arg Glu Glu Gln Ala Phe Ser Leu Pro Ala His
    130                 135                 140

Pro Pro Arg Glu Glu Lys Ser Lys Tyr Leu Leu Lys Pro Pro Gln Gln
145                 150                 155                 160

Pro Lys Pro Arg Arg Leu Lys Arg Gln Leu Arg Lys Tyr Arg Gln Arg
                165                 170                 175

Val Leu
```

<210> SEQ ID NO 138
<211> LENGTH: 423
<212> TYPE: DNA
<213> ORGANISM: Toxoplasma gondii
<220> FEATURE:
<221> NAME/KEY: misc_feature
<222> LOCATION: (6)..(6)
<223> OTHER INFORMATION: n = unknown
<220> FEATURE:
<221> NAME/KEY: misc_feature
<222> LOCATION: (23)..(23)
<223> OTHER INFORMATION: n = unknown
<220> FEATURE:
<221> NAME/KEY: misc_feature
<222> LOCATION: (34)..(34)
<223> OTHER INFORMATION: n = unknown

<400> SEQUENCE: 138
tggtgntgtt gaggccgcat cgngagggga gacntgctag agccaggggc agagccgcag    60
gtccggtgga ggatgttgtt gagccccgt cgggagtgga agacctgccg cagccagagg    120
cagaggcgca agtaccgacc aagggtgttg accatgccgc gtcggagggg aggacatcg    180 tggagccaga ggcagagccg cagggactgg tggctggcgc tggtgaggcc gcatcgggag    240
gggaggacct gctagagcca ggggcagcgc cgcagggtcc ggtgaaggat gttgatgagg    300
cggcgtcggg agaggaagaa ctgctggagc cagaggcaaa gccgcagggt tcggtggagg    360
atgttgatga ggcagcgtcg ggaggggagg acctgctaga gccagaggca gaggcgcaag    420
tcc                                                                   423

<210> SEQ ID NO 139
<211> LENGTH: 327
<212> TYPE: DNA
<213> ORGANISM: Toxoplasma gondii
<220> FEATURE:
<221> NAME/KEY: CDS
<222> LOCATION: (1)..(327)
<223> OTHER INFORMATION:

<400> SEQUENCE: 139

```
cgc tct caa tca aca aag cca ccc gcg cct tca gac gta gag gac aca      48
Arg Ser Gln Ser Thr Lys Pro Pro Ala Pro Ser Asp Val Glu Asp Thr
1               5                   10                  15 ggc tct tct gac aac ccg ggt gac aat gtg aca gag gac aca act gag      96
Gly Ser Ser Asp Asn Pro Gly Asp Asn Val Thr Glu Asp Thr Thr Glu
        20                  25                  30 agt cca tca cag ggc acc gac ggt tca gca tcc gga ccc ggg tcg act     144
Ser Pro Ser Gln Gly Thr Asp Gly Ser Ala Ser Gly Pro Gly Ser Thr
35                  40                  45 cat ccg gaa aac gac gcg ggg gaa cat gag gat ggc gcg tca ctg ggg     192
His Pro Glu Asn Asp Ala Gly Glu His Glu Asp Gly Ala Ser Leu Gly
    50                  55                  60 caa gac cag caa gag cgc atg gat aaa tct tcc cta ggc aaa gaa aca     240
Gln Asp Gln Gln Glu Arg Met Asp Lys Ser Ser Leu Gly Lys Glu Thr
65                  70                  75                  80 ccc atg ctc gat cag gga aat tcg tca cca gca aca acg ggg tcc ggt     288
Pro Met Leu Asp Gln Gly Asn Ser Ser Pro Ala Thr Thr Gly Ser Gly
                85                  90                  95 gcc cat gaa aaa aac gag agc gtg tca gga gtt cca gcg                 327
Ala His Glu Lys Asn Glu Ser Val Ser Gly Val Pro Ala
            100                 105
```

<210> SEQ ID NO 140
<211> LENGTH: 109
<212> TYPE: PRT
<213> ORGANISM: Toxoplasma gondii

<400> SEQUENCE: 140

```
Arg Ser Gln Ser Thr Lys Pro Pro Ala Pro Ser Asp Val Glu Asp Thr
1               5                   10                  15

Gly Ser Ser Asp Asn Pro Gly Asp Asn Val Thr Glu Asp Thr Thr Glu
            20                  25                  30

Ser Pro Ser Gln Gly Thr Asp Gly Ser Ala Ser Gly Pro Gly Ser Thr
35                  40                  45

His Pro Glu Asn Asp Ala Gly Glu His Glu Asp Gly Ala Ser Leu Gly
    50                  55                  60

Gln Asp Gln Gln Glu Arg Met Asp Lys Ser Ser Leu Gly Lys Glu Thr
65                  70                  75                  80

Pro Met Leu Asp Gln Gly Asn Ser Ser Pro Ala Thr Thr Gly Ser Gly
                85                  90                  95

Ala His Glu Lys Asn Glu Ser Val Ser Gly Val Pro Ala
            100                 105
```

<210> SEQ ID NO 141
<211> LENGTH: 444
<212> TYPE: DNA
<213> ORGANISM: Toxoplasma gondii
<220> FEATURE:
<221> NAME/KEY: CDS
<222> LOCATION: (1)..(444)
<223> OTHER INFORMATION:

<400> SEQUENCE: 141

```
ccg gcg cga act ggc gac gcg cag cct gag ggc aga gag ggg cac agc      48
Pro Ala Arg Thr Gly Asp Ala Gln Pro Glu Gly Arg Glu Gly His Ser
1               5                   10                  15 cca ctg gaa gac gaa ggg aga gat gcg ttt gga aga cgc gct gcg gaa      96
Pro Leu Glu Asp Glu Gly Arg Asp Ala Phe Gly Arg Arg Ala Ala Glu
            20                  25                  30 gac gag aga aac aga gga aat ccg aat gcg gct ggc gag act tcc caa     144
Asp Glu Arg Asn Arg Gly Asn Pro Asn Ala Ala Gly Glu Thr Ser Gln
35                  40                  45 gac gag gca gag aac gcg caa gcg tcc ctg cgg ttc gct gcg aga gag     192
Asp Glu Ala Glu Asn Ala Gln Ala Ser Leu Arg Phe Ala Ala Arg Glu
50                  55                  60 aaa cct ctc gaa gtc ctc aga ttc cga gaa gac act gca gac act ctg     240
Lys Pro Leu Glu Val Leu Arg Phe Arg Glu Asp Thr Ala Asp Thr Leu
65                  70                  75                  80 acg tat gca gac tat cca aac agc gtg gag ttc aca ccc gca gac atg     288
Thr Tyr Ala Asp Tyr Pro Asn Ser Val Glu Phe Thr Pro Ala Asp Met
                85                  90                  95 ccg aat gcg aag gac cag acg cct ctg cat gca aag tac aat cac ttt     336
Pro Asn Ala Lys Asp Gln Thr Pro Leu His Ala Lys Tyr Asn His Phe
            100                 105                 110 tgc gcc tac tca tgc tgg ctg acc tcg cgc ttc aac cca gac aac cca     384
Cys Ala Tyr Ser Cys Trp Leu Thr Ser Arg Phe Asn Pro Asp Asn Pro
        115                 120                 125 aac agc cac tgt gga aaa gga aaa aac gag aaa cgc cga ttc gac gac     432
Asn Ser His Cys Gly Lys Gly Lys Asn Glu Lys Arg Arg Phe Asp Asp
130                 135                 140 gac tac gat ccg                                                      444
Asp Tyr Asp Pro
145
```

<210> SEQ ID NO 142
<211> LENGTH: 148
<212> TYPE: PRT
<213> ORGANISM: Toxoplasma gondii

<400> SEQUENCE: 142

```
Pro Ala Arg Thr Gly Asp Ala Gln Pro Glu Gly Arg Glu Gly His Ser
1               5                   10                  15

Pro Leu Glu Asp Glu Gly Arg Asp Ala Phe Gly Arg Arg Ala Ala Glu
            20                  25                  30

Asp Glu Arg Asn Arg Gly Asn Pro Asn Ala Ala Gly Glu Thr Ser Gln
35                  40                  45

Asp Glu Ala Glu Asn Ala Gln Ala Ser Leu Arg Phe Ala Ala Arg Glu
50                  55                  60

Lys Pro Leu Glu Val Leu Arg Phe Arg Glu Asp Thr Ala Asp Thr Leu
65                  70                  75                  80

Thr Tyr Ala Asp Tyr Pro Asn Ser Val Glu Phe Thr Pro Ala Asp Met
                85                  90                  95

Pro Asn Ala Lys Asp Gln Thr Pro Leu His Ala Lys Tyr Asn His Phe
            100                 105                 110
```

```
Cys Ala Tyr Ser Cys Trp Leu Thr Ser Arg Phe Asn Pro Asp Asn Pro
115                 120                 125

Asn Ser His Cys Gly Lys Gly Lys Asn Glu Lys Arg Arg Phe Asp Asp
            130                 135                 140

Asp Tyr Asp Pro
145

<210> SEQ ID NO 143
<211> LENGTH: 928
<212> TYPE: DNA
<213> ORGANISM: Toxoplasma gondii
<220> FEATURE:
<221> NAME/KEY: CDS
<222> LOCATION: (1)..(57)
<223> OTHER INFORMATION:

<400> SEQUENCE: 143 cgg gat ccc gag cgg gac ctc ccg gtg tcc tcg act gct cat aca cca        48
Arg Asp Pro Glu Arg Asp Leu Pro Val Ser Ser Thr Ala His Thr Pro
1               5                   10                  15 gag gag gat tgattcaccg cagaacttaa cccgtgggac gcagcctcca                97
Glu Glu Asp cagagtctgt ggcggacgaa ggaaatgcag gaacagagag acctggaccg aaaaatggca     157
tggacgatgg gtgtccacgg gagaagacgg atactcgtgg aaagccgggg gaaagcgacg     217
gagggaaatg cgcgacaagc tggaaaagcg agctcacaac gacgaaacac gcactgtgca     277
tccgaacgac aatgacctgt ccttagtaga cgagaggggg taggcaacaa ttcctcagaa     337
gtccaccagc gaccggacag cgaccgcggc agcacgttga gggaggtctt actagcggcc     397
gagactcagg acaacaggag ccctctaccg ccatgcgaca cacgcagaac aacgctttag     457
attaaggtcg aaaaaggaaa cctcaacgca gaacgagtca cttctttccc acaaaagtgc     517
tgtgaaaaaa cagcgcatgc ggggctgggt gactcgaaaa tctgggaacg cgtctggcag     577
gcatcctgcc cgaacccgat accagagaaa cggaacccgt actggctgga attcaacagt     637
acggacaaaa aacccaccgt gtaaagtgga caaaagccga caatgaaca actacttggg      697 agaaagcaaa tgctgcgttc accaggccag tgtcacgccg cgtcgtaaag aaggcggctc     757
agcgttgccg gtgtgcctgg cgttgtcgga cggcttccgt gtgtacccaa cagaaaagct     817
tttacactct tactattttc atttggccac gatttctttt ttgcctatct actgtaccta     877
gccacgtcgc cattctaagg aagttgtccc gttgcaacgc agaacgcgga g              928

<210> SEQ ID NO 144
<211> LENGTH: 19
<212> TYPE: PRT
<213> ORGANISM: Toxoplasma gondii

<400> SEQUENCE: 144

Arg Asp Pro Glu Arg Asp Leu Pro Val Ser Ser Thr Ala His Thr Pro
1               5                   10                  15

Glu Glu Asp

<210> SEQ ID NO 145
<211> LENGTH: 18
<212> TYPE: DNA
<213> ORGANISM: Artificial sequence
<220> FEATURE:
<223> OTHER INFORMATION: Synthetic Primer

<400> SEQUENCE: 145
```

```
cgcttcttgt gtcacctg                                                   18

<210> SEQ ID NO 146
<211> LENGTH: 23
<212> TYPE: DNA
<213> ORGANISM: Artificial sequence
<220> FEATURE:
<223> OTHER INFORMATION: Synthetic Primer

<400> SEQUENCE: 146
gcaccttgtt ctctctcttc gcc                                             23

<210> SEQ ID NO 147
<211> LENGTH: 18
<212> TYPE: DNA
<213> ORGANISM: Artificial sequence
<220> FEATURE:
<223> OTHER INFORMATION: Synthetic Primer

<400> SEQUENCE: 147
cgaggagacg gtgggagc                                                   18

<210> SEQ ID NO 148
<211> LENGTH: 21
<212> TYPE: DNA
<213> ORGANISM: Artificial sequence
<220> FEATURE:
<223> OTHER INFORMATION: Synthetic Primer

<400> SEQUENCE: 148
tgcccaagat gccgatctct g                                               21

<210> SEQ ID NO 149
<211> LENGTH: 20
<212> TYPE: DNA
<213> ORGANISM: Artificial sequence
<220> FEATURE:
<223> OTHER INFORMATION: Synthetic Primer

<400> SEQUENCE: 149
tctcccccat cgacgaaaac                                                 20

<210> SEQ ID NO 150
<211> LENGTH: 22
<212> TYPE: DNA
<213> ORGANISM: Artificial sequence
<220> FEATURE:
<223> OTHER INFORMATION: Synthetic Primer

<400> SEQUENCE: 150
gctcatttcc tccgcaattt gg                                              22

<210> SEQ ID NO 151
<211> LENGTH: 23
<212> TYPE: DNA
<213> ORGANISM: Artificial sequence
<220> FEATURE:
<223> OTHER INFORMATION: Synthetic Primer

<400> SEQUENCE: 151
agctggcaga aataccaaag ctc                                             23

<210> SEQ ID NO 152
<211> LENGTH: 20
<212> TYPE: DNA
```

<213> ORGANISM: Artificial sequence
<220> FEATURE:
<223> OTHER INFORMATION: Synthetic Primer

<400> SEQUENCE: 152
tgtcggcaat actgggcatg                                               20

<210> SEQ ID NO 153
<211> LENGTH: 24
<212> TYPE: DNA
<213> ORGANISM: Artificial sequence
<220> FEATURE:
<223> OTHER INFORMATION: Synthetic Primer

<400> SEQUENCE: 153
actggagtgg aaagtctggt tttg                                          24

<210> SEQ ID NO 154
<211> LENGTH: 23
<212> TYPE: DNA
<213> ORGANISM: Artificial sequence
<220> FEATURE:
<223> OTHER INFORMATION: Synthetic Primer

<400> SEQUENCE: 154
gacgcagaga agaaagaaga gcc                                           23

<210> SEQ ID NO 155
<211> LENGTH: 22
<212> TYPE: DNA
<213> ORGANISM: Artificial sequence
<220> FEATURE:
<223> OTHER INFORMATION: Synthetic Primer

<400> SEQUENCE: 155
tccaaaactg tctcgtctcc cc                                            22

<210> SEQ ID NO 156
<211> LENGTH: 21
<212> TYPE: DNA
<213> ORGANISM: Artificial sequence
<220> FEATURE:
<223> OTHER INFORMATION: Synthetic Primer

<400> SEQUENCE: 156
tctggatacg ccgttccttt g                                             21

<210> SEQ ID NO 157
<211> LENGTH: 25
<212> TYPE: DNA
<213> ORGANISM: Artificial sequence
<220> FEATURE:
<223> OTHER INFORMATION: Synthetic Primer

<400> SEQUENCE: 157
gacatctacc tgtgagtgaa ccagg                                         25

<210> SEQ ID NO 158
<211> LENGTH: 22
<212> TYPE: DNA
<213> ORGANISM: Artificial sequence
<220> FEATURE:
<223> OTHER INFORMATION: Synthetic Primer

<400> SEQUENCE: 158
gtcaaaacct tgccagcatc tc                                            22

```
<210> SEQ ID NO 159
<211> LENGTH: 24
<212> TYPE: DNA
<213> ORGANISM: Artificial sequence
<220> FEATURE:
<223> OTHER INFORMATION: Synthetic Primer

<400> SEQUENCE: 159
tccgactgaa tgactacctc tttc                                          24

<210> SEQ ID NO 160
<211> LENGTH: 22
<212> TYPE: DNA
<213> ORGANISM: Artificial sequence
<220> FEATURE:
<223> OTHER INFORMATION: Synthetic Primer

<400> SEQUENCE: 160
tccgaccaag tcctcagtga ac                                            22

<210> SEQ ID NO 161
<211> LENGTH: 20
<212> TYPE: DNA
<213> ORGANISM: Artificial sequence
<220> FEATURE:
<223> OTHER INFORMATION: Synthetic Primer

<400> SEQUENCE: 161
tgggcatttc ctggaagagg                                               20

<210> SEQ ID NO 162
<211> LENGTH: 21
<212> TYPE: DNA
<213> ORGANISM: Artificial sequence
<220> FEATURE:
<223> OTHER INFORMATION: Synthetic Primer

<400> SEQUENCE: 162
gaatccatct cgtgcaaacg g                                             21

<210> SEQ ID NO 163
<211> LENGTH: 21
<212> TYPE: DNA
<213> ORGANISM: Artificial sequence
<220> FEATURE:
<223> OTHER INFORMATION: Synthetic Primer

<400> SEQUENCE: 163
caagacacag ggaaacgttg g                                             21

<210> SEQ ID NO 164
<211> LENGTH: 22
<212> TYPE: DNA
<213> ORGANISM: Artificial sequence
<220> FEATURE:
<223> OTHER INFORMATION: Synthetic Primer

<400> SEQUENCE: 164
gaaagaatcg cacctcctct cc                                            22

<210> SEQ ID NO 165
<211> LENGTH: 23
<212> TYPE: DNA
<213> ORGANISM: Artificial sequence
<220> FEATURE:
```

<223> OTHER INFORMATION: Synthetic Primer

<400> SEQUENCE: 165
tttgagtcta accgccgtat gtc                                                  23

<210> SEQ ID NO 166
<211> LENGTH: 23
<212> TYPE: DNA
<213> ORGANISM: Artificial sequence
<220> FEATURE:
<223> OTHER INFORMATION: Synthetic Primer

<400> SEQUENCE: 166
tcagacgatt ctcccattgt acg                                                  23

<210> SEQ ID NO 167
<211> LENGTH: 22
<212> TYPE: DNA
<213> ORGANISM: Artificial sequence
<220> FEATURE:
<223> OTHER INFORMATION: Synthetic Primer

<400> SEQUENCE: 167
tcgacttggg tccgattgtt ag                                                   22

<210> SEQ ID NO 168
<211> LENGTH: 24
<212> TYPE: DNA
<213> ORGANISM: Artificial sequence
<220> FEATURE:
<223> OTHER INFORMATION: Synthetic Primer

<400> SEQUENCE: 168
gatcttttgc gtgactttgt ctgc                                                 24

<210> SEQ ID NO 169
<211> LENGTH: 24
<212> TYPE: DNA
<213> ORGANISM: Artificial sequence
<220> FEATURE:
<223> OTHER INFORMATION: Synthetic Primer

<400> SEQUENCE: 169
gaagatgctt gtcttgttcg gttc                                                 24

<210> SEQ ID NO 170
<211> LENGTH: 23
<212> TYPE: DNA
<213> ORGANISM: Artificial sequence
<220> FEATURE:
<223> OTHER INFORMATION: Synthetic Primer

<400> SEQUENCE: 170
gaggggtttc cttctttatt gcc                                                  23

<210> SEQ ID NO 171
<211> LENGTH: 20
<212> TYPE: DNA
<213> ORGANISM: Artificial sequence
<220> FEATURE:
<223> OTHER INFORMATION: Synthetic Primer

<400> SEQUENCE: 171
tgttggacat cccgagcatc                                                      20

-continued

```
<210> SEQ ID NO 172
<211> LENGTH: 20
<212> TYPE: DNA
<213> ORGANISM: Artificial sequence
<220> FEATURE:
<223> OTHER INFORMATION: Synthetic Primer

<400> SEQUENCE: 172
ggtccttgtt tttcaggcgg                                               20

<210> SEQ ID NO 173
<211> LENGTH: 22
<212> TYPE: DNA
<213> ORGANISM: Artificial sequence
<220> FEATURE:
<223> OTHER INFORMATION: Synthetic Primer

<400> SEQUENCE: 173
tcgtgcagac agtgaagcaa tg                                            22

<210> SEQ ID NO 174
<211> LENGTH: 21
<212> TYPE: DNA
<213> ORGANISM: Artificial sequence
<220> FEATURE:
<223> OTHER INFORMATION: Synthetic Primer

<400> SEQUENCE: 174
ttttgtcagc acagagtggc g                                             21

<210> SEQ ID NO 175
<211> LENGTH: 23
<212> TYPE: DNA
<213> ORGANISM: Artificial sequence
<220> FEATURE:
<223> OTHER INFORMATION: Synthetic Primer

<400> SEQUENCE: 175
cgcaagtgag ttttggcttt acc                                           23

<210> SEQ ID NO 176
<211> LENGTH: 22
<212> TYPE: DNA
<213> ORGANISM: Artificial sequence
<220> FEATURE:
<223> OTHER INFORMATION: Synthetic Primer

<400> SEQUENCE: 176
cctggaagag atatgcagac ac                                            22

<210> SEQ ID NO 177
<211> LENGTH: 22
<212> TYPE: DNA
<213> ORGANISM: Artificial sequence
<220> FEATURE:
<223> OTHER INFORMATION: Synthetic Primer

<400> SEQUENCE: 177
tcaccgttcg ctcttctttc tc                                            22

<210> SEQ ID NO 178
<211> LENGTH: 20
<212> TYPE: DNA
<213> ORGANISM: Artificial sequence
<220> FEATURE:
<223> OTHER INFORMATION: Synthetic Primer
```

```
<400> SEQUENCE: 178
cgactgaagc atggattgcc                                              20

<210> SEQ ID NO 179
<211> LENGTH: 24
<212> TYPE: DNA
<213> ORGANISM: Artificial sequence
<220> FEATURE:
<223> OTHER INFORMATION: Synthetic Primer

<400> SEQUENCE: 179
acatattcct gaggaggagt tccc                                         24

<210> SEQ ID NO 180
<211> LENGTH: 22
<212> TYPE: DNA
<213> ORGANISM: Artificial sequence
<220> FEATURE:
<223> OTHER INFORMATION: Synthetic Primer

<400> SEQUENCE: 180
aacacacctc cgacgacacc ac                                           22

<210> SEQ ID NO 181
<211> LENGTH: 22
<212> TYPE: DNA
<213> ORGANISM: Artificial sequence
<220> FEATURE:
<223> OTHER INFORMATION: Synthetic Primer

<400> SEQUENCE: 181
ctcggcttct ccacatacaa gg                                           22

<210> SEQ ID NO 182
<211> LENGTH: 23
<212> TYPE: DNA
<213> ORGANISM: Artificial sequence
<220> FEATURE:
<223> OTHER INFORMATION: Synthetic Primer

<400> SEQUENCE: 182
ggatctaggc atttgggttt cac                                          23

<210> SEQ ID NO 183
<211> LENGTH: 21
<212> TYPE: DNA
<213> ORGANISM: Artificial sequence
<220> FEATURE:
<223> OTHER INFORMATION: Synthetic Primer

<400> SEQUENCE: 183
atcgaagaag ctgaagcgga g                                            21

<210> SEQ ID NO 184
<211> LENGTH: 22
<212> TYPE: DNA
<213> ORGANISM: Artificial sequence
<220> FEATURE:
<223> OTHER INFORMATION: Synthetic Primer

<400> SEQUENCE: 184
gtgcttgtct ctgacgaaac cc                                           22

<210> SEQ ID NO 185
<211> LENGTH: 22
```

```
<212> TYPE: DNA
<213> ORGANISM: Artificial sequence
<220> FEATURE:
<223> OTHER INFORMATION: Synthetic Primer

<400> SEQUENCE: 185
tatcattgta tcccgtcgtc cc                                              22

<210> SEQ ID NO 186
<211> LENGTH: 21
<212> TYPE: DNA
<213> ORGANISM: Artificial sequence
<220> FEATURE:
<223> OTHER INFORMATION: Synthetic Primer

<400> SEQUENCE: 186
tgatgcctgg atttgcacaa c                                               21

<210> SEQ ID NO 187
<211> LENGTH: 22
<212> TYPE: DNA
<213> ORGANISM: Artificial sequence
<220> FEATURE:
<223> OTHER INFORMATION: Synthetic Primer

<400> SEQUENCE: 187
cggatcgctc tgagtctctt tg                                              22

<210> SEQ ID NO 188
<211> LENGTH: 23
<212> TYPE: DNA
<213> ORGANISM: Artificial sequence
<220> FEATURE:
<223> OTHER INFORMATION: Synthetic Primer

<400> SEQUENCE: 188
atcctgtgtc ttctcttcga ccc                                             23

<210> SEQ ID NO 189
<211> LENGTH: 20
<212> TYPE: DNA
<213> ORGANISM: Artificial sequence
<220> FEATURE:
<223> OTHER INFORMATION: Synthetic Primer

<400> SEQUENCE: 189
gatcgctctg agtctctttg                                                 20

<210> SEQ ID NO 190
<211> LENGTH: 24
<212> TYPE: DNA
<213> ORGANISM: Artificial sequence
<220> FEATURE:
<223> OTHER INFORMATION: Synthetic Primer

<400> SEQUENCE: 190
acgtgaggga gaagaagaga gtgc                                            24

<210> SEQ ID NO 191
<211> LENGTH: 22
<212> TYPE: DNA
<213> ORGANISM: Artificial sequence
<220> FEATURE:
<223> OTHER INFORMATION: Synthetic Primer

<400> SEQUENCE: 191
```

```
ttcatcgtcg cctctgatgt cc                                              22

<210> SEQ ID NO 192
<211> LENGTH: 23
<212> TYPE: DNA
<213> ORGANISM: Artificial sequence
<220> FEATURE:
<223> OTHER INFORMATION: Synthetic Primer

<400> SEQUENCE: 192
tgtagacagc gtttagggag tgc                                             23

<210> SEQ ID NO 193
<211> LENGTH: 22
<212> TYPE: DNA
<213> ORGANISM: Artificial sequence
<220> FEATURE:
<223> OTHER INFORMATION: Synthetic Primer

<400> SEQUENCE: 193
gtccttggaa gtgcagaagc ag                                              22

<210> SEQ ID NO 194
<211> LENGTH: 21
<212> TYPE: DNA
<213> ORGANISM: Artificial sequence
<220> FEATURE:
<223> OTHER INFORMATION: Synthetic Primer

<400> SEQUENCE: 194
aagcgaggaa aaggaggtgt c                                               21

<210> SEQ ID NO 195
<211> LENGTH: 23
<212> TYPE: DNA
<213> ORGANISM: Artificial sequence
<220> FEATURE:
<223> OTHER INFORMATION: Synthetic Primer

<400> SEQUENCE: 195
cgggaaggtt ggtgatgtct gtg                                             23

<210> SEQ ID NO 196
<211> LENGTH: 18
<212> TYPE: DNA
<213> ORGANISM: Artificial sequence
<220> FEATURE:
<223> OTHER INFORMATION: Synthetic Primer

<400> SEQUENCE: 196
cccgaagact ttgacctg                                                   18

<210> SEQ ID NO 197
<211> LENGTH: 18
<212> TYPE: DNA
<213> ORGANISM: Artificial sequence
<220> FEATURE:
<223> OTHER INFORMATION: Synthetic Primer

<400> SEQUENCE: 197
agtggcatag gaggctgg                                                   18

<210> SEQ ID NO 198
<211> LENGTH: 23
<212> TYPE: DNA
<213> ORGANISM: Artificial sequence
```

```
<220> FEATURE:
<223> OTHER INFORMATION: Synthetic Primer

<400> SEQUENCE: 198
gcaccttcaa tgccacaggt atc                                              23

<210> SEQ ID NO 199
<211> LENGTH: 22
<212> TYPE: DNA
<213> ORGANISM: Artificial sequence
<220> FEATURE:
<223> OTHER INFORMATION: Synthetic Primer

<400> SEQUENCE: 199
tcgtgtgctt ctcgcttctc tg                                               22

<210> SEQ ID NO 200
<211> LENGTH: 25
<212> TYPE: DNA
<213> ORGANISM: Artificial sequence
<220> FEATURE:
<223> OTHER INFORMATION: Synthetic Primer

<400> SEQUENCE: 200
cactgtcgat cagaagaagg cttac                                            25

<210> SEQ ID NO 201
<211> LENGTH: 20
<212> TYPE: DNA
<213> ORGANISM: Artificial sequence
<220> FEATURE:
<223> OTHER INFORMATION: Synthetic Primer

<400> SEQUENCE: 201
gctccgtggg cacattttg                                                   20

<210> SEQ ID NO 202
<211> LENGTH: 25
<212> TYPE: DNA
<213> ORGANISM: Artificial sequence
<220> FEATURE:
<223> OTHER INFORMATION: Synthetic Primer

<400> SEQUENCE: 202
cagtttacga ggtacaaggc aacag                                            25

<210> SEQ ID NO 203
<211> LENGTH: 22
<212> TYPE: DNA
<213> ORGANISM: Artificial sequence
<220> FEATURE:
<223> OTHER INFORMATION: Synthetic Primer

<400> SEQUENCE: 203
gattgcgtgg gcagtgtaga ag                                               22

<210> SEQ ID NO 204
<211> LENGTH: 23
<212> TYPE: DNA
<213> ORGANISM: Artificial sequence
<220> FEATURE:
<223> OTHER INFORMATION: Synthetic Primer

<400> SEQUENCE: 204
tgtttgtttc cccagtcaac gac                                              23
```

<210> SEQ ID NO 205
<211> LENGTH: 24
<212> TYPE: DNA
<213> ORGANISM: Artificial sequence
<220> FEATURE:
<223> OTHER INFORMATION: Synthetic Primer

<400> SEQUENCE: 205
cggaagaggt tgttggactc cttc                                              24

<210> SEQ ID NO 206
<211> LENGTH: 25
<212> TYPE: DNA
<213> ORGANISM: Artificial sequence
<220> FEATURE:
<223> OTHER INFORMATION: Synthetic Primer

<400> SEQUENCE: 206
caaccgagag agaagagagg aacag                                             25

<210> SEQ ID NO 207
<211> LENGTH: 22
<212> TYPE: DNA
<213> ORGANISM: Artificial sequence
<220> FEATURE:
<223> OTHER INFORMATION: Synthetic Primer

<400> SEQUENCE: 207
tggggagaac agcagacatc ag                                                22

<210> SEQ ID NO 208
<211> LENGTH: 22
<212> TYPE: DNA
<213> ORGANISM: Artificial sequence
<220> FEATURE:
<223> OTHER INFORMATION: Synthetic Primer

<400> SEQUENCE: 208
ggatgaacac tggtgcatca tg                                                22

<210> SEQ ID NO 209
<211> LENGTH: 15
<212> TYPE: DNA
<213> ORGANISM: Artificial sequence
<220> FEATURE:
<223> OTHER INFORMATION: Synthetic Primer

<400> SEQUENCE: 209
cgacttggtc cgctc                                                        15

<210> SEQ ID NO 210
<211> LENGTH: 18
<212> TYPE: DNA
<213> ORGANISM: Artificial sequence
<220> FEATURE:
<223> OTHER INFORMATION: Synthetic Primer

<400> SEQUENCE: 210
cggcggcaac aaatgggc                                                     18

<210> SEQ ID NO 211
<211> LENGTH: 22
<212> TYPE: DNA
<213> ORGANISM: Artificial sequence
<220> FEATURE:
<223> OTHER INFORMATION: Synthetic Primer

```
<400> SEQUENCE: 211
gtccgagata tgaggatgcg ac                                          22

<210> SEQ ID NO 212
<211> LENGTH: 21
<212> TYPE: DNA
<213> ORGANISM: Artificial sequence
<220> FEATURE:
<223> OTHER INFORMATION: Synthetic Primer

<400> SEQUENCE: 212
tcagagcacc attgttgcga c                                           21

<210> SEQ ID NO 213
<211> LENGTH: 22
<212> TYPE: DNA
<213> ORGANISM: Artificial sequence
<220> FEATURE:
<223> OTHER INFORMATION: Synthetic Primer

<400> SEQUENCE: 213
tttgacgctc aagtggaggc tg                                          22

<210> SEQ ID NO 214
<211> LENGTH: 19
<212> TYPE: DNA
<213> ORGANISM: Artificial sequence
<220> FEATURE:
<223> OTHER INFORMATION: Synthetic Primer

<400> SEQUENCE: 214
gcctgcaacg ctcgatggc                                              19

<210> SEQ ID NO 215
<211> LENGTH: 23
<212> TYPE: DNA
<213> ORGANISM: Artificial sequence
<220> FEATURE:
<223> OTHER INFORMATION: Synthetic Primer

<400> SEQUENCE: 215
cttcttgact accttcacgt ctg                                         23

<210> SEQ ID NO 216
<211> LENGTH: 18
<212> TYPE: DNA
<213> ORGANISM: Artificial sequence
<220> FEATURE:
<223> OTHER INFORMATION: Synthetic Primer

<400> SEQUENCE: 216
aaggacaagc ctggtttg                                               18

<210> SEQ ID NO 217
<211> LENGTH: 18
<212> TYPE: DNA
<213> ORGANISM: Artificial sequence
<220> FEATURE:
<223> OTHER INFORMATION: Synthetic Primer

<400> SEQUENCE: 217
tttgcccttc gcacaatc                                               18

<210> SEQ ID NO 218
```

```
<211> LENGTH: 22
<212> TYPE: DNA
<213> ORGANISM: Artificial sequence
<220> FEATURE:
<223> OTHER INFORMATION: Synthetic Primer

<400> SEQUENCE: 218
ccagttttgc cagaggaaga cc                                              22

<210> SEQ ID NO 219
<211> LENGTH: 22
<212> TYPE: DNA
<213> ORGANISM: Artificial sequence
<220> FEATURE:
<223> OTHER INFORMATION: Synthetic Primer

<400> SEQUENCE: 219
atccgtcaat gcaggtttca tc                                              22

<210> SEQ ID NO 220
<211> LENGTH: 23
<212> TYPE: DNA
<213> ORGANISM: Artificial sequence
<220> FEATURE:
<223> OTHER INFORMATION: Synthetic Primer

<400> SEQUENCE: 220
agacaccaga gacagcagca gtc                                             23

<210> SEQ ID NO 221
<211> LENGTH: 23
<212> TYPE: DNA
<213> ORGANISM: Artificial sequence
<220> FEATURE:
<223> OTHER INFORMATION: Synthetic Primer

<400> SEQUENCE: 221
acttcgcccg acaatcgctt tcc                                             23

<210> SEQ ID NO 222
<211> LENGTH: 18
<212> TYPE: DNA
<213> ORGANISM: Artificial sequence
<220> FEATURE:
<223> OTHER INFORMATION: Synthetic Primer

<400> SEQUENCE: 222
cgatcctccc gagggacc                                                   18

<210> SEQ ID NO 223
<211> LENGTH: 22
<212> TYPE: DNA
<213> ORGANISM: Artificial sequence
<220> FEATURE:
<223> OTHER INFORMATION: Synthetic Primer

<400> SEQUENCE: 223
gcctttacgc attcaagtcg tg                                              22

<210> SEQ ID NO 224
<211> LENGTH: 20
<212> TYPE: DNA
<213> ORGANISM: Artificial sequence
<220> FEATURE:
<223> OTHER INFORMATION: Synthetic Primer

<400> SEQUENCE: 224
```

```
ttcagcgggt ctttcctcac                                              20
```

<210> SEQ ID NO 225
<211> LENGTH: 22
<212> TYPE: DNA
<213> ORGANISM: Artificial sequence
<220> FEATURE:
<223> OTHER INFORMATION: Synthetic Primer

<400> SEQUENCE: 225

```
caacgagaaa gatggagctt cg                                           22
```

<210> SEQ ID NO 226
<211> LENGTH: 21
<212> TYPE: DNA
<213> ORGANISM: Artificial sequence
<220> FEATURE:
<223> OTHER INFORMATION: Synthetic Primer

<400> SEQUENCE: 226

```
aacttcttgc acttggtccc g                                            21
```

<210> SEQ ID NO 227
<211> LENGTH: 23
<212> TYPE: DNA
<213> ORGANISM: Artificial sequence
<220> FEATURE:
<223> OTHER INFORMATION: Synthetic Primer

<400> SEQUENCE: 227

```
aagcgaggaa aaggaggtgt ctc                                          23
```

<210> SEQ ID NO 228
<211> LENGTH: 21
<212> TYPE: DNA
<213> ORGANISM: Artificial sequence
<220> FEATURE:
<223> OTHER INFORMATION: Synthetic Primer

<400> SEQUENCE: 228

```
ggaaggttgg tgatgtctgt g                                            21
```

<210> SEQ ID NO 229
<211> LENGTH: 23
<212> TYPE: DNA
<213> ORGANISM: Artificial sequence
<220> FEATURE:
<223> OTHER INFORMATION: Synthetic Primer

<400> SEQUENCE: 229

```
tcccccagga attgttgaaa cag                                          23
```

<210> SEQ ID NO 230
<211> LENGTH: 25
<212> TYPE: DNA
<213> ORGANISM: Artificial sequence
<220> FEATURE:
<223> OTHER INFORMATION: Synthetic Primer

<400> SEQUENCE: 230

```
actaccgaca acgtctcagt ccttc                                        25
```

<210> SEQ ID NO 231
<211> LENGTH: 22
<212> TYPE: DNA

```
<213> ORGANISM: Artificial sequence
<220> FEATURE:
<223> OTHER INFORMATION: Synthetic Primer

<400> SEQUENCE: 231
cgtgcgtctg tgaggaaaag tg                                          22

<210> SEQ ID NO 232
<211> LENGTH: 22
<212> TYPE: DNA
<213> ORGANISM: Artificial sequence
<220> FEATURE:
<223> OTHER INFORMATION: Synthetic Primer

<400> SEQUENCE: 232
ttgttgctcg tgttgcaggt gc                                          22

<210> SEQ ID NO 233
<211> LENGTH: 20
<212> TYPE: DNA
<213> ORGANISM: Artificial sequence
<220> FEATURE:
<223> OTHER INFORMATION: Synthetic Primer

<400> SEQUENCE: 233
ttgttctcga acccgcagag                                             20

<210> SEQ ID NO 234
<211> LENGTH: 20
<212> TYPE: DNA
<213> ORGANISM: Artificial sequence
<220> FEATURE:
<223> OTHER INFORMATION: Synthetic Primer

<400> SEQUENCE: 234
tggcaagaga ccgaatcgtg                                             20

<210> SEQ ID NO 235
<211> LENGTH: 20
<212> TYPE: DNA
<213> ORGANISM: Artificial sequence
<220> FEATURE:
<223> OTHER INFORMATION: Synthetic Primer

<400> SEQUENCE: 235
aaacttggca aagggaacg                                              20

<210> SEQ ID NO 236
<211> LENGTH: 21
<212> TYPE: DNA
<213> ORGANISM: Artificial sequence
<220> FEATURE:
<223> OTHER INFORMATION: Synthetic Primer

<400> SEQUENCE: 236
tgctgtggag aatgatggct g                                           21

<210> SEQ ID NO 237
<211> LENGTH: 17
<212> TYPE: DNA
<213> ORGANISM: Artificial sequence
<220> FEATURE:
<223> OTHER INFORMATION: Synthetic Primer

<400> SEQUENCE: 237
tttccgacga agctgcc                                                17
```

```
<210> SEQ ID NO 238
<211> LENGTH: 19
<212> TYPE: DNA
<213> ORGANISM: Artificial sequence
<220> FEATURE:
<223> OTHER INFORMATION: Synthetic Primer

<400> SEQUENCE: 238
gactccaacg aaagcctcg                                                19

<210> SEQ ID NO 239
<211> LENGTH: 20
<212> TYPE: DNA
<213> ORGANISM: Artificial sequence
<220> FEATURE:
<223> OTHER INFORMATION: Synthetic Primer

<400> SEQUENCE: 239
ggaaagggat aaagacgccg                                               20

<210> SEQ ID NO 240
<211> LENGTH: 24
<212> TYPE: DNA
<213> ORGANISM: Artificial sequence
<220> FEATURE:
<223> OTHER INFORMATION: Synthetic Primer

<400> SEQUENCE: 240
aagcagagga gagacgagac gaag                                          24

<210> SEQ ID NO 241
<211> LENGTH: 24
<212> TYPE: DNA
<213> ORGANISM: Artificial sequence
<220> FEATURE:
<223> OTHER INFORMATION: Synthetic Primer

<400> SEQUENCE: 241
ctgcaccatt tctcacttct tgtg                                          24

<210> SEQ ID NO 242
<211> LENGTH: 24
<212> TYPE: DNA
<213> ORGANISM: Artificial sequence
<220> FEATURE:
<223> OTHER INFORMATION: Synthetic Primer

<400> SEQUENCE: 242
gcaaaagcgg actcgattct attg                                          24

<210> SEQ ID NO 243
<211> LENGTH: 20
<212> TYPE: DNA
<213> ORGANISM: Artificial sequence
<220> FEATURE:
<223> OTHER INFORMATION: Synthetic Primer

<400> SEQUENCE: 243
tgtggcagag caaaaggctc                                               20

<210> SEQ ID NO 244
<211> LENGTH: 22
<212> TYPE: DNA
<213> ORGANISM: Artificial sequence
<220> FEATURE:
```

```
<223> OTHER INFORMATION: Synthetic Primer

<400> SEQUENCE: 244
ctgtggatgc tcctttgcga ct                                              22

<210> SEQ ID NO 245
<211> LENGTH: 20
<212> TYPE: DNA
<213> ORGANISM: Artificial sequence
<220> FEATURE:
<223> OTHER INFORMATION: Synthetic Primer

<400> SEQUENCE: 245
cgaggcaccc gaagaatttg                                                 20

<210> SEQ ID NO 246
<211> LENGTH: 22
<212> TYPE: DNA
<213> ORGANISM: Artificial sequence
<220> FEATURE:
<223> OTHER INFORMATION: Synthetic Primer

<400> SEQUENCE: 246
cttctcaggt tcacttcctg cg                                              22

<210> SEQ ID NO 247
<211> LENGTH: 21
<212> TYPE: DNA
<213> ORGANISM: Artificial sequence
<220> FEATURE:
<223> OTHER INFORMATION: Synthetic Primer

<400> SEQUENCE: 247
tcacgcaacg aacaagtcct c                                               21

<210> SEQ ID NO 248
<211> LENGTH: 20
<212> TYPE: DNA
<213> ORGANISM: Artificial sequence
<220> FEATURE:
<223> OTHER INFORMATION: Synthetic Primer

<400> SEQUENCE: 248 cccattttg cttggcttgc                                                  20

<210> SEQ ID NO 249
<211> LENGTH: 20
<212> TYPE: DNA
<213> ORGANISM: Artificial sequence
<220> FEATURE:
<223> OTHER INFORMATION: Synthetic Primer

<400> SEQUENCE: 249
agcggcaaac cagttcgttg                                                 20

<210> SEQ ID NO 250
<211> LENGTH: 20
<212> TYPE: DNA
<213> ORGANISM: Artificial sequence
<220> FEATURE:
<223> OTHER INFORMATION: Synthetic Primer

<400> SEQUENCE: 250
caccaccttt ttcgttgcgg                                                 20
```

<210> SEQ ID NO 251
<211> LENGTH: 16
<212> TYPE: DNA
<213> ORGANISM: Artificial sequence
<220> FEATURE:
<223> OTHER INFORMATION: Synthetic Primer

<400> SEQUENCE: 251
cggcgactca gatggg                                                         16

<210> SEQ ID NO 252
<211> LENGTH: 23
<212> TYPE: DNA
<213> ORGANISM: Artificial sequence
<220> FEATURE:
<223> OTHER INFORMATION: Synthetic Primer

<400> SEQUENCE: 252
ggggctgtgt cttctctatt tcg                                                 23

<210> SEQ ID NO 253
<211> LENGTH: 20
<212> TYPE: DNA
<213> ORGANISM: Artificial sequence
<220> FEATURE:
<223> OTHER INFORMATION: Synthetic Primer

<400> SEQUENCE: 253
aagcaaacag gctcggaagc                                                     20

<210> SEQ ID NO 254
<211> LENGTH: 20
<212> TYPE: DNA
<213> ORGANISM: Artificial sequence
<220> FEATURE:
<223> OTHER INFORMATION: Synthetic Primer

<400> SEQUENCE: 254
tcatgttgga ggcgtcgttc                                                     20

<210> SEQ ID NO 255
<211> LENGTH: 21
<212> TYPE: DNA
<213> ORGANISM: Artificial sequence
<220> FEATURE:
<223> OTHER INFORMATION: Synthetic Primer

<400> SEQUENCE: 255
tgtgcagtgg aggacaaatg g                                                   21

<210> SEQ ID NO 256
<211> LENGTH: 21
<212> TYPE: DNA
<213> ORGANISM: Artificial sequence
<220> FEATURE:
<223> OTHER INFORMATION: Synthetic Primer

<400> SEQUENCE: 256
gaatcagggt gttttagggc g                                                   21

<210> SEQ ID NO 257
<211> LENGTH: 19
<212> TYPE: DNA
<213> ORGANISM: Artificial sequence
<220> FEATURE:
<223> OTHER INFORMATION: Synthetic Primer

```
<400> SEQUENCE: 257
attctgtgca agcccagag                                              19

<210> SEQ ID NO 258
<211> LENGTH: 20
<212> TYPE: DNA
<213> ORGANISM: Artificial sequence
<220> FEATURE:
<223> OTHER INFORMATION: Synthetic Primer

<400> SEQUENCE: 258
cgaccaaggg tgttgaccat                                             20

<210> SEQ ID NO 259
<211> LENGTH: 22
<212> TYPE: DNA
<213> ORGANISM: Artificial sequence
<220> FEATURE:
<223> OTHER INFORMATION: Synthetic Primer

<400> SEQUENCE: 259
ctaggcaaag aaacacccat gc                                          22

<210> SEQ ID NO 260
<211> LENGTH: 18
<212> TYPE: DNA
<213> ORGANISM: Artificial sequence
<220> FEATURE:
<223> OTHER INFORMATION: Synthetic Primer

<400> SEQUENCE: 260
cgctggaact cctgacac                                               18

<210> SEQ ID NO 261
<211> LENGTH: 21
<212> TYPE: DNA
<213> ORGANISM: Artificial sequence
<220> FEATURE:
<223> OTHER INFORMATION: Synthetic Primer

<400> SEQUENCE: 261
acgaagggag agatgcgttt g                                           21

<210> SEQ ID NO 262
<211> LENGTH: 20
<212> TYPE: DNA
<213> ORGANISM: Artificial sequence
<220> FEATURE:
<223> OTHER INFORMATION: Synthetic Primer

<400> SEQUENCE: 262
tggctgtttg ggttgtctgg                                             20

<210> SEQ ID NO 263
<211> LENGTH: 20
<212> TYPE: DNA
<213> ORGANISM: Artificial sequence
<220> FEATURE:
<223> OTHER INFORMATION: Synthetic Primer

<400> SEQUENCE: 263
tcaccgcaga acttaacccg                                             20

<210> SEQ ID NO 264
<211> LENGTH: 20
```

```
<212> TYPE: DNA
<213> ORGANISM: Artificial sequence
<220> FEATURE:
<223> OTHER INFORMATION: Synthetic Primer

<400> SEQUENCE: 264
ctcgcttttc cagcttgtcg                                                    20

<210> SEQ ID NO 265
<211> LENGTH: 311
<212> TYPE: DNA
<213> ORGANISM: Toxoplasma gondii
<220> FEATURE:
<221> NAME/KEY: CDS
<222> LOCATION: (1)..(288)
<223> OTHER INFORMATION:

<400> SEQUENCE: 265
```

| cgg | gat | cca | gct | gca | cct | aac | agc | aca | cag | gct | gtg | gca | gcc | gct | cgt | 48 |
|---|---|---|---|---|---|---|---|---|---|---|---|---|---|---|---|---|
| Arg | Asp | Pro | Ala | Ala | Pro | Asn | Ser | Thr | Gln | Ala | Val | Ala | Ala | Ala | Arg | |
| 1 | | | | 5 | | | | | 10 | | | | | 15 | | |

| acc | gtg | gta | gtg | atg | aaa | acc | gac | gca | gaa | gtg | tcc | ggt | gac | aac | ctc | 96 |
|---|---|---|---|---|---|---|---|---|---|---|---|---|---|---|---|---|
| Thr | Val | Val | Val | Met | Lys | Thr | Asp | Ala | Glu | Val | Ser | Gly | Asp | Asn | Leu | |
| 20 | | | | | 25 | | | | | 30 | | | | | | |

| agt | cag | ccg | ggt | agg | cgt | ccg | ccg | tcg | cca | aag | ccg | caa | acg | acg | aag | 144 |
|---|---|---|---|---|---|---|---|---|---|---|---|---|---|---|---|---|
| Ser | Gln | Pro | Gly | Arg | Arg | Pro | Pro | Ser | Pro | Lys | Pro | Gln | Thr | Thr | Lys | |
| 35 | | | | 40 | | | | | 45 | | | | | | | |

| ttt | ccg | cgg | aga | gag | tca | cca | gac | cgc | agg | ggg | acg | agg | cgg | aga | act | 192 |
|---|---|---|---|---|---|---|---|---|---|---|---|---|---|---|---|---|
| Phe | Pro | Arg | Arg | Glu | Ser | Pro | Asp | Arg | Arg | Gly | Thr | Arg | Arg | Thr | | |
| 50 | | | | 55 | | | | | 60 | | | | | | | |

| gaa | agc | cga | ggc | gct | gtt | agc | agg | gta | tgg | cca | ggg | gaa | aac | cag | cga | 240 |
|---|---|---|---|---|---|---|---|---|---|---|---|---|---|---|---|---|
| Glu | Ser | Arg | Gly | Ala | Val | Ser | Arg | Val | Trp | Pro | Gly | Glu | Asn | Gln | Arg | |
| 65 | | | | 70 | | | | | 75 | | | | | 80 | | |

| aga | cgg | tct | gcc | gtc | gac | gat | tcg | ata | ccg | gct | aac | ccc | atc | gct | ttg | 288 |
|---|---|---|---|---|---|---|---|---|---|---|---|---|---|---|---|---|
| Arg | Arg | Ser | Ala | Val | Asp | Asp | Ser | Ile | Pro | Ala | Asn | Pro | Ile | Ala | Leu | |
| 85 | | | | 90 | | | | | 95 | | | | | | | |

```
aacgcgtggc gccctgcgat ccg                                                311

<210> SEQ ID NO 266
<211> LENGTH: 96
<212> TYPE: PRT
<213> ORGANISM: Toxoplasma gondii

<400> SEQUENCE: 266

Arg Asp Pro Ala Ala Pro Asn Ser Thr Gln Ala Val Ala Ala Ala Arg
1               5                   10                  15

Thr Val Val Val Met Lys Thr Asp Ala Glu Val Ser Gly Asp Asn Leu
            20                  25                  30

Ser Gln Pro Gly Arg Arg Pro Pro Ser Pro Lys Pro Gln Thr Thr Lys
        35                  40                  45

Phe Pro Arg Arg Glu Ser Pro Asp Arg Arg Gly Thr Arg Arg Thr
    50                  55                  60

Glu Ser Arg Gly Ala Val Ser Arg Val Trp Pro Gly Glu Asn Gln Arg
65                  70                  75                  80

Arg Arg Ser Ala Val Asp Asp Ser Ile Pro Ala Asn Pro Ile Ala Leu
                85                  90                  95

<210> SEQ ID NO 267
<211> LENGTH: 303
<212> TYPE: DNA
<213> ORGANISM: Toxoplasma gondii
<220> FEATURE:
```

```
<221> NAME/KEY: CDS
<222> LOCATION: (1)..(303)
<223> OTHER INFORMATION:

<400> SEQUENCE: 267 gac gaa gct ctt cct ctc ttt gga gca aac gat gga acc tca gtt cgg      48
Asp Glu Ala Leu Pro Leu Phe Gly Ala Asn Asp Gly Thr Ser Val Arg
1               5                   10                  15 ctc tcc ctc gac cgc agc gtc ctg ctt gtt ctc gaa ccc gca gag ccc      96
Leu Ser Leu Asp Arg Ser Val Leu Leu Val Leu Glu Pro Ala Glu Pro
            20                  25                  30 ctg cta tcc tct tgg ccc cac ccg ggg aga aga gac act ttt ctt gaa     144
Leu Leu Ser Ser Trp Pro His Pro Gly Arg Arg Asp Thr Phe Leu Glu
35                  40                  45 ggc gat ggc gcg ggc atc ccg tct cct tca tct cgg ccg agt cgc gcg     192
Gly Asp Gly Ala Gly Ile Pro Ser Pro Ser Ser Arg Pro Ser Arg Ala
50                  55                  60 gcc gac cat tac acg aga ctc tcc acg att cgg tct ctt gcc agg gat     240
Ala Asp His Tyr Thr Arg Leu Ser Thr Ile Arg Ser Leu Ala Arg Asp
65                  70                  75                  80 gga gag gtc gac tcc gag ctg gcg ggg gga ccg cag gaa aga gaa agt     288
Gly Glu Val Asp Ser Glu Leu Ala Gly Gly Pro Gln Glu Arg Glu Ser
            85                  90                  95 gtc aga gtg gat ccg                                                 303
Val Arg Val Asp Pro
100

<210> SEQ ID NO 268
<211> LENGTH: 101
<212> TYPE: PRT
<213> ORGANISM: Toxoplasma gondii

<400> SEQUENCE: 268

Asp Glu Ala Leu Pro Leu Phe Gly Ala Asn Asp Gly Thr Ser Val Arg
1               5                   10                  15

Leu Ser Leu Asp Arg Ser Val Leu Leu Val Leu Glu Pro Ala Glu Pro
            20                  25                  30

Leu Leu Ser Ser Trp Pro His Pro Gly Arg Arg Asp Thr Phe Leu Glu
35                  40                  45

Gly Asp Gly Ala Gly Ile Pro Ser Pro Ser Ser Arg Pro Ser Arg Ala
50                  55                  60

Ala Asp His Tyr Thr Arg Leu Ser Thr Ile Arg Ser Leu Ala Arg Asp
65                  70                  75                  80

Gly Glu Val Asp Ser Glu Leu Ala Gly Gly Pro Gln Glu Arg Glu Ser
            85                  90                  95

Val Arg Val Asp Pro
100

<210> SEQ ID NO 269
<211> LENGTH: 236
<212> TYPE: DNA
<213> ORGANISM: Toxoplasma gondii
<220> FEATURE:
<221> NAME/KEY: CDS
<222> LOCATION: (1)..(234)
<223> OTHER INFORMATION:

<400> SEQUENCE: 269 cgc gga gag ggg gag act gag aga ggg cag aat gag gag act cac gca      48
Arg Gly Glu Gly Glu Thr Glu Arg Gly Gln Asn Glu Glu Thr His Ala
1               5                   10                  15
```

| | | |
|---|---|---|
| acg aac aag tcc tca ggc gtc gcc agt ttg gag gca cca gcg tcg ttc<br>Thr Asn Lys Ser Ser Gly Val Ala Ser Leu Glu Ala Pro Ala Ser Phe<br>20                        25                      30 | | 96 |
| gcg cag gag ggc gac gga ggg cgg aga gaa gaa gca agc caa gca aaa<br>Ala Gln Glu Gly Asp Gly Gly Arg Arg Glu Glu Ala Ser Gln Ala Lys<br>35                        40                      45 | | 144 |
| atg ggg acg tct tcc ccg tcg aat cag gtg atc aac gtt gta gac gaa<br>Met Gly Thr Ser Ser Pro Ser Asn Gln Val Ile Asn Val Val Asp Glu<br>50                        55                      60 | | 192 |
| gac gag gag gac gac gag gaa gca gag gcg caa gag gca ccc gg<br>Asp Glu Glu Asp Asp Glu Glu Ala Glu Ala Gln Glu Ala Pro<br>65                        70                      75 | | 236 |

<210> SEQ ID NO 270
<211> LENGTH: 78
<212> TYPE: PRT
<213> ORGANISM: Toxoplasma gondii

<400> SEQUENCE: 270

Arg Gly Glu Gly Glu Thr Glu Arg Gly Gln Asn Glu Gly Thr His Ala
1               5                   10                  15

Thr Asn Lys Ser Ser Gly Val Ala Ser Leu Glu Ala Pro Ala Ser Phe
            20                  25                  30

Ala Gln Glu Gly Asp Gly Gly Arg Arg Glu Glu Ala Ser Gln Ala Lys
        35                  40                  45

Met Gly Thr Ser Ser Pro Ser Asn Gln Val Ile Asn Val Val Asp Glu
    50                  55                  60

Asp Glu Glu Asp Asp Glu Glu Ala Glu Ala Gln Glu Ala Pro
65                  70                  75

<210> SEQ ID NO 271
<211> LENGTH: 423
<212> TYPE: DNA
<213> ORGANISM: Toxoplasma gondii
<220> FEATURE:
<221> NAME/KEY: CDS
<222> LOCATION: (1)..(423)
<223> OTHER INFORMATION:

<400> SEQUENCE: 271

| | | |
|---|---|---|
| cgc gga att ccg gat cag cgt agc agt cgc agc cac act gga gtg gaa<br>Arg Gly Ile Pro Asp Gln Arg Ser Ser Arg Ser His Thr Gly Val Glu<br>1                5                      10                      15 | | 48 |
| agt ctg gtt ttg ccc tcc aga ggg gag gaa gag gcg aga gag gag acg<br>Ser Leu Val Leu Pro Ser Arg Gly Glu Glu Glu Ala Arg Glu Glu Thr<br>20                        25                      30 | | 96 |
| tct gca acg cgc cag atg ccg acg ctt ctc tct tcg ccg agg cct cca<br>Ser Ala Thr Arg Gln Met Pro Thr Leu Leu Ser Ser Pro Arg Pro Pro<br>35                        40                      45 | | 144 |
| ctc gcg ctg ggg ttg gga gac gag tct ccc tgc gga gag tgg gtg tcg<br>Leu Ala Leu Gly Leu Gly Asp Glu Ser Pro Cys Gly Glu Trp Val Ser<br>50                        55                      60 | | 192 |
| ccg aat gac atg gtt tct gcg ttg tcc ctc tgg gaa gca ggc gag gct<br>Pro Asn Asp Met Val Ser Ala Leu Ser Leu Trp Glu Ala Gly Glu Ala<br>65                        70                      75                      80 | | 240 |
| tgg cag ttc aag aca gcg aaa att ctt gac tct ttc gaa ggg gag acc<br>Trp Gln Phe Lys Thr Ala Lys Ile Leu Asp Ser Phe Glu Gly Glu Thr<br>85                        90                      95 | | 288 |
| cca gaa ggg gag gga tgc ggc gca cag gaa aag gac agc cgc atg caa<br>Pro Glu Gly Glu Gly Cys Gly Ala Gln Glu Lys Asp Ser Arg Met Gln<br>100                      105                    110 | | 336 |

```
gct ggt gcg act ccc ggt gaa cgt gga ggg gcg gtc gac gaa ggt gtg      384
Ala Gly Ala Thr Pro Gly Glu Arg Gly Gly Ala Val Asp Glu Gly Val
115                 120                 125 gag ctt ggc tct tct ttc ttc tct gcg tct gaa gat ccg                  423
Glu Leu Gly Ser Ser Phe Phe Ser Ala Ser Glu Asp Pro
130                 135                 140

<210> SEQ ID NO 272
<211> LENGTH: 141
<212> TYPE: PRT
<213> ORGANISM: Toxoplasma gondii

<400> SEQUENCE: 272

Arg Gly Ile Pro Asp Gln Arg Ser Ser Arg Ser His Thr Gly Val Glu
1               5                   10                  15

Ser Leu Val Leu Pro Ser Arg Gly Glu Glu Ala Arg Glu Glu Thr
        20                  25                  30

Ser Ala Thr Arg Gln Met Pro Thr Leu Leu Ser Ser Pro Arg Pro Pro
    35                  40                  45

Leu Ala Leu Gly Leu Gly Asp Glu Ser Pro Cys Gly Glu Trp Val Ser
    50                  55                  60

Pro Asn Asp Met Val Ser Ala Leu Ser Leu Trp Glu Ala Gly Glu Ala
65                  70                  75                  80

Trp Gln Phe Lys Thr Ala Lys Ile Leu Asp Ser Phe Glu Gly Glu Thr
            85                  90                  95

Pro Glu Gly Glu Gly Cys Gly Ala Gln Glu Lys Asp Ser Arg Met Gln
        100                 105                 110

Ala Gly Ala Thr Pro Gly Glu Arg Gly Gly Ala Val Asp Glu Gly Val
    115                 120                 125

Glu Leu Gly Ser Ser Phe Phe Ser Ala Ser Glu Asp Pro
    130                 135                 140

<210> SEQ ID NO 273
<211> LENGTH: 514
<212> TYPE: DNA
<213> ORGANISM: Toxoplasma gondii
<220> FEATURE:
<221> NAME/KEY: CDS
<222> LOCATION: (1)..(513)
<223> OTHER INFORMATION:

<400> SEQUENCE: 273 cgg gat cag gct tct atg cca ctg ccc ccg gcc ccc gaa gac ttt gac      48
Arg Asp Gln Ala Ser Met Pro Leu Pro Pro Ala Pro Glu Asp Phe Asp
1               5                   10                  15 ctg cct cct atg cca ctg ccc gaa gca ccc gaa gac ttt gac cag gct      96
Leu Pro Pro Met Pro Leu Pro Glu Ala Pro Glu Asp Phe Asp Gln Ala
            20                  25                  30 cct atg cca ctg ccc gag gca ccc gaa gac ttt gac cag gct cct atg     144
Pro Met Pro Leu Pro Glu Ala Pro Glu Asp Phe Asp Gln Ala Pro Met
    35                  40                  45 cca ctg ccc gag gca ccc gaa gac ttt gac cag cct cct atg cca ctg     192
Pro Leu Pro Glu Ala Pro Glu Asp Phe Asp Gln Pro Pro Met Pro Leu
    50                  55                  60 ccc gag gca ccc gaa gac ttt gac cag gct cct atg cca ctg ccc gaa     240
Pro Glu Ala Pro Glu Asp Phe Asp Gln Ala Pro Met Pro Leu Pro Glu
65                  70                  75                  80 gca ccc gaa gtc ttt gac cag gct cct atg cca ctg ccc gag gca ccc     288
Ala Pro Glu Val Phe Asp Gln Ala Pro Met Pro Leu Pro Glu Ala Pro
            85                  90                  95
```

```
gaa gtc ttt gac cag gct cct atg cca ctg ccc gaa gca ccc gaa gac       336
Glu Val Phe Asp Gln Ala Pro Met Pro Leu Pro Glu Ala Pro Glu Asp
100                 105                 110 ttt gac cag gct cct atg cca ctg ccc gaa gca ccc gaa gtc ttt gac       384
Phe Asp Gln Ala Pro Met Pro Leu Pro Glu Ala Pro Glu Val Phe Asp
115                 120                 125 cag gct cct atg cca ctg ccc gag gca ccc gaa gac ttt gac cag gct       432
Gln Ala Pro Met Pro Leu Pro Glu Ala Pro Glu Asp Phe Asp Gln Ala
130                 135                 140 cct atg cca gtg ccc gag gca ccc gaa gac ttt gac cag gct cct gag       480
Pro Met Pro Val Pro Glu Ala Pro Glu Asp Phe Asp Gln Ala Pro Glu
145                 150                 155                 160 cca ctg ccc gag gca gcc gaa gaa ttt gat ccc g                         514
Pro Leu Pro Glu Ala Ala Glu Glu Phe Asp Pro
165                 170

<210> SEQ ID NO 274
<211> LENGTH: 171
<212> TYPE: PRT
<213> ORGANISM: Toxoplasma gondii

<400> SEQUENCE: 274

Arg Asp Gln Ala Ser Met Pro Leu Pro Pro Ala Pro Glu Asp Phe Asp
1               5                   10                  15

Leu Pro Pro Met Pro Leu Pro Glu Ala Pro Glu Asp Phe Asp Gln Ala
            20                  25                  30

Pro Met Pro Leu Pro Glu Ala Pro Glu Asp Phe Asp Gln Ala Pro Met
        35                  40                  45

Pro Leu Pro Glu Ala Pro Glu Asp Phe Asp Gln Pro Pro Met Pro Leu
    50                  55                  60

Pro Glu Ala Pro Glu Asp Phe Asp Gln Ala Pro Met Pro Leu Pro Glu
65                  70                  75                  80

Ala Pro Glu Val Phe Asp Gln Ala Pro Met Pro Leu Pro Glu Ala Pro
                85                  90                  95

Glu Val Phe Asp Gln Ala Pro Met Pro Leu Pro Glu Ala Pro Glu Asp
            100                 105                 110

Phe Asp Gln Ala Pro Met Pro Leu Pro Glu Ala Pro Glu Val Phe Asp
        115                 120                 125

Gln Ala Pro Met Pro Leu Pro Glu Ala Pro Glu Asp Phe Asp Gln Ala
    130                 135                 140

Pro Met Pro Val Pro Glu Ala Pro Glu Asp Phe Asp Gln Ala Pro Glu
145                 150                 155                 160

Pro Leu Pro Glu Ala Ala Glu Glu Phe Asp Pro
165                 170

<210> SEQ ID NO 275
<211> LENGTH: 16
<212> TYPE: DNA
<213> ORGANISM: Artificial sequence
<220> FEATURE:
<223> OTHER INFORMATION: Synthetic Primer

<400> SEQUENCE: 275
tgcttctcaa aagccg                                                      16

<210> SEQ ID NO 276
<211> LENGTH: 21
<212> TYPE: DNA
<213> ORGANISM: Artificial sequence
<220> FEATURE:
```

<210> SEQ ID NO 277
<211> LENGTH: 20
<212> TYPE: DNA
<213> ORGANISM: Artificial sequence
<220> FEATURE:
<223> OTHER INFORMATION: Synthetic Primer

<400> SEQUENCE: 276
cgattgcctg caagaagtgt g                                           21

<210> SEQ ID NO 277
<211> LENGTH: 20
<212> TYPE: DNA
<213> ORGANISM: Artificial sequence
<220> FEATURE:
<223> OTHER INFORMATION: Synthetic Primer

<400> SEQUENCE: 277
acagttttct ccatttcagg                                             20

<210> SEQ ID NO 278
<211> LENGTH: 19
<212> TYPE: DNA
<213> ORGANISM: Artificial sequence
<220> FEATURE:
<223> OTHER INFORMATION: Synthetic Primer

<400> SEQUENCE: 278
atatactttg cgtgggcgg                                              19

<210> SEQ ID NO 279
<211> LENGTH: 17
<212> TYPE: DNA
<213> ORGANISM: Artificial sequence
<220> FEATURE:
<223> OTHER INFORMATION: Synthetic Primer

<400> SEQUENCE: 279
tcctgggttt gatgctg                                                17

<210> SEQ ID NO 280
<211> LENGTH: 20
<212> TYPE: DNA
<213> ORGANISM: Artificial sequence
<220> FEATURE:
<223> OTHER INFORMATION: Synthetic Primer

<400> SEQUENCE: 280
ctgttctgaa aacggtgcgg                                             20

<210> SEQ ID NO 281
<211> LENGTH: 18
<212> TYPE: DNA
<213> ORGANISM: Artificial sequence
<220> FEATURE:
<223> OTHER INFORMATION: Synthetic Primer

<400> SEQUENCE: 281
gaaaacggtg ccctaaag                                               18

<210> SEQ ID NO 282
<211> LENGTH: 1225
<212> TYPE: DNA
<213> ORGANISM: Toxoplasma gondii
<220> FEATURE:
<221> NAME/KEY: CDS
<222> LOCATION: (1)..(87)
<223> OTHER INFORMATION:

<400> SEQUENCE: 282 ggt cga gtg tcg cag aaa aag acg ctt gtc tgt gcc cgg cgt aga caa    48

```
Gly Arg Val Ser Gln Lys Lys Thr Leu Val Cys Ala Arg Arg Arg Gln
1               5                   10                  15 tct ctt cgg cct ctc gga cga acc gag ttt tca cgg tga accttttgtg       97
Ser Leu Arg Pro Leu Gly Arg Thr Glu Phe Ser Arg
20                  25 cttactttc gtctcagact gtgttgttgt tccctgcttc tcaaaagccg cccttccctc    157
acttcttgtt cgccgattgc cttcaagaag tgtggagttc ccttcctttt ttccgggttc    217
tccggaagcc tcctgtagca aaatgcgctg aaattttgga cacttctcga cggtgtctcg    277
ctttaggacg gacctcatgg tctttagggc accgttttct ttcactttt ctaggaacat     337 cacagttttc tccatttcag ggaacgaaca atctgcaagc gtccacttgt cctgtggctg    397
ctgggctcgg atgccgcctc tgtttagcaa ttgtagcagg caccggatgg caagctaggt    457
ccacttcact gcagtttcaa cttccaaacc aaggcatctc aatttgtatc gtgttctctg    517
tcaacaagct gttgaacctg tcgacggagt gtcgtcccgg ctcctatccc gcgttcgcaa    577
gccgcaccgt tttcagaaca gtgttccccg tggtgttgaa agcgggctgc gaagcgcgag    637
cgtttcgttt tgtggttttt ctgggaaaac gatggggatc tcttcgtgtg gcgagacgct    697
tgcctcctgt ttcaaggcgg tgaagtccgg aaccgttgac ttcaagggc aggagcgagt     757 atactcgtgg ttgatatact ttgcgtgggc gggtggcctc agcgggtttt tcgtcggagg    817
gattctggaa gacttcacgg tcacagtgta cacgatcttg atgtgcatgg ccattgcggc    877
gattctctgt tttccgtcgt ggccatgttt ccacagacac cctgtcgagt ggacgccgca    937 cgacccgcc aggctggctg ctctcttcac gcagcatcaa acccaggaag aaactcctca     997
gaaaggtgcg gggaaaaaac gagggaagaa gagcgctgaa gtgcaacgga aaaactgagt   1057
gtgtgtgcgt atgtagacaa gtgagtcttc ccagagttcg tccggattgt tgcgtggatc   1117
gtgtcaactg gacttctcgt tcgtcaaaga cctggtcgtc tgacccatct gctctccata   1177
aaaaagcttg ttaacgctcc taaaaaaaaa aaaaaaaaa aaaaaaaa                  1225
```

<210> SEQ ID NO 283
<211> LENGTH: 28
<212> TYPE: PRT
<213> ORGANISM: Toxoplasma gondii

<400> SEQUENCE: 283

```
Gly Arg Val Ser Gln Lys Lys Thr Leu Val Cys Ala Arg Arg Arg Gln
1               5                   10                  15

Ser Leu Arg Pro Leu Gly Arg Thr Glu Phe Ser Arg
20                  25
```

<210> SEQ ID NO 284
<211> LENGTH: 1225
<212> TYPE: DNA
<213> ORGANISM: Toxoplasma gondii

<400> SEQUENCE: 284

```
tttttttttt tttttttttt tttttttagg agcgttaaca agcttttta tggagagcag     60 atgggtcaga cgaccaggtc tttgacgaac gagaagtcca gttgacacga tccacgcaac   120
aatccggacg aactctggga agactcactt gtctacatac gcacacacac tcagttttc    180 cgttgcactt cagcgctctt cttccctcgt ttttccccg cacctttctg aggagtttct    240
tcctgggttt gatgctgcgt gaagagagca gccagcctgg cggggtcgtg cggcgtccac   300
tcgacagggt gtctgtggaa acatggccac gacggaaaac agagaatcgc cgcaatggcc   360
```

```
atgcacatca agatcgtgta cactgtgacc gtgaagtctt ccagaatccc tccgacgaaa      420
aacccgctga ggccacccgc ccacgcaaag tatatcaacc acgagtatac tcgctcctgc      480
cccttgaagt caacggttcc ggacttcacc gccttgaaac aggaggcaag cgtctcgcca      540
cacgaagaga tccccatcgt tcccagaaaa aaccacaaa acgaaacgct cgcgcttcgc       600
agcccgcttt caacaccacg gggaacactg ttctgaaaac ggtgcggctt gcgaacgcgg      660
gataggagcc gggacgacac tccgtcgaca ggttcaacag cttgttgaca gagaacacga     720
tacaaattga gatgccttgg tttggaagtt gaaactgcag tgaagtggac ctagcttgcc      780
atccggtgcc tgctacaatt gctaaacaga ggcggcatcc gagcccagca gccacaggac      840
aagtggacgc ttgcagattg ttcgttccct gaaatggaga aaactgtgat gttcctagaa      900
aaagtgaaag aaaacggtgc cctaaagacc atgaggtccg tcctaaagcg agacaccgtc      960
gagaagtgtc caaatttca gcgcattttg ctacaggagg cttccggaga acccggaaaa      1020
aaggaaggga actccacact tcttgaaggc aatcggcgaa caagaagtga gggaagggcg      1080
gcttttgaga agcagggaac aacaacacag tctgagacga aaagtaagca caaaaggttc      1140
accgtgaaaa ctcggttcgt ccgagaggcc gaagagattg tctacgccgg gcacagacaa      1200
gcgtcttttt ctgcgacact cgacc                                            1225

<210> SEQ ID NO 285
<211> LENGTH: 20
<212> TYPE: DNA
<213> ORGANISM: Artificial sequence
<220> FEATURE:
<223> OTHER INFORMATION: Synthetic Primer

<400> SEQUENCE: 285
gggcgagaac atcaccattg                                                   20

<210> SEQ ID NO 286
<211> LENGTH: 19
<212> TYPE: DNA
<213> ORGANISM: Artificial sequence
<220> FEATURE:
<223> OTHER INFORMATION: Synthetic Primer

<400> SEQUENCE: 286
acacgaagga cctgtatgg                                                    19

<210> SEQ ID NO 287
<211> LENGTH: 19
<212> TYPE: DNA
<213> ORGANISM: Artificial sequence
<220> FEATURE:
<223> OTHER INFORMATION: Synthetic Primer

<400> SEQUENCE: 287
gtgcttcgat ttgaatgcg                                                    19

<210> SEQ ID NO 288
<211> LENGTH: 17
<212> TYPE: DNA
<213> ORGANISM: Artificial sequence
<220> FEATURE:
<223> OTHER INFORMATION: Synthetic Primer

<400> SEQUENCE: 288
tcaaatcgaa gcacatg                                                      17
```

```
<210> SEQ ID NO 289
<211> LENGTH: 19
<212> TYPE: DNA
<213> ORGANISM: Artificial sequence
<220> FEATURE:
<223> OTHER INFORMATION: Synthetic Primer

<400> SEQUENCE: 289
tttcccagac cttgctgtc                                                    19

<210> SEQ ID NO 290
<211> LENGTH: 20
<212> TYPE: DNA
<213> ORGANISM: Artificial sequence
<220> FEATURE:
<223> OTHER INFORMATION: Synthetic Primer

<400> SEQUENCE: 290
tcattcaggt ccatcgtcgg                                                   20

<210> SEQ ID NO 291
<211> LENGTH: 20
<212> TYPE: DNA
<213> ORGANISM: Artificial sequence
<220> FEATURE:
<223> OTHER INFORMATION: Synthetic Primer

<400> SEQUENCE: 291
cgaggcacaa gtctgcaatg                                                   20

<210> SEQ ID NO 292
<211> LENGTH: 1573
<212> TYPE: DNA
<213> ORGANISM: Toxoplasma gondii
<220> FEATURE:
<221> NAME/KEY: CDS
<222> LOCATION: (1)..(222)
<223> OTHER INFORMATION:

<400> SEQUENCE: 292 gca gcc tct ctc ttc acc ctc cgt aaa aat gaa act cct gac gcc caa         48
Ala Ala Ser Leu Phe Thr Leu Arg Lys Asn Glu Thr Pro Asp Ala Gln
1               5                   10                  15 gga cga tgt gcg cgg ccg gaa ggt gca gtt ggt ggc ggc ttt cct gga         96
Gly Arg Cys Ala Arg Pro Glu Gly Ala Val Gly Gly Gly Phe Pro Gly
            20                  25                  30 cct gcc gct gca gac tgt gcc ttt cac cgt ggg gaa gga cga caa gga        144
Pro Ala Ala Ala Asp Cys Ala Phe His Arg Gly Glu Gly Arg Gln Gly
        35                  40                  45 tcc ggc gtt ctt ggc caa gtc gcc tct ggg gcg tct gcc cct gtt gga        192
Ser Gly Val Leu Gly Gln Val Ala Ser Gly Ala Ser Ala Pro Val Gly
    50                  55                  60 gtc cga ggt cgg cgg cgt gtg tct gtt tga aagcaacgcg atttgccgct          242
Val Arg Gly Arg Arg Val Ser Val
65                  70 tcctcgcgcg acttcgcgcc gacaagtgcc tgtacggcga acgcttgcg gagcagggac       302 aagtggacat gtggttggac ttctcgaccc tcgaagtcga gattccgatg tgttgcttgg      362
tgcagggggg aaaggttgcg gagcgcgcgc agagcgacct ggcgcaggca ctgaacgcgg      422
tcgacgccca cctgaagacg cgcaccttca tggtgggcga gaacatcacc attgcagact     482
tgtgcctcgt cgcggtgctg agctacggct ccggtccgg caaggtggac gccgcagcgc      542
tgctcgagaa gcgtccgtac ttgaagcgct tctacgagac cgtggtgaat cagaagagct    602
```

```
tcaagaagat cttcggcgag gcgaaggcag cgccacaggc cgccgccaag aaggagactc      662
ccaaagccgc ggcgaagcct gcacagagcg ccggcgatga cgaagaaccg gcgaagaagc      722
ctgcagtcaa gtgcgagttg gacttgctcc cagagccgac gatggacctg aatgagtgga      782
agcgcgtgta ctccaacacg aaggacctgt atggcacagc gatgaaatgg ttctgggaac      842
acctcgacgc ggcagggtat tccttgtggt acatgaaata tcagaaactc gagggcgagt      902
gcaccgtcgc gttcgtcacc tcgaaccagc tcggcggctt cctgcagcgg atcgacccgg      962
ccttccgcaa atactccttc ggcgtcgtcg acgtgatggg cgagaacggc tgcttcgaca     1022
tcgagggtgt ctggctgttc cgcggccaag acgtacccag cttgatgaag gaccaccgt      1082 cgtacgagta ccacacttgg cagaaactcg acgtcgccag cgcaaaagac aagcaactcg     1142
tcgcagactt ttggtgcgcg tgcgacgaca tccaaggtcg ccccatcgcc gacagcaagg     1202
tctggaaata aaaggaaata acgcacttcg cgaaacgaag gggcggcaac agaggtgtgt     1262
gtctttggtg ctgtgaaaaa aagcgacgcg taaaaaacgg cgagaaatgt tcgtggcgtg     1322
gcgtgcggtg agagggtac agtggcgaag ggtcacaaac ccatgtgctt cgatttgaat      1382
gcgcttccat ctgtacacct ggctcttccg tgcgtccttt cagtctctcc taaaaatctc     1442
gtttcacgcg ggtgcagttg cggtacttca ggagcttcgc aggcgccgct cgcgcgcgct     1502
ccccgctcta ggaactctca cacgacccca tttatgtcaa ctcgaaaaaa aaaaaaaaa      1562 aaaaaaaaa a                                                            1573

<210> SEQ ID NO 293
<211> LENGTH: 73
<212> TYPE: PRT
<213> ORGANISM: Toxoplasma gondii

<400> SEQUENCE: 293

Ala Ala Ser Leu Phe Thr Leu Arg Lys Asn Glu Thr Pro Asp Ala Gln
1               5                   10                  15

Gly Arg Cys Ala Arg Pro Glu Gly Ala Val Gly Gly Phe Pro Gly
            20                  25                  30

Pro Ala Ala Ala Asp Cys Ala Phe His Arg Gly Glu Gly Arg Gln Gly
    35                  40                  45

Ser Gly Val Leu Gly Gln Val Ala Ser Gly Ala Ser Ala Pro Val Gly
50                  55                  60

Val Arg Gly Arg Arg Val Ser Val
65                  70

<210> SEQ ID NO 294
<211> LENGTH: 1573
<212> TYPE: DNA
<213> ORGANISM: Toxoplasma gondii

<400> SEQUENCE: 294
tttttttttt tttttttttt ttttttcga gttgacataa atggggtcgt gtgagagttc       60
ctagagcggg gagcgcgcgc gagcggcgcc tgcgaagctc ctgaagtacc gcaactgcac      120
ccgcgtgaaa cgagatttt aggagagact gaaaggacgc acggaagagc caggtgtaca      180
gatggaagcg cattcaaatc gaagcacatg ggtttgtgac ccttcgccac tgtacccctc      240
tcaccgcacg ccacgccacg aacatttctc gccgtttttt acgcgtcgct ttttttcaca      300
gcaccaaaga cacacacctc tgttgccgcc ccttcgtttc gcgaagtgcg ttatttcctt      360
ttatttccag accttgctgt cggcgatggg cgaccttgg atgtcgtcgc acgcgcacca      420
```

-continued

```
aaagtctgcg acgagttgct tgtcttttgc gctggcgacg tcgagtttct gccaagtgtg      480
gtactcgtac gacgggtggt ccttcatcaa gctgggtacg tcttggccgc ggaacagcca      540
gacaccctcg atgtcgaagc agccgttctc gcccatcacg tcgacgacgc cgaaggagta      600
tttgcggaag gccgggtcga tccgctgcag gaagccgccg agctggttcg aggtgacgaa      660
cgcgacggtg cactcgccct cgagtttctg atatttcatg taccacaagg aatacccctgc    720
cgcgtcgagg tgttcccaga accatttcat cgctgtgcca tacaggtcct tcgtgttgga     780
gtacacgcgc ttccactcat tcaggtccat cgtcggctct gggagcaagt ccaactcgca     840
cttgactgca ggcttcttcg ccggttcttc gtcatcgccg gcgctctgtg caggcttcgc     900
cgcggctttg ggagtctcct tcttggcggc ggcctgtggc gctgccttcg cctcgccgaa     960
gatcttcttg aagctcttct gattcaccac ggtctcgtag aagcgcttca agtacggacg    1020
cttctcgagc agcgctgcgg cgtccacctt gccggaccgg aagccgtagc tcagcaccgc    1080
gacgaggcac aagtctgcaa tggtgatgtt ctcgcccacc atgaaggtgc gcgtcttcag    1140
gtgggcgtcg accgcgttca gtgcctgcgc caggtcgctc tgcgcgcgct ccgcaacctt    1200
tccccctgc accaagcaac acatcggaat ctcgacttcg agggtcgaga agtccaacca     1260
catgtccact tgtccctgct ccgcaagcgt ctcgccgtac aggcacttgt cggcgcgaag    1320
tcgcgcgagg aagcggcaaa tcgcgttgct ttcaaacaga cacacgccgc cgacctcgga    1380
ctccaacagg ggcagacgcc ccagaggcga cttggccaag aacgccggat ccttgtcgtc    1440
cttcccacg gtgaaaggca cagtctgcag cggcaggtcc aggaaagccg ccaccaactg     1500
caccttccgg ccgcgcacat cgtccttggg cgtcaggagt ttcatttttta cggagggtga   1560
agagagaggc tgc                                                        1573

<210> SEQ ID NO 295
<211> LENGTH: 20
<212> TYPE: DNA
<213> ORGANISM: Artificial sequence
<220> FEATURE:
<223> OTHER INFORMATION: Synthetic Primer

<400> SEQUENCE: 295
ttatttcccc gcctcgtctc                                                   20

<210> SEQ ID NO 296
<211> LENGTH: 20
<212> TYPE: DNA
<213> ORGANISM: Artificial sequence
<220> FEATURE:
<223> OTHER INFORMATION: Synthetic Primer

<400> SEQUENCE: 296
cctactgtga ctcccatcac                                                   20

<210> SEQ ID NO 297
<211> LENGTH: 19
<212> TYPE: DNA
<213> ORGANISM: Artificial sequence
<220> FEATURE:
<223> OTHER INFORMATION: Synthetic Primer

<400> SEQUENCE: 297
atcaccacta agcgtaggg                                                    19

<210> SEQ ID NO 298
<211> LENGTH: 19
```

```
<212> TYPE: DNA
<213> ORGANISM: Artificial sequence
<220> FEATURE:
<223> OTHER INFORMATION: Synthetic Primer

<400> SEQUENCE: 298
tcgaaagaac gaagctgcc                                              19

<210> SEQ ID NO 299
<211> LENGTH: 20
<212> TYPE: DNA
<213> ORGANISM: Artificial sequence
<220> FEATURE:
<223> OTHER INFORMATION: Synthetic Primer

<400> SEQUENCE: 299
cgaagggtgt catcctctac                                             20

<210> SEQ ID NO 300
<211> LENGTH: 21
<212> TYPE: DNA
<213> ORGANISM: Artificial sequence
<220> FEATURE:
<223> OTHER INFORMATION: Synthetic Primer

<400> SEQUENCE: 300
tatcgccaac agagtgaacc g                                           21

<210> SEQ ID NO 301
<211> LENGTH: 22
<212> TYPE: DNA
<213> ORGANISM: Artificial sequence
<220> FEATURE:
<223> OTHER INFORMATION: Synthetic Primer

<400> SEQUENCE: 301
gtggacccaa gcatttgtgt gg                                          22

<210> SEQ ID NO 302
<211> LENGTH: 21
<212> TYPE: DNA
<213> ORGANISM: Artificial sequence
<220> FEATURE:
<223> OTHER INFORMATION: Synthetic Primer

<400> SEQUENCE: 302
gcgtttcgac agttctatca c                                           21

<210> SEQ ID NO 303
<211> LENGTH: 20
<212> TYPE: DNA
<213> ORGANISM: Artificial sequence
<220> FEATURE:
<223> OTHER INFORMATION: Synthetic Primer

<400> SEQUENCE: 303
acggaagaag acggagatgg                                             20

<210> SEQ ID NO 304
<211> LENGTH: 20
<212> TYPE: DNA
<213> ORGANISM: Artificial sequence
<220> FEATURE:
<223> OTHER INFORMATION: Synthetic Primer

<400> SEQUENCE: 304
```

```
gagattccct acgcttagtg                                                      20

<210> SEQ ID NO 305
<211> LENGTH: 19
<212> TYPE: DNA
<213> ORGANISM: Artificial sequence
<220> FEATURE:
<223> OTHER INFORMATION: Synthetic Primer

<400> SEQUENCE: 305
gttcgtcttt cgccataac                                                       19

<210> SEQ ID NO 306
<211> LENGTH: 2417
<212> TYPE: DNA
<213> ORGANISM: Toxoplasma gondii
<220> FEATURE:
<221> NAME/KEY: CDS
<222> LOCATION: (1)..(27)
<223> OTHER INFORMATION:

<400> SEQUENCE: 306 gtt tcc tcc gtt ctt ctt cgt ttt aaa ctgcaggaag tttctcctcg                  47
Val Ser Ser Val Leu Leu Arg Phe Lys
1               5 ccttcgaccg cgtccgggga ctgaggtctg ctgtccacgc aggacttcct cttctccttt         107
ttcgcgccgc cagacgaggt cttcccgact tttcgtctgc acgcttctcc gcatctccgc         167
atctccccat ctccgtcttc ttccgttttt gactgtctgc gctctttctc cgacctcgct         227
cgaacgccgc gattctcgcc ttttatttcc ccgcctcgtc tccggccgtt ccacgcacct         287
tcctcggccg ttgcctcgcg ttcctcgggt gtacagacac ctgagcgctc tgcgttgtcg         347
cagcatttct ctgagccgca acatggggaa tgcgcagcct cgcggcggag gcttcccagg         407
aggctctgaa gaagacaaga agaaggagag aaagagactt gaagctgcgc ctccaacgca         467
cattggaaaa agaaagaaga aggaaaagg ccccgtcggt cacagcagac ttcctactgt          527
gactcccatc accaagtgtc gcctgcgtct gctccgactc gagcgcataa agactacct          587 tcttctggag gaagagtata ttctcaacca ggagcagcgg aagccggcgg aggagaagaa         647
cgaagaagat gtgaatcgcg tggacgagct ccgtggatca ccactaagcg tagggaatct         707
cgaggaaatc atcgatgaac agcatgcaat cgtttcttcc tccatcggtc ccgagtacta         767
cgtcaacatc ctctctttcg tcgacaaaga cctgctcgag cctggatgca gtgtccttct         827
tcacaacaaa acgagcagca ttgtcggaat tttgaacgac gaggtggacc ctctcatctc         887
ggtcatgaaa gtggagaagg caccgcttga cgtatgca gacatcggcg gactggagaa          947
gcagattcag gaggtgaagg aggccgtgga atttcctctc acgcatccgg agttcttcga        1007
cgacatcggt atcagccctc cgaagggtgt catcctctac ggaccccccg ggacaggaaa        1067
gactctgctc gcgaaggccg tggcgaacga cgtcggct acgttccttc gcgtcgtcgg         1127
aagtgaactc attcaaaaat atttgggaga cggcccgaag ctggtccggg aaatgtttaa        1187
actcgctcac gagcacgcgc cgagcatcgt cttcatcgtc ttcatcgaga gtctagaccc        1247
tgcgctcatt cggcctggac gcattgatcg gaaaattcaa ctccccaatc cggacgcgaa        1307
aaccaagcga aaaatcttcc agatcccacac agcgaaaatg accatggccg acgacgtcga       1367
cctcgaggaa tttgttatgg cgaaagacga actgtcgggt gcagatatca aggcgacatg        1427
cacggaggcg ggggttgctgg ccttgcgaga gcgacgcatg aaaatcaccc aggaagatct      1487
gcggaaggcg aaggagaagg cgctgtatca gaagaaaggg aacattccag agagtctgta      1547
```

| | |
|---|---|
| tctgtgaaga ggcgggagaa acaatggtg tctccccaga gcgtcgagac agctcgaaga | 1607 |
| acgaagctgc ctcttcagca ccctccagat ctgagccagg agcccaactc gatttgtggc | 1667 |
| ctcccaagaa ggactgacat ctcgaggcga agaagagact ggaaaatgtc acagcaggct | 1727 |
| tcagagacat cttctgctga agaaaaggc tgtgcgagcg ctttcgactc gtcagttttg | 1787 |
| aggcgccgcc ggtagcgcac accctgtggc ttcggtttct ctgtgataga actgtcgaaa | 1847 |
| cgctgcgaaa atagaaatga cgaggtcgca ctgcaagaag acaagagaga ttcaaaagaa | 1907 |
| aaggttgttt gcccgaaaac ttagcgtctg cgtgtctgat tttttcgagt tgagttgcca | 1967 |
| gtgtggacac gcatgatcgc ggagtggggg cactcaaagc gaaaccgttt atcgccaaca | 2027 |
| gagtgaaccg ttcagaccttt ttttcttggc gcatgcaaga aaaaagatgt gaactgcgta | 2087 |
| gtcgcactcg gcgattcccg cgggtgaggg agtgggagta gcgaattcag tcgaaagcga | 2147 |
| agaggctttc cagagcgcag acgcgacaga tttgccgaag gaaaaaagtc acgaacgtgt | 2207 |
| ctgtttgaga gaagaaccag ggccggcaca ggttctccgt gtattttta ggaaggatcg | 2267 |
| tgttgacagc gacaagaaag ccacacaaat gcttgggtcc acgggagcgc tgtcccccag | 2327 |
| acacacgcag aaatacgagt gaaacttact ctgcttcctg cgacaacttt cgcaattacg | 2387 |
| agtggaacgc ttcaaaaaaa aaaaaaaaaa | 2417 |

<210> SEQ ID NO 307
<211> LENGTH: 9
<212> TYPE: PRT
<213> ORGANISM: Toxoplasma gondii

<400> SEQUENCE: 307

Val Ser Ser Val Leu Leu Arg Phe Lys
1               5

<210> SEQ ID NO 308
<211> LENGTH: 2417
<212> TYPE: DNA
<213> ORGANISM: Toxoplasma gondii

<400> SEQUENCE: 308

| | |
|---|---|
| tttttttttt tttttttgaa gcgttccact cgtaattgcg aaagttgtcg caggaagcag | 60 |
| agtaagtttc actcgtattt ctgcgtgtgt ctgggggaca gcgctcccgt ggacccaagc | 120 |
| atttgtgtgg cttttcttgtc gctgtcaaca cgatccttcc taaaaaatac acggagaacc | 180 |
| tgtgccggcc ctgttcttc tctcaaacag acacgttcgt gactttttc cttcggcaaa | 240 |
| tctgtcgcgt ctgcgctctg gaaagcctct tcgctttcga ctgaattcgc tactcccact | 300 |
| ccctcacccg cgggaatcgc cgagtgcgac tacgcagttc acatcttttt tcttgcatgc | 360 |
| gccaagaaaa aaggtctgaa cggttcactc tgttggcgat aaacggtttc gctttgagtg | 420 |
| ccccccactcc gcgatcatgc gtgtccacac tggcaactca actcgaaaaa atcagacacg | 480 |
| cagacgctaa gttttcgggc aaacaacctt ttcttttgaa tctctcttgt cttcttgcag | 540 |
| tgcgacctcg tcatttctat tttcgcagcg tttcgacagt tctatcacag agaaaccgaa | 600 |
| gccacagggt gtgcgctacc ggcggcgcct caaaactgac gagtcgaaag cgctcgcaca | 660 |
| gcctttcttc tcagcagaag atgtctctga agcctgctgt gacattttcc agtctcttct | 720 |
| tcgcctcgag atgtcagtcc ttcttgggag gccacaaatc gagttgggct cctggctcag | 780 |
| atctggaggt gctgaagag gcagcttcgt tcttcgagct gtctcgacgc ctgggggaga | 840 |
| caccattgtt ttctcccgcc tcttcacaga tacagactct ctggaatgtt ccctttcttc | 900 |

-continued

```
tgatacagcg ccttctcctt cgccttccgc agatcttcct gggtgatttt catgcgtcgc    960
tctcgcaagg ccagcaaccc cgcctccgtg catgtcgcct tgatatctgc acccgacagt   1020
tcgtctttcg ccataacaaa ttcctcgagg tcgacgtcgt cggccatggt cattttcgct   1080
gtgtggatct ggaagatttt tcgcttggtt ttcgcgtccg gattggggag ttgaattttc   1140
cgatcaatgc gtccaggccg aatgagcgca gggtctagac tctcgatgaa gacgatgaag   1200
acgatgctcg gcgcgtgctc gtgagcgagt ttaaacattt cccggaccag cttcgggccg   1260
tctcccaaat atttttgaat gagttcactt ccgacgacgc gaaggaacgt agccgacgtc   1320
tcgttcgcca cggccttcgc gagcagagtc tttcctgtcc cgggggtcc gtagaggatg    1380
acacccttcg gagggctgat accgatgtcg tcgaagaact ccggatgcgt gagaggaaat   1440
tccacggcct ccttcacctc ctgaatctgc ttctccagtc cgccgatgtc tgcatacgtc   1500
tcaagcggtg ccttctccac tttcatgacc gagatgagag ggtccacctc gtcgttcaaa   1560
attccgacaa tgctgctcgt tttgttgtga agaaggacac tgcatccagg ctcgagcagg   1620
tctttgtcga cgaaagagag gatgttgacg tagtactcgg gaccgatgga ggaagaaacg   1680
attgcatgct gttcatcgat gatttcctcg agattcccta cgcttagtgg tgatccacgg   1740
agctcgtcca cgcgattcac atcttcttcg ttcttctcct ccgccggctt ccgctgctcc   1800
tggttgagaa tatactcttc ctccagaaga aggtagtctt ttatgcgctc gagtcggagc   1860
agacgcaggc gacacttggt gatgggagtc acagtaggaa gtctgctgtg accgacgggg   1920
ccttttcctt tcttctttct ttttccaatg tgcgttggag gcgcagcttc aagtctcttt   1980
ctctccttct tcttgtcttc ttcagagcct cctgggaagc ctccgccgcg aggctgcgca   2040
ttccccatgt tgcggctcag agaaatgctg cgacaacgca gagcgctcag gtgtctgtac   2100
acccgaggaa cgcgaggcaa cggccgagga aggtgcgtgg aacggccgga gacgaggcgg   2160
ggaaataaaa ggcgagaatc gcggcgttcg agcgaggtcg gagaaagagc gcagacagtc   2220
aaaaacggaa gaagacggag atggggagat gcggagatgc ggagaagcgt gcagacgaaa   2280
agtcgggaag acctcgtctg gcggcgcgaa aaaggagaag aggaagtcct gcgtggacag   2340
cagacctcag tccccggacg cggtcgaagg cgaggagaaa cttcctgcag tttaaaacga   2400
agaagaacgg aggaaac                                                 2417
```

<210> SEQ ID NO 309  
<211> LENGTH: 20  
<212> TYPE: DNA  
<213> ORGANISM: Artificial sequence  
<220> FEATURE:  
<223> OTHER INFORMATION: Synthetic Primer

<400> SEQUENCE: 309

```
cggactgcgt tatcgttacc                                                 20
```

<210> SEQ ID NO 310  
<211> LENGTH: 18  
<212> TYPE: DNA  
<213> ORGANISM: Artificial sequence  
<220> FEATURE:  
<223> OTHER INFORMATION: Synthetic Primer

<400> SEQUENCE: 310

```
ctgttgcctt cggatatg                                                   18
```

<210> SEQ ID NO 311

```
<211> LENGTH: 1785
<212> TYPE: DNA
<213> ORGANISM: Toxoplasma gondii
<220> FEATURE:
<221> NAME/KEY: CDS
<222> LOCATION: (1)..(75)
<223> OTHER INFORMATION:

<400> SEQUENCE: 311 gaa ccg gtg cac ttt tgc acg tgt acg caa gac agc ttc gca gac aac         48
Glu Pro Val His Phe Cys Thr Cys Thr Gln Asp Ser Phe Ala Asp Asn
1               5                   10                  15 atc tgg cag cct ccc gct cat ttt tag tcagcaaaaa tggcacccgc                95
Ile Trp Gln Pro Pro Ala His Phe
            20 acttgtgcag aggagaaaga aggtggccat gattggctct ggcatgattg gtggcactat       155 gggctacctg tgcgctctcc gtgagctcgc tgacgtcgtt ctctacgatg ttgtcaaagg       215 tatgcccgag ggtaaggctc ttgacctgag ccatgtgacc tccgtggtcg acaccaacgt       275 ttccgtccgt gctgagtact cttacgaggc cgcgctcacc ggtgcggact gcgttatcgt       335 taccgccggt ctgaccaagg tgccgggcaa gcccgactcc gagtggagcc gaaacgatct       395 gctcccgttc aactcgaaga tcattcgcga gatcggtcag aacatcaaga gtactgccc        455 caagaccttc atcatcgtgg tcaccaaccc gctggactgc atggtcaagg tcatgtgcga       515 ggcctctggc gtcccgacca acatgatctg cggtatggcc tgcatgctcg actctggtcg       575 cttccgccga tacgtcgccg acgcgctgtc tgtctctccc cgcgacgtcc aggccaccgt       635 catcggcaca cacggcgact gcatggtccc gcttgtccgg tacattaccg tgaacgacta       695 cccgatccag aagttcatca aggacggcgt agtcacggag aagcagctcg aggagatcgc       755 tgagcacacc aaagtgtctg cggcgagat cgtccgcttc ctcggccagg gttccgctta        815 ctacgccccc gccgcatccg ctgtcgccat ggcaacatcc ttcttgaacg acgaaaagcg       875 cgtcatcccg tgcagtgtgt actgcaacgg agagtacggc ttgaaggaca tgttcattgg       935 tctcccggcc gtcattggag cgccggcat cgagcgcgtc atcgagctcg agctgaacga        995 ggaggagaag aagcagttcc agaagtccgt cgacgacgtc atggcgctca acaaggcggt      1055 tgctgctctt caggcgtaag cgttggcaaa acaggagcgg aatgccactt tactgcgcgg      1115 ggcccatgat ttatacacgc gtttgcaacg gaagcgaaaa gacggttccg gttcgcacca      1175 cgcgctcgtc ccgaaaaagg gaagtcgcgg cgctgtcggt caacgctgtg cgggttgcag      1235 gtgcgtgctt aagcatcaca aagtggcaga gccattttgt ccaggaagt agcgtctcaa       1295 acaggtgaac gcgtgcaagc atgagaggca tccgtcgctg cgttcgctca catatccgaa      1355 ggcaacagat tttggtcggc aaaagcctct gcacaaccgt ggcaagatga tggaaacagt      1415 tcgtgtttgg acagcaaccg cgttcgctct cactcaaaac cctgtagtcg agagggtgt       1475 cgcatgactt ggcttttgtg ggagtgccca atcgtctgt gttcgaggtg aagatcacat       1535 gtccgctgca gtactgaaaa acacttggtg cgcagaggcg agcgataggt gcgctgactt      1595 tttttttgtt tgttcaagga aggcatcttt tttttttta ccggttgtcc actgtcatgt       1655 cgaaaacgta gtccgtgtga agtggttggt cccctgttgt cctttgtcta gccgcgcgtg      1715 tctcatggag cattttcaa cgttgcttca aacgaatgct ggtttcaaac aaaaaaaaa        1775 aaaaaaaaa                                                              1785

<210> SEQ ID NO 312
<211> LENGTH: 24
```

```
<212> TYPE: PRT
<213> ORGANISM: Toxoplasma gondii

<400> SEQUENCE: 312

Glu Pro Val His Phe Cys Thr Cys Thr Gln Asp Ser Phe Ala Asp Asn
1               5                   10                  15

Ile Trp Gln Pro Pro Ala His Phe
            20

<210> SEQ ID NO 313
<211> LENGTH: 1785
<212> TYPE: DNA
<213> ORGANISM: Toxoplasma gondii

<400> SEQUENCE: 313
gaaccggtgc acttttgcac gtgtacgcaa gacagcttcg cagacaacat ctggcagcct      60
cccgctcatt tttagtcagc aaaaatggca cccgcacttg tgcagaggag aaagaaggtg     120
gccatgattg gctctggcat gattggtggc actatgggct acctgtgcgc tctccgtgag     180
ctcgctgacg tcgttctcta cgatgttgtc aaaggtatgc ccgagggtaa ggctcttgac     240
ctgagccatg tgacctccgt ggtcgacacc aacgtttccg tccgtgctga gtactcttac     300
gaggccgcgc tcaccggtgc ggactgcgtt atcgttaccg ccgtctgac caaggtgccg      360
ggcaagcccg actccgagtg gagccgaaac gatctgctcc cgttcaactc gaagatcatt     420
cgcgagatcg tcagaacat caagaagtac tgccccaaga ccttcatcat cgtggtcacc      480
aacccgctgg actgcatggt caaggtcatg tgcgaggcct ctggcgtccc gaccaacatg     540
atctgcggta tggcctgcat gctcgactct ggtcgcttcc gccgatacgt cgccgacgcg     600
ctgtctgtct ctccccgcga cgtccaggcc accgtcatcg gcacacacgg cgactgcatg     660
gtcccgcttg tccggtacat taccgtgaac gactacccga tccagaagtt catcaaggac     720
ggcgtagtca cggagaagca gctcgaggag atcgctgagc acaccaaagt gtctggcggc     780
gagatcgtcc gcttcctcgg ccagggttcc gcttactacg ccccgccgc atccgctgtc      840
gccatggcaa catccttctt gaacgacgaa aagcgcgtca tcccgtgcag tgtgtactgc     900
aacggagagt acggcttgaa ggacatgttc attggtctcc cggccgtcat ggaggcgcc      960
ggcatcgagc gcgtcatcga gctcgagctg aacgaggagg agaagaagca gttccagaag    1020
tccgtcgacg acgtcatggc gctcaacaag gcggttgctg ctcttcaggc gtaagcgttg    1080
gcaaaacagg agcggaatgc cactttactg cgcggggccc atgatttata cacgcgtttg    1140
caacggaagc gaaaagacgg ttccggttcg caccacgcgc tcgtcccgaa aagggaagt    1200
cgcggcgctc tcggtcaacg ctgtgcgggt gcaggtgcg tgcttaagca tcacaaagtg     1260
gcagagccat tttgtccagg gaagtagcgt ctcaaacagg tgaacgcgtg caagcatgag    1320
aggcatccgt cgctgcgttc gctcacatat ccgaaggcaa cagatttggg tcggcaaaag    1380
cctctgcaca accgtggcaa gatgatggaa acagttcgtg tttggacagc aaccgcgttc    1440
gctctcactc aaaaccctgt agtcgagagg ggtgtcgcat gacttggctt ttgtgggagt    1500
gcccaaatcg tctgtgttcg aggtgaagat cacatgtccg ctgcagtact gaaaaacact    1560
tggtgcgcag aggcgagcga taggtgcgct gactttttt ttgtttgttc aaggaaggca     1620
tcttttttttt ttttaccggt tgtccactgt catgtcgaaa acgtagtccg tgtgaagtgg    1680
ttggtcccct gttgtccttt gtctagccgc gcgtgtctca tggagcattt ttcaacgttg    1740
cttcaaacga atgctggttt caaacaaaaa aaaaaaaaaa aaaaa                     1785
```

<210> SEQ ID NO 314
<211> LENGTH: 18
<212> TYPE: DNA
<213> ORGANISM: Artificial sequence
<220> FEATURE:
<223> OTHER INFORMATION: Synthetic Primer

<400> SEQUENCE: 314
tctccgactg tggagtgc                                                 18

<210> SEQ ID NO 315
<211> LENGTH: 18
<212> TYPE: DNA
<213> ORGANISM: Artificial sequence
<220> FEATURE:
<223> OTHER INFORMATION: Synthetic Primer

<400> SEQUENCE: 315
gatggcatgg atttgacc                                                 18

<210> SEQ ID NO 316
<211> LENGTH: 17
<212> TYPE: DNA
<213> ORGANISM: Artificial sequence
<220> FEATURE:
<223> OTHER INFORMATION: Synthetic Primer

<400> SEQUENCE: 316
tgaggagacc gaaaagg                                                  17

<210> SEQ ID NO 317
<211> LENGTH: 19
<212> TYPE: DNA
<213> ORGANISM: Artificial sequence
<220> FEATURE:
<223> OTHER INFORMATION: Synthetic Primer

<400> SEQUENCE: 317
tcagtgctct gacgaatcc                                                19

<210> SEQ ID NO 318
<211> LENGTH: 20
<212> TYPE: DNA
<213> ORGANISM: Artificial sequence
<220> FEATURE:
<223> OTHER INFORMATION: Synthetic Primer

<400> SEQUENCE: 318
gccttcagga gagaagctac                                               20

<210> SEQ ID NO 319
<211> LENGTH: 20
<212> TYPE: DNA
<213> ORGANISM: Artificial sequence
<220> FEATURE:
<223> OTHER INFORMATION: Synthetic Primer

<400> SEQUENCE: 319
gatcgaagat gacgcatggg                                               20

<210> SEQ ID NO 320
<211> LENGTH: 20
<212> TYPE: DNA
<213> ORGANISM: Artificial sequence
<220> FEATURE:
<223> OTHER INFORMATION: Synthetic Primer

<400> SEQUENCE: 320
gaaactctgg ggaaaacggc                                                 20

<210> SEQ ID NO 321
<211> LENGTH: 20
<212> TYPE: DNA
<213> ORGANISM: Artificial sequence
<220> FEATURE:
<223> OTHER INFORMATION: Synthetic Primer

<400> SEQUENCE: 321
cttcttcgct ctcaaacatc                                                 20

<210> SEQ ID NO 322
<211> LENGTH: 17
<212> TYPE: DNA
<213> ORGANISM: Artificial sequence
<220> FEATURE:
<223> OTHER INFORMATION: Synthetic Primer

<400> SEQUENCE: 322
atcacggttt gtcgcac                                                    17

<210> SEQ ID NO 323
<211> LENGTH: 19
<212> TYPE: DNA
<213> ORGANISM: Artificial sequence
<220> FEATURE:
<223> OTHER INFORMATION: Synthetic Primer

<400> SEQUENCE: 323
cggacttcct tatgatcgg                                                  19

<210> SEQ ID NO 324
<211> LENGTH: 20
<212> TYPE: DNA
<213> ORGANISM: Artificial sequence
<220> FEATURE:
<223> OTHER INFORMATION: Synthetic Primer

<400> SEQUENCE: 324
agtcggagaa ggcaccatag                                                 20

<210> SEQ ID NO 325
<211> LENGTH: 17
<212> TYPE: DNA
<213> ORGANISM: Artificial sequence
<220> FEATURE:
<223> OTHER INFORMATION: Synthetic Primer

<400> SEQUENCE: 325
ttcctcctcc ttttcgg                                                    17

<210> SEQ ID NO 326
<211> LENGTH: 2167
<212> TYPE: DNA
<213> ORGANISM: Toxoplasma gondii
<220> FEATURE:
<221> NAME/KEY: CDS
<222> LOCATION: (1)..(1716)
<223> OTHER INFORMATION:

<400> SEQUENCE: 326 gtg agc acc cgc cgg aga gaa gac acc gag agc gag gcg tgc gtc aac      48
Val Ser Thr Arg Arg Arg Glu Asp Thr Glu Ser Glu Ala Cys Val Asn -continued

```
1               5               10              15 caa gtc gaa acc atg gag tgc cca act cag gct ggg caa gca tgc ggc       96
Gln Val Glu Thr Met Glu Cys Pro Thr Gln Ala Gly Gln Ala Cys Gly
 20              25              30 aac tat ggt gcc ttc tcc gac tgt gga gtg cct ctt cgc ggc ttc gcc      144
Asn Tyr Gly Ala Phe Ser Asp Cys Gly Val Pro Leu Arg Gly Phe Ala
 35              40              45 atg gcc ttc ccc gag aac tgc cca gag ctc gtg gcc ttc gcc gcc tgc      192
Met Ala Phe Pro Glu Asn Cys Pro Glu Leu Val Ala Phe Ala Ala Cys
 50              55              60 gat gct ccc gcg cct ccc caa gag gac cgc tgc cat tct ttc tcg gcc      240
Asp Ala Pro Ala Pro Pro Gln Glu Asp Arg Cys His Ser Phe Ser Ala
 65              70              75              80 tgg tcc aag tgc aca cac ata ccc ggc act act ctg tac gag cag acg      288
Trp Ser Lys Cys Thr His Ile Pro Gly Thr Thr Leu Tyr Glu Gln Thr
 85              90              95 cgc tcc tgc gat ggc atg gat ttg acc gag tcc cgc ttc tgc act ccc      336
Arg Ser Cys Asp Gly Met Asp Leu Thr Glu Ser Arg Phe Cys Thr Pro
100             105             110 gac gag gag gtc ggc tcg gac gtt tcc act gac gtc gct tcc gaa tgc      384
Asp Glu Glu Val Gly Ser Asp Val Ser Thr Asp Val Ala Ser Glu Cys
115             120             125 ggt tcc ctc ggc gag ttc ggc gag tgt gtg aac ggc ctt cag gag aga      432
Gly Ser Leu Gly Glu Phe Gly Glu Cys Val Asn Gly Leu Gln Glu Arg
130             135             140 agc tac tcg gac tgc ccc gat cat aag gaa gtc cgt cag tgc tct gac      480
Ser Tyr Ser Asp Cys Pro Asp His Lys Glu Val Arg Gln Cys Ser Asp
145             150             155             160 gaa tcc tgc tct gcc ttc ggc gag tgg tca ccc tgc ggg gaa ccc cag      528
Glu Ser Cys Ser Ala Phe Gly Glu Trp Ser Pro Cys Gly Glu Pro Gln
165             170             175 caa ggc ctg cgt atc cgc aag aga cgt gca tgc gac aac gtg cac tgc      576
Gln Gly Leu Arg Ile Arg Lys Arg Arg Ala Cys Asp Asn Val His Cys
180             185             190 gcc tgt gtc gag gcc gag gtc tgc ggc gat gtc acc cca gag att gag      624
Ala Cys Val Glu Ala Glu Val Cys Gly Asp Val Thr Pro Glu Ile Glu
195             200             205 gag gaa gaa ggc gaa cat ttc ccc cct gaa gaa ggc gag gtc ttg cct      672
Glu Glu Glu Gly Glu His Phe Pro Pro Glu Glu Gly Glu Val Leu Pro
210             215             220 cca tat gaa gag ggt cct ggt gag ggt gag ctt gtt cct ccc gag gag      720
Pro Tyr Glu Glu Gly Pro Gly Glu Gly Glu Leu Val Pro Pro Glu Glu
225             230             235             240 gag atc cct gaa gga gaa cat gtt cct gag gag gaa atc cct gaa gga      768
Glu Ile Pro Glu Gly Glu His Val Pro Glu Glu Ile Pro Glu Gly
245             250             255 gaa cat att cct gaa gag ctc cca gaa ggc gag cat gtt cct gag gag      816
Glu His Ile Pro Glu Glu Leu Pro Gly Glu His Val Pro Glu Glu
260             265             270 gaa atc cct gaa gga gaa cat gtt cct gaa gag gaa atc cct gaa gga      864
Glu Ile Pro Glu Gly Glu His Val Pro Glu Glu Ile Pro Glu Gly
275             280             285 gag cat gtt cct gaa gag ttc cca gaa ggc gag cat gtt cct gag gag      912
Glu His Val Pro Glu Glu Phe Pro Gly Glu His Val Pro Glu Glu
290             295             300 gaa atc cct gaa gga gaa cat gtt cct gaa gag gaa atc cct gaa gga      960
Glu Ile Pro Glu Gly Glu His Val Pro Glu Glu Ile Pro Glu Gly
305             310             315             320 gag cat gtt cct gaa gag ttc cct gaa gga gag cat att cct gag gag     1008
```

```
Glu His Val Pro Glu Glu Phe Pro Glu Gly Glu His Ile Pro Glu Glu
325                 330                 335 ctc cct gaa ggc gag cat atc cct gaa gag ttc cct gaa gga gag cat    1056
Leu Pro Glu Gly Glu His Ile Pro Glu Glu Phe Pro Glu Gly Glu His
340                 345                 350 att cct gag gag ctc cct gaa ggc gag cat gtt cct gag gag gag atc    1104
Ile Pro Glu Glu Leu Pro Glu Gly Glu His Val Pro Glu Glu Glu Ile
355                 360                 365 cct gaa gga gag cat att cct gaa gag ttc cca gaa ggc gag cat gtt    1152
Pro Glu Gly Glu His Ile Pro Glu Glu Phe Pro Glu Gly Glu His Val
370                 375                 380 cct gag gag gaa atc cct gaa gga gaa cat att cct gag gag gag ttc    1200
Pro Glu Glu Glu Ile Pro Glu Gly Glu His Ile Pro Glu Glu Glu Phe
385                 390                 395                 400 cct gaa gga gag cat gtt cct gag gag gag atc cct gaa ggc gag cat    1248
Pro Glu Gly Glu His Val Pro Glu Glu Glu Ile Pro Glu Gly Glu His
405                 410                 415 gtt cct gag gag gag ctc cct gga gga gaa ctt att cct gag gag gag    1296
Val Pro Glu Glu Glu Leu Pro Gly Gly Glu Leu Ile Pro Glu Glu Glu
420                 425                 430 atc cct gaa gga gag cat gtt cct gaa gag ctc cct gaa ggc gag cat    1344
Ile Pro Glu Gly Glu His Val Pro Glu Glu Leu Pro Glu Gly Glu His
435                 440                 445 gtt cct gag gag gag atc cct gaa gga gag cat gtt cct gaa gag gaa    1392
Val Pro Glu Glu Glu Ile Pro Glu Gly Glu His Val Pro Glu Glu Glu
450                 455                 460 atc cct gaa ggc gag cat gtt cct gag gag gag acc cct gaa gga gaa    1440
Ile Pro Glu Gly Glu His Val Pro Glu Glu Glu Thr Pro Glu Gly Glu
465                 470                 475                 480 cat gct cca gag gaa gag act cct gca cct gag gag acc gaa aag gag    1488
His Ala Pro Glu Glu Glu Thr Pro Ala Pro Glu Glu Thr Glu Lys Glu
485                 490                 495 gag gaa gaa ggc gtg cca gtc gca gcg att gcc ggt ggt gtc gtc gga    1536
Glu Glu Glu Gly Val Pro Val Ala Ala Ile Ala Gly Gly Val Val Gly
500                 505                 510 ggt gtg ttg ctc att gct ggt ggt gca ggt gct gcc gtg tac gca aac    1584
Gly Val Leu Leu Ile Ala Gly Gly Ala Gly Ala Ala Val Tyr Ala Asn
515                 520                 525 caa ggt ggc gtt gaa gca gct gaa gac gaa gtg atg ttt gag agc gaa    1632
Gln Gly Gly Val Glu Ala Ala Glu Asp Glu Val Met Phe Glu Ser Glu
530                 535                 540 gaa gac gga acc cag gct ggc gag aac cgc gag agc gag acg gtc att    1680
Glu Asp Gly Thr Gln Ala Gly Glu Asn Arg Glu Ser Glu Thr Val Ile
545                 550                 555                 560 gag atc gaa gat gac gca tgg gca gac atg gac taa agtagactag          1726
Glu Ile Glu Asp Asp Ala Trp Ala Asp Met Asp
565                 570 tagtctgtgt gggcacatgc aggcgtgcga caaaaccgtg atcgcgaggt attctgtgtt    1786
acgggcggag cgtctgcggc tgtccttcga aggggaggcg gcgtgacact ctgagctagg    1846
taccagacga acgcagccat tgtgtccgt ccgctctttc ttgatcacgt gccatttat      1906 tttacgtttt ccactggtgt atcttttcca gcagcttata tataggctgc cgcagcttcg    1966
tgtgtcacaa gccgctgtag acagtaagcc tactgcggcc tccttgtgga aagccgtttt    2026
ccccagagtt tcctgttttc cttccctccg cgtgccatct tgtttttcgc ccgcgcggat    2086
gtgttaatgc gataaataac taatgaagca aggttatgaa cagcttcgtg agctatattc    2146
ccagccaaaa aaaaaaaaaa a                                              2167
```

<210> SEQ ID NO 327
<211> LENGTH: 571
<212> TYPE: PRT
<213> ORGANISM: Toxoplasma gondii

<400> SEQUENCE: 327

| | | | | | | | | | | | | | | |
|---|---|---|---|---|---|---|---|---|---|---|---|---|---|---|
| Val | Ser | Thr | Arg | Arg | Glu | Asp | Thr | Glu | Ser | Glu | Ala | Cys | Val | Asn |
| 1 | | | | 5 | | | | | 10 | | | | | 15 |
| Gln | Val | Glu | Thr | Met | Glu | Cys | Pro | Thr | Gln | Ala | Gly | Gln | Ala | Cys | Gly |
| | 20 | | | | 25 | | | | | 30 | | | | | |
| Asn | Tyr | Gly | Ala | Phe | Ser | Asp | Cys | Gly | Val | Pro | Leu | Arg | Gly | Phe | Ala |
| 35 | | | | | 40 | | | | | 45 | | | | | |
| Met | Ala | Phe | Pro | Glu | Asn | Cys | Pro | Glu | Leu | Val | Ala | Phe | Ala | Ala | Cys |
| 50 | | | | | 55 | | | | | 60 | | | | | |
| Asp | Ala | Pro | Ala | Pro | Gln | Glu | Asp | Arg | Cys | His | Ser | Phe | Ser | Ala |
| 65 | | | | | 70 | | | | | 75 | | | | | 80 |
| Trp | Ser | Lys | Cys | Thr | His | Ile | Pro | Gly | Thr | Thr | Leu | Tyr | Glu | Gln | Thr |
| 85 | | | | | 90 | | | | | 95 | | | | | |
| Arg | Ser | Cys | Asp | Gly | Met | Asp | Leu | Thr | Glu | Ser | Arg | Phe | Cys | Thr | Pro |
| 100 | | | | | 105 | | | | | 110 | | | | | |
| Asp | Glu | Glu | Val | Gly | Ser | Asp | Val | Ser | Thr | Asp | Val | Ala | Ser | Glu | Cys |
| 115 | | | | | 120 | | | | | 125 | | | | | |
| Gly | Ser | Leu | Gly | Glu | Phe | Gly | Glu | Cys | Val | Asn | Gly | Leu | Gln | Glu | Arg |
| 130 | | | | | 135 | | | | | 140 | | | | | |
| Ser | Tyr | Ser | Asp | Cys | Pro | Asp | His | Lys | Glu | Val | Arg | Gln | Cys | Ser | Asp |
| 145 | | | | | 150 | | | | | 155 | | | | | 160 |
| Glu | Ser | Cys | Ser | Ala | Phe | Gly | Glu | Trp | Ser | Pro | Cys | Gly | Glu | Pro | Gln |
| 165 | | | | | 170 | | | | | 175 | | | | | |
| Gln | Gly | Leu | Arg | Ile | Arg | Lys | Arg | Arg | Ala | Cys | Asp | Asn | Val | His | Cys |
| 180 | | | | | 185 | | | | | 190 | | | | | |
| Ala | Cys | Val | Glu | Ala | Glu | Val | Cys | Gly | Asp | Val | Thr | Pro | Glu | Ile | Glu |
| 195 | | | | | 200 | | | | | 205 | | | | | |
| Glu | Glu | Glu | Gly | Glu | His | Phe | Pro | Pro | Glu | Glu | Gly | Glu | Val | Leu | Pro |
| 210 | | | | | 215 | | | | | 220 | | | | | |
| Pro | Tyr | Glu | Glu | Gly | Pro | Gly | Glu | Gly | Glu | Leu | Val | Pro | Pro | Glu | Glu |
| 225 | | | | | 230 | | | | | 235 | | | | | 240 |
| Glu | Ile | Pro | Glu | Gly | Glu | His | Val | Pro | Glu | Glu | Ile | Pro | Glu | Gly |
| 245 | | | | | 250 | | | | | 255 | | | | | |
| Glu | His | Ile | Pro | Glu | Glu | Leu | Pro | Glu | Gly | Glu | His | Val | Pro | Glu | Glu |
| 260 | | | | | 265 | | | | | 270 | | | | | |
| Glu | Ile | Pro | Glu | Gly | Glu | His | Val | Pro | Glu | Glu | Ile | Pro | Glu | Gly |
| 275 | | | | | 280 | | | | | 285 | | | | | |
| Glu | His | Val | Pro | Glu | Glu | Phe | Pro | Glu | Gly | Glu | His | Val | Pro | Glu | Glu |
| 290 | | | | | 295 | | | | | 300 | | | | | |
| Glu | Ile | Pro | Glu | Gly | Glu | His | Val | Pro | Glu | Glu | Ile | Pro | Glu | Gly |
| 305 | | | | | 310 | | | | | 315 | | | | | 320 |
| Glu | His | Val | Pro | Glu | Glu | Phe | Pro | Glu | Gly | Glu | His | Ile | Pro | Glu | Glu |
| 325 | | | | | 330 | | | | | 335 | | | | | |
| Leu | Pro | Glu | Gly | Glu | His | Ile | Pro | Glu | Glu | Phe | Pro | Glu | Gly | Glu | His |
| 340 | | | | | 345 | | | | | 350 | | | | | |
| Ile | Pro | Glu | Glu | Leu | Pro | Glu | Gly | Glu | His | Val | Pro | Glu | Glu | Ile |
| 355 | | | | | 360 | | | | | 365 | | | | | |
| Pro | Glu | Gly | Glu | His | Ile | Pro | Glu | Glu | Phe | Pro | Glu | Gly | Glu | His | Val |
| 370 | | | | | 375 | | | | | 380 | | | | | |

```
Pro Glu Glu Glu Ile Pro Glu Gly Glu His Ile Pro Glu Glu Glu Phe
385                 390                 395                 400

Pro Glu Gly Glu His Val Pro Glu Glu Ile Pro Glu Gly Glu His
        405                 410                 415

Val Pro Glu Glu Glu Leu Pro Gly Gly Glu Leu Ile Pro Glu Glu Glu
420                 425                 430

Ile Pro Glu Gly Glu His Val Pro Glu Glu Leu Pro Gly Glu His
435                 440                 445

Val Pro Glu Glu Ile Pro Glu Gly Glu His Val Pro Glu Glu
450                 455                 460

Ile Pro Glu Gly Glu His Val Pro Glu Glu Thr Pro Gly Glu
465                 470                 475                 480

His Ala Pro Glu Glu Glu Thr Pro Ala Pro Glu Thr Glu Lys Glu
485                 490                 495

Glu Glu Glu Gly Val Pro Val Ala Ala Ile Ala Gly Gly Val Val Gly
500                 505                 510

Gly Val Leu Leu Ile Ala Gly Gly Ala Gly Ala Ala Val Tyr Ala Asn
515                 520                 525

Gln Gly Gly Val Glu Ala Ala Glu Asp Glu Val Met Phe Glu Ser Glu
530                 535                 540

Glu Asp Gly Thr Gln Ala Gly Glu Asn Arg Glu Ser Glu Thr Val Ile
545                 550                 555                 560

Glu Ile Glu Asp Asp Ala Trp Ala Asp Met Asp
565                 570

<210> SEQ ID NO 328
<211> LENGTH: 2167
<212> TYPE: DNA
<213> ORGANISM: Toxoplasma gondii

<400> SEQUENCE: 328
tttttttttt ttttggctg ggaatatagc tcacgaagct gttcataacc ttgcttcatt      60
agttatttat cgcattaaca catccgcgcg ggcgaaaaac aagatggcac gcggagggaa     120
ggaaaacagg aaactctggg aaaacggct tccacaagg aggccgcagt aggcttactg      180
tctacagcgg cttgtgacac acgaagctgc ggcagcctat atataagctg ctggaaaaga     240
tacaccagtg gaaaacgtaa aataaaatgg cacgtgatca agaaagagcg gacggacaca     300
aatggctgcg ttcgtctggt acctagctca gagtgtcacg ccgcctcccc ttcgaaggac     360
agccgcagac gctccgcccg taacacagaa tacctcgcga tcacggtttt gtcgcacgcc     420
tgcatgtgcc cacacagact actagtctac tttagtccat gtctgcccat gcgtcatctt     480
cgatctcaat gaccgtctcg ctctcgcggt tctcgccagc ctgggttccg tcttcttcgc     540
tctcaaacat cacttcgtct tcagctgctt caacgccacc ttggtttgcg tacacggcag     600
cacctgcacc accagcaatg agcaacacac ctccgacgac accaccggca atcgctgcga     660
ctggcacgcc ttcttcctcc tccttttcgg tctcctcagg tgcaggagtc tcttcctctg     720
gagcatgttc tccttcaggg gtctcctcct caggaacatg ctcgccttca gggatttcct     780
cttcaggaac atgctctcct tcagggatct cctcctcagg aacatgctcg ccttcaggga     840
gctcttcagg aacatgctct ccttcaggga tctcctcctc aggaataagt tctcctccag     900
ggagctcctc tcaggaaca tgctcgcctt cagggatctc ctcctcagga acatgctctc     960
cttcagggaa ctcctcctca ggaatatgtt ctccttcagg gatttcctcc tcaggaacat    1020
```

-continued

```
gctcgccttc tgggaactct tcaggaatat gctctccttc agggatctcc tcctcaggaa      1080
catgctcgcc ttcagggagc tcctcaggaa atgctctcc ttcagggaac tcttcaggga      1140
tatgctcgcc ttcagggagc tcctcaggaa tatgctctcc ttcagggaac tcttcaggaa      1200
catgctctcc ttcagggatt tcctcttcag gaacatgttc tccttcaggg atttcctcct      1260
caggaacatg ctcgccttct gggaactctt caggaacatg ctctccttca gggatttcct      1320
cttcaggaac atgttctcct tcaggatttt cctcctcagg aacatgctcg ccttctggga      1380
gctcttcagg aatatgttct ccttcaggga tttcctcctc aggaacatgt tctccttcag      1440
ggatctcctc tcgggagga acaagctcac cctcaccagg accctcttca tatggaggca      1500
agacctcgcc ttcttcaggg gggaaatgtt cgccttcttc ctcctcaatc tctgggtga      1560 catcgccgca gacctcggcc tcgacacagg cgcagtgcac gttgtcgcat gcacgtctct      1620 tgccggatacg caggccttgc tggggttccc cgcagggtga ccactcgccg aaggcagagc      1680
aggattcgtc agagcactga cggacttcct tatgatcggg gcagtccgag tagcttctct      1740
cctgaaggcc gttcacacac tcgccgaact cgccgaggga accgcattcg aagcgacgt      1800 cagtggaaac gtccgagccg acctcctcgt cgggagtgca gaagcgggac tcggtcaaat      1860
ccatgccatc gcaggagcgc gtctgctcgt acagagtagt gccgggtatg tgtgtgcact      1920
tggaccaggc cgagaaagaa tggcagcggt cctcttgggg aggcgcggga gcatcgcagg      1980
cggcgaaggc cacgagctct gggcagttct cggggaaggc catggcgaag ccgcgaagag      2040
gcactccaca gtcggagaag gcaccatagt tgccgcatgc ttgcccagcc tgagttgggc      2100
actccatggt ttcgacttgg ttgacgcacg cctcgctctc ggtgtcttct ctccggcggg      2160
tgctcac                                                              2167
```

<210> SEQ ID NO 329
<211> LENGTH: 2393
<212> TYPE: DNA
<213> ORGANISM: Toxoplasma gondii
<220> FEATURE:
<221> NAME/KEY: CDS
<222> LOCATION: (1)..(594)
<223> OTHER INFORMATION:

<400> SEQUENCE: 329

```
gca gga att ctt gca acc act gga gtg cat tca ctc gct gcg atc ccg        48
Ala Gly Ile Leu Ala Thr Thr Gly Val His Ser Leu Ala Ala Ile Pro
1               5                   10                  15 aga ctc acc tca gca gcc gct act gtg tgg acc tcc cag aca agg ttg       96
Arg Leu Thr Ser Ala Ala Ala Thr Val Trp Thr Ser Gln Thr Arg Leu
            20                  25                  30 agt cga tca cct gcg aag tcg gct ccc tgc ccc agc ccc cga ctg tcg      144
Ser Arg Ser Pro Ala Lys Ser Ala Pro Cys Pro Ser Pro Arg Leu Ser
35                  40                  45 ccc ccg gcg agg gtg gtg agg aag acg gca acg cat gtg gac cgt ggg      192
Pro Pro Ala Arg Val Val Arg Lys Thr Ala Thr His Val Asp Arg Gly
50                  55                  60 tcc gtg gag ccc gtg tcc cgg cga agg aaa caa cat gag cac ccg ccg      240
Ser Val Glu Pro Val Ser Arg Arg Lys Gln His Glu His Pro Pro
65                  70                  75                  80 gag aga aga cac cga gag cga ggc gtg cgt caa cca agt cga aac cat      288
Glu Arg Arg His Arg Glu Arg Gly Val Arg Gln Pro Ser Arg Asn His
            85                  90                  95 gga gtg ccc aac tca ggc tgg gca agc atg cgg caa cta tgg tgc ctt      336
Gly Val Pro Asn Ser Gly Trp Ala Ser Met Arg Gln Leu Trp Cys Leu
            100                 105                 110
```

```
ctc cga ctg tgg aat gcc tct tcg cgg ctt cgc cat ggc ctt ccc cga        384
Leu Arg Leu Trp Asn Ala Ser Ser Arg Leu Arg His Gly Leu Pro Arg
115                 120                 125 gaa ctg ccc aga gct cgt ggc ctt cgc cgc ctg cga tgc tcc cgc gcc        432
Glu Leu Pro Arg Ala Arg Gly Leu Arg Arg Leu Arg Cys Ser Arg Ala
130                 135                 140 tcc cca aga gga ccg ctg cca ttc ttt ctc ggc ctg gtc caa gtg cac        480
Ser Pro Arg Gly Pro Leu Pro Phe Phe Leu Gly Leu Val Gln Val His
145                 150                 155                 160 aca cat acc cgg cac tac tct gta cga gca gac gcg ctc ctg cga tgg        528
Thr His Thr Arg His Tyr Ser Val Arg Ala Asp Ala Leu Leu Arg Trp
165                 170                 175 cat gga ttt gac cga gtc ccg ctt ctg cac tcc cga cga gga ggt cgg        576
His Gly Phe Asp Arg Val Pro Leu Leu His Ser Arg Arg Gly Gly Arg
180                 185                 190 ctc gga cgt ttc cac tga cgtcgcttcc gaatgcggtt ccctcggcga               624
Leu Gly Arg Phe His
195 gttcggcgag tgtgtgaacg gccttcagga gagaagctac tcggactgcc ccgatcataa       684
ggaagtccgt cagtgctctg acgaatcctg ctctgccttc ggcgagtggt caccctgcgg       744
ggaaccccag caaggcctgc gtatccgcaa gagacgtgca tgcgacaacg tgcactgcgc       804
ctgtgtcgag gccgaggtct gcggcgatgt caccccagag attgaggagg aagaaggcga       864
acatttcccc cctgaagaag gcgaggtctt gcctccatat gaagagggtc tggtgaggg        924
tgagcttgtt cctcccgagg aggagatccc tgaaggagaa catgttcctg aggagaaat        984
ccctgaagga gaacatattc ctgaagagct cccagaaggc gagcatgttc ctgaggagga      1044
aatccctgaa ggagaacatg ttcctgaaga ggaaatccct gaaggagagc atgttcctga      1104
agagttccca gaaggcgaac atgttcctga ggaggaaatc cctgaaggag aacatgttcc      1164
tgaagaggaa atccctgaag gagaacatgt tcctgaagag ttccctgaag gagaacatat      1224
tcctgaggag ctccctgaag gagagcatat tcatgaagag ttccctgaag gagagcatat      1284
tcatgaggag ctccctgaag gcgagcatgt tcctgaagag gagatccctg aaggagaaca      1344
tattcctgag gagttccctg aaggcgagca tgttcctgag gagaaatcc ctgaaggaga       1404
acatattcct gaggaggagt cccctgaagg agagcatgtt cctgaggagg agatccctga      1464
aggcgagcat gttcctgagg aggagctccc tggaggagaa cttattcctg aggaggagat      1524
ccctgaagga gagcatgttc ctgaagagct ccctgaaggc gagcatgttc ctgaggagga      1584
gatccctgaa ggagagcatg ttcctgaaga ggaaatccct gaaggcgagc atgttcctga      1644
ggaggagacc cctgaaggag aacatgctcc agaggaagag actcctgcac ctgaggagac      1704
cgaaaaggag gaggaagaag gcgtgccagt cgcagcgatt gccggtggtg tcgtcggagg      1764
tgtgttgctc attgctggtg gtgcaggtgc tgccgtgtac gcaaaccaag gtggcgttga      1824
agcagctgaa gacgaagtga tgtttgagag cgaagaagac ggaacccagg ctggcgagaa      1884
ccgcgagagc gagacggtca ttgagatcga agatgacgca tgggcagaca tggactaaag      1944
tagactagta gtctgtgtgg gcacatgcag gcgtgcgaca aaaccgtgat cgcgaggtat      2004
tctgtgttac gggcggagcg tctgcggctg tccttcgaag gggaggcggc gtgacactct      2064
gagctaggta ccagacgaac gcagccattt gtgtccgtcc gctctttctt gatcacgtgc      2124
cattttattt tacgttttcc actggtgtat cttttccagc agcttatata taggctgccg      2184
cagcttcgtg tgtcacaagc cgctgtagac agtaagccta ctgcgcctc cttgtggaaa       2244
```

```
gccgttttcc ccagagtttc ctgttttcct tccctccgcg tgccatcttg tttttcgccc    2304
gcgcggatgt gttaatgcga taaataacta atgaagcaag gttatgaaca gcttcgtgag    2364
ctatattccc agccaaaaaa aaaaaaaaa                                       2393

<210> SEQ ID NO 330
<211> LENGTH: 197
<212> TYPE: PRT
<213> ORGANISM: Toxoplasma gondii

<400> SEQUENCE: 330

Ala Gly Ile Leu Ala Thr Thr Gly Val His Ser Leu Ala Ala Ile Pro
1               5                   10                  15

Arg Leu Thr Ser Ala Ala Ala Thr Val Trp Thr Ser Gln Thr Arg Leu
            20                  25                  30

Ser Arg Ser Pro Ala Lys Ser Ala Pro Cys Pro Ser Pro Arg Leu Ser
        35                  40                  45

Pro Pro Ala Arg Val Val Arg Lys Thr Ala Thr His Val Asp Arg Gly
    50                  55                  60

Ser Val Glu Pro Val Ser Arg Arg Lys Gln His Glu His Pro Pro
65                  70                  75                  80

Glu Arg Arg His Arg Glu Arg Gly Val Arg Gln Pro Ser Arg Asn His
                85                  90                  95

Gly Val Pro Asn Ser Gly Trp Ala Ser Met Arg Gln Leu Trp Cys Leu
            100                 105                 110

Leu Arg Leu Trp Asn Ala Ser Ser Arg Leu Arg His Gly Leu Pro Arg
        115                 120                 125

Glu Leu Pro Arg Ala Arg Gly Leu Arg Arg Leu Arg Cys Ser Arg Ala
    130                 135                 140

Ser Pro Arg Gly Pro Leu Pro Phe Phe Leu Gly Leu Val Gln Val His
145                 150                 155                 160

Thr His Thr Arg His Tyr Ser Val Arg Ala Asp Ala Leu Leu Arg Trp
                165                 170                 175

His Gly Phe Asp Arg Val Pro Leu Leu His Ser Arg Arg Gly Gly Arg
            180                 185                 190

Leu Gly Arg Phe His
195

<210> SEQ ID NO 331
<211> LENGTH: 2392
<212> TYPE: DNA
<213> ORGANISM: Toxoplasma gondii

<400> SEQUENCE: 331
tttttttttt ttttggctg ggaatatagc tcacgaagct gttcataacc ttgcttcatt      60
agttatttat cgcattaaca catccgcgcg ggcgaaaaac aagatggcac gcggagggaa    120
ggaaaacagg aaactctggg gaaaacggct tccacaagg aggccgcagt aggcttactg     180
tctacagcgg cttgtgacac acgaagctgc ggcagcctat atataagctg ctggaaaaga    240
tacaccagtg gaaaacgtaa aataaaatgg cacgtgatca agaaagagcg gacggacaca    300
aatggctgcg ttcgtctggt acctagctca gagtgtcacg ccgcctcccc ttcgaaggac    360
agccgcagac gctccgcccg taacacagaa tacctcgcga tcacggtttt gtcgcacgcc    420
tgcatgtgcc cacacagact actagtctac tttagtccat gtctgcccat gcgtcatctt    480
cgatctcaat gaccgtctcg ctctcgcggt tctcgccagc ctgggttccg tcttcttcgc    540
```

-continued

```
tctcaaacat cacttcgtct tcagctgctt caacgccacc ttggtttgcg tacacggcag    600
cacctgcacc accagcaatg agcaacacac ctccgacgac accaccggca atcgctgcga    660
ctggcacgcc ttcttcctcc tccttttcgg tctcctcagg tgcaggagtc tcttcctctg    720
gagcatgttc tccttcaggg gtctcctcct caggaacatg ctcgccttca gggatttcct    780
cttcaggaac atgctctcct tcagggatct cctcctcagg aacatgctcg ccttcaggga    840
gctcttcagg aacatgctct ccttcaggga tctcctcctc aggaataagt tctcctccag    900
ggagctcctc ctcaggaaca tgctcgcctt cagggatctc ctcctcagga acatgctctc    960
cttcagggaa ctcctcctca ggaatatgtt ctccttcagg gatttcctcc tcaggaacat   1020
gctcgccttc agggaactcc tcaggaatat gttctccttc agggatctcc tcttcaggaa   1080
catgctcgcc ttcagggagc tcctcatgaa tatgctctcc ttcagggaac tcttcatgaa   1140
tatgctctcc ttcagggagc tcctcaggaa tatgttctcc ttcagggaac tcttcaggaa   1200
catgttctcc ttcagggatt tcctcttcag gaacatgttc tccttcaggg atttcctcct   1260
caggaacatg ttcgccttct gggaactctt caggaacatg ctctccttca gggatttcct   1320
cttcaggaac atgttctcct tcagggattt cctcctcagg aacatgctcg ccttctggga   1380
gctcttcagg aatatgttct ccttcaggga tttcctcctc aggaacatgt tctccttcag   1440
ggatctcctc ctcgggagga acaagctcac cctcaccagg accctcttca tatggaggca   1500
agacctcgcc ttcttcaggg gggaaatgtt cgccttcttc ctcctcaatc tctggggtga   1560
catcgccgca gacctcggcc tcgacacagg cgcagtgcac gttgtcgcat gcacgtctct   1620
tgcggatacg caggccttgc tggggttccc cgcagggtga ccactcgccg aaggcagagc   1680
aggattcgtc agagcactga cggacttcct tatgatcggg gcagtccgag tagcttctct   1740
cctgaaggcc gttcacacac tcgccgaact cgccgaggga accgcattcg gaagcgacgt   1800
cagtggaaac gtccgagccg acctcctcgt cgggagtgca gaagcgggac tcggtcaaat   1860
ccatgccatc gcaggagcgc gtctgctcgt acagagtagt gccgggtatg tgtgtgcact   1920
tggaccaggc cgagaaagaa tggcagcggt cctcttgggg aggcgcggga gcatcgcagg   1980
cggcgaaggc cacgagctct gggcagttct cggggaaggc catggcgaag ccgcgaagag   2040
gcattccaca gtcggagaag gcaccatagt tgccgcatgc ttgcccagcc tgagttgggc   2100
actccatggt ttcgacttgg ttgacgcacg cctcgctctc ggtgtcttct ctccggcggg   2160
tgctcatgtt gtttccttcg ccgggacacg ggctccacgg acccacgtc cacatgcgtt    2220 gccgtcttcc tcaccaccct cgccggggggc gacagtcggg ggctggggca gggagccgac   2280
ttcgcaggtg atcgactcaa ccttgtctgg gaggtccaca cagtagcggc tgctgaggtg   2340
agtctcggga tcgcagcgag tgaatgcact ccagtggttg caagaattcc tg            2392
```

<210> SEQ ID NO 332
<211> LENGTH: 21
<212> TYPE: DNA
<213> ORGANISM: Artificial sequence
<220> FEATURE:
<223> OTHER INFORMATION: Synthetic Primer

<400> SEQUENCE: 332

```
ggaactgcat ccgttcatga g                                               21
```

<210> SEQ ID NO 333
<211> LENGTH: 19
<212> TYPE: DNA
<213> ORGANISM: Artificial sequence -continued

```
<220> FEATURE:
<223> OTHER INFORMATION: Synthetic Primer

<400> SEQUENCE: 333
tcttaaagcg ttcgtggtc                                                      19

<210> SEQ ID NO 334
<211> LENGTH: 23
<212> TYPE: DNA
<213> ORGANISM: Artificial sequence
<220> FEATURE:
<223> OTHER INFORMATION: Synthetic Primer

<400> SEQUENCE: 334
ggcgaccaat ctgcgaatac acc                                                 23

<210> SEQ ID NO 335
<211> LENGTH: 24
<212> TYPE: DNA
<213> ORGANISM: Artificial sequence
<220> FEATURE:
<223> OTHER INFORMATION: Synthetic Primer

<400> SEQUENCE: 335
gcatccttgg agacagagct tgag                                                24

<210> SEQ ID NO 336
<211> LENGTH: 24
<212> TYPE: DNA
<213> ORGANISM: Artificial sequence
<220> FEATURE:
<223> OTHER INFORMATION: Synthetic Primer

<400> SEQUENCE: 336
gggttctctt ctcgctcatc tttc                                                24

<210> SEQ ID NO 337
<211> LENGTH: 19
<212> TYPE: DNA
<213> ORGANISM: Artificial sequence
<220> FEATURE:
<223> OTHER INFORMATION: Synthetic Primer

<400> SEQUENCE: 337
agtcagaagc agtcaaggc                                                      19

<210> SEQ ID NO 338
<211> LENGTH: 647
<212> TYPE: DNA
<213> ORGANISM: Toxoplasma gondii

<400> SEQUENCE: 338
gatcctttag ccacttagac cgattcccca gacttgctcg gagatagtgt cagtgtcact          60
actacacagc tcaaagaagc cacatcccgt gaaaaatttt atcgtctaca agcgtgggcc         120
ggttctttgt tcactgttca cgtcacgtgt ggacatgccg ttgtgtcgtg gcagcaaata        180
cgaagaagcc aaagacatcc gaaaccgccc gttcagagtc ggggagactg cctgggtttt        240
cccacgagct gcatgttcca gctagatgca agcacctgca gtgggatgt atctccgaaa        300 aggcgagcaa ttttgtccaa aaagggtgag ctaatcgtga aatgtccact gacatgcagc        360
gtccgcttct gtctcagtac cgatcttcac ttcgcgtgct acccgcgttc gtttcgtttc        420
cccccattcc agatatccct gccgctgtgg cgcctggaag cgctcctcga ctgcattgag        480
```

```
cattccgccg tcacaagact ttttttttccc ttttgccaac gtcgagaacc tctcacgggc    540
gagcaaagtc tagtgtttgg tttcagtacg gcggtcgctg gctctgtgta tgactgacct    600
gaagaagcaa agacttcttg caacgtagaa acgcaaaggc gcttctt                  647

<210> SEQ ID NO 339
<211> LENGTH: 647
<212> TYPE: DNA
<213> ORGANISM: Toxoplasma gondii

<400> SEQUENCE: 339
aagaagcgcc tttgcgtttc tacgttgcaa gaagtctttg cttcttcagg tcagtcatac     60
acagagccag cgaccgccgt actgaaacca acactagac tttgctcgcc cgtgagaggt    120
tctcgacgtt ggcaaaaggg aaaaaaaagt cttgtgacgg cggaatgctc aatgcagtcg    180
aggagcgctt ccaggcgcca cagcggcagg gatatctgga atgggggaa acgaaacgaa    240 cgcgggtagc acgcgaagtg aagatcggta ctgagacaga gcggacgct gcatgtcagt    300 ggacatttca cgattagctc acccttttttg gacaaaattg ctcgcctttt cggagataca    360
tccccactgc aggtgcttgc atctagctgg aacatgcagc tcgtgggaaa acccaggcag    420
tctccccgac tctgaacggg cggtttcgga tgtctttggc ttcttcgtat tgctgccac    480 gacacaacgg catgtccaca cgtgacgtga acagtgaaca aagaaccggc ccacgcttgt    540
agacgataaa attttttcacg ggatgtggct tctttgagct gtgtagtagt gacactgaca    600
ctatctccga gcaagtctgg ggaatcggtc taagtggcta aaggatc                  647

<210> SEQ ID NO 340
<211> LENGTH: 867
<212> TYPE: DNA
<213> ORGANISM: Toxoplasma gondii
<220> FEATURE:
<221> NAME/KEY: CDS
<222> LOCATION: (1)..(867)
<223> OTHER INFORMATION:

<400> SEQUENCE: 340 atg gca gga agg cag gcg gcg ttg ttt ttg gtg gtg ctg tct gtg gcg     48
Met Ala Gly Arg Gln Ala Ala Leu Phe Leu Val Val Leu Ser Val Ala
1               5                   10                  15 gcg ggc cct gtc tcc cag ctt gct cgg gcg agc gac gac agc gtc gac     96
Ala Gly Pro Val Ser Gln Leu Ala Arg Ala Ser Asp Asp Ser Val Asp
            20                  25                  30 agc gtc gaa acc gcg cgt cag cac atg gag ctg gct atc gag gct gac    144
Ser Val Glu Thr Ala Arg Gln His Met Glu Leu Ala Ile Glu Ala Asp
        35                  40                  45 gaa gag atg cac gag gcc tac gac cct ttg ttg gaa ttc gtt gag acg    192
Glu Glu Met His Glu Ala Tyr Asp Pro Leu Leu Glu Phe Val Glu Thr
    50                  55                  60 ttt cgg gaa atc aaa aaa gct gtt gag gaa gat gcg gct ctg agt aca    240
Phe Arg Glu Ile Lys Lys Ala Val Glu Glu Asp Ala Ala Leu Ser Thr
65                  70                  75                  80 gat gcg atc gac cgc gtg tcc cag ttc gat ctg gtt tcc ctc cta gat    288
Asp Ala Ile Asp Arg Val Ser Gln Phe Asp Leu Val Ser Leu Leu Asp
                85                  90                  95 gtc atc cga gag gct gca caa gca aag ttc gat ctc ctc gga cgc ctc    336
Val Ile Arg Glu Ala Ala Gln Ala Lys Phe Asp Leu Leu Gly Arg Leu
            100                 105                 110 att aca gac atc gcc agc gga atc ggc gag ggt gcc atg gct ctg atg    384
Ile Thr Asp Ile Ala Ser Gly Ile Gly Glu Gly Ala Met Ala Leu Met
        115                 120                 125
```

```
gga gag gag gct gcg ttc att agg cca agg agg tca aag aga ggg aaa    432
Gly Glu Glu Ala Ala Phe Ile Arg Pro Arg Arg Ser Lys Arg Gly Lys
130                 135                 140 aag act aca act aca acc agt tca tcc aca agt acg agt aca acg acc    480
Lys Thr Thr Thr Thr Thr Ser Ser Ser Thr Ser Thr Ser Thr Thr Thr
145                 150                 155                 160 acg aca tca act acc act act acc act acc acc act acg act act act    528
Thr Thr Ser Thr Thr Thr Thr Thr Thr Thr Thr Thr Thr Thr Thr Thr
165                 170                 175 aca act acg aca cca aca aca act aca aca acc aca aca act aca cca    576
Thr Thr Thr Thr Pro Thr Thr Thr Thr Thr Thr Thr Thr Thr Thr Pro
180                 185                 190 aca aca acg aca aca acc aca aca act aca cca aca aca acg aca aca    624
Thr Thr Thr Thr Thr Thr Thr Thr Thr Thr Pro Thr Thr Thr Thr Thr
195                 200                 205 acc aca aca act aca cca aca aca acg aca aca acc aca acg cca act    672
Thr Thr Thr Thr Thr Pro Thr Thr Thr Thr Thr Thr Thr Thr Pro Thr
210                 215                 220 aca acg aca tct acg aca acc act acg act acc aca act act act aca    720
Thr Thr Thr Ser Thr Thr Thr Thr Thr Thr Thr Thr Thr Thr Thr Thr
225                 230                 235                 240 cca act aca aca acg aca acc acg gaa cca aca act aca aca aca acc    768
Pro Thr Thr Thr Thr Thr Thr Thr Glu Pro Thr Thr Thr Thr Thr Thr
245                 250                 255 acg gaa cca acc aca act aca agc aca acg acg act acg aca act aca    816
Thr Glu Pro Thr Thr Thr Thr Ser Thr Thr Thr Thr Thr Thr Thr Thr
260                 265                 270 acg act acg aca cca tct acg acg aca tcc acc acc act acc ctc gat    864
Thr Thr Thr Thr Pro Ser Thr Thr Thr Ser Thr Thr Thr Thr Leu Asp
275                 280                 285 tag                                                                867
```

<210> SEQ ID NO 341
<211> LENGTH: 288
<212> TYPE: PRT
<213> ORGANISM: Toxoplasma gondii

<400> SEQUENCE: 341

```
Met Ala Gly Arg Gln Ala Ala Leu Phe Leu Val Val Leu Ser Val Ala
1               5                   10                  15

Ala Gly Pro Val Ser Gln Leu Ala Arg Ala Ser Asp Asp Ser Val Asp
            20                  25                  30

Ser Val Glu Thr Ala Arg Gln His Met Glu Leu Ala Ile Glu Ala Asp
        35                  40                  45

Glu Glu Met His Glu Ala Tyr Asp Pro Leu Leu Glu Phe Val Glu Thr
    50                  55                  60

Phe Arg Glu Ile Lys Lys Ala Val Glu Glu Asp Ala Ala Leu Ser Thr
65                  70                  75                  80

Asp Ala Ile Asp Arg Val Ser Gln Phe Asp Leu Val Ser Leu Leu Asp
                85                  90                  95

Val Ile Arg Glu Ala Ala Gln Ala Lys Phe Asp Leu Leu Gly Arg Leu
            100                 105                 110

Ile Thr Asp Ile Ala Ser Gly Ile Gly Glu Gly Ala Met Ala Leu Met
        115                 120                 125

Gly Glu Glu Ala Ala Phe Ile Arg Pro Arg Arg Ser Lys Arg Gly Lys
    130                 135                 140

Lys Thr Thr Thr Thr Thr Ser Ser Ser Thr Ser Thr Ser Thr Thr Thr
```

```
                    145                 150                 155                 160
Thr Thr Ser Thr Thr Thr Thr Thr Thr Thr Thr Thr Thr Thr Thr Thr
165                 170                 175
Thr Thr Thr Thr Pro Thr Thr Thr Thr Thr Thr Thr Thr Thr Thr Pro
180                 185                 190
Thr Thr Thr Thr Thr Thr Thr Thr Thr Thr Pro Thr Thr Thr Thr Thr
195                 200                 205
Thr Thr Thr Thr Thr Pro Thr Thr Thr Thr Thr Thr Thr Thr Pro Thr
210                 215                 220
Thr Thr Thr Ser Thr Thr Thr Thr Thr Thr Thr Thr Thr Thr Thr Thr
225                 230                 235                 240
Pro Thr Thr Thr Thr Thr Thr Thr Glu Pro Thr Thr Thr Thr Thr Thr
245                 250                 255
Thr Glu Pro Thr Thr Thr Thr Ser Thr Thr Thr Thr Thr Thr Thr Thr
260                 265                 270
Thr Thr Thr Thr Pro Ser Thr Thr Thr Ser Thr Thr Thr Thr Leu Asp
275                 280                 285
```

```
<210> SEQ ID NO 342
<211> LENGTH: 867
<212> TYPE: DNA
<213> ORGANISM: Toxoplasma gondii

<400> SEQUENCE: 342
atggcaggaa ggcaggcggc gttgttttttg gtggtgctgt ctgtggcggc gggccctgtc      60
tcccagcttg ctcgggcgag cgacgacagc gtcgacagcg tcgaaaccgc gcgtcagcac     120
atggagctgg ctatcgaggc tgacgaagag atgcacgagg cctacgaccc tttgttggaa     180
ttcgttgaga cgtttcggga atcaaaaaaa gctgttgagg aagatgcggc tctgagtaca     240
gatgcgatcg accgcgtgtc ccagttcgat ctggtttccc tcctagatgt catccgagag     300
gctgcacaag caaagttcga tctcctcgga cgcctcatta cagacatcgc cagcggaatc     360
ggcgagggtg ccatggctct gatgggagag gaggctgcgt tcattaggcc aaggaggtca     420
aagagaggga aaaagactac aactacaacc agttcatcca caagtacgag tacaacgacc     480
acgacatcaa ctaccactac taccactacc accactacga ctactactac aactacgaca     540
ccaacaacaa ctacaacaac cacaacaact acaccaacaa caacgacaac aaccacaaca     600
actacaccaa caacgacgac aacaaccaca caactacac caacaacaac gacaacaacc     660
acaacgccaa ctacaacgac atctacgaca accactacga ctaccacaac tactactaca     720
ccaactacaa caacgacaac cacggaacca acaactacaa caacaaccac ggaaccaacc     780
acaactacaa gcaacgacga ctacgacaa actacaacga ctacgacacc atctacgacg     840
acatccacca ccactaccct cgattag                                         867

<210> SEQ ID NO 343
<211> LENGTH: 1397
<212> TYPE: DNA
<213> ORGANISM: Toxoplasma gondii
<220> FEATURE:
<221> NAME/KEY: CDS
<222> LOCATION: (238)..(1104)
<223> OTHER INFORMATION:

<400> SEQUENCE: 343
ccccattcca gatatccctg ccgctgtggc gcctggaagc gctcctcgac tgcattgagc      60
attccgccgt cacaagactt ttttttccct tttgccaacg tcgagaacct ctcacggacg     120
```

-continued

```
agcaaagtct agtgtttggt ttcagtacgg cggtcgctgg ctctgtgtat gactgacctg      180
aagaagcaaa gacttcttgc aacgtagaaa cgcaaaggcg cttcttttt gtgcaat         237 atg gca gga agg cag gcg gcg ttg ttt ttg gtg gtg ctg tct gtg gcg       285
Met Ala Gly Arg Gln Ala Ala Leu Phe Leu Val Val Leu Ser Val Ala
1               5                   10                  15 gcg ggc cct gtc tcc cag ctt gct cgg gcg agc gac gac agc gtc gac       333
Ala Gly Pro Val Ser Gln Leu Ala Arg Ala Ser Asp Asp Ser Val Asp
 20                  25                  30 agc gtc gaa acc gcg cgt cag cac atg gag ctg gct atc gag gct gac       381
Ser Val Glu Thr Ala Arg Gln His Met Glu Leu Ala Ile Glu Ala Asp
 35                  40                  45 gaa gag atg cac gag gcc tac gac cct ttg ttg gaa ttc gtt gag acg       429
Glu Glu Met His Glu Ala Tyr Asp Pro Leu Leu Glu Phe Val Glu Thr
 50                  55                  60 ttt cgg gaa atc aaa aaa gct gtt gag gaa gat gcg gct ctg agt aca       477
Phe Arg Glu Ile Lys Lys Ala Val Glu Glu Asp Ala Ala Leu Ser Thr
 65                  70                  75                  80 gat gcg atc gac cgc gtg tcc cag ttc gat ctg gtt tcc ctc cta gat       525
Asp Ala Ile Asp Arg Val Ser Gln Phe Asp Leu Val Ser Leu Leu Asp
 85                  90                  95 gtc atc cga gag gct gca caa gca aag ttc gat ctc ctc gga cgc ctc       573
Val Ile Arg Glu Ala Ala Gln Ala Lys Phe Asp Leu Leu Gly Arg Leu
100                 105                 110 att aca gac atc gcc agc gga atc ggc gag ggt gcc atg gct ctg atg       621
Ile Thr Asp Ile Ala Ser Gly Ile Gly Glu Gly Ala Met Ala Leu Met
115                 120                 125 gga gag gag gct gcg ttc att agg cca agg agg tca aag aga ggg aaa       669
Gly Glu Glu Ala Ala Phe Ile Arg Pro Arg Arg Ser Lys Arg Gly Lys
130                 135                 140 aag act aca act aca acc agt tca tcc aca agt acg agt aca acg acc       717
Lys Thr Thr Thr Thr Ser Ser Ser Thr Ser Thr Ser Thr Thr Thr
145                 150                 155                 160 acg aca tca act acc act act acc act acc act acg act act act            765
Thr Thr Ser Thr Thr Thr Thr Thr Thr Thr Thr Thr Thr Thr Thr
165                 170                 175 aca act acg aca cca aca aca act aca aca acc aca aca act aca cca       813
Thr Thr Thr Thr Pro Thr Thr Thr Thr Thr Thr Thr Thr Thr Pro
180                 185                 190 aca aca acg aca aca acc aca aca act aca cca aca aca acg aca aca       861
Thr Thr Thr Thr Thr Thr Thr Thr Thr Pro Thr Thr Thr Thr Thr
195                 200                 205 acc aca aca act aca cca aca aca acg aca aca acc aca acg cca act       909
Thr Thr Thr Thr Thr Pro Thr Thr Thr Thr Thr Thr Thr Pro Thr
210                 215                 220 aca acg aca tct acg aca acc act acg act acc aca act act act aca       957
Thr Thr Thr Ser Thr Thr Thr Thr Thr Thr Thr Thr Thr Thr Thr
225                 230                 235                 240 cca act aca aca acg aca acc acg gaa cca aca act aca aca aca acc       1005
Pro Thr Thr Thr Thr Thr Thr Thr Glu Pro Thr Thr Thr Thr Thr Thr
245                 250                 255 acg gaa cca acc aca act aca agc aca acg acg act acg aca act aca       1053
Thr Glu Pro Thr Thr Thr Thr Ser Thr Thr Thr Thr Thr Thr Thr
260                 265                 270 acg act acg aca cca tct acg acg aca tcc acc acc act acc ctc gat       1101
Thr Thr Thr Thr Pro Ser Thr Thr Thr Ser Thr Thr Thr Leu Asp
275                 280                 285 tag accaaagtgt ttttgccgca cagattgtac atgcatcaaa aaacgcgata             1154
```

```
tttctttctc gtttgcgctg gcgtcatctg cgtctgccat ttgaatctgt cagcgctgcc      1214
agctccatag ggcgtgctcc ctgattacgt atttgcacga agggatgtct tggcttctac      1274
attggcgaac cgtttttggc actccaaaat ttttattaac acaaagcctt gcactggcct      1334
cattgtctat tcatagaacg ataatgtgtt gacctcgaaa aaaaaaaaaa aaaaaaaaa       1394 aaa                                                                   1397
```

<210> SEQ ID NO 344
<211> LENGTH: 288
<212> TYPE: PRT
<213> ORGANISM: Toxoplasma gondii

<400> SEQUENCE: 344

```
Met Ala Gly Arg Gln Ala Ala Leu Phe Leu Val Val Leu Ser Val Ala
1               5                   10                  15

Ala Gly Pro Val Ser Gln Leu Ala Arg Ala Ser Asp Asp Ser Val Asp
            20                  25                  30

Ser Val Glu Thr Ala Arg Gln His Met Glu Leu Ala Ile Glu Ala Asp
        35                  40                  45

Glu Glu Met His Glu Ala Tyr Asp Pro Leu Leu Glu Phe Val Glu Thr
    50                  55                  60

Phe Arg Glu Ile Lys Lys Ala Val Glu Glu Asp Ala Ala Leu Ser Thr
65                  70                  75                  80

Asp Ala Ile Asp Arg Val Ser Gln Phe Asp Leu Val Ser Leu Leu Asp
                85                  90                  95

Val Ile Arg Glu Ala Ala Gln Ala Lys Phe Asp Leu Leu Gly Arg Leu
            100                 105                 110

Ile Thr Asp Ile Ala Ser Gly Ile Gly Glu Gly Ala Met Ala Leu Met
        115                 120                 125

Gly Glu Glu Ala Ala Phe Ile Arg Pro Arg Arg Ser Lys Arg Gly Lys
    130                 135                 140

Lys Thr Thr Thr Thr Thr Ser Ser Ser Thr Ser Thr Ser Thr Thr Thr
145                 150                 155                 160

Thr Thr Ser Thr Thr Thr Thr Thr Thr Thr Thr Thr Thr Thr Thr Thr
                165                 170                 175

Thr Thr Thr Thr Pro Thr Thr Thr Thr Thr Thr Thr Thr Thr Thr Pro
            180                 185                 190

Thr Thr Thr Thr Thr Thr Thr Thr Thr Pro Thr Thr Thr Thr Thr Thr
        195                 200                 205

Thr Thr Thr Thr Thr Pro Thr Thr Thr Thr Thr Thr Thr Thr Pro Thr
    210                 215                 220

Thr Thr Ser Thr Thr Thr Thr Thr Thr Thr Thr Thr Thr Thr Thr Thr
225                 230                 235                 240

Pro Thr Thr Thr Thr Thr Thr Thr Glu Pro Thr Thr Thr Thr Thr Thr
                245                 250                 255

Thr Glu Pro Thr Thr Thr Thr Ser Thr Thr Thr Thr Thr Thr Thr Thr
            260                 265                 270

Thr Thr Thr Thr Pro Ser Thr Thr Thr Ser Thr Thr Thr Thr Leu Asp
        275                 280                 285
```

<210> SEQ ID NO 345
<211> LENGTH: 1397
<212> TYPE: DNA
<213> ORGANISM: Toxoplasma gondii

<400> SEQUENCE: 345

-continued

```
tttttttttt tttttttttt tttttcgag gtcaacacat tatcgttcta tgaatagaca      60
atgaggccag tgcaaggctt tgtgttaata aaaattttgg agtgccaaaa acggttcgcc    120
aatgtagaag ccaagacatc ccttcgtgca aatacgtaat cagggagcac gccctatgga    180
gctggcagcg ctgacagatt caaatggcag acgcagatga cgccagcgca acgagaaag    240 aaatatcgcg ttttttgatg catgtacaat ctgtgcggca aaaacacttt ggtctaatcg    300
agggtagtgg tggtggatgt cgtcgtagat ggtgtcgtag tcgttgtagt tgtcgtagtc    360
gtcgttgtgc ttgtagttgt ggttggttcc gtggttgttg ttgtagttgt tggttccgtg    420
gttgtcgttg ttgtagttgg tgtagtagta gttgtggtag tcgtagtggt tgtcgtagat    480
gtcgttgtag ttggcgttgt ggttgttgtc gttgttgttg gtgtagttgt tgtggttgtt    540
gtcgttgttg ttggtgtagt tgttgtggtt gttgtcgttg ttgttggtgt agttgttgtg    600
gttgttgtag ttgttgttgg tgtcgtagtt gtagtagtag tcgtagtggt ggtagtggta    660
gtagtggtag ttgatgtcgt ggtcgttgta ctcgtacttg tggatgaact ggttgtagtt    720
gtagtctttt tccctctctt tgacctcctt ggcctaatga acgcagcctc ctctcccatc    780
agagccatgg caccctcgcc gattccgctg gcgatgtctg taatgaggcg tccgaggaga    840
tcgaactttg cttgtgcagc ctctcggatg acatctagga gggaaaccag atcgaactgg    900
gacacgcggt cgatcgcatc tgtactcaga gccgcatctt cctcaacagc ttttttgatt    960
tcccgaaacg tctcaacgaa ttccaacaaa gggtcgtagg cctcgtgcat ctcttcgtca   1020
gcctcgatag ccagctccat gtgctgacgc gcggtttcga cgctgtcgac gctgtcgtcg   1080
ctcgcccgag caagctggga gacagggccc gccgccacag acagcaccac caaaaacaac   1140
gccgcctgcc ttcctgccat attgcacaaa aaagaagcgc ctttgcgttt ctacgttgca   1200
agaagtcttt gcttcttcag gtcagtcata cacagagcca gcgaccgccg tactgaaacc   1260
aaacactaga ctttgctcgt ccgtgagagg ttctcgacgt tggcaaaagg gaaaaaaaag   1320
tcttgtgacg gcggaatgct caatgcagtc gaggagcgct tccaggcgcc acagcggcag   1380
ggatatctgg aatgggg                                                  1397
```

<210> SEQ ID NO 346
<211> LENGTH: 18
<212> TYPE: DNA
<213> ORGANISM: Artificial sequence
<220> FEATURE:
<223> OTHER INFORMATION: Synthetic Primer

<400> SEQUENCE: 346

```
caggaaacag ctatgacc                                                   18
```

<210> SEQ ID NO 347
<211> LENGTH: 20
<212> TYPE: DNA
<213> ORGANISM: Artificial sequence
<220> FEATURE:
<223> OTHER INFORMATION: Synthetic Primer

<400> SEQUENCE: 347

```
attaaccctc actaaaggga                                                 20
```

<210> SEQ ID NO 348
<211> LENGTH: 20
<212> TYPE: DNA
<213> ORGANISM: Artificial sequence
<220> FEATURE:

-continued

<223> OTHER INFORMATION: Synthetic Primer

<400> SEQUENCE: 348
taatacgact cactataggg   20

<210> SEQ ID NO 349
<211> LENGTH: 23
<212> TYPE: DNA
<213> ORGANISM: Artificial sequence
<220> FEATURE:
<223> OTHER INFORMATION: Synthetic Primer

<400> SEQUENCE: 349
gccagtgtga tggatatctg cag   23

<210> SEQ ID NO 350
<211> LENGTH: 18
<212> TYPE: DNA
<213> ORGANISM: Artificial sequence
<220> FEATURE:
<223> OTHER INFORMATION: Synthetic Primer

<400> SEQUENCE: 350
cgagctcgga tccactag   18

<210> SEQ ID NO 351
<211> LENGTH: 23
<212> TYPE: DNA
<213> ORGANISM: Artificial sequence
<220> FEATURE:
<223> OTHER INFORMATION: Synthetic Primer

<400> SEQUENCE: 351
ggttctctcc agaggttcat tac   23

<210> SEQ ID NO 352
<211> LENGTH: 22
<212> TYPE: DNA
<213> ORGANISM: Artificial sequence
<220> FEATURE:
<223> OTHER INFORMATION: Synthetic Primer

<400> SEQUENCE: 352
ggatgcaatg aagagagggc tc   22

<210> SEQ ID NO 353
<211> LENGTH: 24
<212> TYPE: DNA
<213> ORGANISM: Artificial sequence
<220> FEATURE:
<223> OTHER INFORMATION: Synthetic Primer

<400> SEQUENCE: 353
aactagaagg cacagtcgag gctg   24

<210> SEQ ID NO 354
<211> LENGTH: 24
<212> TYPE: DNA
<213> ORGANISM: Artificial sequence
<220> FEATURE:
<223> OTHER INFORMATION: Synthetic Primer

<400> SEQUENCE: 354
gggaacaaaa gctggagctc cacc   24

```
<210> SEQ ID NO 355
<211> LENGTH: 23
<212> TYPE: DNA
<213> ORGANISM: Artificial sequence
<220> FEATURE:
<223> OTHER INFORMATION: Synthetic Primer

<400> SEQUENCE: 355
cggacgttgc atgtcagtgg aca                                             23

<210> SEQ ID NO 356
<211> LENGTH: 24
<212> TYPE: DNA
<213> ORGANISM: Artificial sequence
<220> FEATURE:
<223> OTHER INFORMATION: Synthetic Primer

<400> SEQUENCE: 356
cacgaagctg catgttccag ctag                                            24

<210> SEQ ID NO 357
<211> LENGTH: 24
<212> TYPE: DNA
<213> ORGANISM: Artificial sequence
<220> FEATURE:
<223> OTHER INFORMATION: Synthetic Primer

<400> SEQUENCE: 357
acactttggt ctaatcgagg gtag                                            24

<210> SEQ ID NO 358
<211> LENGTH: 23
<212> TYPE: DNA
<213> ORGANISM: Artificial sequence
<220> FEATURE:
<223> OTHER INFORMATION: Synthetic Primer

<400> SEQUENCE: 358
acaacgacca cgacatcaac tac                                             23

<210> SEQ ID NO 359
<211> LENGTH: 24
<212> TYPE: DNA
<213> ORGANISM: Artificial sequence
<220> FEATURE:
<223> OTHER INFORMATION: Synthetic Primer

<400> SEQUENCE: 359
gttgtcgtag atgtcgttgt agtt                                            24

<210> SEQ ID NO 360
<211> LENGTH: 24
<212> TYPE: DNA
<213> ORGANISM: Artificial sequence
<220> FEATURE:
<223> OTHER INFORMATION: Synthetic Primer

<400> SEQUENCE: 360
agaagcgcct ttgcgtttct acgt                                            24

<210> SEQ ID NO 361
<211> LENGTH: 24
<212> TYPE: DNA
<213> ORGANISM: Artificial sequence
<220> FEATURE:
<223> OTHER INFORMATION: Synthetic Primer
```

```
<400> SEQUENCE: 361
gaggagatcg aactttgctt gtgc                                              24

<210> SEQ ID NO 362
<211> LENGTH: 46
<212> TYPE: DNA
<213> ORGANISM: Artificial sequence
<220> FEATURE:
<223> OTHER INFORMATION: Synthetic Primer

<400> SEQUENCE: 362
aaggataggc ggccgcaggt accatggcag gaaggcaggc ggcgtt                      46

<210> SEQ ID NO 363
<211> LENGTH: 40
<212> TYPE: DNA
<213> ORGANISM: Artificial sequence
<220> FEATURE:
<223> OTHER INFORMATION: Synthetic Primer

<400> SEQUENCE: 363
accgctcgag aagcttgaag ccaagacatc ccttcgtgca                             40

<210> SEQ ID NO 364
<211> LENGTH: 34
<212> TYPE: DNA
<213> ORGANISM: Artificial sequence
<220> FEATURE:
<223> OTHER INFORMATION: Synthetic Primer

<400> SEQUENCE: 364
ggccacgcgt cgactacttt tttttttttt tttt                                   34

<210> SEQ ID NO 365
<211> LENGTH: 20
<212> TYPE: DNA
<213> ORGANISM: Artificial sequence
<220> FEATURE:
<223> OTHER INFORMATION: ggtggcgacg actcctggag

<400> SEQUENCE: 365
ggtggcgacg actcctggag                                                   20

<210> SEQ ID NO 366
<211> LENGTH: 22
<212> TYPE: DNA
<213> ORGANISM: Artificial sequence
<220> FEATURE:
<223> OTHER INFORMATION: ccagaccaac tggtaatggt ag

<400> SEQUENCE: 366
ccagaccaac tggtaatggt ag                                                22
```